US012714678B2

(12) United States Patent
Du et al.

(10) Patent No.: US 12,714,678 B2
(45) Date of Patent: Aug. 25, 2026

(54) PEPTIDES AND METHODS OF TREATING SEPSIS, ATHEROSCLEROSIS, THROMBOSIS, STROKE, HEART ATTACK AND INFLAMMATION

(71) Applicant: THE BOARD OF TRUSTEES OF THE UNIVERSITY OF ILLINOIS, Urbana, IL (US)

(72) Inventors: Xiaoping Du, Willowbrook, IL (US); Ni Cheng, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 867 days.

(21) Appl. No.: 17/773,882

(22) PCT Filed: Nov. 9, 2020

(86) PCT No.: PCT/US2020/059729

§ 371 (c)(1),
(2) Date: May 3, 2022

(87) PCT Pub. No.: WO2021/092580

PCT Pub. Date: May 14, 2021

(65) Prior Publication Data

US 2022/0347113 A1 Nov. 3, 2022

Related U.S. Application Data

(60) Provisional application No. 62/932,024, filed on Nov. 7, 2019.

(51) Int. Cl.

| | |
|---|---|
| ***A61P 7/02*** | (2006.01) |
| ***A61K 9/51*** | (2006.01) |
| ***A61K 38/00*** | (2006.01) |
| ***A61P 29/00*** | (2006.01) |
| ***C07K 14/705*** | (2006.01) |

(52) U.S. Cl.

CPC .......... *A61K 9/5123* (2013.01); *A61K 9/5146* (2013.01); *A61P 7/02* (2018.01); *A61P 29/00* (2018.01); *C07K 14/70557* (2013.01); *A61K 38/00* (2013.01)

(58) Field of Classification Search

CPC ......... A61K 9/5123; A61K 38/00; A61P 7/02; C07K 14/70557

See application file for complete search history.

(56) References Cited

U.S. PATENT DOCUMENTS

| | | | | |
|---|---|---|---|---|
| 8,685,921 | B2 | 4/2014 | Du | |
| 9,156,884 | B2 | 10/2015 | Du | |
| 10,011,634 | B2 | 7/2018 | Du et al. | |
| 10,738,080 | B2 | 8/2020 | Du et al. | |
| 2013/0072433 | A1 * | 3/2013 | Du | C07K 14/70546 514/13.8 |
| 2021/0054026 | A1 | 2/2021 | Du et al. | |

FOREIGN PATENT DOCUMENTS

| | | | | |
|---|---|---|---|---|
| CN | 101258166 | A | 9/2008 | |
| WO | WO-2004091723 | A1 * | 10/2004 | A61P 7/02 |
| WO | WO-2005113601 | A2 | 12/2005 | |
| WO | WO-2008120998 | A2 * | 10/2008 | A61K 9/0009 |
| WO | WO-2010005723 | A2 * | 1/2010 | A61P 35/00 |
| WO | WO-2011084518 | A2 * | 7/2011 | A61K 31/56 |
| WO | WO-2011116026 | A2 * | 9/2011 | A61K 38/08 |
| WO | WO-2012166923 | A2 * | 12/2012 | A61K 35/02 |
| WO | WO-2014/043594 | A1 | 3/2014 | |
| WO | WO-2014043618 | A1 * | 3/2014 | A61P 35/02 |
| WO | WO-2017064276 | A1 * | 4/2017 | A61K 9/0019 |
| WO | WO-2019010422 | A1 * | 1/2019 | C12N 15/102 |

OTHER PUBLICATIONS

Lei et al., 2018, Self-Assembling Myristoylated Human alpha-Defensin 5 as a Next-Generation Nanobiotics Potentiates Therapeutic Efficacy in Bacterial Infection, ACS Nano, 12: 5284-5296.*

Nelson et al., 2007, Myristoyl-Based Transport of Peptides into Living Cells, Biochemistry, 46(51): 14771-14781.*

Lin et al., 2003, PEG-Containing Surfactants Enhance the Ultrasonic Permeabilizability of Liposomes, Mat Res Soc Symp Proc, 774: 8 pages.*

Lin et al., 2003, PEG-Lipids and Oligo(ethylene glycol) Surfactants Enhance the Ultrasonic Permeabilizability of Liposomes, Langmuir, 19: 1098-1105.*

Angus et al., Severe sepsis and septic shock, N Engl J Med., 369(9):840-51 (Aug. 2013).

Bargatze et al., Neutrophils Roll on Adherent Neutrophils Bound to Cytokine-induced Endothelial Cells via L-Selectin on the rolling cells, J Exp Med, 180:1785-1792 (1994).

Benefield et al., A multicenter evaluation of the safety of drotrecogin alfa (activated) in patients with baseline bleeding precautions, Curr. Drug Saf., 7(1):3-7 (Feb. 2012).

Berger et al., Bleeding complications with dual antiplatelet therapy among patients with stable vascular disease or risk factors for vascular disease: results from the Clopidogrel for High Atherothrombotic Risk and Ischemic Stabilization, Management, and Avoidance (CHARISMA) trial, Circulation, 121(23):2575-83 (Jun. 2010).

(Continued)

*Primary Examiner* — Amber D Steele

(74) *Attorney, Agent, or Firm* — MARSHALL, GERSTEIN & BORUN LLP

(57) ABSTRACT

The present disclosure provides peptides that inhibit a binding interaction between a β integrin and a G protein subunit, as well as compositions, e.g., pharmaceutical compositions, particularly nanoparticle compositions, comprising the same and to methods of using the peptides to treat atherosclerosis, thrombosis, stroke, heart attack, inflammation, acute respiratory distress syndrome (ARDS), autoimmune diseases, AV Fistula for hemodialysis or organ transplantation.

16 Claims, 58 Drawing Sheets

Specification includes a Sequence Listing.

(56) References Cited

OTHER PUBLICATIONS

Bernard et al., Efficacy and safety of recombinant human activated protein C for severe sepsis, N Engl. J. Med., 344(10):699-709 (Mar. 2001).
Bhargava et al., Acute lung injury and acute kidney injury are established by four hours in experimental sepsis and are improved with pre, but not post, sepsis administration of TNF-a antibodies, PLoS One, 8(11):e79037 (Nov. 2013).
Bhatt et al., Effect of platelet inhibition with cangrelor during PCI on ischemic events, N. Eng. J. Med., 368(14):1303-13 (Apr. 2013).
Bhatt et al., Intravenous platelet blockade with cangrelor during PCI, N. Eng. J. Med., 361(24):2330-41 (Dec. 2009).
Bian et al., The G12/13-RhoA signaling pathway contributes to efficient lysophosphatidic acid-stimulated cell migration, Oncogene, 25:2234-2244 (2006).
Bledzka et al., Integrin allbß3: from discovery to efficacious therapeutic target, Circ. Res., 112(8):1189-200 (Apr. 2013).
Brooks et al., Buccal mucosa bleeding time is prolonged in canine models of primary hemostatic disorders, Thromb. Haemost., 70(5):777-80 (Nov. 1993).
Call et al., Ratio of local to systemic chemokine concentrations regulates neutrophil recruitment, Am J Pathol, 158:715-721 (2001).
Chen et al., Activation of p115-RhoGEF requires direct association of G?13and the Dbl homology domain, J Biol Chem, 287:25490-25500 (Jul. 2012).
Cheng et al., Serum amyloid A promotes LPS clearance and suppresses LPS-induced inflammation and tissue injury, EMBO Rep., 19:e45517 (Oct. 2018).
Coller, Anti-GPIIb/IIIa drugs: current strategies and future directions, Thromb. Haemost., 86(1):427-43 (Jul. 2001).
Coller, Historical perspective and future directions in platelet research, J. Thromb. Haemost., 9 Suppl 1(Suppl 1):374-95 (Jul. 2011).
Cuenca et al., Cecal ligation and puncture, Curr. Protoc. Immunol., Chapter 19, Unit 19 13 (Nov. 2010).
Dave et al., Lipid-polymer hybrid nanoparticles: synthesis strategies and biomedical applications, J. Microbiological Methods, 160:130-42 (May 2019).
Davis et al., Platelets and coagulation in infection, Clin. Transl. Immunology, 5(7):e89 (Jul. 2016).
Davis, Isolation, culture, and functional evaluation of bone marrow-derived macrophages, Methods Mol. Biol., 1031:27-35 (2013).
Day et al., Murine thrombosis models, Thromb. Haemost., 92(3):486-94 (Sep. 2004).
Diacovo et al., Neutrophil rolling, arrest, and transmigration across activated, surface-adherent platelets via sequential action of P-selectin and the beta 2-integrin CD11b/CD18, Blood, 88:146-157 (1996).
Ding et al., Relative contribution of LFA-1 and Mac-1 to neutrophil adhesion and migration. J Immunol., 163:5029-38 (1999).
Donovan et al., Size-controlled synthesis of granular polyphosphate nanoparticles at physiologic salt concentrations for blood clotting, Biomacromolecules, 15(11):3976-84 (Nov. 2014).
Dorward et al., The role of formylated peptides and formyl peptide receptor 1 in governing neutrophil function during acute inflammation, Am J Pathol, 185:1172-1184 (May 2015).
Esmon, Crosstalk between inflammation and thrombosis, Maturitas, 47:305-14 (2004).
Estevez et al., LIM kinase-1 selectively promotes glycoprotein Ib-IX-mediated TXA2 synthesis, platelet activation, and thrombosis, Blood, 121(22):4586-94 (May 2013).
Estevez et al., New Concepts and Mechanisms of Platelet Activation Signaling, Physiology (Betheseda), 32(2):162-77 (Mar. 2017).
Estevez et al., Signaling-mediated cooperativity between glycoprotein Ib-IX and protease-activated receptors in thrombin-induced platelet activation, Blood, 127(5):626-36 (Feb. 2016).
Estevez et al., Targeting integrin and integrin signaling in treating thrombosis, Arterioscler. Thromb. Vasc. Biol., 35(1):24-9 (Jan. 2015).
Fink et al., Strategies to improve drug development for sepsis, Nat. Rev. Drug Discov., 13(10):741-58 (Oct. 2014).
Flick et al., Leukocyte engagement of fibrin(ogen) via the integrin receptor ?M?2/Mac-1 is critical for host inflammatory response in vivo, J Clin Invest, 113:1596-1606 (2004).
Fosgerau et al., Peptide therapeutics: current status and future directions, Drug Discov. Today, 20(1):122-8 (2015).
Francis et al., Rho GEF Lsc is required for normal polarization, migration, and adhesion of formyl-peptide-stimulated neutrophils. Blood 107:1627-1635 (Feb. 2006).
French et al., Approval of the first protease-activated receptor antagonist: Rationale, development, significance, and considerations of a novel anti-platelet agent, Blood Rev., 29(3):179-89 (May 2015).
Gill et al., Pulmonary microvascular albumin leak is associated with endothelial cell death in murine sepsis-induced lung injury in vivo, PLoS One, 9(2):e88501 (Feb. 2014).
Gong et al., G protein subunit Galpha13 binds to integrin alphallb-beta3 and mediates integrin “outside-in” signaling, Science, 327(5963):340-3 (2010).
Goulimari et al., Ga12/13 is essential for directed cell migration and localized rho-dia1 function. J Biol Chem, 280:42242-42251 (Dec. 2005).
Heit et al., An intracellular signaling hierarchy determines direction of migration in opposing chemotactic gradients. J Cell Biol 159:91-102 (Oct. 2002).
Hind et al., Leading from the Back: The Role of the Uropod in Neutrophil Polarization and Migration, Dev Cell, 38:161-169 (Jul. 2016).
Huttenlocher et al., Integrins in cell migration. Cold Spring Harb Perspect Biol 3 VN-re:1-16 (2011).
Hynes, Integrins: A family of cell surface receptors. Cell 48:549-554 (1987).
Hynes, Integrins: bidirectional, allosteric signaling machines, Cell, 110(6):673-87 (Sep. 2002).
Hynes, The emergence of integrins: A personal and historical perspective, Matrix Biol, 23:333-340 (2004).
International Application No. PCT/US2020/059729, International Search Report and Written Opinion, mailed Apr. 16, 2021.
Ivanciu et al., New insights into the spatiotemporal localization of prothrombinase in vivo, Blood, 124(11):1705-14 (Sep. 2014).
Jasuja et al., Endothelium-derived but not platelet-derived protein disulfide isomerase is required for thrombus formation in vivo, Blood, 116(22):4665-74 (Nov. 2010).
Kiosses et al., Rac recruits high-affinity integrin ? v ? 3 to lamellipodia in endothelial cell migration, Nat cell, 3(3):316-20 (2001).
Kolaczkowska, Neutrophil recruitment and function in health and inflammation. Nat Rev Immunol, 13:159-175 (2013).
Kourtzelis et al., From leukocyte recruitment to resolution of inflammation?: the cardinal role of integrins, J Leukoc Biol., 102:677-683 (2017).
Kozasa et al., Signalling mechanisms of RhoGTPase regulation by the heterotrimeric G proteins G12 and G13, J Biochem, 150:357-369 (2011).
Kreutz et al., Distinct regions of G?13 participate in its regulatory interactions with RGS homology domain-containing RhoGEFs, Cell Signal, 19:1681-1689 (2007).
Kroon et al., Inflammation-Sensitive Myosin-X Functionally Supports Leukocyte Extravasation by Cdc42-Mediated ICAM-1—Rich Endothelial Filopodia Formation. J Immunol, 200(5):1790-1801 (Mar. 2018).
Kumar et al., Cdc42 regulates neutrophil migration via crosstalk between WASp, CD11b, and microtubules, Blood, 120(17):3563-74 (Oct. 2012).
Lagarrigue et al., The Rap1-RIAM-talin axis of integrin activation and blood cell function, Blood, 128:479-487 (2016).
Languino et al., Fibrinogen mediates leukocyte adhesion to vascular endothelium through an ICAM-1-dependent pathway, Cell, 73:1423-1434 (1993).
Levi et al., Inflammation and coagulation, Crit Care Med., 38(2 Suppl):S26-34 (Feb. 2010).
Levi et al., Coagulation and sepsis, Thrombosis Res., 149(2017):38-44 (2017).
Ley et al., Getting to the site of inflammation: The leukocyte adhesion cascade updated, Nat Rev Immunol, 7:678-689 (2007).

(56) References Cited

OTHER PUBLICATIONS

Li et al., Signaling during platelet adhesion and activation, Arterioscler. Thromb. Vasc. Biol., 30(12):2341-9 (Dec. 2010).
Li et al., Two waves of platelet secretion induced by thromboxane A2 receptor and a critical role for phosphoinositide 3-kinases, J. Biol. Chem., 278(33):30725-31 (Aug. 2003).
Libby, Mechanisms of acute coronary syndromes and their implications for therapy, N. Eng. J. Med., 368(21):2004-13 (May 2013).
Liverani et al., P2Y12 Receptor Modulates Sepsis-Induced Inflammation, Arterioscler. Thromb. Vasc. Biol., 36(5):961-71 (May 2016).
Muller et al., Assays of Transendothelial Migration in vitro, Methods Enzymol, 6879:155-176 (2008).
Lämmermann et al., Mechanical modes of "amoeboid" cell migration. Curr Opin Cell Biol., 21(5):636-44 (Oct. 2009).
Lämmermann et al., Rapid leukocyte migration by integrin-independent flowing and squeezing, Nature, 453:51-55 (2008).
Margadant et al., Integrin-TGF-beta crosstalk in fibrosis, cancer and wound healing, EMBO Rep., 11:97-105 (Jan. 2010).
Marjanovic et al., Stimulatory roles of nitric-oxide synthase 3 and guanylyl cyclase in platelet activation, J. Biol. Chem., 280(45):37430-8 (Nov. 2005).
McDowall et al., The I domain of integrin leukocyte function-associated antigen-1 is involved in a conformational change leading to high affinity binding to ligand intercellular adhesion molecule 1 (ICAM-1), J Biol Chem., 273:27396-27403 (Oct. 1998).
Mehilli et al., Abciximab in patients with acute ST-segment-elevation myocardial infarction undergoing primary percutaneous coronary intervention after clopidogrel loading: a randomized double-blind trial, Circulation, 119(14):1933-40 (Apr. 2009).
Mehran et al., Impact of bleeding on mortality after percutaneous coronary intervention results from a patient-level pooled analysis of the REPLACE-2 (randomized evaluation of PCI linking angiomax to reduced clinical events), ACUITY (acute catheterization and urgent intervention triage strategy), and HORIZONS-AMI (harmonizing outcomes with revascularization and stents in acute myocardial infarction) trials, JACC Cardiovasc. Interv., 4(6):654-64 (Jun. 2011).
Metharom et al., Current state and novel approaches of antiplatelet therapy, Arterioscler. Thromb. Vasc. Biol., 35(6):1327-38 (Jun. 2015).
Moers et al., G13 is an essential mediator of platelet activation in hemostasis and thrombosis, Nat. Med., 9(11):1418-22 (Nov. 2003).
Moscucci, Frequency and costs of ischemic and bleeding complications after percutaneous coronary interventions: rationale for new antithrombotic agents, J. Invasive Cardiol., 14 Suppl B:55B-64B (Apr. 2002).
Ndrepepa et al., Bleeding complications in patients undergoing percutaneous coronary interventions: current status and perspective, Coron. Artery Dis., 25(3):247-57 (May 2014).
Ndrepepa et al., Weight of the bleeding impact on early and late mortality after percutaneous coronary intervention, J. Thromb. Thrombolysis, 39(1):35-42 (Jan. 2015).
Nourshargh et al., Leukocyte Migration into Inflamed Tissues, Immunity, 41:694-707 (2014).
Nuzzi et al., Analysis of Neutrophil Chemotaxis, IN: Coutts (ed.), Adhesion Protein Protocols, Second edition, Humana Press (2007).
O'Brien et al., An important role for Akt3 in platelet activation and thrombosis, Blood, 118(15):4215-23 (Oct. 2011).
O'Gara et al., 2013 ACCF/AHA guideline for the management of ST-elevation myocardial infarction: a report of the American College of Cardiology Foundation/American Heart Association Task Force on Practice Guidelines, J. Am. Coll. Cardiol., 61(4):e78-e140 (Jan. 2013).
Pang et al., Shear-induced integrin signaling in platelet phosphatidylserine exposure, microvesicle release, and coagulation, Blood, 132(5):533-43 (Aug. 2018).
Radhika et al., G?13 stimulates cell migration through cortactin-interacting protein Hax-1. J Biol Chem, 279:49406-49413 (2004).
Ray et al., Isolation of mouse peritoneal cavity cells, J Vis Exp, (35):1488 (Jan. 2010).
Reutershan, Sequential recruitment of neutrophils into lung and bronchoalveolar lavage fluid in LPS-induced acute lung injury. AJP Lung Cell Mol Physiol., 289:L807-L815 (Jun. 2005).
Rieken et al., G 12 /G 13 Family G Proteins Regulate Marginal Zone B Cell Maturation, Migration, and Polarization, J Immunol., 177:2985-2993 (2006).
Ruggeri, Platelets in atherothrombosis, Nat. Med., 8(11):1227-34 (Nov. 2002).
Safley et al., Impact of Glycoprotein IIb/IIIa Inhibition in Contemporary Percutaneous Coronary Intervention for Acute Coronary Syndromes: Insights From the National Cardiovascular Data Registry, JACC Cardiovasc. Interv., 8(12):1574-82 (Oct. 2015).
Seemann et al., Comprehensive comparison of three different animal models for systemic inflammation, J. Biomed. Sci., 24(1):60 (Aug. 2017).
Seguin et al., Integrins and cancer: Regulators of cancer stemness, metastasis, and drug resistance. Trends Cell Biol 25:234-240 (2015).
Seidel et al., Beneficial effect of clopidogrel in a mouse model of polymicrobial sepsis, J. Thromb. Haemost., 7(6):1030-2 (Jun. 2009).
Semeraro et al., Sepsis, thrombosis and organ dysfunction, Thromb. Res., 129(3):290-5 (Mar. 2012).
Shan et al., The G Protein G?13 Is Required for Growth Factor-Induced Cell Migration, Dev Cell, 10:707-718 (2006).
Shattil et al., The final steps of integrin activation: the end game, Nat. Rev. Mol. Cell Biol., 11(4):288-300 (Apr. 2010).
Shen et al. A directional switch of integrin signalizing and a new anti-thrombotic strategy, Nature, 503(7474): 131-5 (2013).
Shen et al., The interaction of Ga13 with integrin ß1 mediates cell migration by dynamic regulation of RhoA, Mol. Biol. Cell, 26(20):3658-70 (Oct. 2015).
Singer et al., Platelet recruitment in the murine hepatic microvasculature during experimental sepsis: role of neutrophils, Microcirculation, 13(2):89-97 (Mar. 2006).
Southgate et al., Identification of Formyl Peptides from Listeria monocytogenes and *Staphylococcus aureus* as Potent Chemoattractants for Mouse Neutrophils. J Immunol 181:1429-1437 (2008).
Speyer et al., Novel chemokine responsiveness and mobilization of neutrophils during sepsis, Am. J. Pathol., 165(6):2187-96 (Dec. 2004).
Storey et al., Lower mortality following pulmonary adverse events and sepsis with ticagrelor compared to clopidogrel in the PLATO study, Platelets, 25(7):517-25 (2014).
Surve et al., Dynamic regulation of neutrophil polarity and migration by the heterotrimeric G protein subunits G alpha i-GTP and G beta gamma. Sci Signal 9:1-10 (2016).
Suzuki et al., G?12 activates Rho GTPase through tyrosine-phosphorylated leukemia-associated RhoGEF. Proc Natl Acad Sci U S A 100:733-738 (2003).
Szczur et al., The small Rho GTPase Cdc42 regulates neutrophil polarity via CD11b integrin signaling. Blood 114:4527-4537 (2009).
Tan et al., Recent developments in liposomes, microparticles and nanoparticles for protein and peptide drug delivery, Peptides, 31(1):184-93 (Jan. 2010).
Tan et al., The Ga13-Rho signaling axis is required for SDF-1-induced migration through CXCR. J Biol Chem, 281:39542-39549 (2006).
Thelen et al., How chemokines invite leukocytes to dance. Nat Immunol 9:953-959 (2008).
Tsai et al., Association of prior antiplatelet agents with mortality in sepsis patients: a nationwide population-based cohort study, Intensive Care Med., 41(5):806-13 (May 2015).
Vestweber, Review: How leukocytes cross the vascular endothelium, Nat Rev Immunol, 15:692-704 (2015).
Wang et al., Application of poly(ethylene glycol)-distearoylphosphatidylethanolamine (PEG-DSPE) block copolymers and their derivatives as nanomaterials in drug delivery, Int. J. Nanomedicine, pp. 4185-4198 (Aug. 2012).
Weckmann et al., SiMA: A simplified migration assay for analyzing neutrophil migration, Cytom Part A, 91:675-685 (2017).
Winning et al., Antiplatelet drugs and outcome in mixed admissions to an intensive care unit, Crit Care Med., 38(1):32-7 (Jan. 2010).

(56) References Cited

OTHER PUBLICATIONS

Wong et al., Blockade of protease-activated receptor-4 (PAR4) provides robust antithrombotic activity with low bleeding, Sci. Transl. Med., 9(371):eaaf5294 (Jan. 2017).
Xu et al., A murine model of myocardial ischemia-reperfusion injury through ligation of the left anterior descending artery, J. Vis. Exp., (86):51329 (Apr. 2014).
Yamahashi et al., Integrin associated proteins differentially regulate neutrophil polarity and directed migration in 2D and 3D, Biomed Microdevices, 17(5):100 (Oct. 2015).
Yin et al., Role for platelet glycoprotein Ib-IX and effects of its inhibition in endotoxemia-induced thrombosis, thrombocytopenia, and mortality, Arterioscler. Thromb. Vasc. Biol., 33(11):2529-37 (Nov. 2013).
Zhu et al., The cyclooxygenase-1/mPGES-1/endothelial prostaglandin EP4 receptor pathway constrains myocardial ischemia-reperfusion injury, Nat. Commun., 10(1):1888 (Apr. 2019).
Cheng et al., Targeting Galpha13-integrin interaction ameliorates systemic inflammation, Nat. Comm., 12:3185 (2021).
Liu, Controlled release of therapeutic agents from polymeric particles, University of Illinois at Chicago, PhD Dissertation, (2020).
Luo et al., [Research progress on triptolide functionalized nanoparticulate drug delivery systems for tumor treatment], Zhongguo Zhong Yao Za Zhi (China Journal of Chinese Materia Medica), 44(21):4566-72 (Nov. 2019).

* cited by examiner

M3mP6
PEG
DSPE
PC

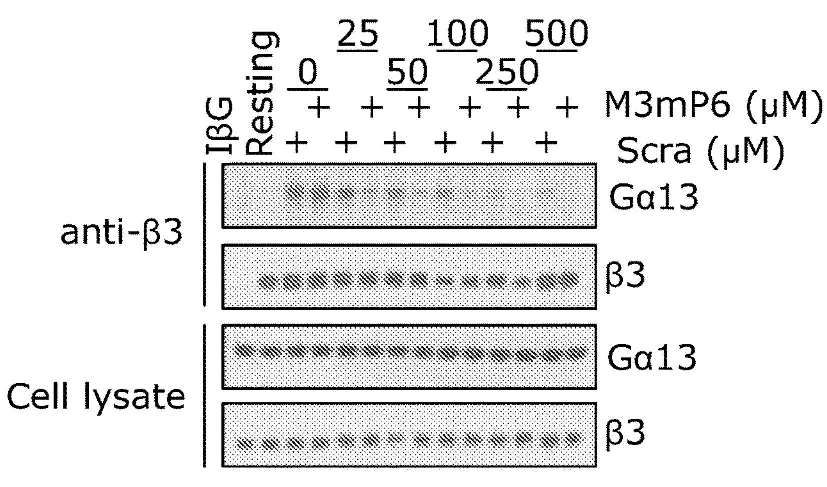
FIG. 1C
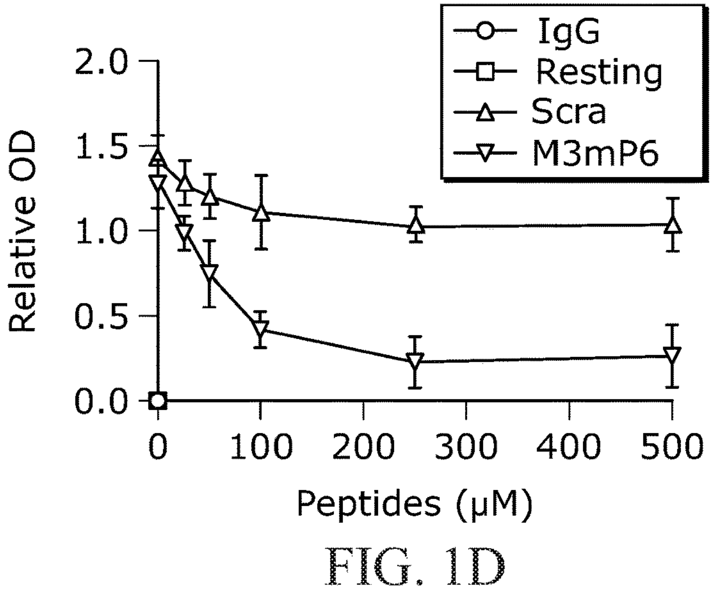
FIG. 1D
Volume
100
80
60
40
20
0
5.0
50
500
5000
Diameter (nm)
FIG. 1E

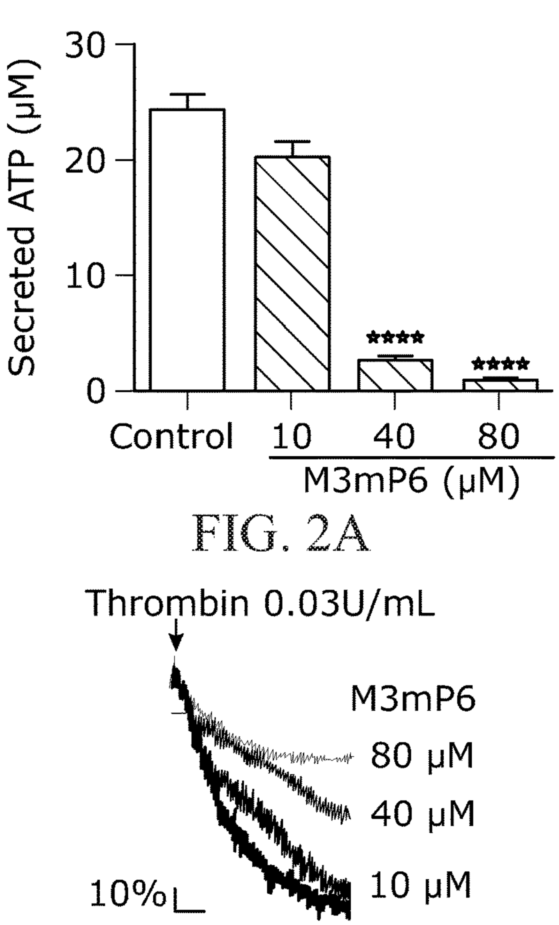
FIG. 2A
Thrombin 0.03U/mL
M3mP6
80 μM
40 μM
10 μM
10%
1min
FIG. 2B
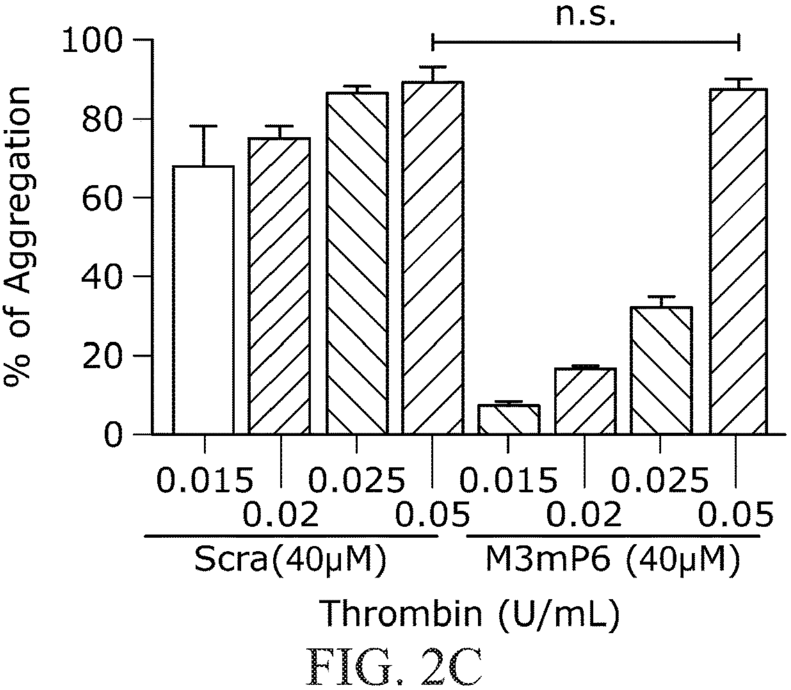
FIG. 2C

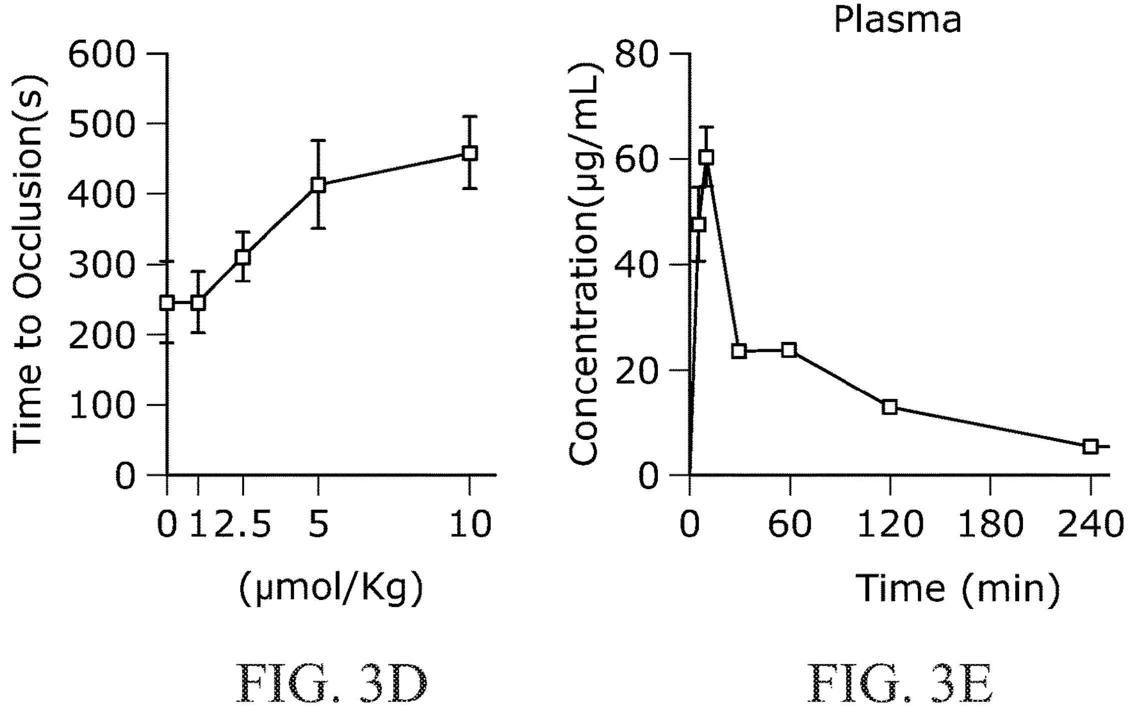
FIG. 3D
FIG. 3E
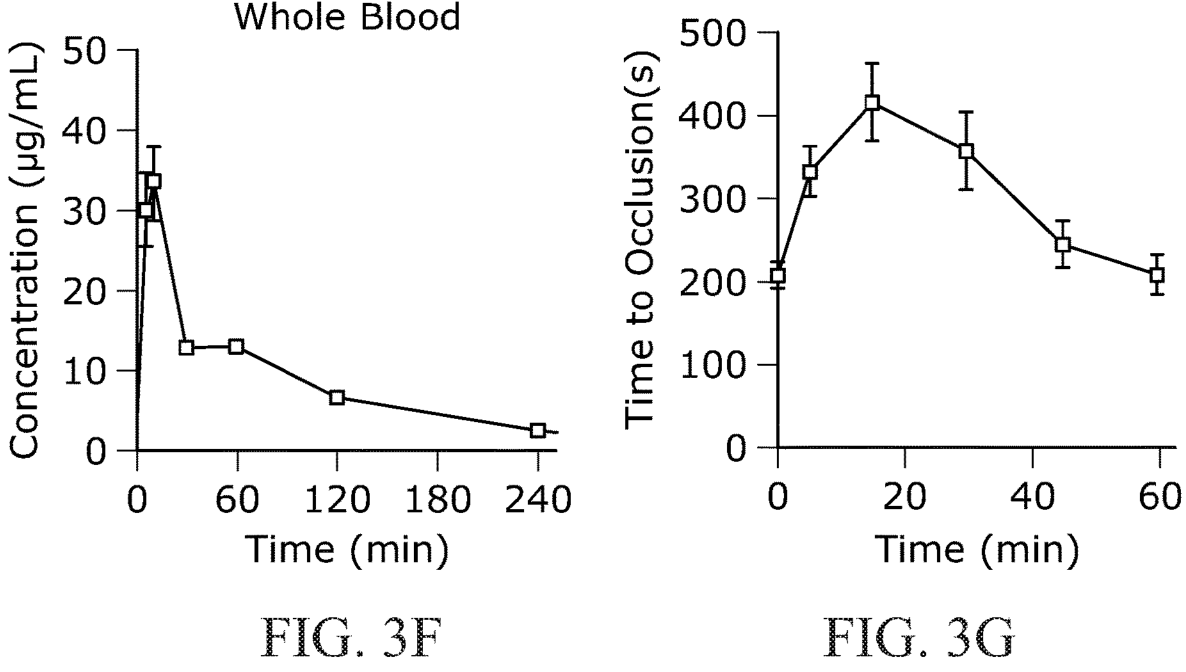
FIG. 3F
FIG. 3G

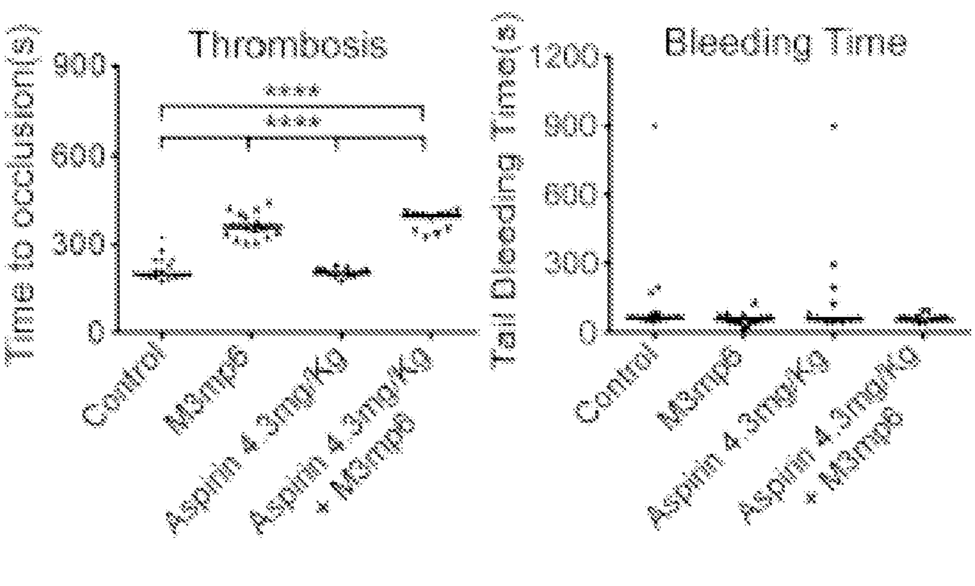
*FIG. 4A*
*FIG. 4B*
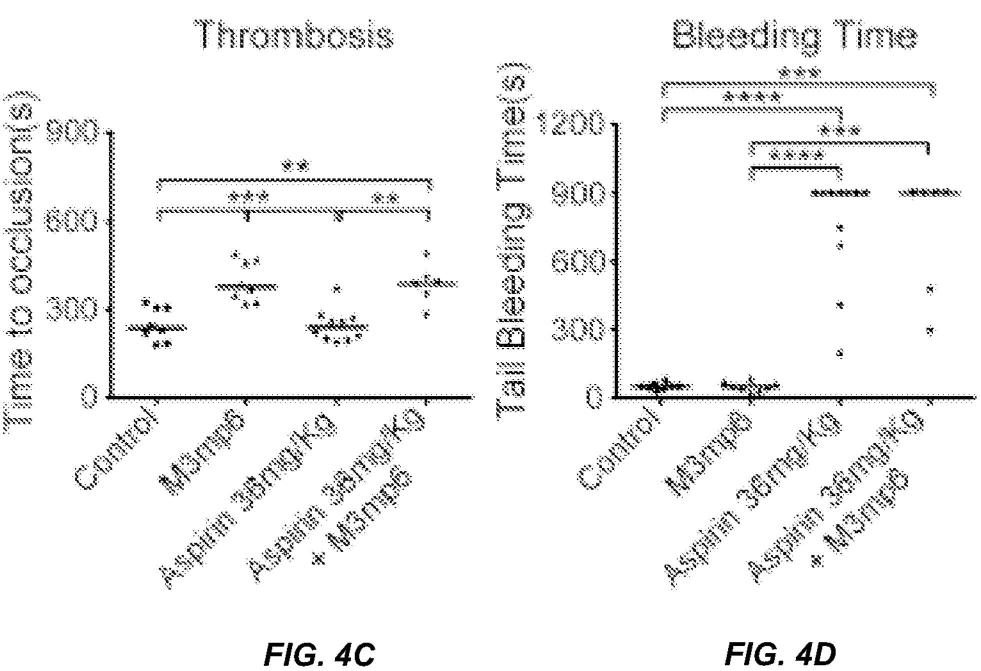
*FIG. 4C*
*FIG. 4D*

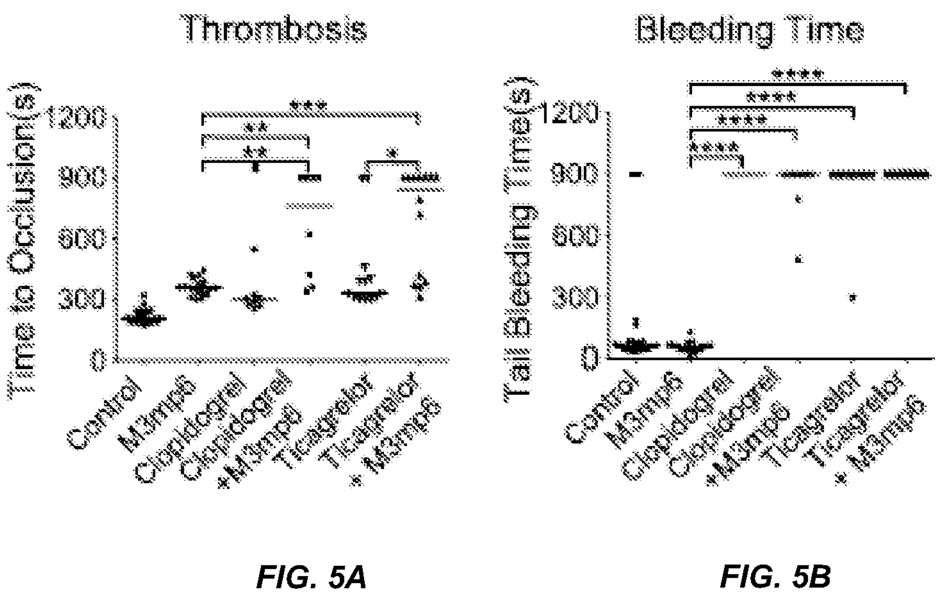
FIG. 5A
FIG. 5B
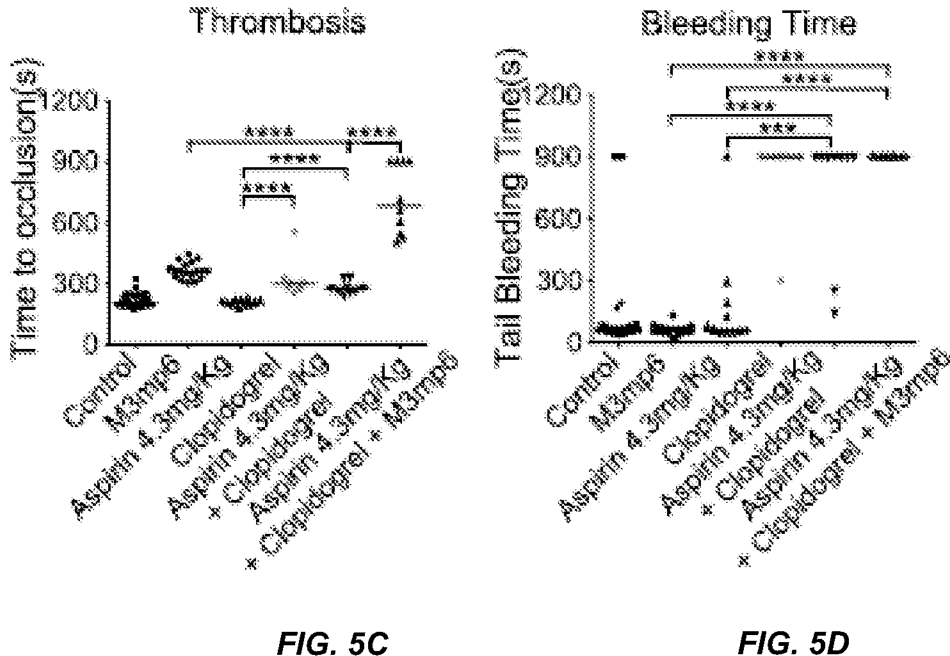
FIG. 5C
FIG. 5D

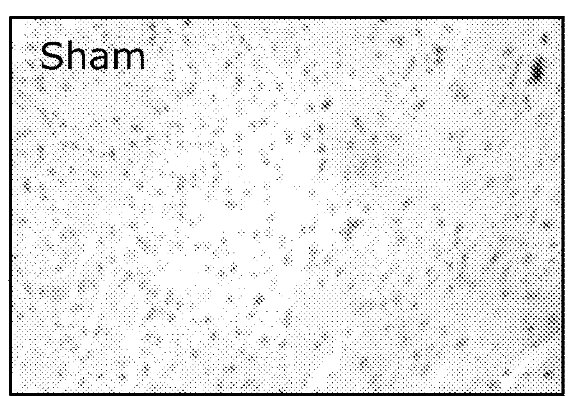
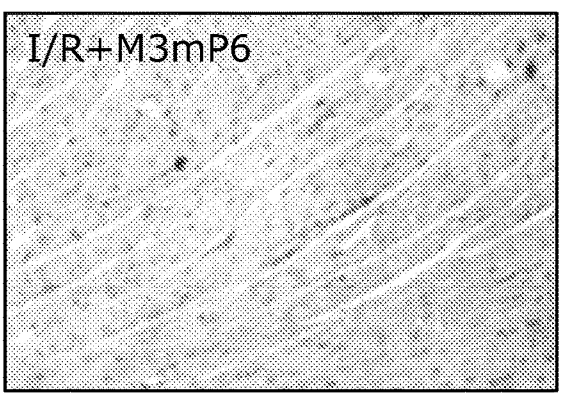
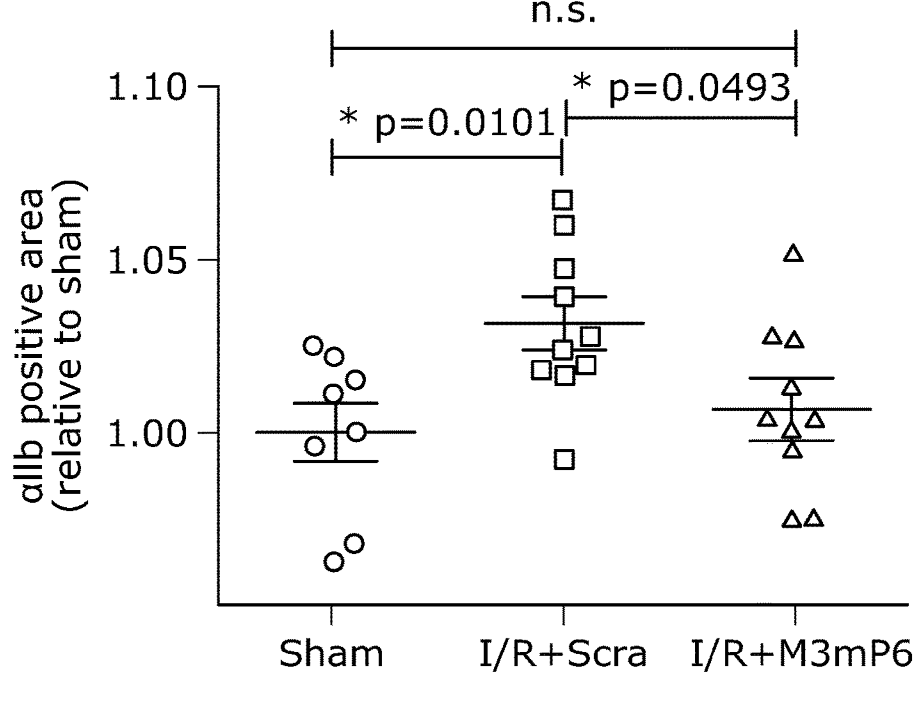
FIG. 8G

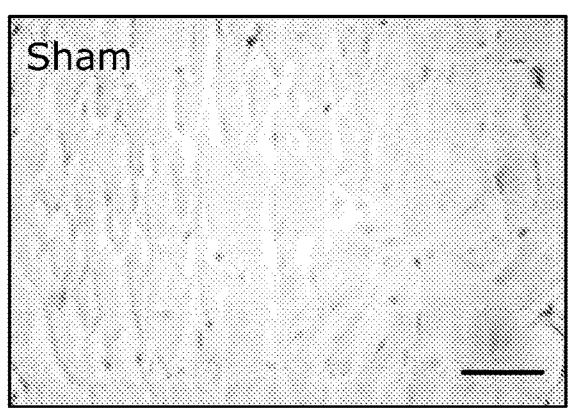
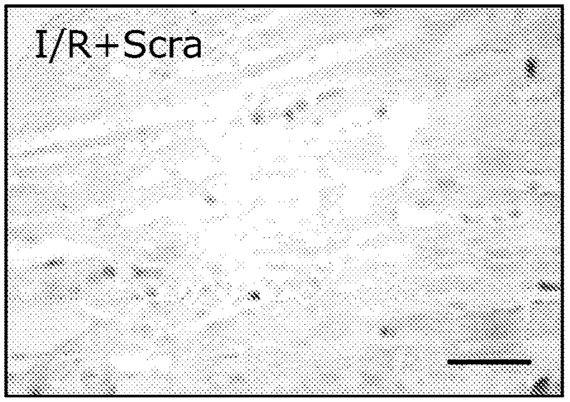
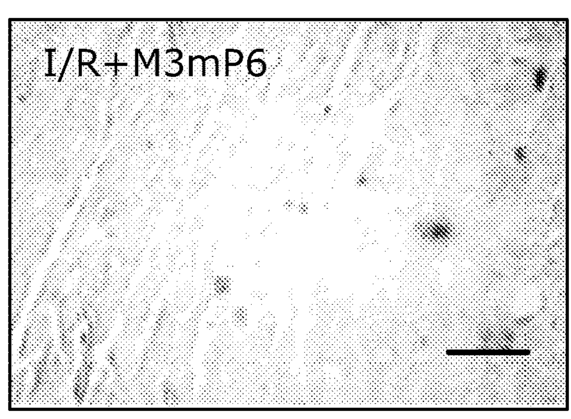
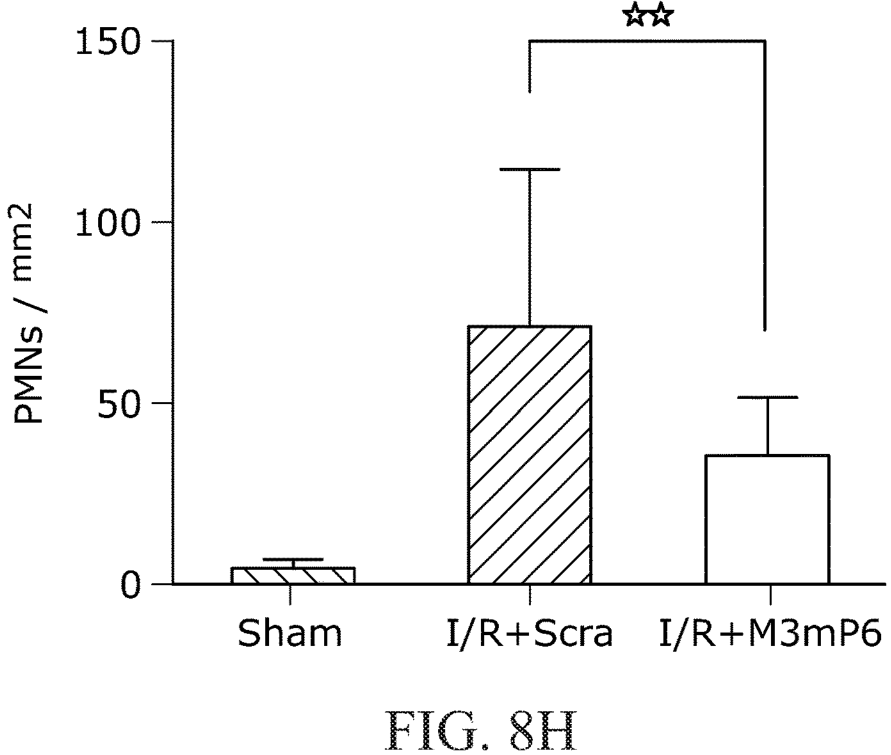
FIG. 8H

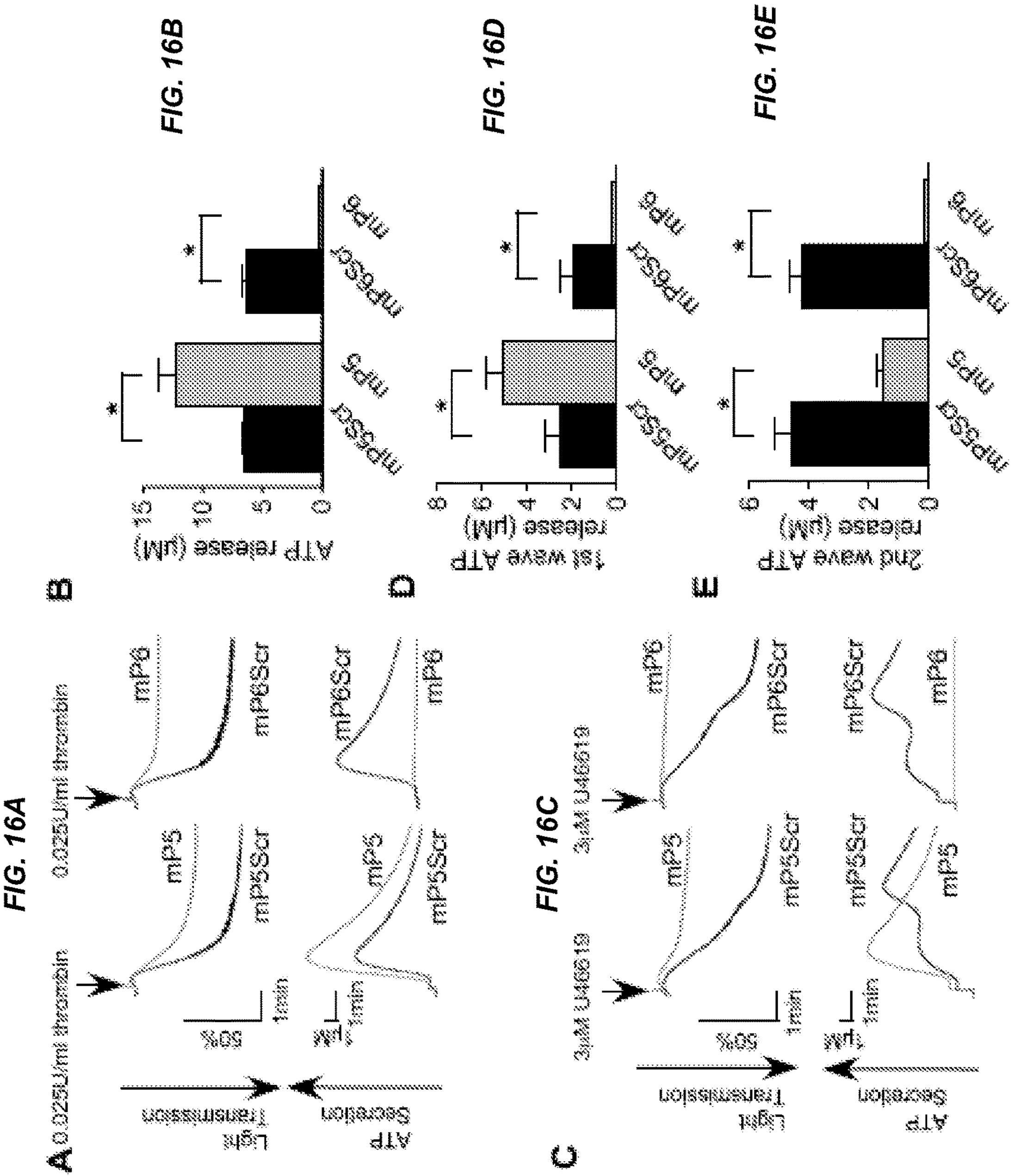
Effects of ExE motif Effects of ExE motif

A 11.8 nm
Start point
Volume
Diameter (nm)

B 18.0 nm
1.5 years at -20°C
Volume
Diameter (nm)

C

*
n.s.
Occlusion Time (s)
Saline
Fresh
1.5 Years

D 20.2 nm
Start point
Volume
Diameter (nm)

E 16.1 nm
2 weeks at RT
Volume
Diameter (nm)

F

*
n.s.
Occlusion Time (s)
Saline
Fresh
2 Weeks RT

| Parameter | Dose: 25 mg/kg IVB/150 mg/kg/day IVI for 5 days | |
|---|---|---|
| | **Female** | **Male** |
| $C_{max}$ (ng/ml) | 193171 (23543)* | 264984 (NA) |
| $T_{max}$ (h) | 0.08 | 0.08 |
| $C_{ss}$ (ng/ml) | 131117 | 77621 |
| $AUC_{0\text{-}last}$ (h-ng/ml) | 17611767 (2160634)* | 9490148 (NA) |
| $AUC_{0\text{-}\infty}$ (h-ng/ml) | 17641938 | 9485816 |
| $\lambda_z$ ($h^{-1}$) | 0.223 | 0.177 |
| $t_{1/2\text{-}\lambda z}$ (h) | 3.1 | 3.9 |
| CL (ml/min/kg) | | |
| $CL_{AUC}$ | 0.7 | 1.4 |
| $CL_{css}$ | 0.8 | 1.3 |
| $V_{\lambda z}$ (l/kg) | 0.20 | 0.46 |

*FIG. 24* a
IgG
Anti-β2
Ctrl-pep
MB2mP6
LPS 0 0 1 2 4 0 1 2 4 hrs
Gα13
β2
IP
Input c
Ctrl
MB2mP6
mIl1β mRNA
Vehicle
LPS (8h)

d
mIl6 mRNA
b FIG. 25B Anti-β3
Ctrl-pep
MB2mP6
Thr 0 0.5 1 2 5 10 0 0.5 1 2 5 10 min
β3
e FIG. 25E
Thrombin 0.03U/mL
MB2mP6
20 μM
10 μM
5 μM
2.5 μM
10%
1min
f FIG. 25F
Secreted ATP (μM)
0 20 40 60 80 (μM)
g FIG. 25G
Time to Occlusion (s)
Ctrl
MB2mP6
M3mP6
h FIG. 25H
Tail bleeding time (s)
ns
i FIG. 25I
Hb concentration (μM)
Sham
Scra
rpA

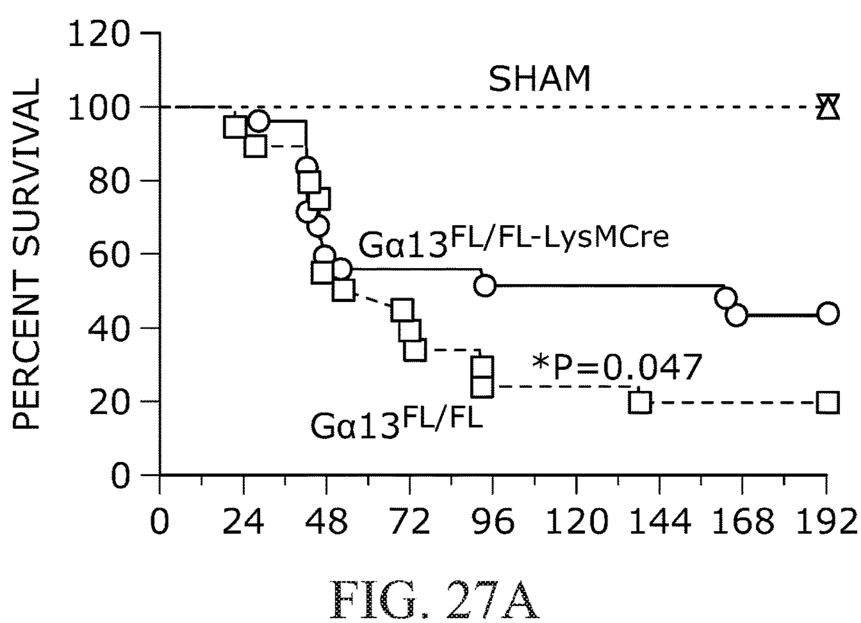
FIG. 27A
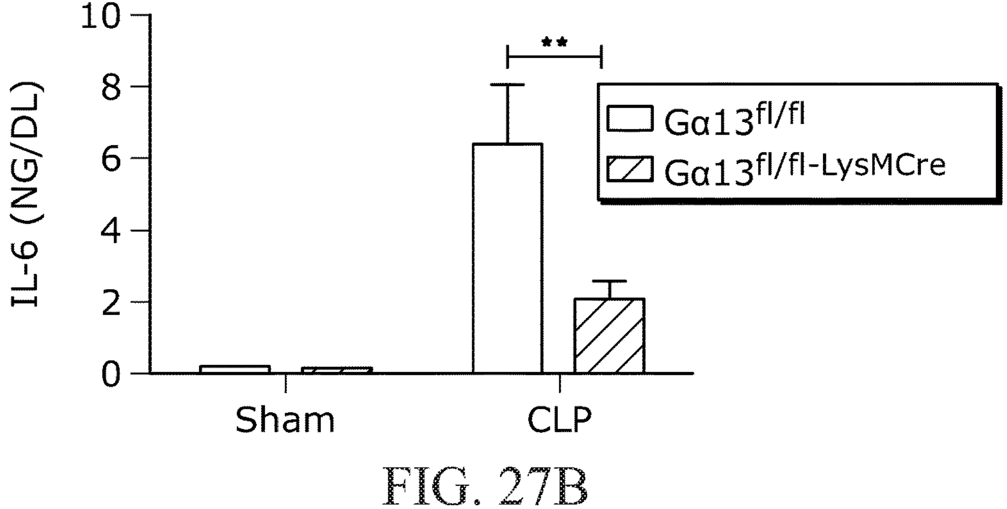
FIG. 27B
TNFα (pg/mL)
300
200
100
0
*
Gα13fl/fl
Gα13fl/fl-LysMCre
Sham
CLP
FIG. 27C BUN (mg/dL)
150
100
50
0
Sham
CLP
☆☆
Gα13fl/fl
Gα13fl/fl-PF4Cre

FIG. 27H

TNFα (pg/mL)
300
200
100
0
Sham
CLP
ns
Gα13fl/fl
Gα13fl/fl-PF4Cre

FIG. 27I

IL-6 (ng/dL)
6
4
2
0
Sham
CLP
☆
Gα13fl/fl
Gα13fl/fl-PF4Cre

FIG. 27J

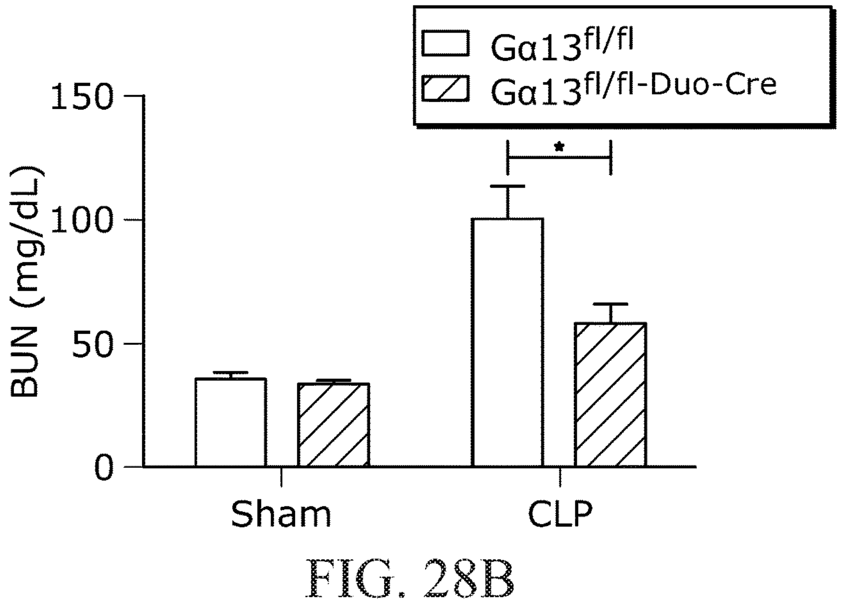
FIG. 28B
FIG. 28C
400
300
200
100
0
TNFα (ng/dL)
* * *
$G\alpha13^{fl/fl}$
$G\alpha13^{fl/fl\text{-}Duo\text{-}Cre}$
Sham
CLP
FIG. 28D

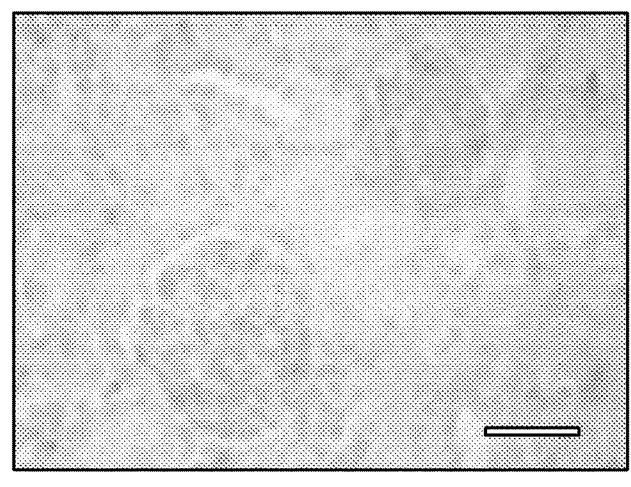
Gα13fl/fl
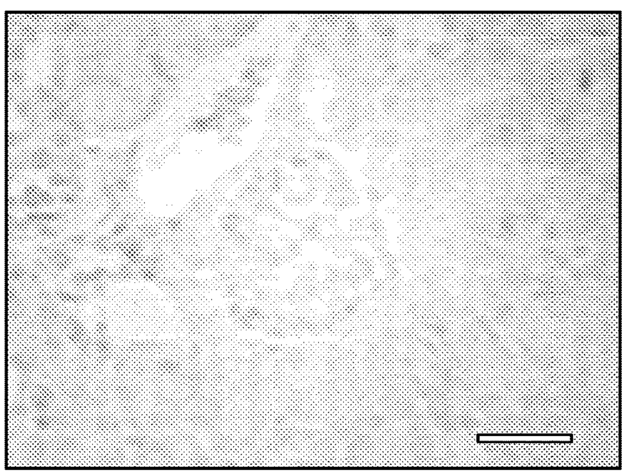
Gα13fl/fl-Duo-Cre
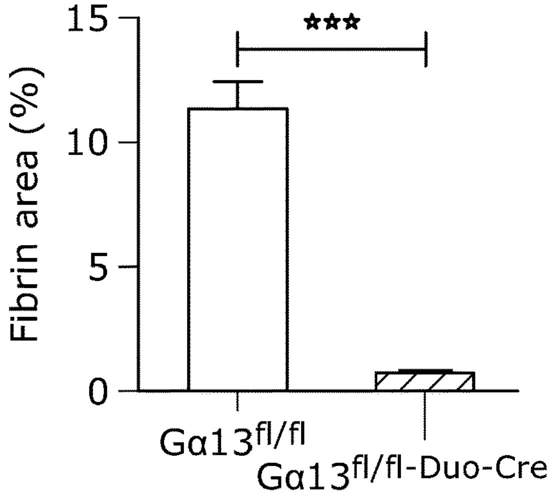
FIG. 28E a

Sham
Scra
MB2mP6
Fibrin area (%)
Sham
Scra
MB2mP6
CLP
b

Sham
Scra
MB2mP6
Sham
Scra
MB2mP6
CLP
c

Creatinine (mg/dL)
Sham
CLP+Scra
CLP+MB2mP6
d

Cystatin (ng/mL)
Sham
CLP+Scra
CLP+MB2mP6

*FIG. 31A* *FIG. 31B*
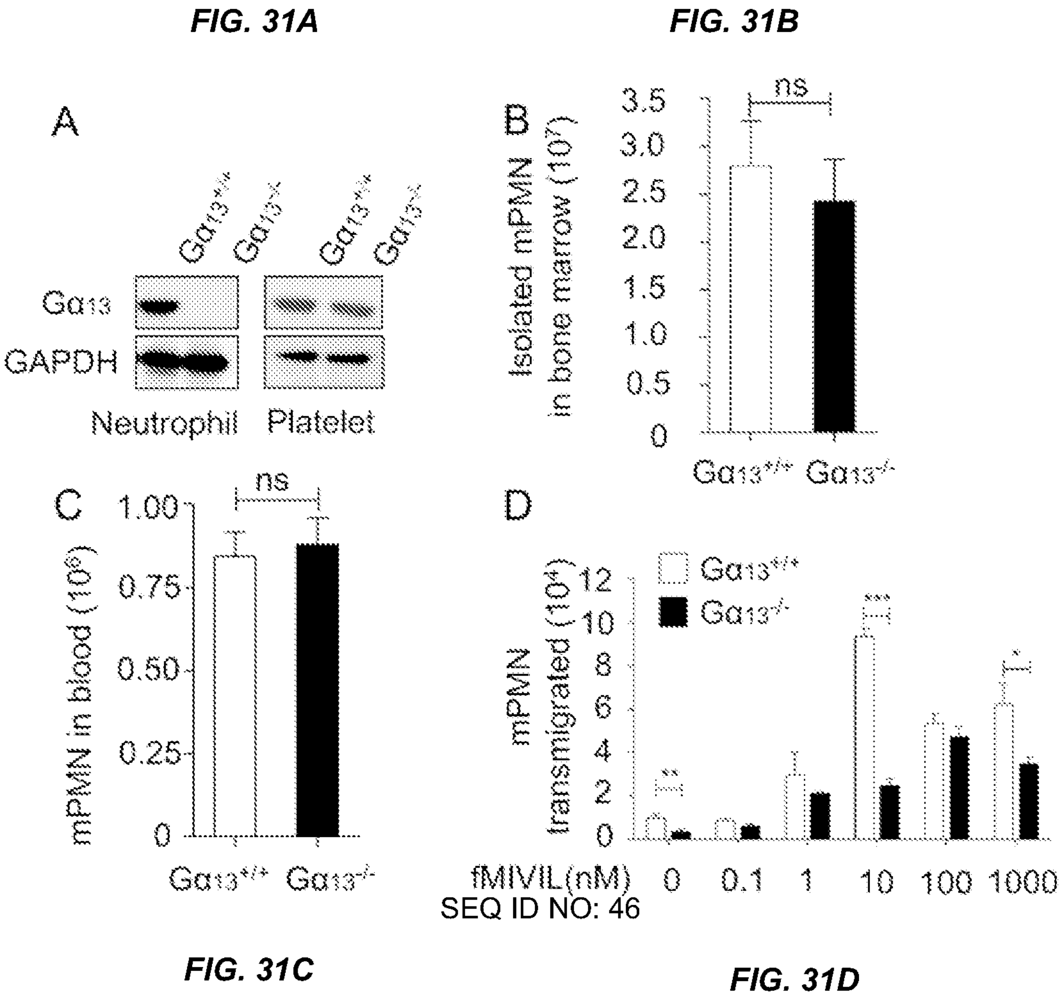
*FIG. 31C* *FIG. 31D*

*FIG. 35A* *FIG. 35B*
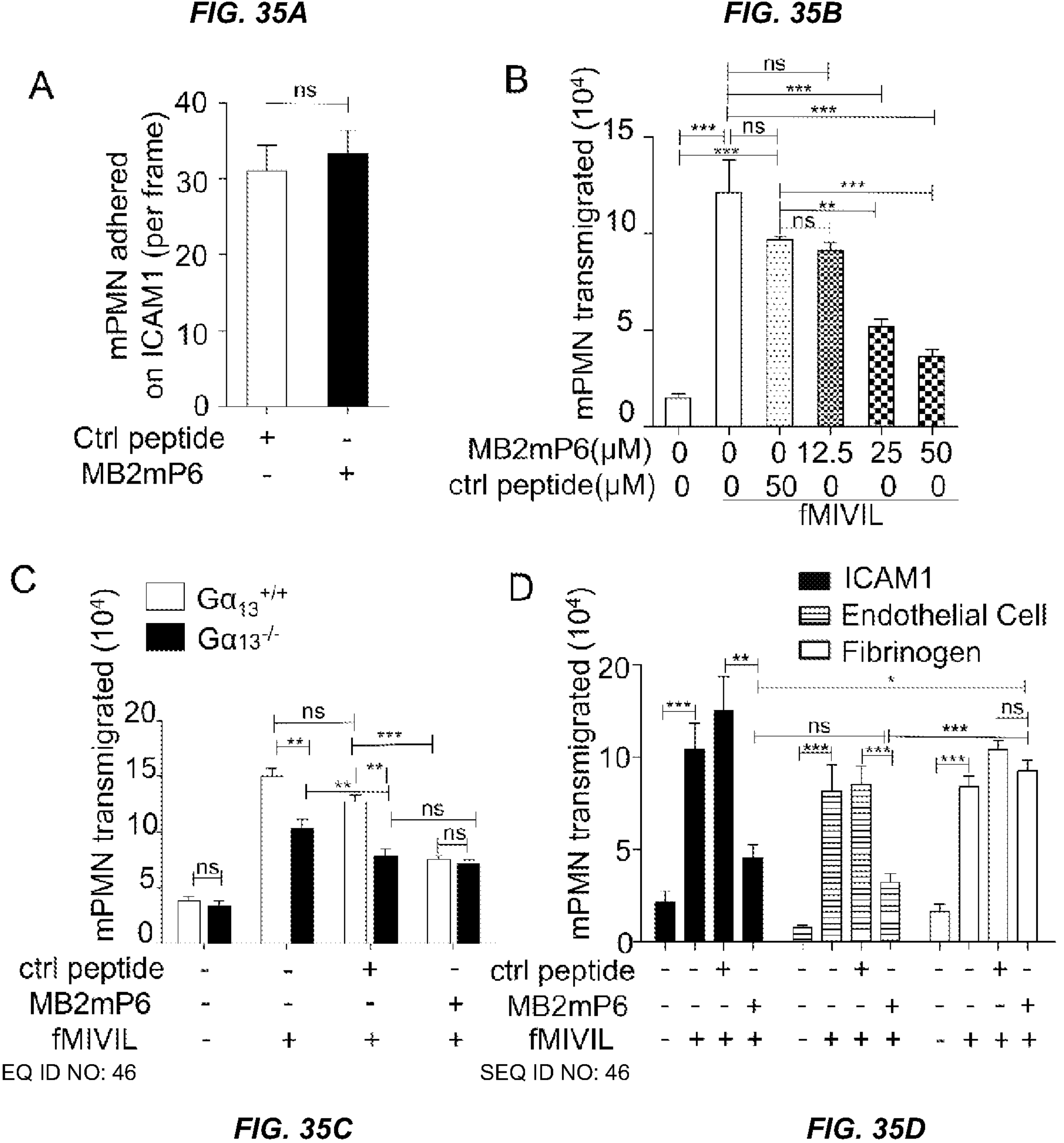
*FIG. 35C* *FIG. 35D*

*FIG. 36A* *FIG. 36B* *FIG. 36C*
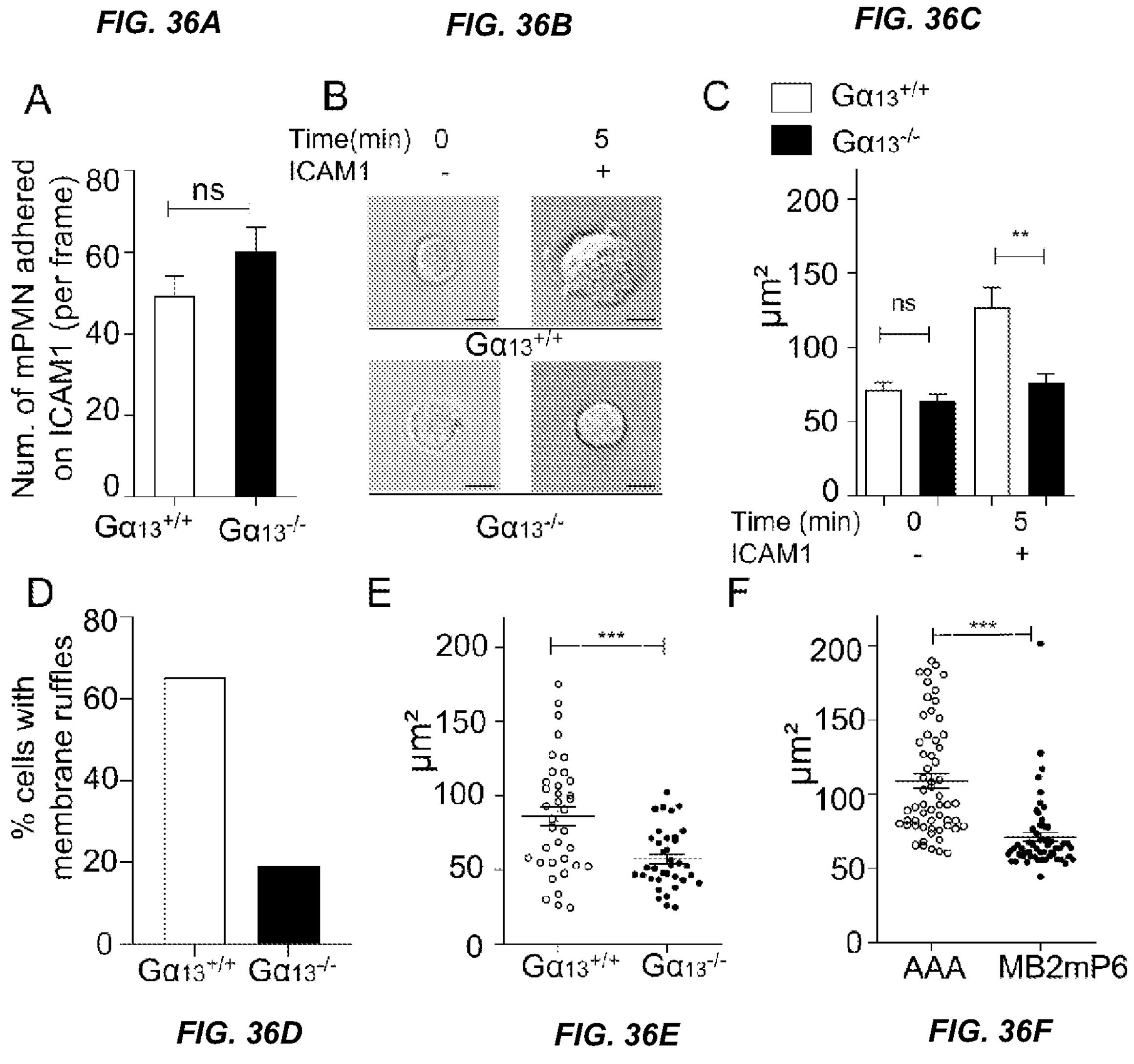
*FIG. 36D* *FIG. 36E* *FIG. 36F*

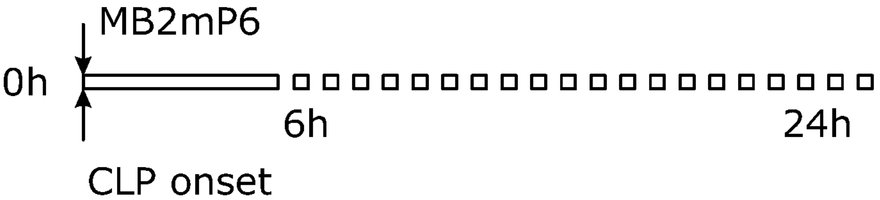
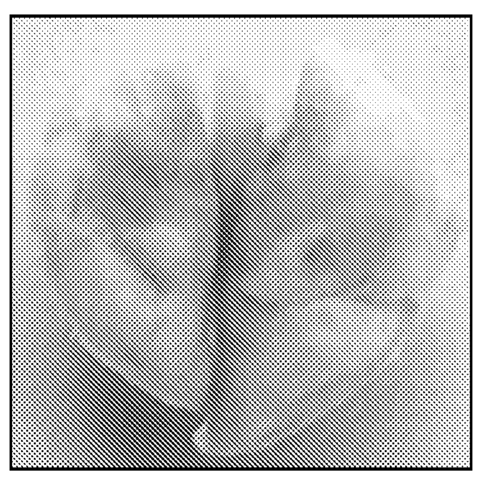
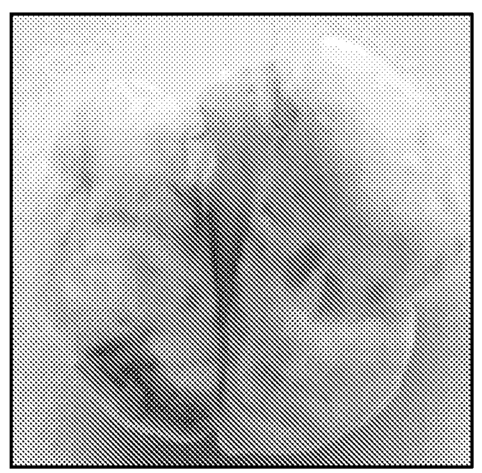
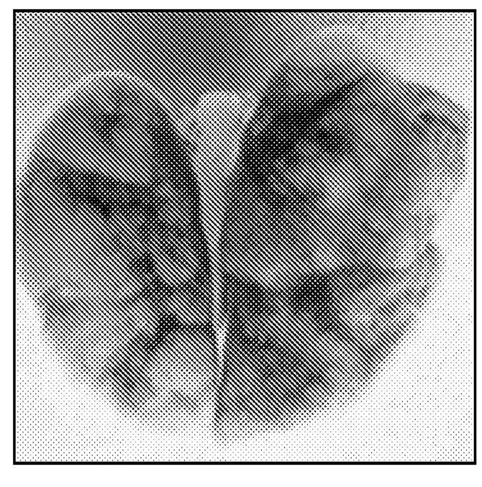
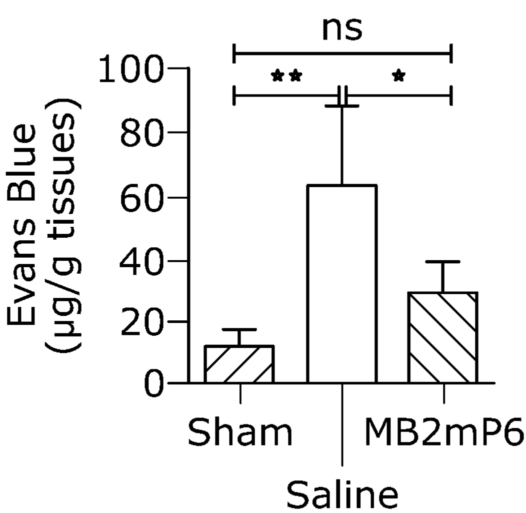
FIG. 38B

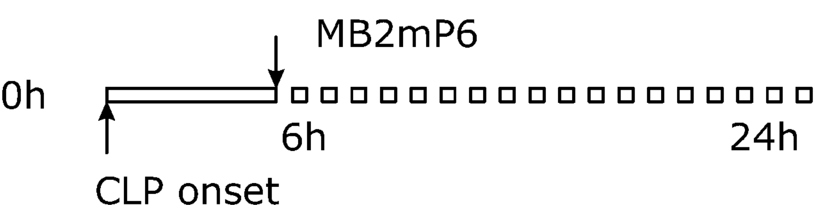
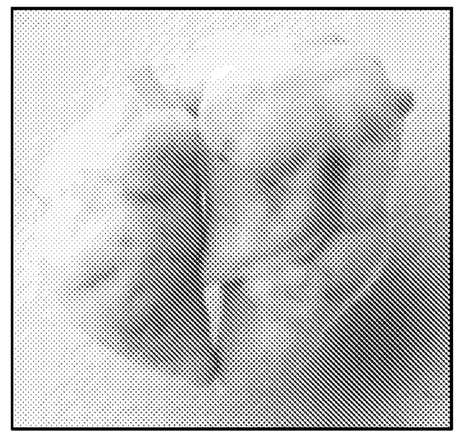
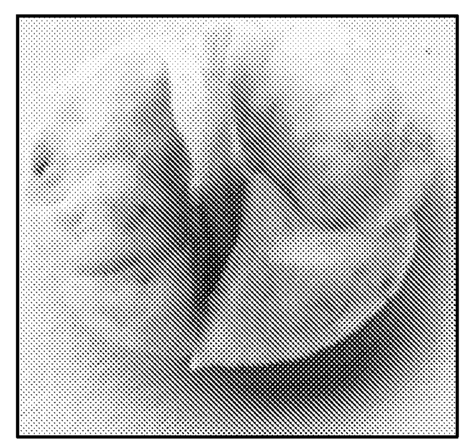
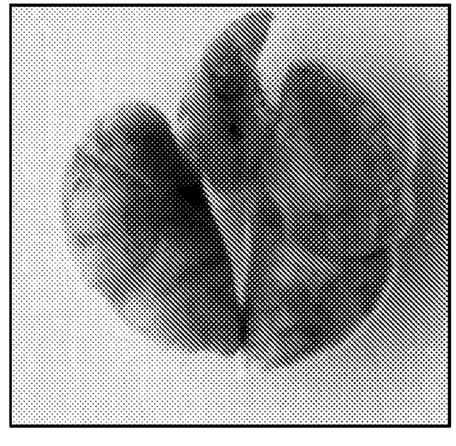
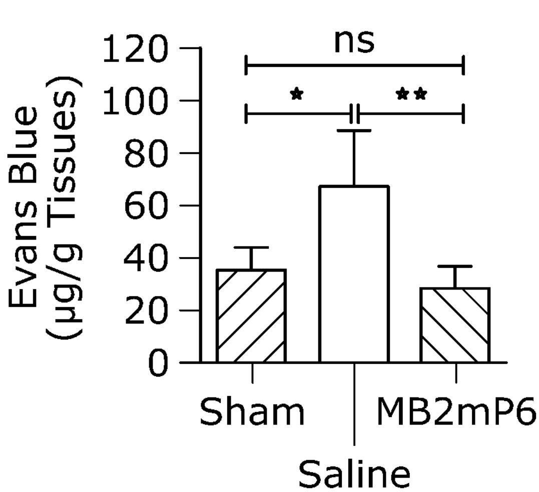
FIG. 38C

SEQUENCE LISTING

```
<160> NUMBER OF SEQ ID NOS: 60

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Phe Glu Xaa Glu Arg Xaa
1               5


<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Phe Glu Glu Glu Arg Ile
1               5


<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Phe Glu Lys Glu Lys Ile
1               5


<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Phe Glu Lys Glu Arg Ile
1               5


<210> SEQ ID NO 5
<211> LENGTH: 5
<212> TYPE: PRT
<213> ORGANISM: Artificial Sequence
```

<220> FEATURE:
<223> OTHER INFORMATION: Synthetic

<400> SEQUENCE: 5

Glu Glu Glu Arg Ala
1 5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Phe Glu Glu Glu Arg Ala
1 5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Phe Glu Glu Glu Arg Met
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Phe Glu Glu Glu Arg Leu
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Phe Glu Lys Glu Lys Met
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Phe Glu Lys Glu Lys Leu
1 5

<210> SEQ ID NO 11
<211> LENGTH: 6
<212> TYPE: PRT
<213> ORGANISM: Artificial Sequence
<220> FEATURE:

<223> OTHER INFORMATION: Synthetic

<400> SEQUENCE: 11

Phe Glu Lys Glu Arg Met
1 5

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Phe Glu Lys Glu Arg Leu
1 5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Cys Phe Glu Glu Glu Arg Ala Cys
1 5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Phe Glu Glu Glu Arg Ala Arg
1 5

<210> SEQ ID NO 15
<211> LENGTH: 8
<212> TYPE: PRT
<213> ORGANISM: Artificial Sequence
<220> FEATURE:
<223> OTHER INFORMATION: Synthetic

<400> SEQUENCE: 15

Phe Glu Glu Glu Arg Ala Arg Ala
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ser Ile Arg Tyr Ser Gly His Ser Leu
1 5

<210> SEQ ID NO 17
<211> LENGTH: 13
<212> TYPE: PRT
<213> ORGANISM: Artificial Sequence
<220> FEATURE:
<223> OTHER INFORMATION: Synthetic

<400> SEQUENCE: 17

Lys Phe Glu Glu Glu Arg Ala Arg Ala Lys Trp Asp Thr
1 5 10

<210> SEQ ID NO 18
<211> LENGTH: 13
<212> TYPE: PRT
<213> ORGANISM: Artificial Sequence
<220> FEATURE:
<223> OTHER INFORMATION: Synthetic

<400> SEQUENCE: 18

Leu Leu Ala Arg Arg Pro Thr Lys Gly Ile His Glu Tyr
1 5 10

<210> SEQ ID NO 19
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 19

Phe Glu Glu Glu Arg Ile
1 5

<210> SEQ ID NO 20
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 20

Phe Glu Lys Glu Lys Ile
1 5

<210> SEQ ID NO 21
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 21

Phe Glu Lys Glu Arg Ile
1 5

<210> SEQ ID NO 22
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 22

Glu Glu Glu Arg Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 23

Phe Glu Glu Glu Arg Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 24

Phe Glu Glu Glu Arg Met
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 25

Phe Glu Glu Glu Arg Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 26

Phe Glu Lys Glu Lys Met
1               5

<210> SEQ ID NO 27
<211> LENGTH: 6

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 27

Phe Glu Lys Glu Lys Leu
1 5

<210> SEQ ID NO 28
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 28

Phe Glu Lys Glu Arg Met
1 5

<210> SEQ ID NO 29
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 29

Phe Glu Lys Glu Arg Leu
1 5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 30

Cys Phe Glu Glu Glu Arg Ala Cys
1 5

<210> SEQ ID NO 31
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 31

Phe Glu Glu Glu Arg Ala Arg
1 5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 32

Phe Glu Glu Glu Arg Ala Arg Ala
1 5

<210> SEQ ID NO 33
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 33

Ser Ile Arg Tyr Ser Gly His Pro Ser Leu
1 5 10

<210> SEQ ID NO 34
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 34

Lys Phe Glu Glu Glu Arg Ala Arg Ala Lys Trp Asp Thr
1 5 10

<210> SEQ ID NO 35
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 35

Leu Leu Ala Arg Arg Pro Thr Lys Gly Ile His Glu Tyr
1 5 10

<210> SEQ ID NO 36
<211> LENGTH: 5
<212> TYPE: PRT
<213> ORGANISM: Artificial Sequence
<220> FEATURE:
<223> OTHER INFORMATION: Synthetic

<400> SEQUENCE: 36

Glu Glu Glu Arg Met
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic

<400> SEQUENCE: 37

Glu Glu Glu Arg Leu
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Glu Lys Glu Lys Met
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic

<400> SEQUENCE: 39

Glu Lys Glu Lys Leu
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Glu Lys Glu Arg Met
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

Glu Lys Glu Arg Leu
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic

<400> SEQUENCE: 42

Cys Glu Glu Glu Arg Ala Cys
1 5

<210> SEQ ID NO 43
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 43

Phe Ala Ala Ala Arg Leu
1 5

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Phe Lys Glu Lys Glu Ile
1 5

<210> SEQ ID NO 45
<211> LENGTH: 6
<212> TYPE: PRT
<213> ORGANISM: Artificial Sequence
<220> FEATURE:
<223> OTHER INFORMATION: Synthetic

<400> SEQUENCE: 45

Arg Cys Leu Leu Pro Ala
1 5

<210> SEQ ID NO 46
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-Formyl

<400> SEQUENCE: 46

Met Ile Val Ile Leu
1 5

<210> SEQ ID NO 47
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 47

Glu Arg Ala Phe Glu Glu 1 5

<210> SEQ ID NO 48
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 48

Glu Phe Lys Lys Leu Glu
1 5

<210> SEQ ID NO 49
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr

<400> SEQUENCE: 49

Phe Lys Lys Glu Lys Leu
1 5

<210> SEQ ID NO 50
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: myr
<220> FEATURE:
<221> NAME/KEY: MISC_FEATURE
<222> LOCATION: (7)..(7)
<223> OTHER INFORMATION: FAM

<400> SEQUENCE: 50

Phe Glu Glu Glu Arg Leu Lys
1 5

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
cgacaaaata cctgtggcct 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ttctttgggt attgcttggg 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
tccagttgcc ttcttgggac 20

<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
gtgtaattaa gcctccgact tg 22

<210> SEQ ID NO 55
<211> LENGTH: 32
<212> TYPE: DNA
<213> ORGANISM: Artificial Sequence
<220> FEATURE:
<223> OTHER INFORMATION: Synthetic

<400> SEQUENCE: 55
ttctgtctac tgaacttcgg ggtgatcggt cc 32

<210> SEQ ID NO 56
<211> LENGTH: 32
<212> TYPE: DNA
<213> ORGANISM: Artificial Sequence
<220> FEATURE:
<223> OTHER INFORMATION: Synthetic

<400> SEQUENCE: 56
gtatgagata gcaaatcggc tgacggtgtg gg 32

<210> SEQ ID NO 57
<211> LENGTH: 24
<212> TYPE: DNA
<213> ORGANISM: Artificial Sequence
<220> FEATURE:
<223> OTHER INFORMATION: Synthetic

<400> SEQUENCE: 57
ggttgccaag ccttatcgga aatg 24

<210> SEQ ID NO 58
<211> LENGTH: 22
<212> TYPE: DNA
<213> ORGANISM: Artificial Sequence
<220> FEATURE:
<223> OTHER INFORMATION: Synthetic

<400> SEQUENCE: 58
cactcttcac ctgctccact gc 22

<210> SEQ ID NO 59
<211> LENGTH: 20
<212> TYPE: DNA
<213> ORGANISM: Artificial Sequence -continued

```
<220> FEATURE:
<223> OTHER INFORMATION: Synthetic

<400> SEQUENCE: 59

tgcgacttca acagcaactc                                                20


<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60

cttgctcagt gtccttgctg                                                20
```

PEPTIDES AND METHODS OF TREATING SEPSIS, ATHEROSCLEROSIS, THROMBOSIS, STROKE, HEART ATTACK AND INFLAMMATION

CROSS REFERENCE TO RELATED APPLICATIONS

This application is a U.S. national phase application of International Application No. PCT/US20/59729, filed on Nov. 9, 2020, which claims priority to U.S. Provisional Patent Application No. 62/932,024, filed on Nov. 7, 2019, the entire contents of which are fully incorporated herein by reference.

STATEMENT REGARDING FEDERALLY FUNDED RESEARCH

The present disclosure was made with government support under Grant Nos. HL080264, HL062350, HL125356, HL150797, HL142396 and Contract Nos. HHSN268201400007C and HHSN268201700002C, awarded by the National Institutes of Health. The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "56205_Seglisting.txt", which was created on Nov. 9, 2020 and is 12,040 bytes in size. The subject matter of the Sequence Listing is incorporated herein in its entirety by reference.

FIELD OF THE DISCLOSURE

The present disclosure relates to peptides that inhibit a binding interaction between a β integrin and a G protein subunit, as well as compositions, e.g., pharmaceutical compositions, particularly nanoparticle compositions, comprising the same. The present disclosure also relates to methods of using the peptides to treat atherosclerosis, thrombosis, stroke, heart attack, inflammation, acute respiratory distress syndrome (ARDS), autoimmune diseases, AV Fistula for hemodialysis or organ transplantation. This disclosure further relates to nanoparticle compositions for delivery of peptides in vitro into cells and in vivo for therapeutic and diagnostic use.

BACKGROUND OF THE DISCLOSURE

Delivering peptides in vivo into cells is currently a major obstacle for the development of peptide-based drugs targeting the intracellular compartments. Thus, successes in developing this type of drugs are scarce, despite the low toxicity and high specificity of natural peptides in general (1, 2). Developing an efficient method for delivering peptides into cells in vivo will have broad significance for the advancement of peptide-based drug development.

Thrombotic cardiovascular disease causes more deaths than any other disease in the world (3). Blood platelets physiologically mediate hemostatic thrombus formation to prevent bleeding but are also critical in the development of occlusive thrombosis (4, 5). Anti-platelet therapy is therefore pivotal in the treatment of thrombotic diseases, and in preventing thrombosis in patients receiving invasive vascular procedures (6, 7). The important role of platelets in hemostasis and thrombosis requires the adhesion receptor integrin αIIbβ3 (also named glycoprotein (GP) IIb-IIIa) (8). Currently available anti-platelet drugs inhibit thrombus formation either by inhibiting the activation of integrin αIIbβ3 (e.g., cyclooxygenase (COX) inhibitor aspirin, inhibitors of adenosine diphosphate (ADP) P2Y12 receptor, clopidogrel, ticagrelor and cangrelor) or directly block the ligand binding function of integrin αIIbβ3 (integrin antagonists abciximab, eptifibatide and tirofiban) (9, 10). The P2Y12 inhibitors such as clopidogrel either with or without aspirin are the current standard of care (9, 10). However, these drugs have the serious adverse effect of excessive bleeding (11-14) because of the importance of integrin-mediated primary platelet adhesion and aggregation in hemostasis. Hemorrhage is strongly associated with poor outcomes and increased mortality (11, 15-17). Thus, there is a need for a new generation of anti-platelet drugs that minimally affect hemostasis (18). Recently, inhibitors of thrombin receptors, the protease-activated receptor (PAR) 1 inhibitor vorapaxar (19) and PAR4 inhibitor BMS-986120 (20), have been reported to partially reduce hemorrhagic effect as compared to P2Y12 inhibitors in animal studies. However, clinical trials revealed significant adverse hemorrhagic effects associated with vorapaxar (19). Although the mechanism for reduced hemorrhage seen with these inhibitors in animal models remains unclear, the presence of remaining but significant hemorrhagic effects of both PAR1 and PAR4 inhibitors is consistent with the knowledge that these thrombin receptors are important for activation of the ligand binding function of integrin αIIbβ3.

Three classes of integrin inhibitors are currently in clinical use or development: monoclonal antibodies targeting the extracellular ligand binding domain of the heterodimer (eg, Reopro, Eli Lilly, Indiapolis, Vitaxin; MedImmune, Gaithersburg, MD), synthetic peptides containing an RGD or KGD sequences (eg, Integrillin, Millennium Pharmaceuticals; cilengitide; Merck KGaA, Darmstadt, Germany), and peptidomimetics (eg, aggrestat (Tirofiban), Merck, White House Station, NJ; S247; Pfizer, St Louis, MO).

The first integrin-specific drugs targeted the integrin αIIbβ3, which is central to hemostasis and plays an important role in platelet adhesion and thrombus formation. αIIbβ3 also functions in the inflammatory response. The first FDA-approved αIIbβ3 antagonists have proven benefit for indications, including acute coronary syndromes and prevention of myocardial infarction. However, the use of some of these drugs are limited due to their pharmacokinetic profiles—some drugs demonstrate rapid plasma clearance, rapid metabolism, poor oral bioavailability, and/or large variation in plasma levels. Also, some antagonists of αIIbβ3 integrin induced thrombocytopenia. See, e.g., *Advances in Immunology*, Volume 91, Elsevier Academic Press (San Diego, CA), 2006. A common and potentially life-threatening adverse effect of integrin inhibitor is bleeding (this is because integrin is important in hemostasis).

A novel $G\alpha_{13}$-dependent mechanism of integrin outside-in signaling was recently discovered, which resulted in new strategy of selectively targeting integrin outside-in signaling without affecting the ligand binding function of integrin αIIbβ3 (21, 22). Indeed, a synthetic peptide (mP6), derived from the $G\alpha_{13}$ binding ExE motif of integrin $\beta_3$ cytoplasmic domain, was shown to inhibit thrombosis without affecting hemostasis (21). However, in vivo delivery of this peptide with liposomes or lipid micelles was inefficient.

SUMMARY OF THE DISCLOSURE

To enhance delivery of the disclosed peptides in vivo, high loading peptide nanoparticles (HLPN) comprising greater than 30 mole percent of one or more amphiphilic peptide, peptide-lipid conjugates, or peptide-hydrophobic molecule conjugates, or a combination thereof (based on total nanoparticle mass) were developed. For certain peptides such as the peptide mP6 (a synthetic 6 amino acid peptide derived $G\alpha_{13}$-binding ExE motif of $\beta_3$ cytoplasmic domain), preparation of the high loading peptide nanoparticle is facilitated by exchanging the C-terminal amino acid residue for an amino acid with a longer hydrophobic side chain (e.g. changing alanine to a leucine, isoleucine or a methionine). This change enables higher concentrations of the peptide to form stable nanoparticles together with phospholipids and PEG-attached phospholipids. The HLPN can be used for efficient delivery of peptides to their intracellular target in vitro and in vivo. The peptide concentration incorporated in the stable nanoparticle suspension is greatly improved to more than 10 mM, enabling bolus injection in human subjects. In contrast to current lipid micelles or liposomes encapsulating peptides, this novel lipid-stabilized HLPN is mainly formed by the lipid-conjugated or amphiphilic peptide (such as M3mP6-Myr-FEEERL (SEQ ID NO: 25)), together with low percentages of phospholipid phosphatidylcholine (PC) (2-10%) and 1,2-Distearoyl-sn-glycero-3-phosphoethanolamine-attached polyethylene glycol (DSPE-PEG) (10-60%).

Using this in vivo delivery technology, the data provided herein demonstrated that the HLPN are effective for inhibiting occlusive thrombosis. For example, the data provided herein demonstrates the superior characteristics of M3mP6 in inhibiting occlusive thrombosis without causing excessive bleeding. M3mP6 HLPN also synergistically enhanced anti-thrombotic effect of the current standard anti-platelet treatment while minimizing the adverse effect of hemorrhage. Furthermore, post-ischemia injection of M3mP6 HLPN significantly improved the outcome of myocardial ischemia/reperfusion injury in mice.

Accordingly, in an aspect, the disclosure provides for a lipid-stabilized, high-loading peptide nanoparticle comprising i) greater than about 10 mole percent, based on total nanoparticle mass, of a peptide; ii) about 2 to about 20 mole percent of one or more lipids free of a water soluble polymer; and iii) about 10 to about 60 mole percent of one or more lipids covalently attached to a water soluble polymer, wherein the peptide is a lipidated peptide, amphiphilic peptide, or peptide-hydrophobic molecule conjugate, and the peptide consists of about 2 to about 50 amino acid residues. In some exemplary aspects, the total nanoparticle mass is 30 mole percent.

In various aspects, the peptide of the lipid-stabilized, high-loading peptide nanoparticle is a lipidated peptide which is conjugated to a fatty acid. In various aspects, the fatty acid is covalently attached to the peptide. In various aspects, the lipidated peptide is myristoylated.

In various aspects, the lipid free of a water soluble polymer of the lipid-stabilized, high-loading peptide nanoparticle is phosphatidylcholine (PC), phosphatidylglycero (PG), phosphatidyl-inositol (PI), phosphatidyl-serine (PS) and phosphatidylethanolamine (PE) or mixtures thereof.

In various aspects, the lipid covalently attached to a water-soluble polymer of the lipid-stabilized, high-loading peptide nanoparticle is peg-phosphatidylethanolamine (PEG-PE), PEG-phosphatidylcholine(PEG-PC), PEG-phosphatidylglycerol (PEG-PG), PEG-phosphatidyl-inositol (PEG-PI), PEG-phosphatidyl-serine (PEG-PS), PEG-1,2-distearoyl-sn-glycero-3-phosphoethanolamine-N-[amino (polyethylene glycol)](PEG-DSPE) or a mixture thereof. In various aspects, the PEG-DSPE may comprise a PEG with a molecular weight of about 200-about 100,000 or other PEGs known in the art, such as PEG200, PEG300, PEG400, PEG500, PEG600, PEG700, PEG800, PEG900, PEG1000, PEG2000, PEG3000, PEG4000, PEG5000, PEG6000, PEG7000, PEG8000, PEG9000, PEG10,000, PEG20,000, PEG30,000, PEG40,000, PEG50,000, PEG60,000, PEG70,000, PEG80,000, PEG90,000 or PEG100,000. In an exemplary aspect, the lipid covalently attached to a water-soluble polymer is PEG-1,2-distearoyl-sn-glycero-3-phosphoethanolamine-N-[amino(polyethylene glycol)-2000](PEG2000-DSPE). In another aspect, the lipid covalently attached to a water-soluble polymer is PEG-1,2-distearoyl-sn-glycero-3-phosphoethanolamine-N-[amino(polyethylene glycol)-2000](PEG2000-DSPE) and the lipid free of a water soluble polymer is phosphatidylcholine.

In various aspects, the peptide of the lipid-stabilized, high-loading peptide nanoparticle comprises the amino acid sequence $FEX_1ERX_2$ (SEQ ID NO: 1) wherein $X_1$ and $X_2$ are selected from natural and unnatural amino acids, wherein the peptide is a 6-mer, 7-mer, 8-mer or 9-mer and wherein the peptide inhibits both the integrin-dependent and integrin-independent platelet granule secretion or wherein the peptide inhibits leukocyte integrin outside-in signaling. In various aspects, $X_1$ is glutamic acid or lysine. In various aspects, $X_2$ is isoleucine, alanine, methionine or lysine. In various aspects, $X_1$ is glutamic acid or lysine and $X_2$ is isoleucine, alanine, methionine or lysine. In related aspects, the peptide is myristoylated.

In various aspects, the peptide of any of the disclosed lipid-stabilized, high-loading peptide nanoparticle is FEEERI (SEQ ID NO: 2), FEKEKI (SEQ ID NO: 3), FEKERI (SEQ ID NO: 4), RGT, EEERA (SEQ ID NO: 5), FEEERA (SEQ ID NO: 6), FEEERM (SEQ ID NO: 7), FEEERL (SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17) or LLARRPTKGIHEY (SEQ ID NO: 18).

In other aspects, the peptide of any of the disclosed lipid-stabilized, high-loading peptide nanoparticle is myr-FEEERI (SEQ ID NO: 19), myr-FEKEKI (SEQ ID NO: 20), myr-FEKERI (SEQ ID NO: 21), myr-RGT, myr-EEERA (SEQ ID NO: 22), myr-FEEERA (SEQ ID NO: 23), myr-FEEERM (SEQ ID NO: 24), myr-FEEERL (SEQ ID NO: 25), myr-FEKEKM (SEQ ID NO: 26), myr-FEKEKL (SEQ ID NO: 27), myr-FEKERM (SEQ ID NO: 28), myr-FEKERL (SEQ ID NO: 29), myr-CFEEERAC (SEQ ID NO: 30), myr-FEEERAR (SEQ ID NO: 31), myr-FEEERARA (SEQ ID NO: 32), myr-SIRYSGHpSL (SEQ ID NO: 33), myr-KFEEERARAKWDT (SEQ ID NO: 34) or myr-LLARRPTKGIHEY (SEQ ID NO: 35).

In various aspects, the lipid-stabilized, high-loading peptide nanoparticle comprises about 10 to about 80 mol %, based on total nanoparticle mass, of peptide. In related aspects the peptide of the lipid-stabilized, high-loading peptide nanoparticle is myr-FEEERL (SEQ ID NO: 25) or myr-FEKEKL (SEQ ID NO: 27).

In an exemplary aspect, the lipid-stabilized, high-loading peptide nanoparticle comprises 2-10% phosphatidylcholine and 10-60% PEG-DSPE.

The disclosure also provides for pharmaceutical compositions comprising any of the lipid-stabilized, high-loading nanoparticles of the disclosure, and a pharmaceutically acceptable carrier, diluent, or excipient.

In another aspect, this disclosure provides for methods of preparing a lipid-stabilized, high-loading peptide nanoparticle comprising contacting a peptide nanoparticle comprising one or more lipidized peptides consisting of about 2 to about 50 amino acid residues with −2-20% of a lipid free of a water soluble polymer based on total nanoparticle mass and 20-50% of a lipid covalently attached to a water soluble polymer based on total nanoparticle mass. The mixture of the above are dissolved in methanol and chloroform followed by evaporation using a rotary evaporator to form a thin film, which will be rehydrated with isotonic saline (0.9% NaCl) or pH-buffered isotonic saline to prepare the lipid-stabilized high-loading nanoparticle.

In addition, the disclosure provides for methods of treating a thrombotic condition or an inflammatory condition in a subject in need thereof comprising administering to the subject an effective amount of any of the disclosed lipid-stabilized, high-loading nanoparticles. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, the thrombotic condition is arterial thrombosis, venous thrombosis and microvascular thrombosis, artificial valve thrombosis, AV-Fistura thrombosis, heart attack, or ischemic stroke.

In another aspect, the disclosure provides for methods of treating a stroke or a heart attack in a subject in need thereof comprising administering to the subject an effective amount of any of the disclosed lipid-stabilized, high-loading nanoparticles.

In a further aspect, the disclosure provides for use of an effective amount of any of the disclosed lipid-stabilized, high-loading nanoparticles nanoparticle or any disclosed pharmaceutical composition for the preparation of a medicament for treating a thrombotic condition or an inflammatory condition in a subject in need thereof. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, thrombotic condition is arterial thrombosis, venous thrombosis and microvascular thrombosis, artificial valve thrombosis, AV-Fistura thrombosis, heart attack, or ischemic stroke.

In another aspect, the disclosure provides for use of an effective amount of any of the disclosed lipid-stabilized, high-loading nanoparticles nanoparticle or any disclosed pharmaceutical compositions for the preparation of a medicament for treating a stroke or a heart attack in a subject in need thereof.

The disclosure also provides for compositions for treating a thrombotic condition or an inflammatory condition in a subject in need thereof, wherein the composition comprises an effective amount of any of the disclosed lipid-stabilized, high-loading nanoparticles nanoparticle or any disclosed pharmaceutical compositions. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, the thrombotic condition is arterial thrombosis, venous thrombosis and microvascular thrombosis, artificial valve thrombosis, AV-Fistura thrombosis, heart attack, or ischemic stroke.

In additional aspects, the disclosure provides compositions for treating a stroke or a heart attack in a subject in need thereof, wherein the composition comprises an effective amount any of the disclosed lipid-stabilized, high-loading nanoparticles nanoparticle or any disclosed pharmaceutical compositions.

In any of the disclosed methods, uses and compositions, the peptide is a lipidated peptide comprising the amino acid sequence of FEEERM (SEQ ID NO: 7), FEEERL (SEQ ID NO: 8), FEEERI (SEQ ID NO: 2), FEKEKM (SEQ ID NO: 9), FEKEKL (SEQ ID NO: 10), FEKEKI (SEQ ID NO: 3), FEKERM (SEQ ID NO: 11), FEKERL (SEQ ID NO: 12), FEKERI (SEQ ID NO: 4) or CFEEERAC (SEQ ID NO: 13).

In any of the disclosed methods, uses and compositions, the peptide is myristoylated an comprises the amino acid sequence of myr-FEEERM (SEQ ID NO: 24), myr-FEEERL (SEQ ID NO: 25), myr-FEEERI (SEQ ID NO: 19), myr-FEKEKM (SEQ ID NO: 26), myr-FEKEKL (SEQ ID NO: 27), myr-FEKEKI (SEQ ID NO: 20), myr-FEKERM (SEQ ID NO: 28), myr-FEKERL (SEQ ID NO: 29), myr-FEKERI (SEQ ID NO: 21) of myr-CFEEERAC (SEQ ID NO: 30).

In another aspect, the disclosure provides for a peptide comprising the amino acid sequence FEEERI (SEQ ID NO: 2), FEKEKI (SEQ ID NO: 3), or FEKERI (SEQ ID NO: 4). In a related aspect, the disclosure provides for a peptide consisting of the amino acid sequence FEEERI (SEQ ID NO: 2), FEKEKI (SEQ ID NO: 3), or FEKERI (SEQ ID NO: 4). In related aspects, the peptide further comprises a membrane permeable moiety. For example, the membrane permeable moiety is a membrane permeable peptide, a membrane permeable synthetic compound or a fatty acid. In certain aspects, the membrane permeable moiety is a fatty acid. In related aspects, the fatty acid is covalently attached to the peptide. In related aspects, the peptide is myristoylated. In related aspects, the peptide is myr-FEEERI (SEQ ID NO: 19), myr-FEKEKI (SEQ ID NO: 20), or myr-FEKERI (SEQ ID NO: 21).

In various aspects, the disclosure provides for pharmaceutical compositions comprising a peptide disclosed herein and a pharmaceutically acceptable carrier, diluent, or excipient. In various aspects, pharmaceutical compositions comprise the amino acid sequence FEEERI (SEQ ID NO: 2), FEKEKI (SEQ ID NO: 3), or FEKERI (SEQ ID NO: 4) and a pharmaceutically acceptable carrier, diluent, or excipient. In various aspects, pharmaceutical compositions comprise the peptide is myr-FEEERI (SEQ ID NO: 19), myr-FEKEKI (SEQ ID NO: 20), or myr-FEKERI (SEQ ID NO: 21) and a pharmaceutically acceptable carrier, diluent, or excipient.

In another aspect, the disclosure provides for methods of treating a thrombotic condition or an inflammatory condition in a subject in need thereof comprising administering to the subject an effective amount of a peptide or a pharmaceutical composition disclosed herein. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, the thrombotic condition is arterial thrombosis, venous thrombosis and microvascular thrombosis, artificial valve thrombosis, AV-Fistura thrombosis, heart attack, or ischemic stroke.

In another aspect, the disclosure provides for methods of treating ischemic events such as stroke or heart attack or AV Fistula thrombosis in a subject in need thereof comprising administering to the subject an effective amount of a peptide or a pharmaceutical composition disclosed herein.

In another aspect, the disclosure provides for use of an effective amount of a peptide or a pharmaceutical composition disclosed herein for the preparation of a medicament for treating a thrombotic condition or an inflammatory condition in a subject in need thereof. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, the thrombotic condition is arterial thrombosis, venous thrombosis and microvascular thrombosis, artificial valve thrombosis, AV-Fistura thrombosis, heart attack, or ischemic stroke.

In another aspect, the disclosure provides for use of an effective amount of a peptide or a pharmaceutical composition disclosed herein for the preparation of a medicament for treating stroke and heart attack or AV Fistula thrombosis in a subject in need thereof.

In another aspect, the disclosure provides compositions for treating a thrombotic condition or an inflammatory condition in a subject in need thereof comprising an effective amount of a peptide or a pharmaceutical composition disclosed herein. In related aspects, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury. In related aspects, the thrombotic condition is arterial thrombosis, venous thrombosis and microvascular thrombosis, artificial valve thrombosis, AV-Fistura thrombosis, heart attack, or ischemic stroke.

In another aspect, the disclosure provides compositions for treating stroke and heart attack in a subject in need thereof comprising an effective amount of a peptide or a pharmaceutical composition disclosed herein.

There are two kinds of granule secretion: integrin-dependent and integrin-independent. The platelet adhesion receptor integrin αIIbβ3 is known to induce integrin-dependent platelet granule secretion. However, it was discovered that blocking the ligand binding function of integrin αIIbβ3 with currently available integrin inhibitors such as Integrilin or mutating the Gα13 binding site in the integrin β3 cytoplasmic domain in fact enhances integrin-independent granule secretion although inhibiting integrin-dependent granule secretion.

Accordingly, in another aspect, the disclosure provides for methods of treating a disease or condition regulated by platelet granule secretion, Gα13 function or leukocyte integrin outside-in signaling in a subject comprising administering to the subject an effective amount of a peptide comprising the amino acid sequence $FEX_1ERX_2$ (SEQ ID NO: 1) wherein $X_1$ and $X_2$ are selected from natural and unnatural amino acids, wherein the peptide is a 6-mer, 7-mer, 8-mer or 9-mer and wherein the peptide inhibits both the integrin-dependent and integrin-independent platelet granule secretion or wherein the peptide inhibits leukocyte integrin outside-in signaling.

In another aspect, the disclosure provides for methods of inhibiting integrin outside-in signaling without inhibiting integrin-independent platelet granule secretion in a subject comprising administering to the subject an effective amount of a peptide consisting of the amino acid sequence of EEERA (SEQ ID NO: 5), EEERM (SEQ ID NO: 36), EEERL (SEQ ID NO: 37), EKEKM (SEQ ID NO: 38), EKEKL (SEQ ID NO: 39), EKERM (SEQ ID NO: 40), EKERL (SEQ ID NO: 41) or CEEERAC (SEQ ID NO: 42). This peptide may be useful under conditions where platelet granule secretion is desired (e.g. for facilitating wound healing) during treatment for thrombosis.

BRIEF DESCRIPTION OF THE DRAWINGS

FIGS. 1A-1E: (FIG. 1A) A schematic of lipid-stabilized, high-loading peptide nanoparticles (HLPN). (FIG. 1B) Structure of M3mP6 (Myr-FEEERL (SEQ ID NO: 25)) peptide. (FIG. 1C) Dose-dependent inhibitory effects of M3mP6 on the coimmunoprecipitation of integrin $\beta_3$ and $G\alpha_{13}$ in α-thrombin (0.025 U/mL) stimulated human platelets compared to scrambled peptide. (FIG. 1D) Quantification of coimmunoprecipitation blots in panel FIG. 1C (n=3). OD, optical density. (FIG. 1E) The size distribution of a single preparation of M3mP6 HLPN (6.6±0.8 nm) as analyzed by dynamic light scattering.

FIGS. 2A-2I show a function analysis of M3mP6 HLPN. (FIG. 2A) M3mP6 HLPN dose-dependently inhibited thrombin-induced human platelet secretion in vitro. Data from 3-4 experiments. (FIG. 2B) Dose-dependent inhibition of thrombin (0.03 U/mL)-induced platelet aggregation by M3mP6 HLPN. (FIG. 2C) Inhibitory effects of M3mP6 HLPN on thrombin-induced human platelet aggregation is limited to the low-dose thrombin (Scra: scrambled control peptide). (FIG. 2D) M3mP6 HLPN inhibited both low-dose and higher-dose induced platelet secretion in human platelets. (FIG. 2E) M3mP6 HLPN partially inhibited collagen (1 μg/mL)-induced mouse platelet aggregation compared to scrambled peptide control. (FIG. 2F) M3mP6 HLPN partially inhibited U46619 (0.5 μM)-induced mouse platelet aggregation compared to scrambled peptide HLPN. (FIG. 2G) M3mP6 HLPN had no effects on ADP (5 μM)-induced human platelet aggregation. (FIG. 2H) M3mP6 HLPN had no effects on PAR4 agonist (PAR4-AP)-induced binding of PE-conjugated antibody against activated αIIbβ3, JON/A, to mouse platelets. (FIG. 2I) M3mP6 HLPN had no effects on PAR4 agonist (PAR4-AP)-induced binding of Oregon Green-labelled fibrinogen to mouse platelets. *P<0.05, ****P<0.0001, n.s., no significance.

FIGS. 3A-3G show the pharmacokinetics of M3mP6 HLPN. (FIG. 3A) Flow cytometry comparison of the intakes of Fluorescence-labeled M3mP6 dissolved in DMSO with that dissolved in HLPN into mouse platelets. (FIG. 3B) Comparable effect of 40 μM M3mP6 in HLPN with 160 μM DMSO-solubilized M3mP6 on human platelet aggregation. (FIG. 3C) M3mP6 HLPN (n=15) inhibited $FeCl_3$-induced carotid artery thrombosis, in contrast to the lack of effect of DMSO-solubilized M3mP6 (n=6) as compared with saline control (n=14). (FIG. 3D) Dose response of M3mP6 HLPN in inhibiting $FeCl_3$-induced carotid artery occlusive thrombosis following retro-orbital injection 15 minutes before procedure (n=3). (FIG. 3E) Pharmacokinetic study on plasma levels of M3mP6 HLPN following retro-orbital injection (5 μmol/kg). (FIG. 3F) Pharmacokinetic study on whole blood levels of M3mP6 HLPN following retro-orbital injection (5 μmol/kg). (FIG. 3G) Kinetics of anti-thrombotic effect of 5 μmol/kg M3mP6 HLPN (retro-orbital injection) in inhibiting $FeCl_3$-induced carotid artery occlusive thrombosis (n=3). P<0.01, **P<0.0001, n.s. no significance.

FIGS. 4A-4D show a comparison of the effect of M3mP6 HLPN with aspirin on thrombosis and hemostasis. (FIGS. 4A and 4B) Comparison of the effects of M3mP6 HLPN (10 μmol/kg, 15 minutes before procedure), aspirin (4.3 mg/kg, oral 2 hours before procedure), and M3mP6 HLPN plus aspirin on $FeCl_3$-induced thrombosis (FIG. 4A) and tail bleeding time (FIG. 4B). (FIG. 4A: n=17 for normal control, n=18 for M3mP6 HLPN, n=11 for aspirin, n=11 for aspirin +M3mP6 HLPN; FIG. 4B: n=16 for normal control, n=18 for M3mP6 HLPN, n=11 for aspirin, n=11 for aspirin +M3mP6 HLPN). (FIGS. 4C and 4D) Comparison of the effects of M3mP6 HLPN (5 μmol/kg), a high dose aspirin (36 mg/kg, i.p. 1 hour before procedure), and M3mP6 HLPN plus high dose aspirin on $FeCl_3$-induced carotid artery thrombosis (FIG. 4C) and tail bleeding time (FIG. 4D). (FIG. 4C: n=8 for normal control, n=8 for M3mP6 HLPN, n=10 for aspirin, n=6 for aspirin +M3mP6 HLPN; D: n=8 for normal control, n=8 for M3mP6 HLPN, n=11 for aspirin, n=6 for aspirin +M3mP6 HLPN). P<0.01, *P<0.001, ****P<0.0001.

FIGS. 5A-5D show a comparison of effects of M3mP6 HLPN with oral P2Y12 inhibitors on thrombosis and hemostasis and their synergistic anti-thrombotic effect. (FIGS. 5A and 5B) Comparison of the effects of M3mP6 HLPN (10 μmol/kg, 15 minutes before procedure) with clopidogrel (4 mg/kg, 2 hours before procedure), M3mP6 HLPN plus clopidogrel, ticagrelor (3 mg/kg, 2 hours before procedure), and M3mP6 HLPN plus ticagrelor on $FeCl_3$-induced carotid artery thrombosis (FIG. 5A) and tail bleeding time (FIG. 5B). (FIGS. 5A and 5B: n=30 for normal control, n=18 for M3mP6 HLPN, n=8 for clopidogrel, n=8 for clopidogrel+ M3mP6 HLPN, n=13 for ticagrelor, n=14 for ticagrelor+ M3mP6 HLPN). (FIGS. 5C and 5D) Comparison of the effects of M3mP6 HLPN, clopidogrel plus aspirin, M3mP6 HLPN and clopidogrel plus aspirin on $FeCl_3$-induced carotid artery thrombosis (FIG. 5C) and tail bleeding time (FIG. 5D). (FIGS. 5C and 5D: n=27 for normal control, n=18 for M3mP6 HLPN, n=11 for aspirin, n=8 for clopidogrel, n=9 for aspirin +clopidogrel, n=10 for aspirin +clopidogrel +M3mP6 HLPN). *P<0.05, P<0.01, *P<0.001, ****P<0.0001.

(FIG. 6A) Effects of M3mP6 HLPN (10 μmol/kg) and cangrelor (30 μg/kg) on occlusive thrombosis when injected 5 minutes after $FeCl_3$ (3.75%)-induced carotid artery injury. (FIG. 6B) Tail bleeding time analysis of mice as described in (FIG. 6A). A and B: n=7 for normal control, n=9 for M3mP6 HLPN, n=6 for cangrelor. (FIGS. 6C and 6D) Comparison of the effects of pre-injury injection of M3mP6 HLPN (10 μmol/kg) with a high dose cangrelor (30 μg/kg), high dose cangrelor (30 μg/kg) plus M3mP6 HLPN, a low dose cangrelor (10 μg/kg), and the low dose cangrelor (10 μg/kg) plus M3mP6 HLPN and with normal controls on $FeCl_3$-induced carotid artery thrombosis (FIG. 6C) and tail bleeding time (FIG. 6D). (FIG. 6C: n=29 for normal control, n=26 for M3mP6 HLPN, n=20 for high dose cangrelor, n=15 for high dose cangrelor+M3mP6 HLPN, n=17 for low dose cangrelor, n=14 for low dose cangrelor+ M3mP6 HLPN; FIG. 6D: n=29 for normal control, n=25 for M3mP6 HLPN, n=17 for cangrelor 30 μg/kg, n=17 for cangrelor 30 μg/kg+ M3mP6 HLPN, n=17 for cangrelor 10 μg/kg, n=14 for cangrelor 10 μg/kg+ M3mP6 HLPN). (FIG. 6E) Comparison of the median integrated platelet fluorescence intensity (DyLight 649-labeled anti-GPIbβ) at the sites of the laser-induced injury in cremaster arterioles of control (black), M3mP6 HLPN (10 μmol/kg)-treated (red) and cangrelor (30 μg/kg)-treated (blue) mice (27 injury sites each for control, M3mP6- and cangrelor-treated groups (Control vs M3mP6 or cangrelor, P<0.0001, M3mP6 vs cangrelor, no significant difference). (FIG. 6F) Comparison of the median integrated fibrin fluorescence intensity (Alexa Fluor 488-labeled anti-fibrin) at the sites of the laser-induced injury in cremaster arterioles of control (black), M3mP6 HLPN (10 μmol/kg)-treated (red) and cangrelor (30 μg/kg)-treated (blue) mice (27 injury sites each for control, M3mP6- and cangrelor-treated groups (Control vs M3mP6 or cangrelor, P<0.0001, M3mP6 vs cangrelor, P<0.01).

(FIG. 7A) Illustration of a novel mouse surgical bleeding model. (FIG. 7B) Comparison of M3mP6 HLPN (10 μmol/kg) with high dose cangrelor (30 μg/kg), high dose cangrelor plus M3mP6 HLPN, low dose cangrelor (10 μg/kg), and low dose cangrelor plus M3mP6 HLPN in the artery perforation model of surgical bleeding (n=27 for normal control, n=20 for M3mP6 HLPN, n=16 for cangrelor 30 μg/kg, n=17 for cangrelor 30 μg/kg+ M3mP6 HLPN, n=11 for cangrelor 10 μg/kg, n=12 for cangrelor 10 μg/kg+ M3mP6 HLPN). (FIG. 7B) BMBT test of the effect of M3mP6 HLPN on hemostasis in dogs. (n=3). (FIG. 7C) Bleeding times were observed between pre- and post-administration of M3mP6 HLPN. ****P<0.0001, n.s., no significance.

FIGS. 8A-8L show the effects of post-ischemia injection of M3mP6 HLPN on myocardial ischemia and reperfusion (MI/R) injury in mice. (FIG. 8A) Schematic protocol of MI/R study. Mouse left anterior descending branch (LAD) was fully ligated for 45 minutes before reopening (repurfusion). Mouse chest was then closed. 35 minutes after LAD ligation, M3mP6 HLPN or scrambled peptide HLPN control (Scra) was bolus injected at 5 μmol/kg through jugular vein and then continuously infused at rate of 2.5 μmol/kg/h for 24 hours. The mice were then subject to echocardiography and/or histological examinations. (FIG. 8B) Representative images of heart sections of M3mP6 HLPN- or scrambled peptide HLPN treated-mice 24 hours after reperfusion. (FIG. 8C) Quantification of the infarct area (white) as percentage of the area at risk (non-blue) as shown in A. (FIG. 8D) Quantification of risk area as percentage of the entire heart section. Viable tissue within the risk area was stained in red. (n=4 for each group, *p<0.05) (FIG. 8E) Representative M-mode long-axis echo images for (i) sham control; (ii) MI/R treated with scrambled control HLPN; and (iii) MI/R treated with M3mP6 HLPN. (FIG. 8F) Mouse left ventricle ejection fraction was detected by echocardiography and calculated by Vevo 2100 software. Data was presented as mean±SEM, statistic was analyzed by one-way ANOVA using Graphpad PRISM 5.0. (FIG. 8G) Immunohistochemistry staining of platelets in mouse heart sections 24 h after MI/R using rat anti-integrin αIIb antibody. The representative sections are from (i) sham control; (ii) MI/R treated with scrambled peptide HLPN; and (iii) MI/R treated with M3mP6 HLPN. (iv) αIIb positive staining was quantified by image J software and presented as percentage of total tissue area. Statistical analysis was examined by Mann-Whitney nonparametric t-test. (FIG. 8H) Immunohistochemistry staining of neutrophils in mouse heart sections 24 h after MI/R using rat anti-Ly6G antibody. The representative sections are from (i) sham control; (ii) MI/R treated with scrambled peptide HLPN; and (iii) MI/R treated with M3mP6 HLPN. (iv) Ly6G-positive cells/mm2 were counted using imageJ software. Statistical analysis was examined by Mann-Whitney nonparametric t-test. p<0.01 (FIG. 8I) Mouse plasma MPO level 24 hours after MI/R. (sham: n=6, scrambled HLPN treatment: n=11, M3mP6 HLPN treatment: n=9) (FIG. 8J) Kaplan-Meier survival curve of mice 7 days after MI/R surgery treated with M3mP6 HLPN or scrambled peptide HLPN. Sham surgery caused no death in 6 tested mice. (FIG. 8K) Left Ventricular Ejection Fraction (LVEF) percentage (%) of mice treated with M3mP6 HLPN, cangrelor, saline or sham. (FIG. 8**L) Kaplan-Meier survival curve of mice showing percent survival for mice treated with M3mP6 HLPN, cangrelor, saline or sham and reperfusion time after MI.

(FIG. 9A) Mouse neutrophil adhesion to β2 integrin ligand ICAM1 were not affected after MB2mP6 (50 μM) as compared to control peptide (n=3). (FIG. 9B) Trans-endothelial migration of neutrophils was dose-dependently inhibited by MB2mP6 peptide treatment. (FIG. 9C) Neutrophil trans-endothelial migration were significantly reduced in MB2mP6 peptide treated control neutrophil (Gα$13^{fl/fl}$), similar to the inhibitory effect of Gα13-knockout neutrophils (Gα$13^{fl/fl}$ LysM cre). Note that MB2mP6 treatment did not further reduce neutrophil transmigration in Gα$13^{fl/flLy}$-$_{sMCre}$ neutrophils, suggesting the inhibition by MB2mP6 is Gα13-specific.

FIGS. 10A-10B show expression of selected cytokine (IL-6 and TNFα) at the protein level in mouse serum measured by ELISA 24 h after CLP. Sham, n=6; Scra, n=8; MB2mP6, n=10. FIGS. 10C-10D show expression of selected cytokines at the mRNA level in mouse lung tissues 24 h after CLP. Sham, n=4; Scra, n=6; MB2mP6, n=6. All data are shown as mean±s.e.m. Data were analyzed by two-tailed unpaired t-test with Welch's correction; * P<0.05, P<0.01, *P<0.001.

(FIG. 12A) Washed wild-type (WT) and β3−/− mouse platelets were solubilized and immunoblotted with a rabbit antibody recognizing integrin β3, and with an anti-Gα13 antibody. (FIG. 12B) Washed wild-type (WT) and β3−/− platelets were stimulated with thrombin. Platelet aggregation and ATP secretion was recorded concomitantly in the presence of luciferin-luciferase agent using a Chronolog platelet aggregometer at 37° C. and 1000 rpm stirring speed. (FIG. 12C) Quantification of secretion. *p<0.05 (n=3, Student t test). (FIG. 12D) Washed human platelets pre-incubated with buffer or μg/ml Integrilin were stimulated with thrombin. Platelet aggregation and ATP secretion was recorded concomitantly in the presence of luciferin-luciferase agent using Chronolog platelet aggregometer. (FIG. 12E) quantification of secretion. *p<0.05, Student t test (n=3).

(FIG. 13A) Washed wild-type (WT) and β3−/− platelets were stimulated with U46619. Platelet aggregation and ATP secretion was monitored using a Chronolog Lumi-aggregometer at 37° C. and 1000 rpm stirring speed. Note the two waves of ATP secretion in wild type platelets and a higher single (first) secretion wave in β3 knockout platelets. (FIGS. 13B and 13C) Quantification of either wave of secretion in (FIG. 13A) was performed using Student t test (n=3). (FIG. 13D) Washed human platelets pre-incubated with buffer or 10 μg/ml Integrilin were stimulated with U46619. Platelet aggregation and ATP secretion was monitored as in (FIG. 13A). (FIG. 13E) Quantification of secretion data from (FIG. 13D) using Student t test (n=3).

(FIG. 14A) Flow cytometric analysis of platelet expression of wild type (EEE) and AAA mutant integrin β3 in β3−/− mice transplanted with bone marrow stem cells transfected with wild type or AAA mutant human β3 cDNA. Platelets were stained with the anti-β3 monoclonal antibody mAb15. (FIG. 14B) Washed wild-type (EEE) and AAA mutant-expressing mouse platelets were stimulated with thrombin. Platelet aggregation/ATP secretion was monitored as in FIG. 1. (FIG. 14C) Quantitative data from (FIG. 14B) using Student t test (n=3). (FIG. 14D) Washed EEE and AAA platelets were stimulated with U46619. Platelet aggregation was monitored as in FIG. 14B. (FIG. 14E) Quantitative data from (FIG. 14D) using Student t test (n=3).

(FIG. 15A) Equal amounts of washed wild-type (WT) and Gα13−/− mouse platelets were solubilized and immunoblotted with a rabbit antibody specifically recognizing Gα13, and integrin β3. (FIG. 15B) Washed wild-type (WT) and Gα13−/− platelets were stimulated with thrombin. Platelet aggregation and ATP secretion was recorded concomitantly in the presence of luciferin-luciferase agent as described in FIG. 1. (FIG. 15C) Quantification of secretion in (FIG. 15B). Student t test (n=3). (FIG. 15D) Washed wild-type (WT) and Gα13−/− platelets were stimulated with U46619. Platelet aggregation and ATP secretion were recorded concomitantly in the presence of luciferin-luciferase agent. (FIG. 15E) Quantification of secretion in (FIG. 15D). Student t test (n=3).

FIGS. 16A-16E shows a comparison of the effects of mP6 and mP5 on platelet granule secretion. (FIG. 16A) Washed human platelets were stimulated with thrombin. Platelet aggregation and ATP secretion was recorded concomitantly in the presence of luciferin-luciferase agent as described above. (FIG. 16B) Quantification of secretion in (FIG. 16A). Student t test (n=3). (FIG. 16C) Washed human platelets were stimulated with U46619. Platelet aggregation and ATP secretion was recorded concomitantly in the presence of luciferin-luciferase agent. Note the two waves of granule secretion and opposing effect on 1st wave by mP5 and mP6 (FIGS. 16D and 16E) Quantification of secretion in (FIG. 16C). Student t test (n=3).

(FIGS. 18A and B) Dynamic light scattering (DLS) analysis of particle sizes of M3mP6 HLPN before (FIG. 18A) and after (FIG. 18B) 18-month storage at −20° C. (FIG. 18C) Anti-thrombotic effects of M3mP6 HLPN in $FeCl_3$-induced carotid artery thrombosis model before and after 18-month storage at −20° C. n=4, *p<0.05. (D and E) DLS-analysis of particle sizes of M3mP6 HLPN before (FIG. 18D) and after (FIG. 18E) 2-week storage at room temperature (~22° C.). (FIG. 18F) Anti-thrombotic effects of M3mP6 HLPN in $FeCl_3$-induced carotid artery thrombosis model before and after 2-week storage at room temperature. *p<0.05.

FIG. 2I shows a dose response analysis of tail vein-injected M3mP6 HLPN in inhibiting occlusive thrombosis using the 7.5% $FeCl_3$-induced carotid artery thrombosis model. Note that efficacious dose is 1.25 μmol peptide/kg and above. (n=3 for M3mP6 HLPN 1.25, 2.5 μmol/kg; n=5 for M3mP6 HLPN 5 μmol/kg; n=6 for M3mP6 HLPN 10 μmol/kg).

FIG. 24 shows a table of mean M3mP6 Peptide Pharmacokinetic Parameters. *standard error; NA—standard error not able to be calculated due to sample sizes <3 IVB-intravenous bolus, IVI—intravenous infusion, Cmax—maximum plasma concentration, Tmax-time of Cmax, Css—steady-state plasma concentration during the continuous IV infusion, AUC0-last—area under the plasma concentration-time curve from time zero (administration of IV bolus) to last plasma concentration (48 h after stopping infusion), AUC0-∞—AUC from time zero to infinity, λz—terminal elimination rate constant, t½-λz—terminal elimination half-life, CLAUC—clearance estimated from the AUC0-∞, CLcss—clearance estimated from Css, Vλz—distribution volume.

FIGS. 25A-25I show that MB2mP6 blocks Gα13 interactions with β2 and β3 integrins and inhibits macrophage and platelet function without causing bleeding. FIG. 25A, Representative immunoblots of co-immunoprecipitation of β2 integrin and Gα13 with anti-β2 antibody in PMA differentiated THP-1 cells pretreated with MB2mP6 or control peptide micelles (50 μM) for 20 min and then stimulated with LPS (100 ng/mL). The immunoprecipitates and total cell lysates were then immunoblotted with both anti-β2-integrin and anti-Gα13 antibodies. FIG. 25B, Representative immunoblots of co-immunoprecipitation of β3 integrin and Gα13 with anti-β3 antibody in human platelets pretreated with MB2mP6 or control peptide micelles (50 μM) for 5 min and then stimulated with thrombin (0.025 U/mL) at various time points. The immunoprecipitates and total cell lysates were immunoblotted with both anti-β3-integrin and anti-Gα13 antibodies respectively. FIGS. 25C and 25D, MB2mP6 micelles inhibited LPS (100 ng/mL) stimulated Il-1β (c) and Il-6 (d) mRNA expression in mouse BMDMs. The mRNA expression level changes were detected by qRT-PCR. All groups, n=4. e, Representative thrombin (0.03 U/mL) induced human platelet aggregation tracing showing a dose-dependent inhibition of aggregation by MB2mP6 micelles. FIG. 25F, Representative study showing thrombin (0.03 U/mL) induced ADP secretion in washed human platelets is dose-dependently inhibited by MB2mP6 micelles. FIGS. 25G and 25H, Comparison of the effects of MB2mP6 and M3mP6 (Myr-FEEERL (SEQ ID NO: 25)) on $FeCl_3$-induced carotid artery thrombosis (FIG. 25G) and tail-bleeding time (FIG. 25H). control, n=29; MB2mP6, n=14; M3mP6, n=29. i, MB2mP6 did not enhance inflammation-induced hemorrhage compared with scrambled peptide in the reverse passive Arthus (rpA) assay. All data are shown as mean±s.e.m. Data in c and d were analyzed by two-way analysis of variance (ANOVA) with the post hoc Tukey's multiple comparison test; p<0.01, *p<0.001. Data in FIGS. 25G, 25H and 25I were analyzed by two-tailed unpaired t-test. ns, no significance, p<0.01, *p<0.001,****p<0.0001.

FIG. 26A, MB2mP6 treatment immediately after CLP surgery enhanced the survival of septic C57BL/6 mice in a CLP model compared to scrambled peptide or saline treatment groups. All mice in the sham group survived. Significance was determined by a Log-rank (Mantel-Cox) test using GraphPad Prism software. Sham, n=6; Scra, n=23; MB2mP6, n=24; Saline, n=18. FIG. 26B, MB2mP6 treatment 6 hours after CLP onset enhanced the survival of septic C57BL/6 mice in a CLP model. All mice in the sham group survived. Significance analysis was determined by a Log-rank (Mantel-Cox) test using GraphPad Prism software. Sham, n=6; Saline, n=24; MB2mP6, n=19. FIGS. 26C-26D, MB2mP6 inhibits expression of selected cytokines IL-6 and TNFα at the protein level in mouse serum measured by ELISA 24 hours after CLP. Sham, n=6; Scra, n=8; MB2mP6, n=10. FIG. 26E, Representative images of fibrin deposition detected by PTAH staining in mouse kidney glomeruli 24 hours after CLP. Bars indicate the percentage of PTAH positive stained area per glomerulus (30 random glomeruli from 6 mice/group). Sham, n=6; Scra, n=30; MB2mP6, n=30. Scale bar, 100 μm. FIG. 26F, Plasma level of BUN in septic mice 24 hours after CLP was inhibited in MB2mP6 treated mice compared to scrambled peptide treated mice. Sham, n=6; Scra, n=9; MB2mP6, n=9. All data are shown as mean±s.e.m. Data in FIGS. 26C, 26D and 26F were analyzed by a two-tailed unpaired t-test with Welch's correction; data in FIG. 26E were analyzed by a two-tailed nonparametric Mann-Whitney test; *p<0.05, p<0.01, *p<0.001.

FIGS. 27A-27J show that Leukocyte- or platelet-specific Gα13 knockout reduces mortality in CLP-induced septic mice. FIG. 27A, The survival rate of mice after CLP-induced was increased in $G\alpha13^{fl/fl\text{-}LysMCre}$ mice compared to $G\alpha13^{fl/fl}$ control mice. All mice in the sham group survived. $G\alpha13^{fl/fl}$ sham, n=6; $G\alpha13^{fl/fl}$ CLP, n=20; $G\alpha13^{fl/fl\text{-}LysMCre}$ sham, n=6; $G\alpha13^{fl/fl\text{-}LysMCre}$ CLP, n=25. Significance was determined by a Log-rank (Mantel-Cox) test using GraphPad Prism software. FIGS. 27B and 27C, Serum levels of selected cytokines IL-6 and TNFα in septic mice 24 hours after CLP in $G\alpha13^{fl/fl\text{-}LysMCre}$ and $G\alpha13^{fl/fl}$ control mice. All sham groups, n=6; all CLP groups, n=10. FIG. 27D, Representative images of immunohistochemical staining of fibrin deposition in mouse kidney 24 hours after CLP. Bars indicate the percentage of fibrin positive stained area per glomerulus (30 random glomeruli from 6 mice/group). All groups, n=30. Scale bar, 100 μm. FIG. 27E, Plasma level of BUN in septic mice 24 hours after CLP showed no difference between $G\alpha13^{fl/fl\text{-}LysMCre}$ mice and $G\alpha13^{fl/fl}$ mice. All sham groups, n=5; all CLP groups, n=10. FIG. 27F, Survival rate in mice after CLP-induced sepsis was increased in $G\alpha13^{fl/fl\text{-}PF4Cre}$ mice compared to $G\alpha13^{fl/fl}$ control mice. All mice in the sham group survived. $G\alpha13^{fl/fl}$ sham, n=6; $G\alpha13^{fl/fl}$ CLP, n=26; $G\alpha13^{fl/fl\text{-}PF4Cre}$ sham, n=7; $G\alpha13^{fl/fl\text{-}PF4Cre}$ CLP, n=17. Significance was determined by a Log-rank (Mantel-Cox) test using GraphPad Prism software. FIG. 27G, Representative images of immunohistochemical staining of fibrin deposition in mouse kidney 24 hours after CLP. Bars indicate the percentage of fibrin positive stained area per glomerulus (30 random glomeruli from 6 mice/group). All groups, n=30. Scale bar, 100 μm. FIG. 27H, Plasma levels of BUN in septic mice 24 hours after CLP were reduced in $G\alpha13^{fl/fl\text{-}PF4Cre}$ mice compared to $G\alpha13^{fl/fl}$ mice. All groups, n=9. FIGS. 27I and 27J, serum levels of selected cytokines TNFα and IL-6 in septic mice 24 hours after CLP in $G\alpha13^{fl/fl\text{-}PF4Cre}$ and $G\alpha13^{fl/fl}$ control mice. All groups, n=8. All data are shown as mean±s.e.m. Data in FIGS. 27B, 27C, 27H-J were analyzed by two-way ANOVA with multiple comparisons; data in d and g were analyzed by a two-tailed nonparametric Mann-Whitney test. ns, no significance, *p<0.05, p<0.01, *p<0.001.

FIGS. 28A-28E show that platelet and leukocyte duo-specific Gα13 knockout protects mice from death in CLP sepsis model. FIG. 28A, Survival rate in mice after CLP-induced sepsis was increased in $G\alpha13^{fl/fl\text{-}PF4/LysMCre}$ mice compared to $G\alpha13^{fl/fl}$ control mice. All mice in the sham group survived. $G\alpha13^{fl/fl}$ sham, n=6; $G\alpha13^{fl/fl}$ CLP, n=17; $G\alpha13^{fl/fl\text{-}PF4/LysMCre}$ sham, n=7; $G\alpha13^{fl/fl\text{-}LysMCre}$ CLP, n=13. Significance was determined by a Log-rank (Mantel-Cox) test using GraphPad Prism software. FIG. 28B, Plasma levels of BUN in septic mice 24 hours after CLP were decreased in $G\alpha13^{fl/fl\text{-}PF4/LysMCre}$ mice compared to $G\alpha13^{fl/fl}$ mice. All groups, n=9. FIGS. 28C and 28D, serum levels of selected cytokines IL-6 and TNFα in septic mice 24 hours after CLP were reduced in $G\alpha13^{fl/fl\text{-}PF4/LysMCre}$ mice compared with $G\alpha13^{fl/fl}$ control mice. All groups, n=9. FIG. 28E, Representative images of immunohistochemical staining of fibrin deposition in mouse kidney 24 hours after CLP. Bars indicate the percentage of fibrin positive stained area per glomerulus (30 random glomeruli from 6 mice/group). All groups, n=30. Scale bar, 100 μm. All data are shown as mean±s.e.m. Data in b-d were analyzed by two-way ANOVA with multiple comparisons; data in e were analyzed by a two-tailed nonparametric Mann-Whitney test; *p<0.05, p<0.01, *p<0.001.

FIG. 29A, Representative images of immunohistochemistry stain of fibrin in mouse lung 24 after CLP. Bars indicate the percentage of fibrin positive stained area per glomerulus (30 random glomeruli from 6 mice/group). Sham, n=6; Scra, n=30; MB2mP6, n=30. Scale bar, 100 mm. FIG. 29B, Representative images of immunohistochemistry stain of platelet αIIb in mouse lung 24 after CLP. Bars indicate the percentage of αIIb positive stained area per glomerulus (30 random glomeruli from 6 mice/group). Sham, n=6; Scra, n=30; MB2mP6, n=30. Scale bar, 100 mm. FIG. 29C, Serum level of Creatinine in septic mice 24 hours after CLP was inhibited in MB2mP6 treated mice compared to scrambled peptide treated mice. Sham, n=6; Scra, n=8; MB2mP6, n=10. FIG. 29D, Serum level of Cystatin C in septic mice 24 hours after CLP was inhibited in MB2mP6 treated mice compared to scrambled peptide treated mice. Sham, n=6; Scra, n=8; MB2mP6, n=10. All data are shown as mean±s.e.m. Data in FIGS. 29A and 29B were analyzed by two-tailed nonparametric Mann-Whitney test; data in c and d were analyzed by two-tailed unpaired t-test with Welch's correction; *p<0.05, p<0.01, *p<0.001.

FIG. 30A, schematic breeding strategies for Gα13 knockout mice. FIG. 30B, Representative western blots for Gα13 protein analysis.

FIGS. 31A-31D: The importance of Gα13 in transendothelial migration of mouse neutrophils. FIG. 31A, Western blot comparison of Gα13 expression in $G\alpha13^{fl/fl}$ ($G\alpha_{13}^{+/+}$) and $G\alpha13^{fl/fl\ LysM\ cre}$ ($G\alpha_{13}^{-/-}$) mouse neutrophils (mPMN) (n=3). FIGS. 31B and 31C, Total number of neutrophils isolated from bone marrow (B) (n=6) and blood (C) (n=6). FIG. 31D, Comparison of in vitro transendothelial migration toward formyl peptide between $G\alpha13^{-/-}$ and $G\alpha13^{+/+}$ neutrophils (n=3). The t-test was used for statistical analysis. *P<0.05, P<0.01, *P<0.001, ns, no significance.

FIG. 32A, Comparison of $G\alpha_{13}^{+/+}$ and $G\alpha_{13}^{-/-}$ neutrophil migration through transwell filters pre-coated with 5% BSA, fibrinogen (60 μg/ml) and ICAM1 (10 μg/ml) in the absence or presence of 10 nM fMIVIL. FIG. 32B, The effect of a function-blocking anti-β2 antibody on transendothelial migration of both $G\alpha13^{fl/fl}$ and $G\alpha13^{fl/fl\ LysM\ cre}$ neutrophils (n=3) in the presence of 10 nM fMIVIL. Two-way ANOVA with Tukey's multiple comparisons test was used for panel A and panel B ****P<0.0001; ns, no significance.

FIG. 33A, Comparison of velocity between the $G\alpha_{13}^{fl/fl}$ ($G\alpha13^{+/+}$,78 cells) $G\alpha_{13}^{fl/flLysM\ cre}$ ($G\alpha_{13}^{-/-}$,47 cells) neutrophil migration on glass slide-coated with ICAM1 (10 μg/ml). FIG. 33B, Comparison of total travel distance between $G\alpha_{13}^{+/+}$ (78 cells) and $G\alpha_{13}^{-/-}$ (47 cells) neutrophil migration. FIG. 33C, Comparison of Euclidean distance (straight line between the initial and final point) between $G\alpha_{13}^{+/+}$ (78 cells) and $G\alpha_{13}^{-/-}$ (47 cells) neutrophil migration. FIG. 33D, The rose diagram representation of the orientation of $G\alpha_{13}^{+/+}$ (cells) and $G\alpha_{13}^{-/-}$ (cells) neutrophil migration trajectories. Dark colored areas indicate frequency of trajectory orientations towards 12 different sections of in 30 minutes. The % of cell in each section are indicated with black font. FIG. 33E, Quantification of positions of cells at 30 minute time point relative to 0 minute time point in three categories: toward, away from or neutral to the fMIVIL loading site. (black text indicates percent of cell in each region) Student's t test was used for FIGS. 33A and 33B, Mann-Whitney test was used for FIG. 33C and Chi square test was used for panel FIG. 33E. ns, no significance, *P<0.05, *P<0.001, **P<0.0001.

FIG. 34A, Representative immunoblots of co-immunoprecipitation of $\beta_2$ integrin and Gα13 with anti-$\beta_2$ antibody in human neutrophils. PMNs were pretreated with MB2mP6 or control peptide micelles (50 mM) for 10 min and then stimulated with fMLP (1 μM)

in the ICAM1 (10 μg/mL) precoated 6-well plates. At indicated time points, the PMN samples were collected. The immunoprecipitates and total cell lysates were then immunoblotted with both anti-$b_2$-integrin and anti-$G\alpha_{13}$ antibodies. FIG. 34B, Quantification of coimmunoprecipitation blots in panel A (n=4) were analyzed by ImageJ software. OD, optical density.

FIGS. 35A-35D: The P2 EXE motif peptide MB2mP6 inhibits transendothelial neutrophil migration. FIG. 35A, Comparison of mouse neutrophil adhesion to ICAM1 after MB2mP6 (50 μM) or control (Ctrl) peptide (50 μM) treatment (n=3). FIG. 35B, Dose-dependent inhibitory effects of MB2mP6 in neutrophil transendothelial migration. FIG. 35C, The effect of MB2mP6 (50 μM) on transendothelial migration of $G\alpha_{13}^{+/+}$ and $G\alpha_{13}^{-/-}$ neutrophils. FIG. 35D, The effects of MB2mP6 (50 μM) pretreatment on neutrophil migration through transwell filters coated with endothelial cells, ICAM1 or fibrinogen (60 μg/ml). One-way ANOVA was used for FIGS. 35B, 35C, and 35D. *P<0.05, P<0.01, *P<0.001, ns, no significance.

FIGS. 36A-36F: The role of $G\alpha_{13}$ in neutrophil adhesion and spreading. FIG. 36A, Comparison of control and $G\alpha_{13}$-knockout neutrophil adhesion on ICAM1(t-test, ns, no significance, randomly selected 20 frames). FIG. 36B, DIC image of mouse neutrophils adherent on ICAM1. (t=0 min, $G\alpha13^{+/+}$ 3 cells, $G\alpha13^{-/-}$ 2 cells, t=5 min, $G\alpha13^{+/+}$ 23 cells, $G\alpha13^{-/-}$ 26 cells) Scale bars, 5 μm. FIG. 36C, Size quantification of live DIC images of neutrophils plated on ICAM-coated surfaces at indicated time points as in (FIG. 36B). Sizes of non-adherent neutrophils (t=0) were estimated by measuring cells on a BSA surface (n=5) One Way ANOVA *P<0.001, ns, no significance. FIG. 36D, Percent of cells with membrane ruffles in FIGS. 36B and 36E, Size quantification of fixed control ($G\alpha_{13}^{+/+}$) and $G\alpha_{13}$-knockout ($G\alpha_{13}^{-/-}$) neutrophils adherent on ICAM1 for 15 min. at 37° C. (n=36, p<0.0005, Mann-Whitney U test). FIG. 36**F, Size quantification of fixed AAA or MB2mP6 peptide-treated human neutrophils adherent on ICAM1 for 15 min. at 37° C. (n=58, p<0.0001, Mann Whitney U Test).

FIG. 37A, Comparison of thioglycolate-induced peritoneal neutrophil infiltration between $G\alpha_{13}^{+/+}$ and $G\alpha_{13}^{-/-}$ (n=4). FIG. 37B, Mouse lung neutrophil migration stimulated by intratracheal installation of LPS in $G\alpha13^{-/-}$ mice compared to control $G\alpha_{13}^{+/+}$ mice (n=5). One-way ANOVA was used for all figures. *P<0.05, ***P<0.001.

FIGS. 38A-38C: MB2mP6 inhibits CLP-induced microvascular thrombosis and vascular leakage in septic mouse lungs. FIG. 38A. C57BL mice were infused with MB2mP6 or scrambled peptides immediately after CLP onset. After 24 h, lungs were removed and sections cut and stained with phosphotungstic acid hematoxylin (PTAH) for fibrin (blue stain). Bars: the mean (±SD) of % stained area per mm2 (P<0.01; t test with Welch correction). FIGS. 38B and 38C. C57BL mice were infused with MB2mP6 or saline immediately after (FIG. 38B) or 6 h after CLP (FIG. 38**C). After 23 h, mice were i.v. injected with Evans blue albumin (EBA; 1%, 25 mg/kg body weight). After 1 h, mouse lungs were harvested and Evans blue was extracted with formamide at 60° C. for 18 h and quantitated by absorbance at 620 nm. Bars: the mean (±SD), (*P<0.05, **P<0.01; One-way ANOVA).

DETAILED DESCRIPTION

Figures 1A, 1B:
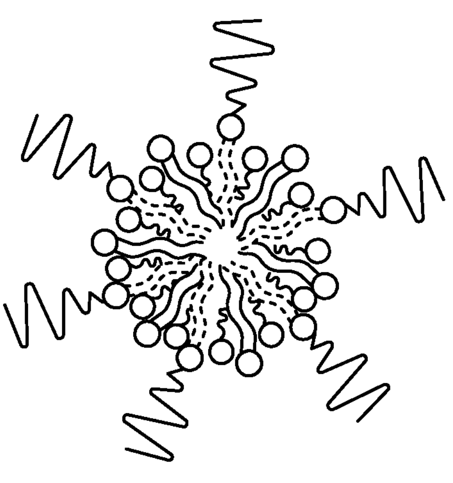

Three significant advances are disclosed herein: (1) the development of novel lipid-stabilized, high-loading peptide nanoparticles (HLPN) for efficient delivery of a new ExE motif peptide (M3mP6) in vivo into the intracellular compartment for therapeutic use; (2) data showing that M3mP6 HLPN potently inhibits occlusive thrombosis without observable adverse effect on hemorrhage; and (3) post-ischemia injection of M3mP6 HLPN also inhibits microvascular thrombosis/inflammation and improves cardiac function and survival in a mouse model of MIR injury. Importantly, this new drug showed not only anti-thrombotic synergism with the current standard of care anti-platelet drugs (P2Y12 inhibitors) while minimizes bleeding risk, but also demonstrated significant therapeutic effect in treating MI/R injury when injected post-ischemically. Thus, the drug M3mP6 HLPN has the potential to greatly advance current anti-platelet therapy in treating heart attack and improve drug safety.

Despite having advantages of high specificity due to unique amino acid sequences and low risk of toxic nonspecific effects, development of peptide-based drugs targeting intracellular compartments has lagged (1, 2). Among the major reasons is the lack of technology to efficiently deliver sufficient amounts of peptides into cells in vivo. Thus, a breakthrough in efficient delivery of peptide into cells should greatly facilitate development and therapeutic use of peptide-based therapeutic agents. Numerous tools have been developed for delivering peptides into cells. Among them, lipidization will render the peptide membrane permeable. However, the myristoylated peptide M3mP6, although membrane permeable and inhibits platelet function in vitro, is ineffective in vivo. Thus membrane permeability is not sufficient to deliver the peptides into platelets in vivo. Liposomes and lipid micelles have been relatively more efficient and often used for drug delivery in vivo (2). However, these approaches usually require large amounts of lipid to encapsulate a limited amount of peptides, thus necessitating unusually high peptide affinity or avidity for its targets. For example, a lipid micellar formulation of the synthetic peptide mP6 contains a maximal 4% (mol/mol) peptide with the maximal concentration of mP6 peptide at <1 mM, which is insufficient for clinical use (21). The lipid-stabilized M3mP6 HLPN in the present study contains up to 70% (mol/mol) peptide and achieves a high peptide concentration of >10 mM suitable for bolus IV injection in humans. Importantly, the lipid-stabilized HLPN also greatly facilitates peptide drug entry into cells, resulting in much less peptide being required for comparable anti-platelet efficacy attained with the peptide alone. These superior characteristics rendered M3mP6 HLPN a potent anti-thrombotic in vivo. Thus, these data demonstrate that the lipid-stabilized HLPN greatly improves efficiency of intracellular delivery of a peptide-based drug in vivo and enables effective in vivo use of the peptide drugs having relatively moderate affinity for their intracellular targets. Thus, this new technology may be of general significance in facilitating development of peptide-based drugs targeting the intracellular compartment for therapeutic use.

Platelets circulating in blood vessels are normally in a resting state and become activated only when exposed to platelet agonists. Platelet agonists elicit platelet activation via various receptor-mediated intracellular signaling pathways (28, 29). These intracellular signals converge as an "inside-out" signal to transform $\alpha IIb\beta 3$ from a 'resting' state to an 'activated' state (8, 30). This enables integrin ligand binding function, a requirement for platelet adhesion and aggregation (12). Current anti-platelet drugs either inhibit platelet activation signaling pathways leading to integrin activation or directly inhibit the ligand binding function of the integrin αIIbβ3 (10, 12). Although these drugs have become cornerstones in the treatment of patients with cardiovascular diseases (6, 12), they also inhibit hemostasis causing excessive bleeding, which can be life-threatening (11-14). Bleeding effects of these drugs limits the optimal use of efficacious doses and therefore their anti-thrombotic efficacy. Thus, bleeding in thrombotic patients receiving peripheral coronary intervention is associated with poor prognosis and increased mortality (11, 15-17). Hence the balance of optimal platelet inhibition with minimal bleeding complications is a significant current clinical challenge, particularly for patients requiring traumatic procedures or suffering from thrombotic stroke, in which hemorrhage is life-threatening. Recently, various thrombin receptor inhibitors have been shown to have reduced adverse effects on hemorrhage in animal models (19, 20). However, the reduction in adverse effect on hemorrhage is partial and relative to clopidogrel (19, 20). Animals administered with these drugs still have significantly increased bleeding compared to normal controls (19, 20). In contrast, no difference was observed in bleeding between normal controls and animals administered M3mP6 HLPN. Importantly, clinical trials of the PAR1 inhibitor vorapaxar demonstrated significantly increased bleeding in human patients (19), suggesting that the reduced hemorrhagic adverse effect of thrombin receptor inhibitors still pose a clinically relevant risk. The hemorrhagic effects of these drugs are consistent with these drugs inhibiting the activation of the ligand binding function of integrin αIIbβ3 and are thus not fundamentally different from the current anti-platelet drugs (29). The new peptides disclosed herein are conceptually based on a totally different concept that integrin outside-in signaling is selectively targeted without affecting the binding of integrin ligands to platelets. Based on this concept, the disclosed peptides permit primary platelet adhesion and aggregation to occur but prevents pathological thrombus expansion (21, 22). With the HLPN delivery system for this peptide-based new drug as described above, it was demonstrated that HLPN comprising the peptides potently inhibited occlusive thrombosis without any observable effect on hemostasis in mice and dogs, and in mice, this was shown using both tail bleeding time and carotid artery perforation bleeding analysis. Thus, by engineering a lipid-stabilized HLPN delivery system, disclosed herein is a potentially clinically usable drug likely to be superior to current anti-platelet drugs in clinical use or in development.

This disclosure provides a lipid-stabilized, high-loading peptide nanoparticle comprising i) greater than about 10 mole percent, based on total nanoparticle mass, of a lipidated peptide, amphiphilic peptide, or peptide-hydrophobic molecule conjugate; ii) about 2 to about 20 mole percent of one or more lipids free of a water soluble polymer; and iii) about 10 to about 60 mole percent of one or more lipids covalently attached to a water soluble polymer. For example, the lipidated peptide consists of about 2 to about 50 amino acid residues, or about 2 to 45 amino acids, or about 2 to about 40 amino acids, or about 2 to about 35 amino acids, or about 2 to about 30 amino acids, or about 2 to about 25 amino acids, or about 2 to about 20 amino acids, or about 2 to about 15 amino acids, or about 2 to about 10 amino acids, or about 2 to about 5 amino acids, or about 3 to about 40 amino acids, or about 3 to about 25 amino acids, or about 4 to about 35 amino acids, or about 4 to about 25 amino acids, or about 5 to about 50 amino acids, or about 5 to about 25 amino acids, or about 6 to about 50 amino acids, or about 6 to about 25 amino acids, or about 10 amino acids to about 25 amino acids.

In certain embodiments, the lipid-stabilized, high-loading peptide nanoparticle comprises about 10 to about 80 mol %, or about 10 to about 75 mol %, or about 10 to about 70 mol %, or about 10 to about 65 mol %, or about 10 to about 60 mol %, or about 10 to about 55 mol %, or about 10 to about 50 mol %, or about 10 to about 45 mol %, or about 10 to about 40 mol %, or about 40 to about 55 mol %, or about 40 to about 75 mol %, or about 50 to about 80 mol %, or about 60 to about 80 mol %, or about 70 to about 80 mol % based on total nanoparticle mass, of lipidated peptide.

In certain embodiments, the lipid-stabilized, high-loading peptide nanoparticle comprises about 2 to about 20 mole percent, or about 2 to about 15 mole percent, or about 2 to about 10 mole percent, or about 2 to about 5 mole percent, about 5 to about 20 mole percent, about 5 to about 10 mole percent, of one or more lipids free of a water soluble polymer.

In certain embodiments, the lipid-stabilized, high-loading peptide nanoparticle comprises about 10 to about 60 mole percent, or about 10 to about 55, or about 10 to about 50, or about 10 to about 45, or about 10 to about 40, or about 10 to about 35, or about 10 to about 30, or about 10 to about 25, or about 10 to about 20, or about 10 to about 15, of one or more lipids covalently attached to a water soluble polymer.

The foregoing discussion of the disclosure has been presented for purposes of illustration and description. The foregoing is not intended to limit the disclosure to the form or forms disclosed herein. Although the description of the disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Nanoparticles

Suitable lipids for use in preparing micelles and liposomes incapsulating compounds and peptides for drug delivery are known in the art. See, e.g., Banerjee and Onyuksel, Peptide Delivery Using Phospholipid Micelles, WIREs Nanomed Nanobiotechnol 4:562-574 (2012). Representative lipids include phosphatidylcholine (PC), phosphatidylglycerol (PG), phosphatidylethanolamine (PE), phosphatidyl-serine (PS), phosphatidyl-inositol (PI), and the like. Representative lipids attached to a water soluble polymer include a fatty acid or mixture of fatty acids conjugated to PEG (poly(ethylene glycol)-PE, PEG-PC, PEG-PG, PEG-PI, PEG-PS, PEG-DSPE, and the like. In a particular embodiment, the lipid covalently attached to a water soluble polymer is 1,2-distearoyl-sn-glycero-3-phosphoethanolamine-N-[amino(polyethylene glycol)-2000] and the lipid free of a water soluble polymer is phosphatidylcholine. In an exemplary embodiment, the lipid-stabilized, high-loading peptide nanoparticle comprises 2-10% phosphatidylcholine and 10-60% PEG-DSPE. In various aspects, the PEG-DSPE may comprise a PEG with a molecular weight of 200-100,000 or other PEGs known in the art.

In certain embodiments, modification of the peptide allows the peptide to form the main body of compositions of micellar nanoparticles, greatly increasing the concentration of peptides incorporated into micellar nanoparticles and therefore efficiency of delivery in vivo. In exemplary aspects, the peptide of the nanoparticle is covalently attached to a fatty acid or other lipid moiety. The lipidated peptide, amphiphilic peptide, or peptide-hydrophobic molecule conjugates are capable of forming micellar nanoparticles, which can be stabilized by the presence of certain lipids. In certain embodiments, a HLPN-stabilizing lipid can be covalently attached to a water soluble polymer and a lipid free of a water soluble polymer. This lipid-stabilized high loading peptide nanoparticle (HLPN) is different from the peptide-incapsulating lipid micelles in that the high concentrations of peptide forms main body of the micellar nanoparticles, increasing the efficiency of delivery. Suitable lipids for use in micelle synthesis is known in the art. See, e.g., Banerjee and Onyuksel, Peptide Delivery Using Phospholipid Micelles, WIREs Nanomed Nanobiotechnol 4:562-574 (2012). In exemplary aspects, the lipid that is covalently attached to a water soluble polymer is 1,2-distearoyl-sn-glycero-3-phosphoethanolamine-N-[amino(polyethylene glycol)-2000] and the lipid that is free of a water soluble polymer is phophatidylcholine.

In other embodiments, the lipid free of a water soluble polymer is selected from phosphatidylcholine, phosphatidylglycerol and phosphatidylethanolamine. In particular embodiments, the lipid covalently attached to a water-soluble polymer is PEG-DSPE and the lipid free of a water soluble polymer is phosphatidylcholine.

In exemplary aspects, modification of lipidized FEEERA (SEQ ID NO: 6) to lipidized FEEERL (SEQ ID NO: 8), FEEERI (SEQ ID NO: 2), FEKEKL (SEQ ID NO: 10), FKEKEI (SEQ ID NO: 44) or FEEERM (SEQ ID NO: 7) facilitates the formation of stable micellar nanoparticles containing greater than about 4-10 mM in peptide concentrations as compared to the original 1 mM in FEEERA (SEQ ID NO: 6) peptide concentration in micellar formulation. In certain embodiments, the peptide concentration is about 4, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0. 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1. 9.2, 9.3, 9.4. 9.6, 9.6, 9.7, 9.8, 9.9, or about 10 mM.

Representative peptides consisting of about 2 to about 50 amino acid residues suitable for formulating as lipid-stabilized, high-loading peptide nanoparticles include FEEERI (SEQ ID NO: 2), FEKEKI (SEQ ID NO: 3), FEKERI (SEQ ID NO: 4), RGT, EEERA (SEQ ID NO: 5), FEEERA (SEQ ID NO: 6), FEEERM (SEQ ID NO: 7), FEEERL(SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17), and the like. Other peptides can also be formulated as HLPN for delivery into cells, such as RCLLPA(SEQ ID NO: 45) (Rusu et al, Blood 123(3):442-50, 2014), and LLARRPTKGIHEY (SEQ ID NO: 18) (Huang J-S et al, JBC 282, 10210-10222, 2007).

In certain embodiments, the lipidated peptide comprises a peptide consisting of about 2 to about 50 amino acid residues conjugated to a fatty acid. In other embodiments, the fatty acid is covalently attached to the peptide. In other embodiments, the peptide is myristolyated.

In other embodiments, The lipid-stabilized peptide is selected from myr-FEEERI (SEQ ID NO: 19), myr-FEKEKI (SEQ ID NO: 20), myr-FEKERI (SEQ ID NO: 21), myr-RGT, myr-EEERA (SEQ ID NO: 22), myr-FEEERA (SEQ ID NO: 23), myr-FEEERM (SEQ ID NO: 24), myr-FEEERL (SEQ ID NO: 25), myr-FEKEKM (SEQ ID NO: 26), myr-FEKEKL (SEQ ID NO: 27), myr-FEKERM (SEQ ID NO: 28), myr-FEKERL (SEQ ID NO: 29), myr-CFEEERAC (SEQ ID NO: 30), myr-FEEERAR (SEQ ID NO: 31), myr-FEEERARA (SEQ ID NO: 32), myr-SIRYSGHpSL (SEQ ID NO: 33), myr-KFEEERARAKWDT (SEQ ID NO: 34) and myr-LLARRPTKGIHEY (SEQ ID NO: 35). In other embodiments, the lipid stabilized peptide is myr-FEEERL (SEQ ID NO: 25) or myr-FEKEKL (SEQ ID NO: 27).

In certain embodiments, the nanoparticle comprises about 10 to about 80 mol %, based on total nanoparticle mass, of a peptide consisting of the amino acid sequence FEEERM (SEQ ID NO: 7), FEEERL (SEQ ID NO: 8), FEEERI (SEQ ID NO: 2), FEKEKM (SEQ ID NO: 9), FEKEKL (SEQ ID NO: 10), FEKEKI (SEQ ID NO: 3), FEKERM (SEQ ID NO: 11), FEKERL (SEQ ID NO: 12), FEKERI (SEQ ID NO: 4) or CFEEERAC (SEQ ID NO: 13).

In certain embodiments, the nanoparticle comprises about 10 to about 80 mol %, based on total nanoparticle mass, of a peptide is myr-FEEERL (SEQ ID NO: 25) or myr-FEKEKL (SEQ ID NO: 27).

In certain embodiments, the nanoparticle comprises a peptide disclosed in International Patent Application Publication No. WO/2011/116026, U.S. Pat. Nos. 8,685,921, 9,156,884, 10,011,634, and/or 10,738,080, which are all incorporated by reference in their entirety.

Also disclosed herein is a method of preparing a lipid-stabilized, high-loading peptide nanoparticle comprising stabilizing a peptide nanoparticle comprising one or more lipidized peptides consisting of about 2 to about 50 amino acid residues with 2-20% of a lipid free of a water soluble polymer and 10-60% of a lipid covalently attached to a water soluble polymer based on total nanoparticle mass.

Also disclosed herein is a method of treating a thrombotic condition or an inflammatory condition in a subject in need thereof comprising administering to the subject an effective amount of a nanoparticle or peptide disclosed herein. For example, disclosed herein is a method of treating a thrombotic condition or an inflammatory condition in a subject in need thereof comprising administering to the subject an effective amount of a nanoparticle comprising greater than about 10 mole percent, based on total nanoparticle mass, of a lipidated peptide; about 2 to about 20 mole percent of one or more lipids free of a water soluble polymer; and about 10 to about 60 mole percent of one or more lipids covalently attached to a water soluble polymer, wherein the lipidated peptide is myr-FEEERM (SEQ ID NO: 24), myr-FEEERL (SEQ ID NO: 25), myr-FEEERI (SEQ ID NO: 19), myr-FEKEKM (SEQ ID NO: 26), myr-FEKEKL (SEQ ID NO: 27), myr-FEKEKI (SEQ ID NO: 20), myr-FEKERM (SEQ ID NO: 28), myr-FEKERL (SEQ ID NO: 29), myr-FEKERI (SEQ ID NO: 21) or myr-CFEEERAC (SEQ ID NO: 30).

In certain embodiments, the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury.

In various exemplary embodiments, the disclosure provides for methods of treating acute respiratory distress syndrome (ARDS) comprising administering to a subject an effective amount of a nanoparticle or peptide disclosed herein. ARDS can be caused by severe viral infections (such as Coronavirus Disease 2019 (COVID-19)) and bacterial infection (such as in sepsis), or sterile inflammation (such as severe trauma and oxygen deprivation). ARDS are often caused by over-exaggerated inflammation and blood clots blocking small blood vessels in response to severe infection, trauma etc, resulting in leakage of the blood vessels in the lung, causing large amount of fluid flow into the lung aveoli (small air-filled sac lined by blood vessels serving to exchange oxygen/$CO_2$ with blood). The fluid in the aveoli blocks the air exchange, causing oxygen deprivation.

Also disclosed herein is a method of treating a disease or condition regulated by platelet granule secretion, Gα13 function or leukocyte integrin outside-in signaling in a subject comprising administering to the subject an effective amount of a peptide comprising the amino acid sequence $FEX_1ERX_2$ (SEQ ID NO: 1)wherein $X_1$ and $X_2$ are selected from natural and unnatural amino acids, wherein the peptide is a 6-mer, 7-mer, 8-mer or 9-mer and wherein the peptide inhibits both the integrin-dependent and integrin-independent platelet granule secretion or wherein the peptide inhibits its leukocyte integrin outside-in signaling.

In certain embodiments, $X_1$ is glutamic acid (E) and $X_2$ is alanine (A). In other embodiments, the peptide further comprises a membrane permeable moiety. In other embodiments, the membrane permeable moiety is a membrane permeable peptide, a membrane permeable synthetic compound and a fatty acid. In other embodiments, the membrane permeable moiety is a fatty acid. In other embodiments, the fatty acid is covalently attached to the peptide.

In a particular embodiment, the peptide is myr-FEEERA (SEQ ID NO: 23), myr-FEEERM(SEQ ID NO: 24), myr-FEEERL(SEQ ID NO: 25), myr-FEKEKM(SEQ ID NO: 26), myr-FEKEKL(SEQ ID NO: 27), myr-FEKERM(SEQ ID NO: 28), myr-FEKERL(SEQ ID NO: 29), or myr-CFEEERAC(SEQ ID NO: 30). In another particular embodiment, the peptide is incorporated into a nanoparticle, wherein the nanoparticle comprises about 36 to about 80 mol % of the peptide.

In certain embodiments, the disease or condition is regulated by platelet granule secretion. In particular embodiments, the disease or condition regulated by platelet granule secretion is selected from inflammatory conditions. More particularly, the inflammatory conditions are selected from atherosclerosis, autoimmune diseases and inflammation.

In other embodiments, the disease or condition is regulated by leukocyte integrin outside-in signaling. In particular embodiments, the disease or condition regulated by leukocyte integrin outside-in signaling is selected from sepsis, atherosclerosis, vasculitis, deep vein thrombosis, and ischemia-reperfusion injury.

In various embodiments, the peptide disclosed herein anti-inflammatory and inhibits leukocyte migration. In related embodiments, inhibition of migration is achieved without totally abolishing the important cell adhesion function of leukocytes mediated by integrin family of adhesion receptors and without abolishing the function of neutrophils to sense the site of infection or inflammation.

The method of treating a disease or condition regulated by platelet granule secretion, Gα13 function or leukocyte integrin outside-in signaling disclosed herein may further comprise administration of an effective amount of a P2Y12 inhibitor. In certain embodiments, P2Y12 inhibitor is selected from clopidogrel, ticagrelor, presugrel, cangrelor. In other certain embodiments, the method may further comprise administering an effective amount of aspirin.

Also disclosed herein is a method of inhibiting integrin outside-in signaling without inhibiting integrin-independent platelet granule secretion in a subject comprising administering to the subject an effective amount of a peptide consisting of the amino acid sequence of EEERA (SEQ ID NO: 5), EEERM (SEQ ID NO: 36), EEERL (SEQ ID NO: 37). EKEKM (SEQ ID NO: 38), EKEKL (SEQ ID NO: 39), EKERM (SEQ ID NO: 40), EKERL (SEQ ID NO: 41) or CEEERAC (SEQ ID NO: 42). This peptide may be useful under conditions where platelet granule secretion is desired (e.g. for facilitating wound healing) during treatment for thrombosis.

In an embodiment, the peptide that inhibits both integrin-dependent and integrin independent granule secretion and leukocyte function is FEEERA (SEQ ID NO: 6).

Also disclosed herein is a peptide consisting of the amino acid sequence FEEERI (SEQ ID NO: 2), FEKEKI (SEQ ID NO: 3), or FEKERI (SEQ ID NO: 4).

In certain embodiments, the peptide further comprises a membrane permeable moiety. In other embodiments, the membrane permeable moiety is selected from a membrane permeable peptide, a membrane permeable synthetic compound and a fatty acid. In other embodiments, the membrane permeable moiety is a fatty acid. In other embodiments, the fatty acid is covalently attached to the peptide. In a particular embodiment, the peptide is myristoylated. In another particular embodiment, the peptide is selected from myr-FEEERI (SEQ ID NO: 19), myr-FEKEKI (SEQ ID NO: 20), and myr-FEKERI (SEQ ID NO: 21).

The present disclosure also provides a method of treating a thrombotic condition or an inflammatory condition in a subject in need thereof comprising administering to the subject an effective amount of a peptide consisting of the amino acid sequence FEEERI (SEQ ID NO: 2), FEKEKI (SEQ ID NO: 3), or FEKERI (SEQ ID NO: 4).

The disclosed peptides may be obtained by methods known in the art. Suitable methods of de novo synthesizing peptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Additional exemplary methods of making the peptides of the disclosure are set forth herein.

In some embodiments, the peptides described herein are commercially synthesized by companies, such as Synpep (Dublin, Calif.), Peptide Technologies Corp. (Gaithersburg, Md.), Multiple Peptide Systems (San Diego, Calif.), Peptide 2.0 Inc. (Chantilly, Va.), and American Peptide Co. (Sunnyvale, Calif.). In this respect, the peptides can be synthetic, recombinant, isolated, and/or purified.

Also, in some aspects, the peptides are recombinantly produced using a nucleic acid encoding the amino acid sequence of the peptide using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994.

The peptides of the disclosure can be isolated and/or purified. The term "isolated" as used herein means having been removed from its natural environment. The term "purified" as used herein means having been increased in purity, wherein "purity" is a relative term, and not to be necessarily construed as absolute purity. In exemplary aspects, the purity of the compound (e.g., in the composition) is at least or about 50%, at least or about 60%, at least or about 70%, at least or about 80%, at least or about 90%, at least or about 95%, or at least or about 98% or is about 100%.

Additional Peptide Modifications

In certain embodiments, the peptides of the disclosure comprise one or more modifications including without limitation phosphorylation, glycosylation, hydroxylation, esterification, cyclization, sulfonation, amidation, acetylation, carboxylation, lipidation (e.g., myritoylated, palmitoylated), introduction of non-hydrolyzable bonds, disulfide formation and conjugation or linking to a targeting or carrier peptide, or converted into an acid addition salt and/or optionally dimerized or polymerized, or conjugated, as further described herein. The modification may improve the stability and/or activity of the peptides.

For example, the C-terminal may be modified with amidation, addition of peptide alcohols and aldehydes, addition of esters, addition of p-nitorailine and thioesters and multipelantigens peptides. The N-terminal and side chains may be modified by PEGylation, acetylation, formylation, addition of a fatty acid, addition of benzoyl, addition of bromoacetyl, addition of pyroglutamyl, succinylation, addition of tetrabutyoxycarbonyl and addition of 3-mercaptopropyl, acylations (e.g. lipopeptides), biotinylation, phosphorylation, sulfation, glycosylation, introduction of maleimido group, chelating moieties, chromophores and fluorophores.

Conjugates

In some embodiments, the compounds of the disclosure are attached or linked or conjugated to a second moiety (e.g., a heterologous moiety, a conjugate moiety). As used herein, the term “heterologous moiety” is synonomous with “conjugate moiety” and refers to any molecule (chemical or biochemical, naturally-occurring or non-coded) which is different from the disclosed compounds. Exemplary heterologous moieties include, but are not limited to, a polymer, a carbohydrate, a lipid, a nucleic acid, an oligonucleotide, a DNA or RNA, an amino acid, peptide, polypeptide, protein, therapeutic agent, (e.g., a cytotoxic agent, cytokine), or a diagnostic agent. Representative peptides of the disclosure include peptides conjugated to a lipid, peptides conjugated to a second peptide such as a peptide comprising a transmembrane domain such as IL2 receptor alpha transmembrane domain, referred to herein as “amphiphilic peptides”, and peptides conjugated to a hydrophobic moiety such as DSPE.

In some embodiments, the peptides incorporated into HLPN are chemically modified with various substituents. In some embodiments, the chemical modifications impart additional desirable characteristics as discussed herein. Chemical modifications in some aspects take a number of different forms such as heterologous peptides, polysaccarides, lipids, radioisotopes, non-standard amino acid resides and nucleic acids, metal chelates, and various cytotoxic agents. In some embodiments, compounds can be used to mimic the structure the amino acid residues in the peptides described herein.

In some embodiments, the compounds are fused to heterologous peptides to confer various properties, e.g., increased solubility and/or stability and/or half-life, resistance to proteolytic cleavage, modulation of clearance, targeting to particular cell or tissue types. In some embodiments, the compound is linked to a Fc domain of IgG or other immunoglobulin. In some embodiments, the compound is fused to alkaline phosphatase (AP). Methods for making Fc or AP fusion constructs are found in WO 02/060950. By fusing the compound with protein domains that have specific properties (e.g. half-life, bioavailability) it is possible to confer these properties to the compound of the disclosure.

When the compounds are peptides, they can be modified, for instance, by glycosylation, amidation, carboxylation, or phosphorylation, or by the creation of acid addition salts, amides, esters, in particular C-terminal esters, and N-acyl derivatives, as discussed above. The peptides also can be modified to create peptide derivatives by forming covalent or noncovalent complexes with other moieties. Covalently bound complexes can be prepared by linking the chemical moieties to functional groups on the side chains of amino acids comprising the peptides, or at the N- or C-terminus.

Peptides can be conjugated to a reporter group, including, but not limited to a radiolabel, a fluorescent label, an enzyme (e.g., that catalyzes a calorimetric or fluorometric reaction), a substrate, a solid matrix, or a carrier (e.g., biotin or avidin). Examples of analogs are described in WO 98/28621 and in Olofsson, et al, Proc. Nat'l. Acad. Sci. USA, 95:11709-11714 (1998), U.S. Pat. Nos. 5,512,545, and 5,474,982; U.S. Patent Application Nos. 20020164687 and 20020164710.

Cysteinyl residues most commonly are reacted with haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-.beta.(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R1) such as 1-cyclohexyl-3-(2-morpholinyl-(4-ethyl) carbodiimide or 1-ethyl-3 (4 azonia 4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecule Properties, W. H. Freeman & Co., San Francisco, pp. 79-86,1983), acetylation of the N-terminal amine, and, in some instances, amidation of the C-terminal carboxyl groups. Such derivatives are chemically modified polypeptide compositions in which the binding construct polypeptide is linked to a polymer.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the binding construct becomes attached to one or more polymer molecules, and (b) obtaining the reaction product(s). The optimal reaction conditions will be determined based on known parameters and the desired result. For example, the larger the ratio of polymer molecules: protein, the greater the amount of attached polymer molecule. In some embodiments, the compound may have a single polymer molecule moiety at the amino terminus. (See, e.g., U.S. Pat. No. 5,234,784).

Derivatized binding constructs disclosed herein may have additional activities, enhanced or reduced biological activity, or other characteristics, such as increased or decreased half-life, as compared to the non-derivatized molecules.

In some embodiments, the compound is directly joined to a conjugate moiety in the absence of a linker. In alternative aspects, the compound is indirectly connected to the conjugate moiety via one or more linkers. Whether directly joined together or indirectly joined together through a linker, the compound may be connected through covalent bonds (e.g., a peptide, ester, amide, or sulfhydryl bond) or non-covalent bonds (e.g., via hydrophobic interaction, hydrogen bond, van der Waals bond, electrostatic or ionic interaction), or a combination thereof. The compound of the disclosure and conjugate moiety may be connected via any means known in the art, including, but not limited to, via any disclosed linker. See, for example, the section herein entitled "Linkers."

Heterologous Moieties: Polymers, Carbohydrates, and Lipids

In some embodiments, the heterologous moiety is a polymer. The polymer may be branched or unbranched. The polymer may be of any molecular weight. The polymer in some embodiments has an average molecular weight of between about 2 kDa to about 100 kDa (the term "about" indicating that in preparations of a water soluble polymer, some molecules will weigh more, some less, than the stated molecular weight). The average molecular weight of the polymer is in some aspect between about 5 kDa and about 50 kDa, between about 12 kDa to about 40 kDa or between about 20 kDa to about 35 kDa.

In some embodiments, the polymer is modified to have a single reactive group, such as an active ester for acylation or an aldehyde for alkylation, so that the degree of polymerization may be controlled. The polymer in some embodiments is water soluble so that the protein to which it is attached does not precipitate in an aqueous environment, such as a physiological environment. In some embodiments, when, for example, the composition is used for therapeutic use, the polymer is pharmaceutically acceptable. Additionally, in some aspects, the polymer is a mixture of polymers, e.g., a co-polymer, a block co-polymer.

In some embodiments, the polymer is selected from the group consisting of: polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly (octadecyl acrylate).

In some embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In some aspects, the water soluble polymers or mixtures thereof include, but are not limited to, N-linked or O-linked carbohydrates, sugars, phosphates, phosphatidylcholine (PC), phosphatidylglycero (PG), phosphatidyl-inositol (PI), phosphatidyl-serine (PS) and phosphatidylethanolamine (PE), carbohydrates; sugars; phosphates; polyethylene glycol (PEG) (including the forms of PEG that have been used to derivatize proteins, including mono-(C1-C 10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol or mixtures thereof. Also encompassed by the present disclosure are bifunctional crosslinking molecules which may be used to prepare covalently attached multimers.

An exemplary water-soluble polymer for use herein is polyethylene glycol (PEG). As used herein, polyethylene glycol is meant to encompass any of the forms of PEG that can be used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophibic nature, thus creating a water shell or hydration sphere when attached to other proteins or polymer surfaces. PEG is nontoxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., Preparation and Properties of Monomethoxypoly(ethylene glycol)-modified Enzymes for Therapeutic Applications, in J. M. Harris ed., Poly(Ethylene Glycol) Chemistry—Biotechnical and Biomedical Applications, 127-36, 1992, incorporated herein by reference. These phenomena are due to the exclusion properties of PEG in preventing recognition by the immune system. In addition, PEG has been widely used in surface modification procedures to decrease protein adsorption and improve blood compatibility. S. W. Kim et al., Ann. N.Y. Acad. Sci. 516: 116-30 1987; Jacobs et al., Artif. Organs 12: 500-501, 1988; Park et al., J. Poly. Sci, Part A 29:1725-31, 1991, incorporated herein by reference. Hydrophobic polymer surfaces, such as polyurethanes and polystyrene can be modified by the grafting of PEG (MW 3,400) and employed as non-thrombogenic surfaces. Surface properties (contact angle) can be more consistent with hydrophilic surfaces, due to the hydrating effect of PEG. More importantly, protein (albumin and other plasma proteins) adsorption can be greatly reduced, resulting from the high chain motility, hydration sphere, and protein exclusion properties of PEG.

PEG (MW 3,400) was determined as an optimal size in surface immobilization studies, Park et al., J. Biomed. Mat. Res. 26:739-45, 1992, while PEG (MW 5,000) was most beneficial in decreasing protein antigenicity. (F. M. Veronese et al., In J. M. Harris, et al., Poly(Ethylene Glycol) Chemistry—Biotechnical and Biomedical Applications, 127-36.)

Methods for preparing pegylated compounds may comprise the steps of (a) reacting the compound with polyethylene glycol (such as a reactive ester or aldehyde derivative of PEG) under conditions whereby the compound becomes attached to one or more PEG groups, and (b) obtaining the reaction product(s). In general, the optimal reaction conditions for the acylation reactions will be determined based on known parameters and the desired result. For example, the larger the ratio of PEG:compound, the greater the percentage of poly-pegylated product. In some embodiments, the compound will have a single PEG moiety at the N-terminus. See U.S. Pat. No. 8,234,784, herein incorporated by reference.

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid.

Lipidation

In exemplary aspects, the peptide is lipidated, or otherwise, attached to a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, a phospholipid. In some embodiments, the lipidation is performed as described in Kowalczyk et al., Peptides and Peptide-based Biomaterials and their Biomedical Applications. 2017; 1030: 185-227 (Incorporated by reference in its entirety).

In an embodiment, the peptide is conjugated to a fatty acid, e.g. the peptide is myristoylated. For example, a fatty acid may be conjugated to the N-terminus of the peptide, such fatty acids include caprylic acid (C8), capric acid (C10), lauric acid (C12), myristic acid (C14), palmitic acid (C16) and stearic acid (C18) etc. Furthermore cysteines in peptides can be palmitoylated. In an embodiment, the fatty acid is covalently attached to the peptide. In an embodiment, the peptide is myristylated, stearylated or palmitoylated at the N terminal amino acid. In an embodiment, the peptide is myristylated at the N-terminal amino acid.

In exemplary aspects, the peptide is covalently attached to a fatty acid. In some specific embodiments, the fatty acid is a C4 to C30 fatty acid. The fatty acid in exemplary aspects is any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In some embodiments, the fatty acid is a C8 to C20 fatty acid, a C12 to C29 fatty acid, or a C14 to C18 fatty acid, e.g., a C14 fatty acid or a C16 fatty acid.

In exemplary aspects, the peptide is covalently attached to a fatty acid and the fatty acid is attached to the N-terminal amino acid or the C-terminal amino acid. In alternative aspects, the peptide is covalently attached to a fatty acid and the fatty acid is attached to an internal amino acid of the peptide, e.g., via a functional group off of a side chain of the internal amino acid. For example, the fatty acid may be attached to an amine, hydroxyl, or thiol of a side chain of an internal amino acid. In exemplary aspects, the peptide is covalently attached to a fatty acid and the fatty acid is attached to the second third, fourth, fifth, sixth, seventh, eighth, ninth, tenth, eleventh, or twelfth amino acid.

In other embodiments, the peptide may be cyclized. For example, the peptide may comprise two Cys residues, the sulfur atoms of which participate in the formation of a disulfide bridge. In exemplary aspects, the peptide comprises a Cys residue as the terminal residues. In a particular embodiment, the peptide is CFEEERAC (SEQ ID NO: 13). Suitable methods of modifying peptides with disulfide bridges or sulfur-based cyclization are described in, for example, Jackson et al., J. Am. Chem. Soc. 113: 9391-9392 (1991) and Rudinger and Jost, Experientia 20: 570-571 (1964).

Other means of peptide cyclizing are reviewed in Davies, J. Peptide. Sci. 9: 471-501 (2003). Such means include the formation of an amide bridge, thioether bridge, thioester bridge, urea bridge, carbamate bridge, sulfonamide bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof.

The peptide, peptide compositions and nanoparticles of the disclosure are contemplated for therapeutic purposes. For example, certain peptides of the disclosure may be used to treat atherosclerosis, thrombosis, stroke or heart attack, acute respiratory distress syndrome (ARDS), autoimmune diseases, AV Fistula for hemodialysis, organ transplantation, and/or inflammation in a subject in need thereof. The method comprises the step of administering to the subject a peptide or peptide composition of the disclosure to the subject in an amount effective to treat atherosclerosis, thrombosis, stroke or heart attack, acute respiratory distress syndrome (ARDS), autoimmune diseases, AV Fistula for hemodialysis, organ transplantation, and/or inflammation.

In certain embodiments, the peptide, peptide compositions and nanoparticles of the disclosure are administered in combination with an effective amount of a P2Y12 inhibitor and/or aspirin to enhance anti-thrombotic effect while minimizing bleeding.

In certain embodiments, the P2Y12 inhibitor is selected from clopidogrel, ticagrelor, presugrel, cangrelor.

Because blood clotting and thrombosis play a role in stroke and heart attack, the disclosure furthermore provides a method of treating or preventing a stroke or a heart attack in a subject in need thereof. The method comprises the step of administering to the subject a peptide, peptide compositions and nanoparticles of the disclosure an amount effective to treat or prevent stroke or heart attack.

Certain peptides provided herein also may be used for affecting leukocyte function. The disclosure accordingly provides a method of inhibiting leukocyte adhesion, spreading, migration, or chemotaxis. The method comprises the step of contacting a leukocyte with a peptide, peptide compositions and nanoparticles of the disclosure in an amount effective to inhibit leukocyte adhesion, spreading, migration, or chemotaxis. Since these leukocyte functions are related to inflammation, the disclosure additionally provides a method of inhibiting or treating inflammation in a subject in need thereof. The method comprises the step of administering to the subject a peptide, peptide compositions and nanoparticles of the disclosure in an amount effective to inhibit or treat inflammation. In exemplary embodiments, the peptide, peptide compositions or nanoparticles of the disclosure is administered to the subject systemically, e.g., parenterally (e.g., via intravenous injection).

In other embodiments, administration of an effective dose of certain peptides, peptide compositions or nanoparticles of the disclosure provided here can be used to treat sepsis, a systemic inflammatory state caused by entry of miroorganisms or their toxins into circulation.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating atherosclerosis, thrombosis, stroke or heart attack, acute respiratory distress syndrome (ARDS), autoimmune diseases, AV Fistula for hemodialysis, organ transplantation, and/or inflammation of the disclosure can provide any amount or any level of treatment. Furthermore, the treatment provided by the method of the disclosure may include treatment of one or more conditions or symptoms or signs of the atherosclerosis, stroke, heart attack, acute respiratory distress syndrome (ARDS), autoimmune diseases, AV Fistula for hemodialysis, organ transplantation, or inflammation, being treated. Also, the treatment provided by the methods of the disclosure may encompass slowing the progression of the atherosclerosis, stroke, heart attack, acute respiratory distress syndrome (ARDS), autoimmune diseases, AV Fistula for hemodialysis, organ transplantation, or inflammation. "Treat", as used herein also encompasses "inhibit", "inhibition", "prevent" or "prevention".

As used herein, the term "prevent" and words stemming therefrom encompasses delaying the onset of the medical condition being prevented. As used herein, the term "prevent" and words stemming therefrom encompasses reducing the risk of the medical condition being prevented.

As used herein, the term "inhibit" and words stemming therefrom may not be a 100% or complete inhibition or abrogation. Rather, there are varying degrees of inhibition of which one of ordinary skill in the art recognizes as having a potential benefit or therapeutic effect. In this respect, the compounds of the may inhibit the binding interaction between a β integrin and a G protein α subunit to any amount or level. In exemplary embodiments, the inhibition provided by the methods of the disclosure is at least or about a 10% inhibition (e.g., at least or about a 20% inhibition, at least or about a 30% inhibition, at least or about a 40% inhibition, at least or about a 50% inhibition, at least or about a 60% inhibition, at least or about a 70% inhibition, at least or about a 80% inhibition, at least or about a 90% inhibition, at least or about a 95% inhibition, at least or about a 98% inhibition). In some embodiments, the compound completely abrogates the binding interaction between the R integrin and the G protein a subunit, such that no R integrin-G protein α subunit binding complexes are detectable in a sample obtained from a subject, as measured by, for example, immunoprecipitation, Western blotting, immunohistochemistry, and the like.

As used herein, the term "amount effective," "effective amount" or a "therapeutically effective amount" refers to an amount of the peptide of the disclosure or a pharmaceutical composition comprising the inventive peptide sufficient to achieve the stated desired result, for example, treating or limiting development of a condition or disease characterized by excessive vascularity. The amount of the peptide which constitutes an "effective amount" or "therapeutically effective amount" may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 μg/kg to up to about 100 mg/kg or more, depending on the factors mentioned above. In certain embodiments, the dosage may range from 0.1 μg/kg up to about 100 mg/kg, or 1 μg/kg up to about 100 mg/kg, or 5 μg/kg up to about 100 mg/kg.

The pharmaceutical compositions, nanoparticles or the peptides of the disclosure provided herein can be specially formulated for oral administration in solid or liquid form or for intravenous injection. Optimal pharmaceutical compositions can be determined by one skilled in the art depending upon, for example, the intended route of administration, delivery format and desired dosage. See, for example, REMINGTON'S PHARMACEUTICAL SCIENCES, 18th Edition, (A. R. Gennaro, ed.), 1990, Mack Publishing Company.

The peptides of the disclosure can be incorporated in a conventional systemic dosage form, such as a tablet, capsule, soft gelatin capsule, elixir or injectable formulation. The dosage forms may also include the necessary physiologically acceptable carrier material, excipient, lubricant, buffer, surfactant, antibacterial, bulking agent (such as mannitol), antioxidants (ascorbic acid or sodium bisulfite) or the like.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, Id.

The primary vehicle or carrier in a pharmaceutical composition, nanoparticles or the peptides of the disclosure may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Pharmaceutical compositions of the disclosure may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the peptides of the disclosure may be formulated as a lyophilizate using appropriate excipients such as sucrose.

Administration routes for the pharmaceutical compositions, nanoparticles or the peptides of the disclosure include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

The pharmaceutical compositions, nanoparticles or the peptides of the disclosure can be delivered parenterally. When parenteral administration is contemplated, the therapeutic compositions for use in this disclosure may be in the form of a pyrogen-free, parenterally acceptable aqueous solution comprising the desired compound identified in a screening method of the disclosure in a pharmaceutically acceptable vehicle. A particularly suitable vehicle for parenteral injection is sterile distilled water in which the compound identified in a screening method of the disclosure is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions, nanoparticles or the peptides of the disclosure may also be formulated for inhalation. In these embodiments, the nanoparticles or peptides of the disclosure are formulated as a dry powder for inhalation, or inhalation solutions may also be formulated with a propellant for aerosol delivery, such as by nebulization. Pulmonary administration is further described in the International Application No. PCT/US94/001875, which describes pulmonary delivery of chemically modified proteins and is incorporated herein by reference.

The pharmaceutical compositions, nanoparticles or the peptides of the disclosure can be delivered through the digestive tract, such as orally. The preparation of such pharmaceutically acceptable compositions is within the skill of the art. The nanoparticles or peptides of the disclosure that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the peptides of the disclosure disclosed herein. Diluents, flavorings, low melting point waxes, vegetable oils, lubricants, suspending agents, tablet disintegrating agents, and binders may also be employed.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

Pharmaceutically Acceptable Salts

With regard to the disclosure, the compositions, nanoparticles or peptides disclosed herein are in some aspects is in the form of a salt, e.g., a pharmaceutically acceptable salt. Such salts can be prepared in situ during the final isolation and purification of the active agent or separately prepared by reacting a free base function with a suitable acid. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate.

Basic addition salts also can be prepared in situ during the final isolation and purification of the compositions or peptides disclosed herein, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like.

Further, basic nitrogen-containing groups can be quaternized with the compositions or peptides disclosed herein, as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

Timing of Administration

The disclosed pharmaceutical compositions, nanoparticles, peptides or formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi monthly. Timing, like dosing can be fine-tuned based on dose-response studies, efficacy, and toxicity data, and initially gauged based on timing used for other therapeutics.

Combinations

In some embodiments, the compositions, nanoparticles or peptides described herein are administered alone, and in alternative embodiments, the compositions or peptides described herein are administered in combination with another therapeutic agent, e.g., another active agent of the disclosure of different type (e.g., structure), or another therapeutic which does not inhibit a binding interaction between β integrin and G protein a subunit. In some aspects, the other therapeutic aims to treat or prevent diseases disclosed herein. In specific aspects, the other therapeutic is one listed under the section entitled "Heterologous Moieties: Therapeutic Agents."

In exemplary aspects, the compositions, nanoparticles or peptides described herein are administered or packaged in combination with an anti-thrombotic agent. In exemplary embodiments, the anti-thrombotic agent is an anticoagulant, e.g., fondaparinux and bivalirudin.

In exemplary embodiments, the anti-thrombotic agent is an anti-platelet agent, e.g., aspirin, clopidogrel, dipyridamole, and abciximab.

In exemplary aspects, the composition, nanoparticles or peptide described herein is administered or packaged in combination with an anti-platelet drug. In exemplary aspects, the antiplatelet drug is an irreversible cyclooxygenase inhibitor (e.g., aspirin), an adenosine diphosphate (ADP) receptor inhibitor (e.g., clopidogrel, prasugrel, ticagrelor, ticlopidine), a phosphodiesterase inhibitor (e.g., cilostazol), a glycoprotein IIb/IIIa inhibitor (e.g., abciximab, eptifibatide), tirofiban), an adenosine reuptake inhibitor (e.g., dipyridamole), or a thromboxane inhibitor (e.g., a thromboxane synthase inhibitor, a thromboxane receptor antagonist (e.g., terutroban). In exemplary aspects, the antiplatelet drug is aspirin, a thienopyridine, a cylooxygenase inhibitor or a P2Y12 inhibitor.

In exemplary aspects, the composition, nanoparticles or peptide described herein is administered or packaged in combination with an integrin antagonist or integrin inhibitor. The integrin inhibitor in exemplary aspects is eptifibatide In exemplary embodiments, the composition, nanoparticles or peptide is administered simultaneously as the other therapeutic. In alternative embodiments, the composition or peptide is administered either before or after the other therapeutic.

The foregoing may be better understood by reference to the following examples, which are presented for purposes of illustration and not intended to limit the scope of the disclosure.

EXAMPLES

General Methods

Animals

Mice used in this study were 8- to 10-weeks-old C57BL/6. Animal usage and protocol was approved by the Institutional Animal Care Committee of the University of Illinois at Chicago. Mice with similar age, weight and sex ratios (1:1) were used for control and treatment.

Figure 30A:
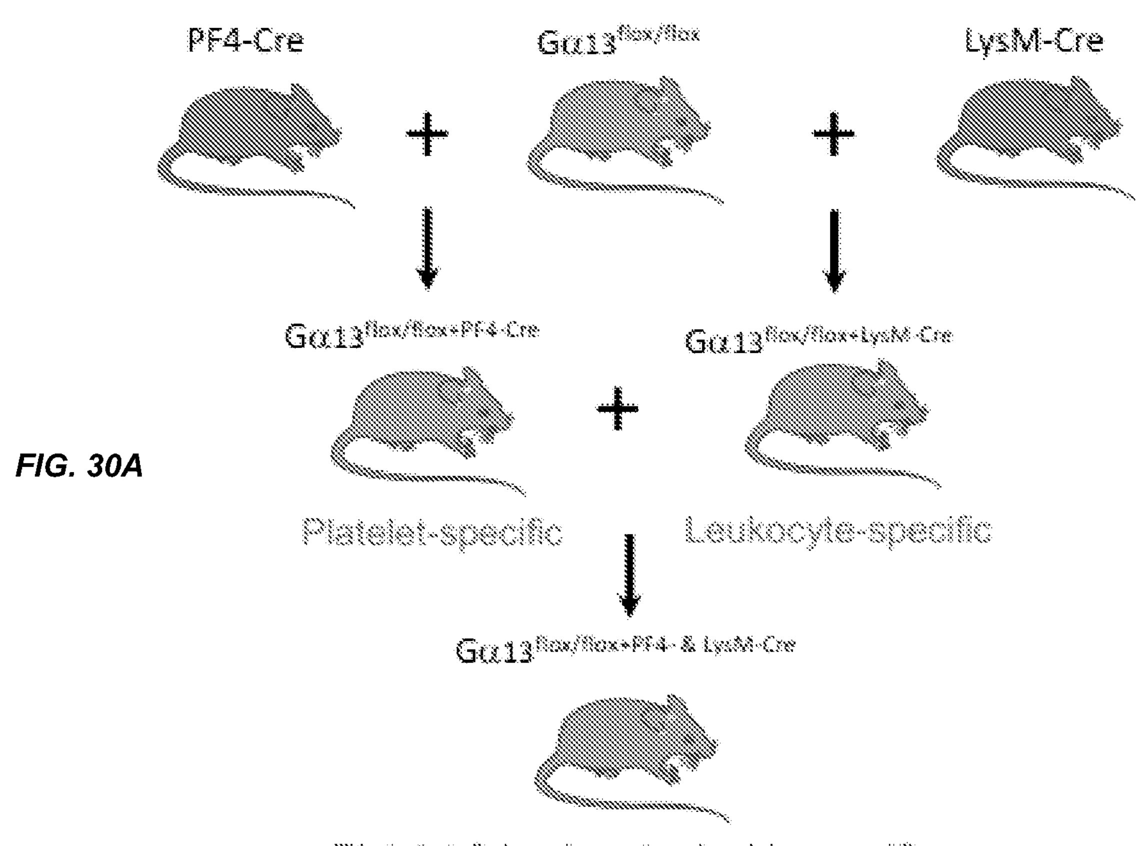
FIGS. 30A-30B: Generation of platelet-specific, leukocyte-specific and platelet & leukocyte-dual-specific Gα13 knockout mice.
Figure 30B:
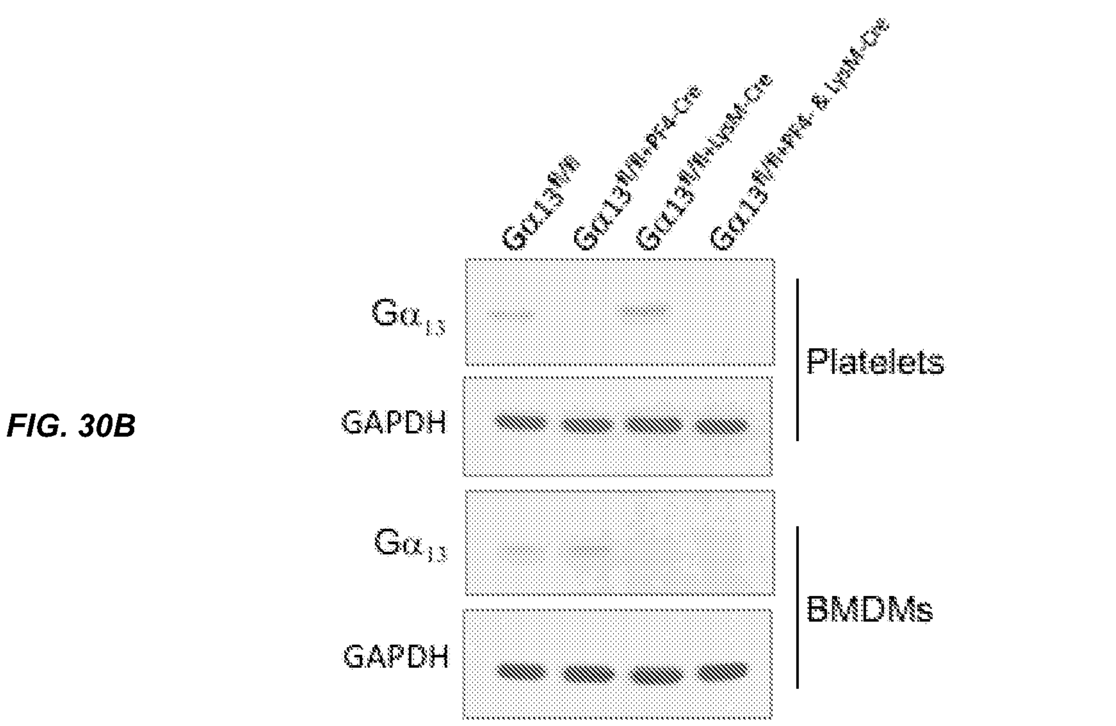

In some experiments 14- to 16-weeks-old mice with an equal sex ratio were used. Gα13$^{fl/fl}$ mice were gifts obtained from Dr. Stefan Offermanns' lab (Max Planck Institute for Heart and Lung Research, Bad Nauheim, Germany). PF4-Cre mice, LysM-Cre (Lyz2-Cre) and C57BL/6 mice were obtained from the Jackson Laboratory. Platelet specific or leukocyte specific Gα13 knockout mice were generated by breeding Gα13$^{fl/fl}$ and PF4-Cre or LysM-Cre mice and confirmed by genotyping and western blot analysis (FIGS. 30A-30B). Control mice were negative for Cre recombinase with matched genetic background, age and sex. Animal usage and protocol were approved by the Institutional Animal Care Committee, University of Illinois at Chicago. A randomized approach of choosing mice was used throughout the study, using all mice with the correct genotype without bias.

Reagents

Peptides were synthesized and purified at the Research Resource Center at the University of Illinois at Chicago or custom-made by the New England Biolabs, MA. A peptide purchased from China Peptide Company (CPC) was also tested in some experiments, but have abandoned using peptides produced by this vendor because of unreliable quality. Clopidogrel bisulfate were purchased from Sigma-Aldrich Co. (St. Louis, MO). Cangrelor was purchased from Adooq Bioscience Co. (York, UK), Brilinta (Ticagrelor) was purchased from AstraZeneca pharmaceutical company (London, UK). Mouse anti-integrin β3 monoclonal antibody M15 was a gift from Dr. Mark Ginsberg (UCSD, CA). Rabbit anti-integrin β3 antibody (Cat. 18309-1-AP) was obtained from Proteintech Group Inc. (Chicago, IL). Rabbit anti-Gα13 antibody (GTX32613) was purchased from GeneTex Inc. (Irving, CA). PE-conjugated rat anti-mouse integrin αIIb $\beta_3$ (active) clone JON/A was obtained from Emfret Analytics (Germany). Rat anti-mouse Ly-6G (clone 1A8) antibody was purchased from BD Biosciences (San Jose, CA).

Mouse anti-integrin β2 antibody (1.BB.246, sc-71397) and rat anti-integrin αIIb antibody (MWReg30, sc-19963) were purchased from Santa Cruz Biotechnology (Dallas, TX). Rabbit anti-integrin β2 monoclonal antibody (D4N5Z, #73663) was purchased from Cell Signaling Technology, Inc. (Danvers, MA). Mouse anti-integrin β3 monoclonal antibody M15 was a gift from Dr. Mark Ginsberg (UCSD, CA). Rabbit anti-integrin β3 antibody (18309-1-AP) was obtained from Proteintech Group Inc. (Chicago, IL). Rabbit anti-Gα13 antibody (GTX32613) was purchased from GeneTex Inc. (Irving, CA). Rabbit anti-fibrin/fibrinogen polyclonal antibody (A0080) was obtained from Dako/Agilent (Santa Clara, CA). Mouse cytokines IL-6, TNFα and IL-10 ELISA kits were obtained from R&D Systems, Inc. (Minneapolis, MN). The DetectX®Urea Nitrogen (BUN) Detection Kit was purchased from Arbor Assays (Ann Arbor, MI). Creatinine and alanine transaminase colorimetric assay kits were from Cayman Chemical (Ann Arbor, MI). Mouse Cystatin C ELISA kit was from ThermoFisher Scientific (Waltham, MA).

Anti-Gα13 antibody (GTX32613) was purchased from GeneTex (Irvine, CA). Integrin β2 antibodies (sc-19624, sc-8420 and sc-71397) were from Santa Cruz Biotechnology (Dallas, TX). Rabbit anti-integrin β2 monoclonal antibody (D4N5Z, #73663) was purchased from Cell Signaling Technology, Inc. (Danvers, MA). N-Formyl-Met-Ile-Val-Ile-Leu (fMIVIL (SEQ ID NO: 46)) was obtained from Dr. Richard Ye (Southgate et al., 2008). Anti-GAPDH (MAB5718) was purchased from R&D Systems. Hank's balanced salt solution (HBSS; with and without $Ca^{2+}$ and $Mg^{2+}$ and phenol red) and RPMI 1640 medium were from Gibco/Life Technologies. Bovine serum albumin (BSA) and bacterial LPS (LPS; *Escherichia coli* 055:B5) were purchased from Sigma-Aldrich (St Louis, MO).

Lipid-Stabilized High-Loading M3mP6 Peptide Nanoparticles

The peptide myr-FEEERL(SEQ ID NO: 25) was modified from the original 03 cytoplasmic domain sequence to make it more suitable to form peptide-based nanoparticle, and was formulated to form lipid-stabilized high-loading peptide nanoparticles together with PEG2000-DSPE (Avanti Polar Lipids Inc. Alabaster, AL), L-α-phosphatidylcholine (egg PC, Type XI-E, Sigma-Aldrich, St. Louis, MO) with a peptide to PEG-DSPE to PC molar ratio of 36.8:51.7:11.5 or 50:40:10 (further improved formulation with identical in vivo effect) using thin-film rehydration (21, 31). The size distribution of nanoparticles were determined using dynamic light scattering (DLS) (Malvern, Zetasizer Nano ZS90, Worcestershire, U.K.) as previously described (32). This method uses light scattering to monitor the Brownian motion of the particles. Particle size is presented as volume weighted diameter distribution. In some studies, M3mP6 HLPN containing 60% (mol/mol, FIG. 3C, FIG. 8) and 70-80% (mol/mol, not shown) M3mP6 produced in scaled manufacturing by Dupage Medical Technology, Inc. were also used with similar anti-thrombotic effects.

Platelet Preparation, Aggregation and Granule Secretion

For human subjects, Institutional Review Board approval was obtained from the University of Illinois at Chicago, and informed consent from volunteers was obtained in accordance with the Declaration of Helsinki. Platelets were prepared as previously described (33). Platelet aggregation and adenosine triphosphate (ATP) secretion were measured simultaneously in a lumiaggregometer (Chronolog) at 37° C. with stirring (1000 rpm), as previously described (34).

Co-Immunoprecipitation

Co-immunoprecipitation of integrin β3 and Gα13 was performed similarly to previously described (21, 22, 35). Briefly, differentiated THP-1 cells (2×10^6) or human platelets (5×10^8/mL, 300 μL) were treated with various concentrations of M3mP6 or scrambled peptide. 10 min after treatment, THP-1 cells or platelets were stimulated with LPS (100 ng/mL) or thrombin (0.025 U/mL) for various time points or for 5 min in aggregometer and solubilized with NP40 lysis buffer (50 mM Tris, pH 7.4, 10 mM MgCl2, 150 mM NaCl, 1% NP-40, 1 mM EGTA, 1 mM sodium orthovanadate, 1 mM NaF) with complete protease inhibitor cocktail tablets (Roche). After centrifugation at 14,000 g for 10 min at 4° C., lysates were then collected and immunoprecipitated with mouse anti-integrin β2 antibody (1.BB.246) or with mouse anti-integrin β3 IgG (M15) or equal amount of mouse IgG overnight at 4° C., and then with protein A/G plus agarose beads (sc-2003, Santa cruz Biotechnology, Inc, Dallas, TX) for 1 hour at 4° C. Following 3 washes with NP40 lysis buffer, immunoprecipitants were analyzed by western blot.

Co-immunoprecipitation of integrin β2 and $G\alpha_{13}$ was performed similarly to the previously described procedure (Gong et al., 2010; Shen et al., 2013). Briefly, human neutrophils (5×10^6) were pre-treated with MB2mP6 (50 μM) or scrambled peptide (50 μM). Ten minutes after treatment, human neutrophils were stimulated with fMLF (1 μM) and loaded into ICAM1 precoated 6-well plate. At indicated time points, the neutrophils in each wells were solubilized with NP40 lysis buffer (50 mM HEPES, pH 7.4, 10 mM MgCl2, 150 mM NaCl, 1% NP-40, 1 mM EGTA, 1 mM sodium orthovanadate, 1 mM NaF) with complete protease inhibitor cocktail tablets (Roche). After centrifugation at 14,000 g for 10 minutes at 4° C., lysates were then collected and immunoprecipitated with mouse anti-integrin β2 antibody (1.BB.246, sc71937 or an equal amount of mouse IgG overnight at 4° C., and then with protein A/G plus agarose beads (sc-2003, Santa Cruz Biotechnology, Inc, Dallas, TX) for 1 hour at 4° C. Following 3 washes with NP40 lysis buffer, immunoprecipitants were analyzed by western blot.

Fibrinogen and JON/A Binding Assay

Washed mouse platelets in modified Tyrode's buffer (5×10^7/mL) were incubated with 10 μg/mL Oregon Green-conjugated fibrinogen (Molecular Probes) and PAR4AP for 30 minutes at room temperature as described previously (21), or with PE-conjugated rat anti-mouse integrin αIIβ3 (active) antibody JON/A (Emfret) and PAR4AP for 15 minutes at room temperature. The reaction was diluted with PBS containing 1% BSA and analyzed by flow cytometry using an Accuri C6 flow cytometry (BD Biosciences).

Drug Administration

C57BL/6 mice were gavaged with aspirin, clopidogrel or ticagrelor using a gavage needle (20 gauge curved metal, Fine Science Tools, Heidelberg, Germany) and syringe 2 hours prior to the initiation of carotid artery injury procedure. In some experiments, high dose aspirin was also administrated via intraperitoneal route. M3mP6 was administered via retro-orbital injection 15 minutes prior to procedure. Cangrelor was injected retro-orbitally prior to the initiation of carotid artery injury. In some experiments determining the M3mP6 dose responses, M3mP6 was also injected intravenously through tail veins.

Maximal Tolerated Doses (MTD) and Pharmacokinetics

CD-1 mice (6-8 weeks old and 20-30 g in weights) were quarantined for at least 3 days upon arrival and group housed under standard conditions (tap water, Harlan Irradiated Diet 7912 and Anderson bed-o'cob bedding). The first mouse was injected IV in the tail vein (Day 0) with the maximal feasible dose (60 mg/kg (60 mol/kg)) of M3mP6. No signs of toxicity were detectable on the next day (Day 1). Four more animals were then injected with the same dose. The animals were observed 2 times per day for 8 days for clinical signs of toxicity. As no clinical signs of toxicity were observed, this maximal feasible dose was considered the MTD.

For pharmacokinetic studies, CD-1 mice were intravenously injected with 5 mg/kg (5 μmol/kg) M3mP6 (potential therapeutic dose). At the following time points: 0 (pre-dose) min, 5 min, 10 min, 30 min, 1, 2, 4, 6, and 24 hours, 3 drug-treated mice were sacrificed, and their blood drawn via vena cava into K2EDTA tubes. Whole blood and plasma were analyzed for M3mP6 concentrations using Agilent 1290 Infinity LC and 6430 triple quadrupole mass spectrometer and MassHunter software.

Toxicological responses to bolus and continuous intravenous infusion of M3mP6 HLPN were performed using jugular vein catheterized (JVC) Sprague-Dawley (SD) rats (6-8 weeks old and 250-350 in weights), which were quarantined for at least 3 day after arrival. Four SD rats (n=2 per sex) was given an IV bolus dose of M3mP6 (100 mg/kg, dose volume 10 mL/kg) followed by IV infusion dose of M3mP6 for 24 hr (25 mg/kg/hr for a total dose of 600 mg/kg/day). Since no toxicity was observed during 3-4 days post dose, this dose level was considered the single dose MTD as this was the maximum feasible dose based on the maximum allowable dosing volume. A pilot 7-day continuous infusion study in rats was performed similarly with lower drug concentrations. The parameters observed include mortality, clinical signs, body weights, hematology, clinical chemistry and organ weights. For pharmacokinetic studies, plasma samples for drug analysis were obtained from blood samples collected in satellite 6 males and 6 females (3 rat/sex per time-point) in the dose Groups 3 and 4 (Phase 2) at the following time-point on Day 1 after the bolus dose and infusion were started: 5, 10 and 30 minutes, and 1, 2, 6 and 24 hours. Additional blood samples were collected prior to the end of 5-day infusion, immediately after stopping the infusion, and at 30 minutes, and 1, 4, 6, 24 and 48 hours after the end of the infusion.

Laser-Induced Mouse Cremaster Arteriolar Thrombosis and Intravital Microscopy

Laser-induced thrombosis and intravital microscopy are performed as previously described using male C57BL/6 mice (6-8 weeks old) anesthetized by intraperitoneal injection of ketamine and xylazine (36). Platelet thrombi were indicated by infusion of DyLight 649-labeled anti-mouse GPlbpEmfrey, Germany). Fibrin deposition was tracked by Alexa Fluor (AF) 488-labeled monoclonal anti-fibrin antibody (clone 59D8) as previously described (25). Suspensions of M3mP6 HLPN (10 μmol/kg) or a control peptide (Myr-ERAFEE (SEQ ID NO: 47)) HLPN in 0.15 M NaCl or cangrelor were injected 15 min or immediately prior to induction of injury. Fluorescence and bright-field images were recorded by an Olympus BX61W microscope with a 603/1.0 NA water immersion objective and a high-speed camera (5 frame/second) through an intensifier at 27-30 injury sites in 7 mice per group. The movies shown are compressed to 100 frame/second.

$FeCl_3$-Induced Mouse Carotid Artery Thrombosis Model

Figure 19:
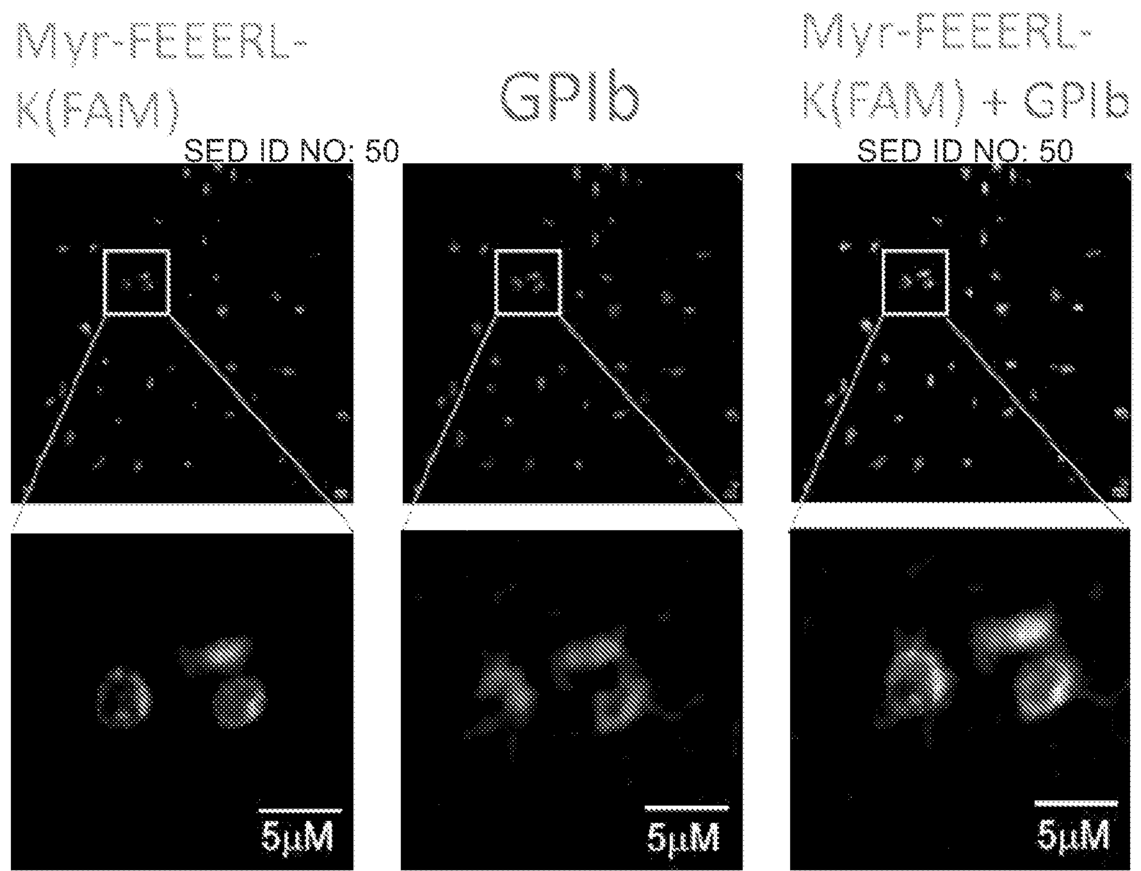
FIG. 19 shows the intake of fluorescently labeled M3mP6 HLPN into mouse platelets. Fluorescently labeled M3mP6 HLPN was incubated with mouse platelets for 30 minutes at 37° C., and then plated on cover glass. The platelets were then stained with PE-conjugated rat anti GPIβP antibody for 30 minutes at room temperature. The intake of M3mP6 into platelets was observed by confocal microscope (Zeiss LSM 710 META).

Eight- to 10-week-old C57BL/6 mice were anesthetized with isoflurane inhalation. The right carotid artery was isolated (34, 37). A MA-0.5SB nanoprobe (Transonic Systems, Ithaca, NY) was hooked to the carotid artery to monitor blood flow with a TS420 flowmeter (Transonic Systems) as previously described (38). After stabilization, carotid arterial thrombosis was induced with 7.5% ferric chloride ($FeCl_3$) (Sigma Aldrich, St. Louis, MO), a filter paper disc (2 mm diameter) soaked with 1.2 μL of 7.5% $FeCl_3$ was placed on top of the artery for 3 minutes, and then removed. M3mP6 HLPN, HLPN of scrambled control peptide, HLPN of a second control peptide carrying AAA mutation or physiological saline solution were injected 15 minutes before procedure retro-orbitally. In a pilot study, both control peptides showed no significant difference from saline solution (FIG. 19). To study the effect of post-injury drug injection on thrombosis development, the filter paper disc soaked with 1.2 μl 3.75% $FeCl_3$ were placed on artery for 2 minutes, and drugs were injected retro-orbitally 3 minutes after removing the filter paper. Blood flow was monitored continuously until 5 minutes after occlusion or for 30 minutes if no occlusion occurred. Time to occlusion was defined as the time between the removal of the filter paper and stable occlusion (no blood flow for 2 minutes). Data were analyzed using Mann-Whitney test to compare medians between treatments.

Tail Bleeding Time

Tail bleeding time was performed as previously described (21, 39). Eight- to 10-week-old C57BL/6 mice were anesthetized with isoflurane. After cutting 0.5-cm-long segment of the distal tip of the tail, their tails were immersed in 0.15 M NaCl immediately at 37° C. Tail bleeding time was defined as the time between cutting tail and stable cessation of bleeding (no rebleeding within 60s). Bleeding was observed for up to 15 minutes. If bleeding persisted at 15 minute time point, bleeding was stopped by application of pressure. Data were analyzed using Mann-Whitney test to compare medians between groups.

Arterial Perforation Bleeding Analysis

To estimate bleeding during vascular procedures, 8- to 10-week-old C57BL/6 mice were anesthetized with isoflurane inhalation. The right carotid artery was isolated as previously described (34, 37) and punctured with a 27½G needle in the middle of carotid artery. The perforating wound was immediately covered with a 4×4 mm hemostatic pad (CERTI-GAUZE™, Kansas City, MO), which serve to absorb extravascular blood and also help stop bleeding similarly to that during vascular procedures. The pad was removed after 15 minutes regardless whether bleeding continued or not. The volume of blood absorbed on the pad during the 15-minute period was quantified by estimating the amount of hemoglobin. To do so, adsorbed blood on the pad was dissolved into 30 mL double distilled water. To 1 mL of dissolved blood, 1 mL of the 2× Drabkin's Solution was added. After fully mixing and incubating for 20 minutes at room temperature, the absorbance of the samples was analyzed at 540 nm wave length with a spectrophotometer. Known volumes of blood were similarly analyzed to establish a standard curve for the calculation of blood volume on the pad. Data were analyzed by Mann-Whitney test for statistical significance.

Dog Buccal Mucosal Bleeding Time (BMBT) test

BMBT in dogs was performed after the administration of M3mP6 HLPN (10 mg M3mP6 peptide/kg) using Jorvet Surgicutt bleeding time device (J522J, Jorgensen Laboratories, Inc. CO) according to the direction of the manufacturer as previous described (40). Normal range of bleeding time for dogs is less than 4 minutes.

Mouse Myocardial Ischemia and Reperfusion Model

MI/R model was performed as previously described (41, 42). C57BL/6 mice were random assigned to surgical and sham groups. Mice were anesthetized with 1.5-3.0% isoflurane inhalation and orally intubated with a 18G angiocath sleeve. Mice were artificially ventilated with a rodent respirator machine. A left thoracotomy was performed by 1 cm careful incision along sternum and 1 mm to the left from a midline between the 2nd and the 4th rib in layers. Mouse left anterior descending branch (LAD) was located and ligated with 8-0 prolene suture 1-2 mm below the ostium. A 4-0 prolene suture was placed under suture to help removing it. 35 minutes after induction of ischemia, M3mP6 or control HLPN was injected at a bolus dose of 5 μmol/Kg followed by 2.5 μmol/kg/hour infusion through jugular vein cannula. After 45 minutes ischemia period, the suture was cut and removed. The successful reperfusion was confirmed by observing a change of the color of the anterior wall from pale to pink-red after 15-20 sec. Chest wound was closed after surgery.

Determination of Infarct Size in MI/R Mice 24 hours post I/R, the LAD was reoccluded in the previous position, and 1% Evans blue dye (Sigma, Darmstadt, Germany) was injected into the heart cavity through the ascending aorta (42). The mouse was then euthanized, and its heart was harvested and rinsed in Saline. The heart was then frozen at −20° C. for 15 minutes and cut transversely into 6-7 slices. The slices were incubated with 1.5% 2, 3, 5-triphenyltetrasolium chloride (TTC, Sigma, America) at 37° C. for 20 minutes in the dark room and then imaged (Nikon SMZ800N). The ischemic area, risk area, and total left ventricular area were measured and calculated using the ImageJ.

Echocardiography

Mouse echocardiography was performed in the Center for Cardiovascular Research Physiology Core (CCVRPC) using VisualSonics Vevo 770 Echocardiography System. 2% of isoflurane was used for sedation during the whole examination. Both 2-dimensional and M-mode images were obtained in the long- and short-axis views. Ejection fraction (EF) was calculated using Vevo 2100 software. Measurements were performed on 3 independently acquired images per animal, by researchers who were blinded to experimental group.

Immunohistochemistry

Mouse hearts were collected after perfusion and then fixed with 10% formalin overnight. 20 h after fixation, mouse hearts were dehydrated in 70% ethyl alcohol and embedded in paraffin. Four micrometer sections were cut and stained with hematoxylin and eosin. Sections were deparaffinized, rehydrated, peroxidase blocked, and antigen retrieval with heating at 95° C. for 20 min in pH 6.0 citrate buffer. Rat anti mouse integrin αIIb antibody (1:250, Clone MWReg 30, Santa Cruz Biotechnology) and anti-rat IgG-avidin-biotin complex kit (Vector Laboratories) were used to stain platelet-rich thrombi. The neutrophils infiltration into mouse heart was stained with rat anti-mouse Ly6G (clone 1A8, BD Biosciences) antibody. The positive stain in each section was quantified with ImageJ software.

Detection of MPO in Mouse Plasma

Mouse blood samples were drawn from the retro-orbital venous sinus of mice into 1.5 ml Eppendorf tubes containing 7.5 μl Heparin 1000 u/ml and centrifuged at 600 g at 4° C. for 15 minutes to obtain plasma. Plasma MPO was detected by mouse myeloperoxidase DuoSet ELISA kit (R&D Systems) according to manufacturer's instructions.

Micellar Peptide Preparation

MB2mP6 (Myr-FEKEKL (SEQ ID NO: 27)) and scrambled control (Myr-EFKKLE (SEQ ID NO: 48)) peptides were synthesized and purified by the Research Resources Center at the University of Illinois at Chicago. PEG2000-DSPE (Avanti Polar Lipids Inc. Alabaster, AL), L-α-phosphatidylcholine (egg PC, Type XI-E, Sigma-Aldrich, St. Louis, MO) and peptides were mixed at a molar ratio of 55.6:11.9:40. Micelles were prepared using a film rehydration method as previously described[16].

Detection of Cytokine Expression in Mouse Bone Marrow Derived Macrophages (BMDMs)

Mouse BMDMs were isolated as previously described26. After differentiating into macrophages by incubating in DMEM medium containing 15% L929-conditioned medium and 10% FBS for 7 days, BMDMs (2×106/mL) were seeded into 6-well plates for 14 hours and serum starved for 4 hours. Eight hours after LPS stimulation, mouse BMDMs were collected and subjected to total RNA extraction and quantitative RT-PCR (qRT-PCR) analysis using SYBR Green (Roche) with various mouse cytokine specific primers.

```
mIl1b forward:
                                    (SEQ ID NO: 51)
5'-CGACAAAATACCTGTGGCCT-3'

mIl1b reverse:
                                    (SEQ ID NO: 52)
5'-TTCTTTGGGTATTGCTTGGG-3'

mIl6 forward:
                                    (SEQ ID NO: 53)
5'-TCCAGTTGCCTTCTTGGGAC-3'

mIl6 reverse:
                                    (SEQ ID NO: 54)
5'-GTGTAATTAAGCCTCCGACTTG-3'

mTnfa forward:
                                    (SEQ ID NO: 55)
5'-TTCTGTCTACTGAACTTCGGGGTGATCGGTCC-3'

mTnfa reverse:
                                    (SEQ ID NO: 56)
5'-GTATGAGATAGCAAATCGGCTGACGGTGTGGG-3'

mIl10 forward:
                                    (SEQ ID NO: 57)
5'-GGTTGCCAAGCCTTATCGGAAATG-3'

mIl10 reverse:
                                    (SEQ ID NO: 58)
5'-CACTCTTCACCTGCTCCACTGC-3'

mGapdh forward:
                                    (SEQ ID NO: 59)
5'-TGCGACTTCAACAGCAACTC-3'

mGapdh reverse:
                                    (SEQ ID NO: 60)
5'-CTTGCTCAGTGTCCTTGCTG-3'
```

Platelet Preparation, Aggregation and Granule Secretion

Human blood was drawn by venipuncture from healthy volunteers. Institutional Review Board approval was obtained from the University of Illinois at Chicago, and informed consent from volunteers was obtained in accordance with the Declaration of Helsinki.

To prepare platelet-rich plasma (PRP), whole blood was anticoagulated with 3.8% trisodium citrate. To prepare human platelets, one-seventh volume of ACD was used as anticoagulant. Platelets were washed twice and resuspended in modified Tyrode's buffer as previously described (27). Platelet aggregation and adenosine triphosphate (ATP) secretion were measured simultaneously in a lumiaggregometer (Chronolog) at 37° C. with stirring (1000 rpm) as previously described (28).

$FeCl_3$-Induced Mouse Carotid Artery Thrombosis Model

Eight- to 10-week-old C57BL/6 mice (20-25 g body weight) were anesthetized by isoflurane inhalation. The right carotid artery was isolated. A MA-0.5SB nanoprobe (Transonic Systems, Ithaca, NY) was hooked to the carotid artery to monitor blood flow with a TS420 flowmeter (Transonic Systems) as previously described (29). After stabilization, a filter paper disc (2 mm diameter) soaked with 1.2 μL of 7.5% $FeCl_3$ (Sigma Aldrich, St. Louis, MO) was placed on top of the carotid artery for 3 minutes to induce thrombosis and then removed. MB2mP6 or scrambled control peptide were injected 15 minutes before the procedure retro-orbitally. Blood flow was monitored continuously until 5 minutes after occlusion or for 15 minutes if no occlusion occurred. Time to occlusion was defined as the time between the removal of the filter paper and stable occlusion (no blood flow for 5 minutes). Data were analyzed using the Mann-Whitney test to compare medians between treatments.

Tail Bleeding Time

Tail bleeding time was performed as previously described (16, 29). Eight- to 10-week-old C57BL/6 mice weighing 20-25 g were anesthetized with isoflurane. After cutting a 0.5-cm-long segment off the distal tip of the tail, their tails were immersed in 0.15 M NaCl immediately at 37° C. Tail bleeding time was defined as the time between cutting the tail and stable cessation of bleeding (no re-bleeding within 60s). Bleeding was observed for up to 15 minutes. If bleeding persisted at 15 minutes, bleeding was stopped by application of pressure. Data were analyzed using the Mann-Whitney test to compare medians between groups.

Reverse Passive Arthus (rpA) Reaction

C57/BL6 mice were anesthetized by i.p. injection of a mixture of ketamine and xylazine (100 mg/kg and 16 mg/kg mouse weight), and the medial surface of the mouse back was shaved. Shaved mice received intradermal injections of rabbit anti-bovine serum albumin (BSA) antibody (6 μg/μL, MP Biomedicals, OH) in 25 μL of 0.9% NaCl, followed by i.v. injection of BSA (75 μg/g mouse weight) as well as the peptide inhibitors (5 μmol/kg mouse weight) in 100 μL sterile 0.9% NaCl. In addition, control sites received 25 μL of PBS in parallel. Four hours after injection, mice were euthanized and inflamed or control skin samples at each injection site were collected. The hemoglobin (Hb) contents in the skin samples were quantified by hemoglobin colorimetric assay kit (Cayman Chemical, Ann Arbor, MI).

Cecal Ligation and Puncture (CLP) Sepsis Model

CLP sepsis was induced as described previously (32, 33). In brief, mice (14- to 16-week-old with equal number of each gender) were anesthetized by intraperitoneal administration of ketamine (100 mg/kg body weight) and xylazine (8 mg/kg). After a midline laparotomy, the cecum was ligated at about 1 cm from the end and then subjected to a double "through and through" perforation with an 18-gauge needle. Sham-operated mice underwent the same procedure except for ligation and puncture of the cecum. After the procedure, an analgesic (buprenorphine, 0.1 mg/kg, s.c.) was given immediately and every 12 h thereafter for 3 d. At these time points, fluid resuscitation (prewarmed 0.9% NaCl, 0.05 ml/g body weight) was given through subcutaneous injection to prevent fluid loss and help the recovery of body temperature. One hour after surgery, antibiotic (Claforan® solution; 10 mg/kg body weight) was subcutaneously administrated (to mimic clinical conditions) for 5 days. The medication was continued until the situation of scheduled sacrifice, death, or study completion in the surviving mice. The survival of mice was observed every 6 h for 8 days and analyzed by the Log Rank test (using Prism GraphPad software (ver. 5.0), San Diego, CA, USA). For CLP-induced mouse organ injury, blood samples and kidney or lung tissues were collected 24 hours after CLP and subjected to cytokine and immunohistochemistry analyses.

Mouse Jugular Vein Cannulation and Continueal Peptide Infusion

Mice were weighed, anesthetized using ketamine/xylazine (100/5 mg/kg), and transferred to a heated platform under a dissection microscope. A 5 mm incision through the skin on the upper part of the mouse back was made posterior to the ears and between the scapulae. The mouse was then placed in a supine position and the skin over the right-side jugular vein was shaved and cleaned with hexachlorophene and 70% ethanol. After a vertical incision over the jugular site, the vein was dissected and exposed. The catheter was tunneled from the upper back incision to jugular incision through a trocar sleeve kit (DSI, St. Paul, MN). The jugular vein was carefully separated, and two sutures were drawn around vessel and tied loosely. Then, a small incision was made in the vein, the beveled catheter was inserted and tied in place with a suture, without closing off the catheter. The wound was closed using 6-0 suture and cleaned with hexachlorophene. For peptide treatment, MB2mP6 or control peptide micelles were injected immediately or 6 hours after CLP surgery in a bolus dose of 2.5 μmol/kg followed by a continuous infusion at rate of 1.25 μmol/kg/hour for 5 days.

Measurement of Organ Injury

Twenty-four hours after CLP, mouse blood was collected and added to an EDTA-rinsed microcentrifuge tube or citrate buffer. The plasma was obtained after centrifugation at 1,000 g at 4° C. for 5 minutes. In some case, mouse serum was collected from blood without adding any anti-coagulant. The kidney function markers BUN, creatinine and cystatin C and mouse liver function marker ALT were detected using corresponding kits according to the manufacturers' instructions. Septic mouse kidney, lung and liver tissue were collected from the sacrificed mice 24 hours after CLP, as well as from sham-operated mice and fixed in 10% formalin.

Immunohistochemistry

Mouse kidney and lung were collected 24 hours after CLP after perfusion with phosphate-buffered saline and then fixed in 10% formalin solution. 20 hours after fixation, mouse tissues were dehydrated in 70% ethyl alcohol and embedded in paraffin. Four to five micrometer sections were cut and stained with hematoxylin and eosin for quality control. Sections were de-paraffinized, rehydrated, peroxidase blocked, and subjected to antigen retrieval by heating at 95° C. for 20 min in pH 6.0 citrate buffer. Rat anti mouse integrin αIIb antibody (1:250, Clone MWReg 30) and rabbit anti fibrin/fibrinogen antibody (1:2,000) and anti-rat or anti-rabbit IgG-avidin-biotin complex kits (Vector Laboratories) were used to stain platelet-rich or fibrin-rich thrombi. The positive stain in each section was quantified with ImageJ software. Slides were also stained with Mallory's phosphotungstic acid hematoxylin (PTAH) (PTAH Stain kit, American MasterTech, McKinney, TX) to identify fibrin deposition and viewed with a Leica DMI RB microscope using a 40×/0.55 NA objective. Total thrombotic area/glomerulus was quantitated by analyzing 20-30 glomeruli from each group using ImageJ software.

Detection of Cytokine Expression

Twenty-four hours after CLP, mouse blood was collected from sham-operated and CLP induced septic mice. The serum was isolated and analyzed for cytokine levels using specific mouse cytokine ELISA kits. Mouse lungs were also collected from those sacrificed mice after PBS perfusion. Cytokine transcripts expressed in lung tissue were detected by real-time PCR using SYBR green.

TABLE 1

Key Resources

| Reagent type(species) or resource | Designation | Source or reference | Identifiers | Additional information |
|---|---|---|---|---|
| Genetic reagent (*M. musculus*) | $G\alpha_{13}^{flox/flox}$ | PMID: 8999798 | | |
| Genetic reagent (*M. musculus*) | B6.129P2-Lyz2tm1(cre)Ifo/J | Jackson Lab | | |
| Antibody | G alpha 13 | Genetex | GTX32613 | FC: 1:1000 |
| Antibody | GAPDH | R&D system | MAB5718 | FC: 1:10000 |
| Antibody | Integrin Beta 2(GAME46) | Santa Cruz | Sc-19624L | FC: 1:300 |
| Antibody | Integrin Beta 2 | Proteintech | 10554-1 AP | 1:500 |
| Antibody | Integrin Beta 2 (1.BB246) | Santa Cruz | sc-71397 | 2 μg/ reaction |
| Antibody | Integrin Beta 2 (CTB104) | Santa Cruz | sc8420 | 1:1000 |
| Antibody | Integrin Beta 2 (D4N5Z) | Cell Signaling | #73663 | 1:1000 |
| Primary Cell | HUVEC | Lonza | C2519A | |
| Peptide, recombinant protein | N-formyl-Met-Ile-Val-Ile-Leu(fMIVIL (SEQ ID NO: 46)) | PMID: 18606697 | | |
| Software, algorithm | Fiji | | | |
| Software, algorithm | Zeiss Zen | | | Image/video acquisition |
| Software, algorithm | R | R code for a standard numerical algorithm to solve the migration direction | This paper: Source code 1 | |

Generation of $G\alpha_{13}$ Deficient Mice

The $G\alpha_{13}^{flox/flox}$ mice were used as described in *Nat Med* 9, 1418-1422 (2003). We used $G\alpha_{13}^{flox/flox}$ crossed with LysM-Cre mice to generate tissue specific $G\alpha_{13}^{fl/fl\ LysM\text{-}Cre}$ mice. Age and gender matched mice were used in the study. Blood was harvested, and white blood cell and neutrophil counts were determined with a Hemavet System (Drew Scientific, Oxford, CT).

Cell Culture

Human umbilical vein endothelial cells (HUVEC) and human lung microvascular endothelial cells (HLMVEC) were purchased from Lonza (Walkersville, MD) and cultured on a 0.2% gelatin coated surface in EGM2 Medium (Lonza, Morrisville, NC).

Cell were washed with phosphate buffered saline (PBS) (0.137M NaCl, 0.01M $Na_2HPO_4$, 0.0027M KCl, 0.9 mM $CaCl_2$), 0.5 mM $MgCl_2$, pH 7.4, Corning). Outgrowing cells were harvested by trypsinization (0.05% porcine trypsin, 0.02% Ethylenediaminetetraacetic acid (EDTA)·4Na in Hanks' Balanced Salt Solution with phenol red, ThermoFisher Scientific). The cells were maintained in endothelial growth medium-2 (EGM-2, Lonza) and supplement bullet kit (0.1% Epidermal Growth Factor (hEGF), Hydrocortisone 0.1%,GA-1000 0.1%, 0.4% bovine brain extract (BBE), 0.1%, Ascorbic acid, 2% FBS, Lonza, Morristown, NJ) and additional 8% fetal bovine serum (FBS) (vol/vol, Lonza).The cells were cultured in T75 flasks and split in a ratio of 1:3. The cells were used within the first four passages in experiments.

All cells were cultured on cell culture dishes to 80-90% confluence in a humidified incubator at 37° C. and 5% $CO_2$.

In Vivo Mouse Neutrophil Migration Models

For the peritonitis model, mice were challenged with an intraperitoneal injection of 1 mL of 3% thioglycollate broth (Sigma-Aldrich, St Louis, MO) or 1 mL of PBS (control). After 4 h, mice were then injected intraperitoneally with 10 mL of saline and massaged for 2 min. The peritoneal lavage fluid was collected with a syringe and the neutrophil number was determined with a HEMAVET (Call et al., 2001; Ray and Dittel, 2010).

Neutrophil recruitment into the lungs was performed by intratracheal installation of LPS (2 mg/Kg). After 6 hours, mice were sacrificed, and cold saline was injected into the lungs intratracheally and then withdrawn to collect bronchoalveolar lavage fluid. This collection procedure was performed twice. Neutrophils were counted with a HEMAVET.(Reutershan, 2005).

Mouse Neutrophil Isolation

Mouse femurs and tibias from 8 to 12-week-old mice were isolated and washed with cold HBSS containing 0.5% BSA on ice. The bones were cleared of all remaining tissues and flushed with HBSS containing 0.5% BSA using 27-G needles. The pooled bone marrow eluates were gently resuspended and filtered through a 70 μm nylon cell strainer to remove cell clumps and bone particles. The filtrate was centrifuged at 1500 rpm for 5 min at 4° C. and the cell pellet was resuspended with 3 mL of HBSS containing 0.5% BSA. Cells were layered over a discontinuous gradient consisting of 3 ml of Nycoprep 1.077 underlayed with 3 ml of 72% Percoll, then centrifuged at 2500 rpm for 20 min at room temperature with slow acceleration and no brake. Neutrophils were isolated from the Nycoprep and 72% Percoll interface and washed with HBSS. After centrifuging, cell pallets were incubated with 2 mL of ACK (Ammonium-Chloride-Potassium) lysing buffer (Lonza Bioscience, Morrisville, NC) for 2 min on ice to remove the red blood cells. After the final wash with HBSS, cells were resuspended in 2 mL of 0.1% BSA-RPMI 1640 and counted. Neutrophils were incubated in a $CO_2$ incubator at 37° C. for 1 hour before the experiments.(Luscinskas, 2008; Southgate et al., 2008)

Human Neutrophil Isolation

Blood were collected from healthy donors with acid citrate-dextrose (citrate buffer containing 2% dextrose) as an anticoagulant. Human neutrophil were isolated from blood using density gradients of Percoll based isolation method with 55% and 74% Percoll. Red blood cells were lysed with RBC lysis buffer. Viability of the cells in a routine preparation was greater than 98% as determined by trypan blue exclusion.

Production of Mouse ICAM-1

293-T cells were transfected with an expression construct in the pVITRO-hygro vector (InvivoGen) consisting of the extracellular region of mouse ICAM1 (Gln28-Asn485) and 6×His tag. Transfected cells were selected by hygromycin (100 μg/ml) and maintained in a serum-free, FreeStyle™ 293 (ThermoFisher Scientific). The ICAM1-6×His fusion protein was purified from cell culture supernatant by Ni-NTA (nickel-nitrilotriacetic acid) chromatography and dialyzed with PBS (pH7.4). The ICAM1 protein concentration was determined with BCA protein assay kit (ThermoFisher Scientific).

Real Time Imaging of Neutrophil Migration

Neutrophils were isolated with mouse neutrophil enrichment kit from Stemcell Technologies Inc (Stemcell Technologies Inc., Cambridge, MA). Neutrophils were plated onto Ibidi chemotaxis chambers precoated with appropriate ligand (Ibidi, Fitchburg, WI). Experiments were conducted according to manufacturer's instruction(Weckmann et al., 2017). Chemoattractant (1 mM fMIVIL (SEQ ID NO: 46)) were loaded to the left side inlet to induce chemotaxis. Neutrophil migration was observed using a Meta 710 BIG microscope with 5% $CO_2$ at 37° C. Data were collected according to Ibidi's instruction. Velocity, distance and Euclidean distance were analyzed using the Image J and R script. (Kroon et al., 2018; RStudio Team, 2020)

Transwell Migration Assay

Confluent endothelial cells grown on transwell inserts with 3 μm pore size (Corning, Lowell, MA) were treated with 10 ng/mL of TNF-α and 10 ng/mL of IFN-γ for 4 hours and then used for neutrophil transendothelial cell migration experiments. For the non-endothelial mediated migration assay, ICAM1 or fibrinogen were coated on transwell inserts overnight at 4° C. The insert was then washed with PBS twice. Neutrophils in 0.1% BSA-RPMI 1640 medium were seeded on the upper chamber of the insert and allowed to migrate toward the lower chamber containing the indicated concentration of formyl peptide (fMIVIL (SEQ ID NO: 46)) for 4 h in a $CO_2$ incubator at 37° C. (Nuzzi, Paul; Lokuta, Mary; Huttenlocher, 2007; Southgate et al., 2008)

Peptide Inhibitor

Myristoylated peptides MB2mP6 (Myr-FEKEKL (SEQ ID NO: 27)) and control peptide (Myr-FKKEKL (SEQ ID NO: 49)) were synthesized and purified in the Research Resources Center of the University of Illinois at Chicago. The micellar peptide formulation was prepared as described previously. (Shen et al., 2013) The micellar peptides were resuspended in RPMI 1640 culture medium or HBSS.

Neutrophil Spreading Area Quantification

Cells spreading area was measured using Image J. Images were adjusted via brightness and contrast to enhance the visibility of the edge of cells. All cells were observed individually to determine if they have membrane ruffles. (FIG. 5B. top right image presented ruffled cells and lower right image presented non ruffled cells)

Neutrophil Migration Towards Chemoattractant in Migration Chamber

Live Cell Imaging

The center channel of ibidi μ-Slide Chemotaxis chamber (ibidi USA, Inc, Fitchburg, WI) were precoated with 10 μL of 10 μg/mL purified ICAM1 (expressed in 293T cells) in PBS for 1 hour at 37° C. Mouse neutrophils were isolated with HBSS (5.33 mM KCl, 0.44 mM $KH_2PO_4$, 4.16 mM $NaHCO_3$, 137.93 mM NaCl, 0.34 mM $Na_2HPO_4$, 5.55 mM D-Glucose, pH7.4, Gibco) and diluted to $10\times10^6$ cell/mL. The side chambers of ibidi g-Slide Chemotaxis chamber were filed with 70 µL RPMI (2 g/L sodium bicarbonate, 2 g/L glucose, 5 mg/L phenol red, 6 g/L NaCl, 2 g/L $NaHCO_3$, 1.512 g/L $Na_2HPO_4$, 400 mg/L KCl, 100 mg/L MgSO4, 100 mg/L $Ca(NO_3)2$, Sigma) with 10 µM HEPES (N-2-Hydroxyethylpiperazine-N-2-Ethane Sulfonic Acid, ThermoFisher Scientific) and non-essential amino acids (0.1 mM glycine, 0.1 mM L-alanine, 0.1 mM L-asparagine, 0.1 mM L-aspartic acid, 0.1 mM L-Glutamine, 0.1 mM L-proline, and 0.1 mM serine, ThermoFisher Scientific) and 10% FBS. 10 mL of neutrophil cells were loaded from the center bottom inlet (inlet A) into the center channel with all other inlets plugged to avoid cells leakage from the observation chamber between A and B (Supplemental Figure I). The ibidi chamber (Weckmann et al., 2017) were then kept in the 37° C. incubator for 15 minutes to allow cell adhesion. N-formyl-Met-Ile-Val-Ile-Leu (fMIVIL (SEQ ID NO: 46))) (Southgate et al., 2008) from *L. monocytogenes* (1 µM) in RPMI medium that were added into lower left side chamber (inlet C) according to ibidi, Inc's recommendation and imaging position were set using Zen software (Carl Zeiss Microscopy GmbH, Germany). The video was recorded every 30 seconds and convert to tiff images for image quantification.

Cell Tracking

The pixel size was set to be 0.55 $\mu m^2$/pixel using Zen software. The tiff images were tracked using image J manual tracking. The migration distance for each cell were calculated by multiplying pixel with 0.55 µm. Cell traces are shown in Supplemental Videos.

Cell Migration Pattern (Accumulated Distance, Euclidean Distance, and Velocity)

The cell position X and Y were determined using Image J manual track and the cell migration distance were calibrated using pixel/µm value. Accumulated distance was determined from an accumulation of individual distance in each 30 seconds. Euclidean distance was calculated using the initial and final position of each cell. Velocity were calculated by Euclidean distance divide by migration time.

Directions of Cell Migration

Cell position were determined using Image J manual track. Position data were adjusted to real distance (0.55 $\mu m^2$/pixel). Cell position were adjusted that the initial position where X=0 and Y=0. Movement and directions of movements were determined by comparing the final position versus the initial position. Initial X position, Xf: final X position, Yi: initial Y position, Yf: final Y position. Cells moving toward the chemoattractant are defined by $Xf-Xi<0$ (cell toward) and $Xf-Xi>0$ (cell away). The percentage of each type of cells going toward and away the chemoattractant were divided by total moving cells (combine cell toward and cell away). The directions of cell migration were also presented using Roseplot, in which number of cells migrated into 12 segments surrounding 0 position were quantified. Rose plot figures were calculated and plotted with R studio (RStudio Team, 2020).

Statistics

For parametric data, statistical significance was analyzed using Student's t-test or ANOVA. For nonparametric data, statistical significance was determined using Mann-Whitney test. Fisher exact test was performed for sample size estimation. Survival analysis was performed using Graphpad software with Kaplan-Meier method. P-value <0.05 was considered as significant.

Example 1: High-Loading ExE Peptide Nanoparticles as a New Anti-Platelet Drug

The $G\alpha_{13}$-binding ExE motif of $\beta_3$ cytoplasmic domain (FEEERA (SEQ ID NO: 6)) selectively mediates outside-in signaling and occlusive thrombosis (21). However, it is a challenge to efficiently deliver a synthetic ExE motif peptide, mP6, in vivo into cells for therapeutic use. Although liposomes or lipid micelles can be used to deliver peptides in vivo, low concentrations of peptide incorporation into liposomes/lipid micelles make it difficult to achieve efficacious doses for clinical use, with the exception for few extremely high affinity drugs. In these studies, only 1 mM mP6 concentration (<4% of total molar content) in the lipid micellar suspension was achieved. This concentration is not practical for clinical uses.

To efficiently deliver the ExE motif peptides into cells in vivo and thus translate the new concept into a clinically usable drug, novel lipid-stabilized, high-loading peptide nanoparticles were developed. The main component of HLPN is an amphiphilic peptide (or a peptide conjugated to a lipid or a hydrophobic molecule), which is capable of self-assembling to form micellar nanoparticle-like structures (although unstable). The peptide micellar nanoparticles are stabilized by a low percentage of phosphatidylcholine and protected by 1,2-Distearoyl-sn-glycero-3-phosphoethanolamine (DSPE)-attached polyethylene glycol (PEG) forming the hydrophilic outer layer (FIG. 1A). A re-engineered mP6 was developed to enhance its incorporation of into HLPN. The new peptide, M3mP6 (Myr-FEEERL (SEQ ID NO: 25)) contains the critical ExE motif, and its N-terminal phenoalanine is attached to a myristoyl group. The C-terminal alanine was changed to a leucine with a long hydrophobic side chain, which helped packing higher concentrations of the peptide together with lipids into nanoparticles (FIG. 1B). This peptide retains the function of mP6 to inhibit $G\alpha_{13}$-$\beta_3$ interaction as indicated by co-immunoprecipitation (FIGS. 1C and 1D). The M3mP6 HLPN achieves a high M3mP6 peptide loading reaching >80% of total nanoparticle (mol/mol) and a high peptide concentration of >10 mM in injectable suspension (>10 times more concentrated than the original lipid micelles formulation of mP6 (21)).

As analyzed by dynamic light scattering (DLS), the vast majority (99.8-100%) of these lipid-stabilized, PEG-coated M3mP6 HLPN have the average size ranging between 6 nm to 20 nm (in different preparations) with occasional appearance of very small populations (0-0.2%) with larger diameters (~50-500 nm) (FIG. 1E). The lyophilized powder of M3mP6 is readily dissolvable in physiological saline for I.V. injection, and is stable for more than 18 months with the similar DLS profile and pharmacological effect when stored at −20° C., and for at least 2 weeks at room temperature (22° C.) (FIG. 18A-18F).

Figure 2D:
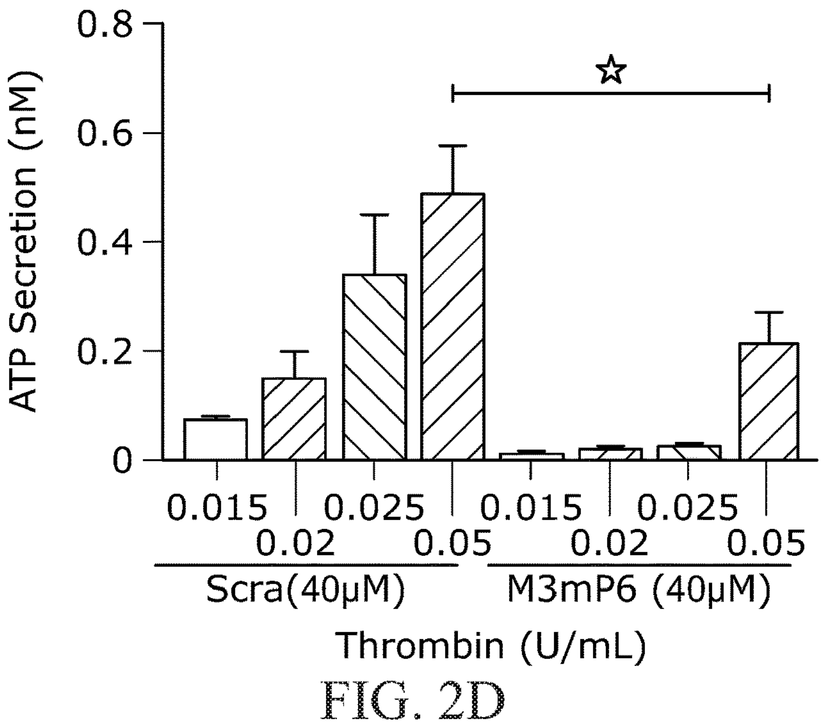

Acute MTD (maximal tolerated dose) studies in mice showed no signs of toxicity after one bolus injection of up to 60 mg peptide/kg (~60 µmol/kg). Further toxicity studies in rats reveals MTD exceeds 100 mg peptide bolus (80× converted efficacy dose), and rats exhibited no observable toxic reaction to M3mP6 HLPN after 5-day continuous infusion at 150 mg/kg/day. M3mP6 HLPN dose-dependently inhibited human platelet granule secretion and secretion-dependent secondary platelet aggregation induced by low dose thrombin in vitro (FIGS. 2A and 2B), but had no effect on platelet aggregation induced by high doses of thrombin (FIGS. 2C and 2D), although platelet granule secretion was still partially inhibited by M3mP6 even at higher thrombin concentrations (FIG. 2D).

Figure 2E:
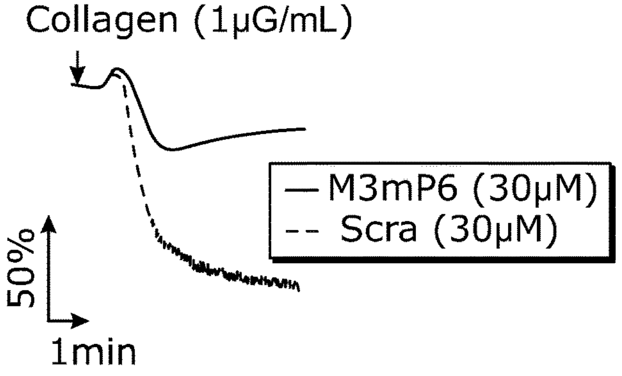
Figure 2F:
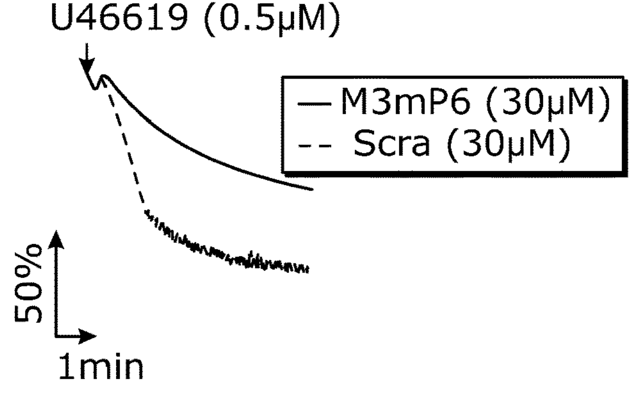
Figure 2G:
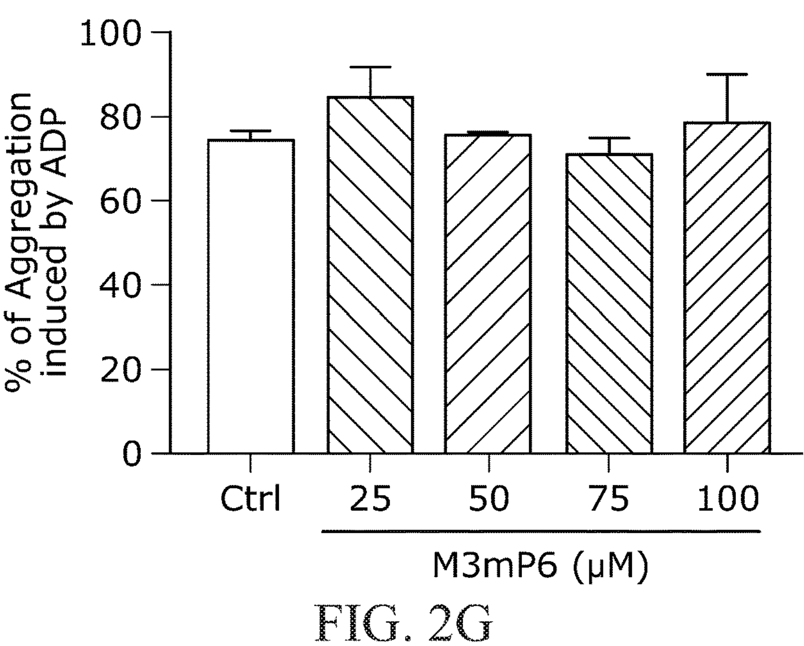
Figure 2H:
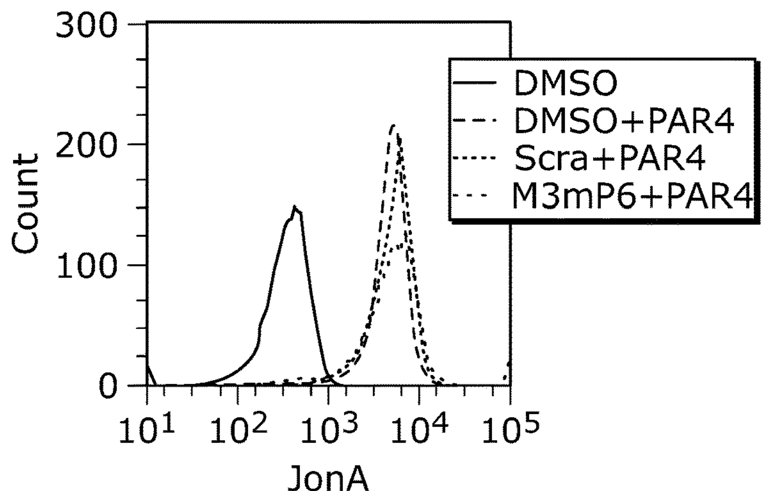
Figure 2I:
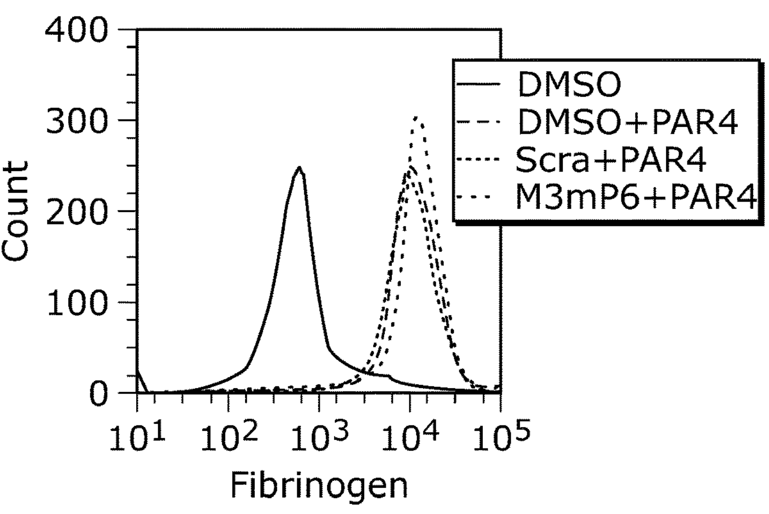

M3mP6 HLPN also partially inhibited collagen (FIG. 2E) and U46619 (thromboxane A2 analog)-induced platelet aggregation (FIG. 2F), but did not affect ADP-induced platelet aggregation (FIG. 2G), nor JonA (FIG. 2H) or fibrinogen (FIG. 2I) binding to platelets induced by PAR4 agonist peptide. These data confirm that M3mP6 does not affect inside-out signaling nor the ligand binding function of $\alpha IIb\beta 3$, but inhibits secondary platelet responses to integrin outside-in signaling.

Figure 3A:
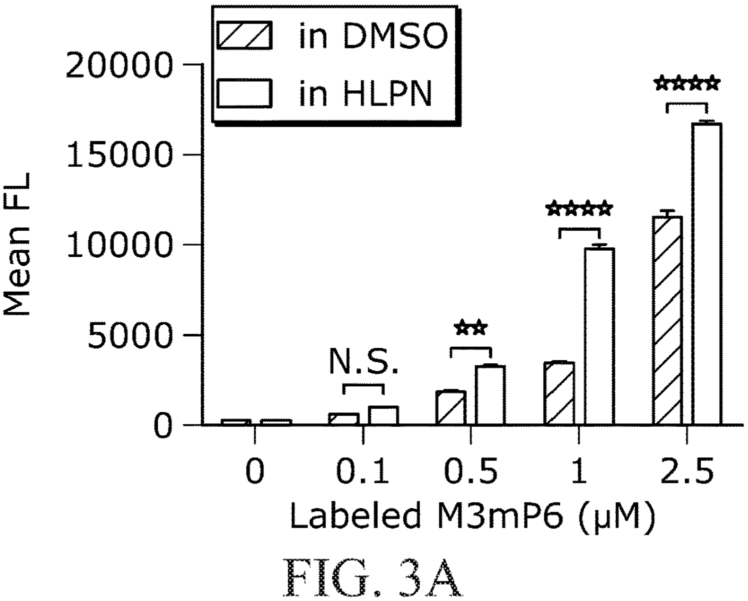
Figure 3B:
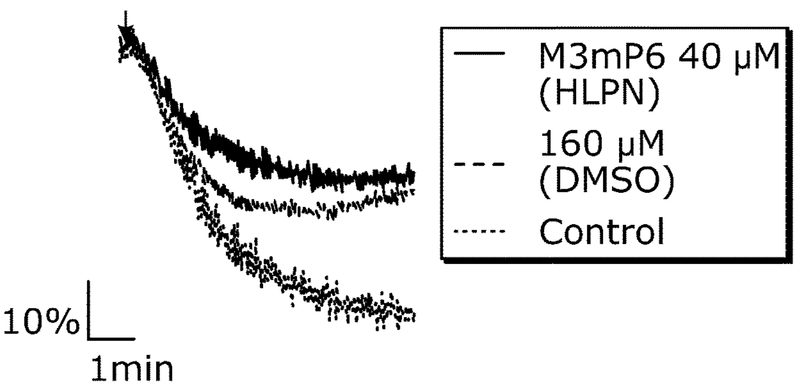
Figure 3C:
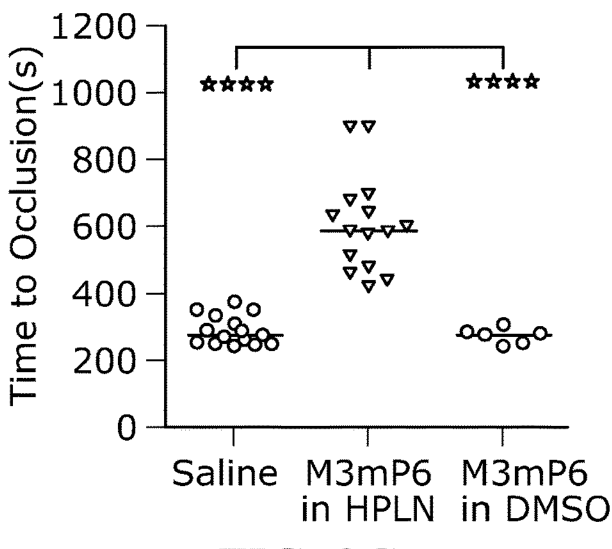
Figure 20A:
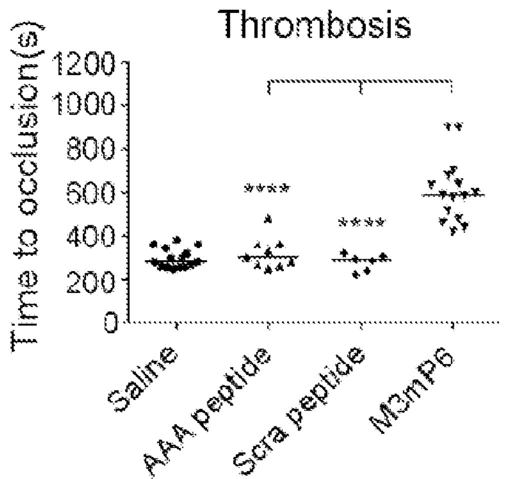
FIGS. 20A-20B show a comparison of the effects of M3mP6 HLPN, scrambled control peptide (Scra) HLPN, AAA mutant peptide (Myr-FAAARL (SEQ ID NO: 43)) HLPN and physiological saline solution on 7.5% $FeCl_3$-induced carotid artery thrombosis (FIG. 20A) and tail bleeding time (FIG. 20B). (saline: n=15, AAA: n=9, scrambled: n=6, M3mP6: n=15). **** p<0.0001.
Figure 20B:
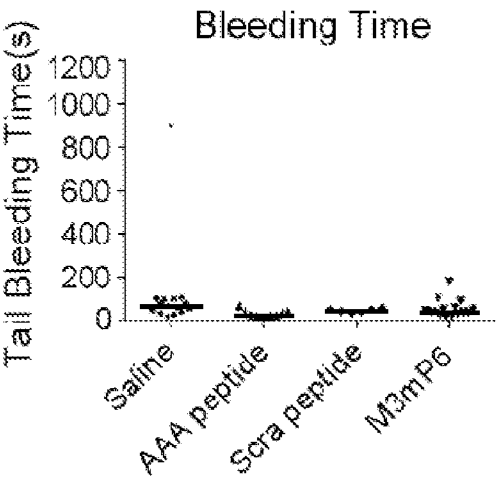
Figure 21:
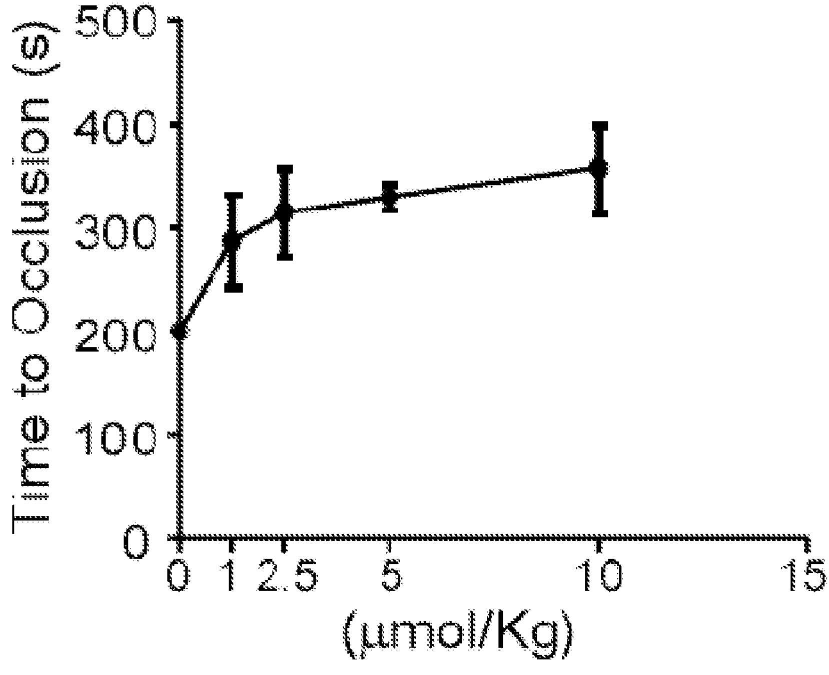
Figure 22:
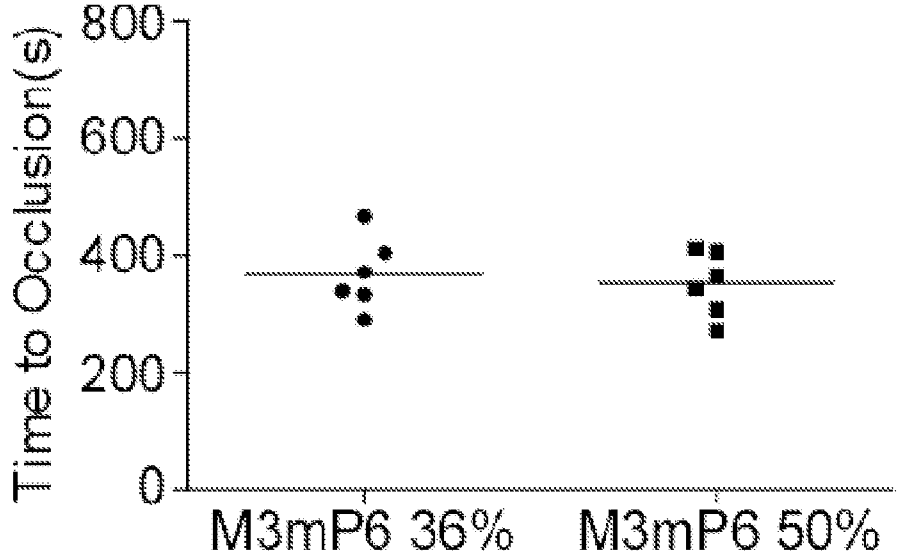
FIG. 22 shows a comparison of effects of 50% vs 36.8% M3mP6 HLPN on $FeCl_3$-induced thrombosis. Comparable anti-thrombotic effects of HLPN composed of 50% (mass/mass) M3mP6 peptide, 40% DSPE-PEG and 10% PC (5 μmol/kg peptide injected) with HLPN composed of 36.8% M3mP6, 51.7% DSPE-PEG and 11.5% PC (5 μmol/kg peptide injected) using $FeCl_3$-induced carotid artery thrombosis model. (n=6).

Fluorescence microscopy of fluorescently labeled M3mP6 demonstrated that M3mP6 HLPN entered platelets after incubation (FIG. 19). When compared with identical concentrations of M3mP6 solubilized in DMSO, significantly increased amount of fluorescent M3mP6 HLPN enters platelets as analyzed using flowcytometry (FIG. 3A). Consistently, only ¼ concentration of M3mP6 in HLPN is required to achieve a comparable inhibitory effect on platelet aggregation as compared to the same peptide dissolved in DMSO (FIG. 3B), suggesting superior intracellular delivery. Importantly, the DMSO-dissolved M3mP6 peptide had no in vivo effect on arterial thrombosis (FIG. 3C). In contrast, M3mP6 HLPN dose-dependently inhibited occlusive thrombosis using a robust $FeCl_3$-induced carotid artery thrombosis model in mice (FIG. 3C, 3D, See FIGS. 20A-20B for comparison with negative control peptides), suggesting the protective effect of the HLPN on peptide viability in vivo. An anti-thrombotic effect of M3mP6 HLPN was observed at doses above 2.5 μmol peptide/kg when administered by retro-orbital injection (FIG. 3D), and 1.25 μmol/kg with tail vein injection (FIG. 21). The HLPN containing 50% (mass/mass) M3mP6 peptide has a similar anti-thrombotic effect to HLPN containing 36% M3mP6 when identical amount of peptide (5 μmol/kg) was injected, confirming that peptide concentrations but not changes in formulation determined the anti-thrombotic effects (FIG. 22). Pharmacokinetic studies indicate that blood and plasma levels of M3mP6 reach maximum within 10 minutes at 59.63 ng/ml in plasma (FIG. 3E) and 33.36 ng/ml in whole blood (FIG. 3F) following intravenous injection of 5 mg/kg M3mP6 (5 μmol/kg) with $t_{1/2-\lambda z}$=2.46 hour (FIG. 24). Consistently, the anti-thrombotic effect of M3mP6 was demonstrated 5 minutes after injection, and lasted until about 45 minutes after injection (FIG. 3G). This window of efficacy is longer than the current intravenous anti-platelet drugs cangrelor and eptifibatide. Rat 5-day infusion study showed a $t_{1/2-\lambda z}$ (half-life after cessation of infusion) of 3.1 (male) and 3.7 (female) hour (See FIG. 24 for PK characteristics). Thus, M3mP6 HLPN is a fast-acting and reversible anti-platelet drug suitable for i.v. injection, and if needed, its therapeutic effect can be prolonged with continuous infusion.

Example 2: M3mP6 HLPN has Superior Anti-Thrombotic Effect as Compared to High Doses of Aspirin but does not Cause Bleeding A robust $FeCl_3$-induced mouse carotid artery thrombosis model was used to compare M3mP6 HLPN with aspirin in inhibiting occlusive thrombosis. Mouse models were used because the $\beta_3$ cytoplasmic domain is identical between humans and mice. In this model, following injury induction by 3-minute contact with a 2 mm diametral filter paper soaked with 1.2 μl of 7.5% $FeCl_3$, wild type C57BL/6 mice had a median time of 199 seconds to form stable occlusive thrombosis as determined by ultrasound Doppler blood flow probe. Formation of a stable occlusive thrombus was significantly delayed by one-time bolus injection of M3mP6 HLPN (5 or 10 mol/kg, 15 min before procedure, retro-orbital) as compared with normal control (FIG. 4A). In contrast, tail bleeding time of M3mP6 HLPN-treated mice (10 μmol/kg) was not significantly different from control group (FIG. 4B). Occlusion time in aspirin-treated mice (4.3 mg/kg, 2 hours prior to the procedure, oral) in this potent thrombosis model as well as tail bleeding time was not significantly different from normal control (FIGS. 4A and 4B). To exclude the possibility of insufficient aspirin dosing, the effect of a very high dose of aspirin (36 mg/kg, i.p., 1 hour prior to experiments) on thrombus formation and hemorrhage was also tested. This dose of aspirin still had no significant effect on the occlusive thrombus formation under this robust thrombotic condition (FIG. 4C), but dramatically increased tail bleeding time (FIG. 4D). These effects contrasted with M3mP6 HLPN (5 μmol/kg), which significantly inhibited occlusive thrombosis but did not affect tail bleeding time (FIGS. 4C and 4D). Combination use of 5 μmol/kg M3mP6 HLPN together with 36 mg/kg aspirin was similar to M3mP6 HLPN alone in significantly inhibiting thrombosis (FIG. 4C) and was similar to aspirin alone in tail bleeding time (FIG. 4D). Thus, M3mP6 HLPN is clearly superior to aspirin in inhibiting $FeCl_3$-induced arterial thrombosis without causing hemorrhage.

Example 3: Comparative and Synergistic Effects of M3mP6 HLPN with Oral P2Y12 Inhibitors on Thrombosis and Hemostasis The anti-thrombotic effect of M3mP6 HLPN was compared with P2Y12 antagonist clopidogrel, which is a current standard of care anti-platelet drug more potent than aspirin. One-time oral administration of the loading dose of clopidogrel (4 mg/kg, 2 hours prior to procedure) caused a moderate but significant delay in occlusive thrombus formation following $FeCl_3$-induced injury. This dose of clopidogrel, however, was significantly less effective than M3mP6 HLPN in inhibiting $FeCl_3$-induced occlusive thrombosis (FIG. 5A). The anti-thrombotic effect of M3mP6 HLPN was compared with the more potent direct oral P2Y12 antagonist, ticagrelor, which does not require hepatic conversion. One-time injection of M3mP6 HLPN had similar anti-thrombotic effects to one-time ingestion of high dose ticagrelor (3 mg/kg, 2 hours, oral) (FIG. 5A). Thus, M3mP6 HLPN, is similar to the potent P2Y12 inhibitor ticagrelor in inhibiting occlusive thrombosis in vivo. Importantly, it was further demonstrated that the median occlusion time in mice treated with M3mP6 HLPN together with clopidogrel or ticagrelor was significantly longer than that of mice treated with each of the drugs alone, and was longer than the additive median occlusion time of M3mP6 HLPN plus clopidogrel or M3mP6 HLPN plus ticagrelor (FIG. 5A). These data suggest that M3mP6 HLPN has synergistic effects with clopidogrel and ticagrelor in inhibiting thrombosis.

P2Y12 receptor inhibitors have been shown to cause excessive bleeding. Indeed, clopidogrel and ticagrelor caused dramatically prolonged tail bleeding time in mice (FIG. 5B) as compared to controls, in contrast to normal bleeding time in M3mP6 HLPN-treated mice (FIG. 5B). Additionally, the bleeding times in mice treated with M3mP6 HLPN in combination with clopidogrel or ticagrelor were similar to that of mice treated with one of the P2Y12 receptor inhibitors alone (FIG. 5B). However, because tail bleeding time analysis was terminated at 900 sec, and high concentrations of clopidogrel or ticagrelor used already caused dramatically increased bleeding, near the maximum limit of the assay, whether M3mP6 HLPN in combination with P2Y12 inhibitors exacerbates bleeding will be further addressed in the following sections. Taken together, these data indicate that intravenous injection of M3mP6 HLPN is superior to oral P2Y12 inhibitors in acute treatment of arterial thrombosis and in reducing bleeding risk. Importantly, M3mP6 HLPN exerts a synergistic anti-thrombotic effect when used in combination with P2Y12 inhibitors.

Example 4: Comparative and Synergistic Effects of M3mP6 HLPN with Clopidogrel Plus Aspirin on Thrombosis and Hemostasis Clopidogrel in combination with aspirin is the recommended anti-platelet treatment for patients with coronary heart disease (CHD). Thus, the comparative and synergistic effects of treatment with M3mP6 in combination with clopidogrel plus aspirin were investigated. One-time oral administration of a loading dose of clopidogrel in combination with aspirin had a similar antithrombotic effect to clopidogrel alone, and was significantly less effective in inhibiting occlusive thrombosis than one-time M3mP6 HLPN injection alone (FIG. 5C). M3mP6 HLPN in combination with aspirin and clopidogrel had significantly enhanced anti-thrombotic effect as compared to clopidogrel in combination with aspirin (FIG. 5C), but was similar to the anti-thrombotic effect of M3mP6 HLPN in combination with clopidogrel in the absence of aspirin (FIG. 5A). In tail bleeding time analysis, clopidogrel plus aspirin had significantly increased bleeding time compared to normal controls or to M3mP6 HLPN alone (FIG. 5D), again highlighting the benefit of M3mP6 HLPN in reducing bleeding risk.

Figures 6A, 6B, 6C, 6D, 6E, 6F:
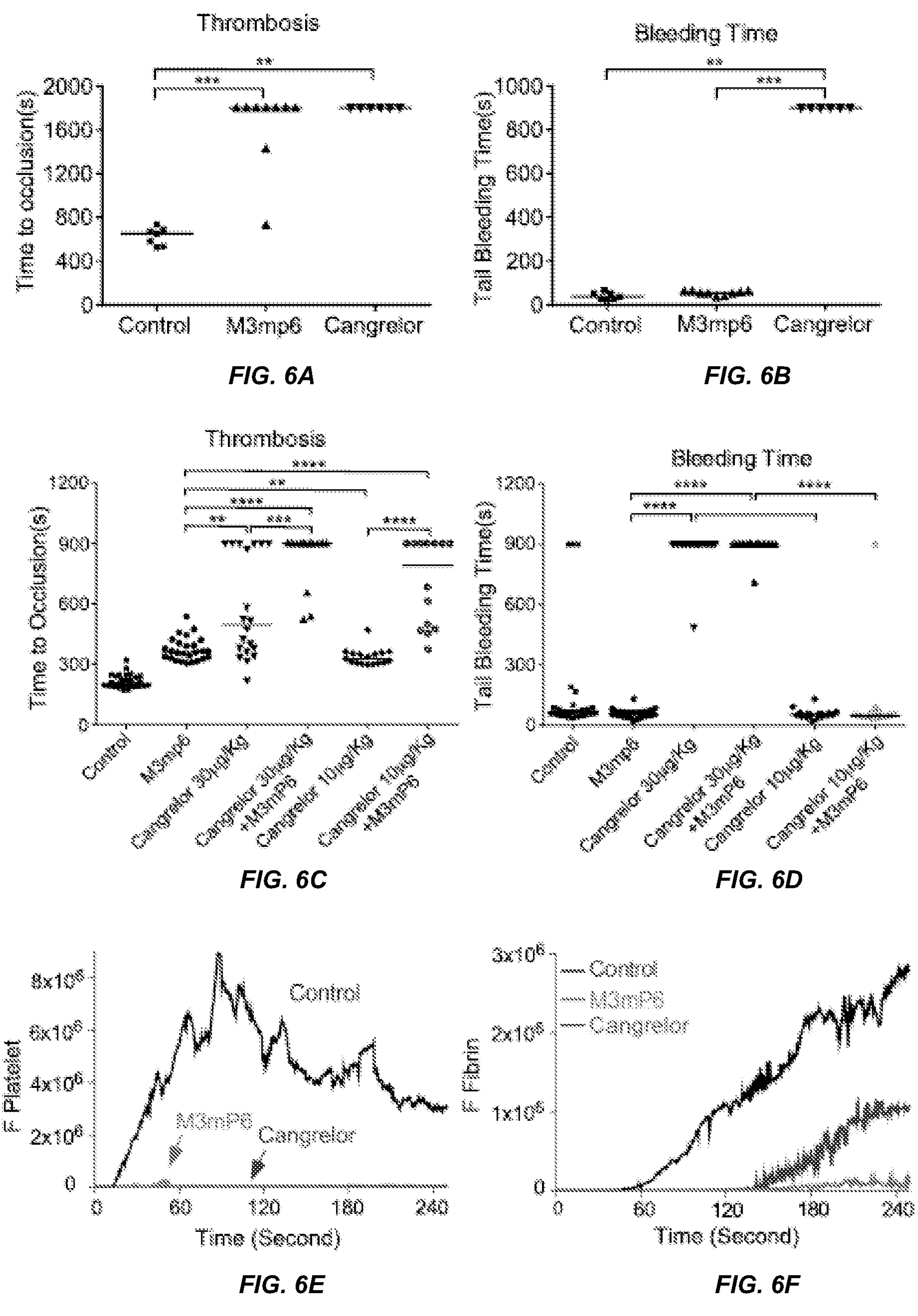
FIGS. 6A-6F show the comparative effects of M3mP6 HLPN with cangrelor on thrombosis, hemostasis, platelet thrombus formation and clotting, and their synergistic anti-thrombotic effects.
Figure 23A:
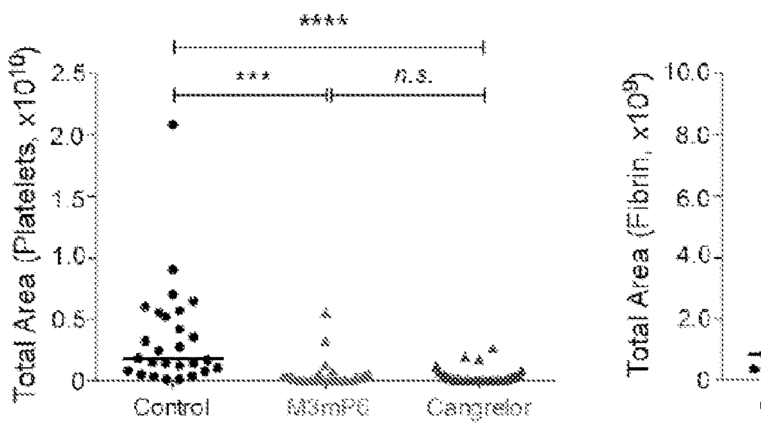
FIGS. 23A-23B show a comparison of platelet thrombus formation and fibrin generation in mice treated with 10 μmol/kg M3mP6 HLPN and with 30 μg/kg cangrelor in laser injury-induced cremaster arteriolar thrombosis model in vivo. The median of the total fluorescence detected over time for platelets (FIG. 23A) or fibrin (FIG. 23B) in total 27 injuries. * p<0.05,  p<0.01, * p<0.001, **** p<0.0001.

Example 5: Comparison and Synergism Between M3mP6 HLPN and the Intravenous P2Y12 Inhibitor Cangrelor More recently, a new intravenous direct P2Y12 inhibitor, cangrelor was approved by the FDA for acute anti-thrombosis treatment. Cangrelor has a faster and more potent anti-thrombotic effect than oral P2Y12 inhibitors, but also significantly causes more severe bleeding (23, 24). The acute anti-thrombotic effect of cangrelor was compared with M3mP6 HLPN under experimental conditions mimicking thrombotic emergency, when the drugs were retro-orbitally injected after the initiation of carotid arterial thrombosis. There was no statistical difference between M3mP6 (10 μmol/kg) and the loading dose cangrelor (30 μg/kg) in their anti-thrombotic effect under these conditions (FIG. 6A). However, this concentration of cangrelor but not M3mP6 caused significant bleeding with tail bleeding analysis (FIG. 6B). Furthermore, when preinjected intravenously, M3mP6 HLPN (10 μmol/kg) is not significantly different from the loading dose cangrelor (30 μg/kg) in completely inhibiting thrombus formation using the laser-induced mouse cremaster arteriolar thrombosis model (FIG. 6E and FIG. 23A). The effect of injecting M3mP6 HLPN was compared with the loading dose cangrelor in preventing occlusive carotid artery thrombosis induced by higher concentrations of $FeCl_3$. Under this condition, the effect of one-time injection of the maximal loading dose of cangrelor (30 μg/kg, retro-orbital) on occlusive thrombosis had broad variations in different individual mice or experiments. In the majority of mice tested, the effect on vessel occlusion was similar to M3mP6 HLPN. However, a small population of mice treated with cangrelor showed much longer occlusion time (FIG. 6C). Thus, the overall effect of cangrelor was moderately but significantly better than M3mP6 HLPN (FIG. 6C). However, cangrelor treatment dramatically increased tail bleeding time, in contrast to M3mP6 HLPN's no effect on bleeding (FIG. 6D). M3mP6 HLPN in combination with cangrelor showed significantly longer median occlusion time than M3mP6 HLPN or cangrelor alone (FIG. 6C), and was longer than the additive effects of M3mP6 HLPN and cangrelor, suggesting a synergism between M3mP6 HLPN and cangrelor, which significantly enhances anti-thrombotic efficacy.

Figure 23B:
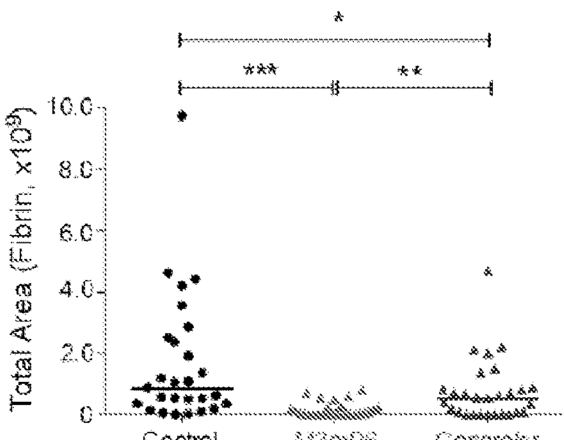

Example 6: Comparative Effect of M3mP6 HLPN and Cangrelor on Intravascular Coagulation Using Laser-Induced Cremaster Arteriolar Thrombosis Model in Mice It was recently shown that outside-in signaling plays an important role in not only platelet thrombus formation but also intravascular coagulation under flow shear, an important aspect of thrombosis (25). This result is in contrast to the previous reports demonstrating the lack of effect of current anti-platelet drugs on intravascular coagulation (26, 27). Thus, the effect of M3mP6 HLPN on platelet thrombus formation and intravascular coagulation in comparison with cangrelor using the laser-induced cremaster arterial thrombosis model was evaluated. Whereas the two drugs have similarly potent effects in inhibiting platelet thrombus formation (FIG. 6E), M3mP6 HLPN almost completely inhibited intravascular fibrin clot formation at the site of vascular injury, whereas cangrelor only has moderate effect (FIG. 6F and FIG. 23B). Thus, M3mP6 HLPN is not only effective in inhibiting thrombus formation but also in inhibiting intravascular coagulation in vivo, and this effect is significantly superior than the most potent P2Y12 inhibitor cangrelor.

Example 7: Synergistic Anti-Thrombotic Effect without Excessive Bleeding Using Combination of M3mP6 HLPN with Low Dose Cangrelor These data demonstrates that the maximal clinical dose of cangrelor had potent anti-thrombotic efficacy (FIG. 6A), but also dramatically increased hemorrhage, which contrasted M3mP6 HLPN's selective effect on thrombosis (FIG. 6B). These data also demonstrated that M3mP6 HLPN in combination with this high dose of cangrelor significantly enhanced anti-thrombotic efficacy compared to high dose cangrelor alone (FIG. 6C), but appears to have a similar adverse effect on bleeding as cangrelor alone (FIG. 6D). Thus, it was hypothesized that the combination of M3mP6 HLPN with low dose cangrelor may synergistically enhance anti-thrombotic efficacy but reduce the adverse effects on bleeding caused by high dose cangrelor. Indeed, when M3mP6 HLPN was used in combination with low dose cangrelor (10 μg/kg), the anti-thrombotic effect was significantly greater than even the maximum clinical dose of cangrelor (FIG. 6C); however, hemorrhage was significantly reduced (FIG. 6D). Thus, M3mP6 HLPN used together with low-dose cangrelor would be an optimal choice for acute anti-thrombotic treatment due to its powerful anti-thrombotic therapeutic effect and reduced bleeding risk.

Figures 7A, 7B, 7C:
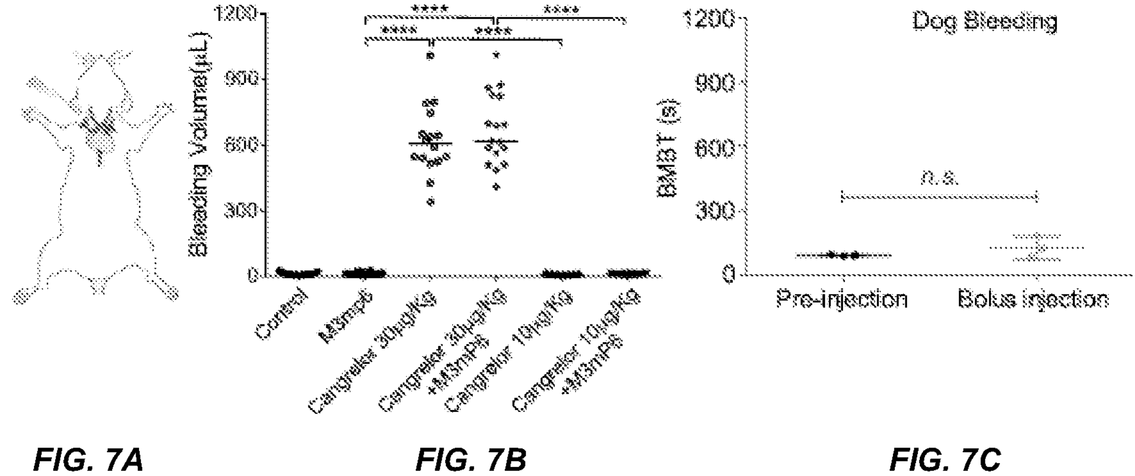
FIGS. 7A-7C shows that M3mP6 did not cause bleeding in mouse artery perforation model of surgical bleeding and dog buccal mucosal bleeding time (BMBT) test.

Example 8: Comparison of M3mP6 HLPN with Cangrelor in an Artery Perforation Model of Surgical Bleeding Clinically, the risk of hemorrhage during anti-platelet therapy is often associated with traumatic intervention, particularly intravascular intervention when perforation of a vascular wall is a necessity. To more closely mimic hemorrhage during intravascular/surgical procedures, a carotid artery perforation model of surgical hemorrhage was designed. In this model, the common carotid artery was surgically exposed, and perforated with a needle. The site of perforation was immediately covered with a hemostatic pad (CERTI-GAUZE™) to stop bleeding in a way similar to that performed during vascular intervention. Blood absorbed on the pad was eluted and quantified to indicate level of hemorrhage. In normal control, bleeding at the perforation site was quickly stopped by the hemostatic pad with the extravasation of a minimal amount of blood (FIG. 3F). The loading dose of cangrelor caused excessive bleeding from the perforated artery even when using the hemostatic pad. In contrast, M3mP6 HLPN-treated mice were not different from control mice in this surgical bleeding model (FIG. 7A), further demonstrating that M3mP6 HLPN is a safe anti-platelet drug that does not cause excessive bleeding under a condition mimicking vascular intervention. To verify that combination use of M3mP6 HLPN with P2Y12 antagonists does not exacerbate the adverse effect of a P2Y12 antagonist, M3mP6 was used in combination with high and low doses of cangrelor. There was no difference in hemorrhage as quantified by blood volume between cangrelor alone and cangrelor plus M3mP6 HLPN. Importantly, the combination of M3mP6 HLPN and low-dose cangrelor were not significantly different from normal controls in hemorrhage (FIG. 7B). These data clearly demonstrate that M3mP6 HLPN is a potent anti-platelet drug that does not cause bleeding, and M3mP6 HLPN in combination of a low-dose cangrelor minimizes bleeding risk caused by cangrelor but has superior anti-thrombotic effect compared to even the highest clinical dose of cangrelor.

Example 9: M3mP6 HLPN Did not Cause Prolonged Bleeding in Dog Buccal Mucosal Bleeding Time (BMBT) Test To determine whether M3mP6 may affect hemostasis in large animals, BMBT, a routine bleeding time test to measure the bleeding time in 3 dogs before and during M3mP6 HLPN infusion, was used. No significant differences in bleeding time were observed between pre- and post-administration of M3mP6 HLPN, both of which falls in the normal bleeding time range (<4 minutes in dogs) (FIG. 7C). These data suggest that M3mP6 HLPN does not cause excessive bleeding not only in rodents but also in dogs.

Figures 8A, 8B, 8C, 8D, 8E:
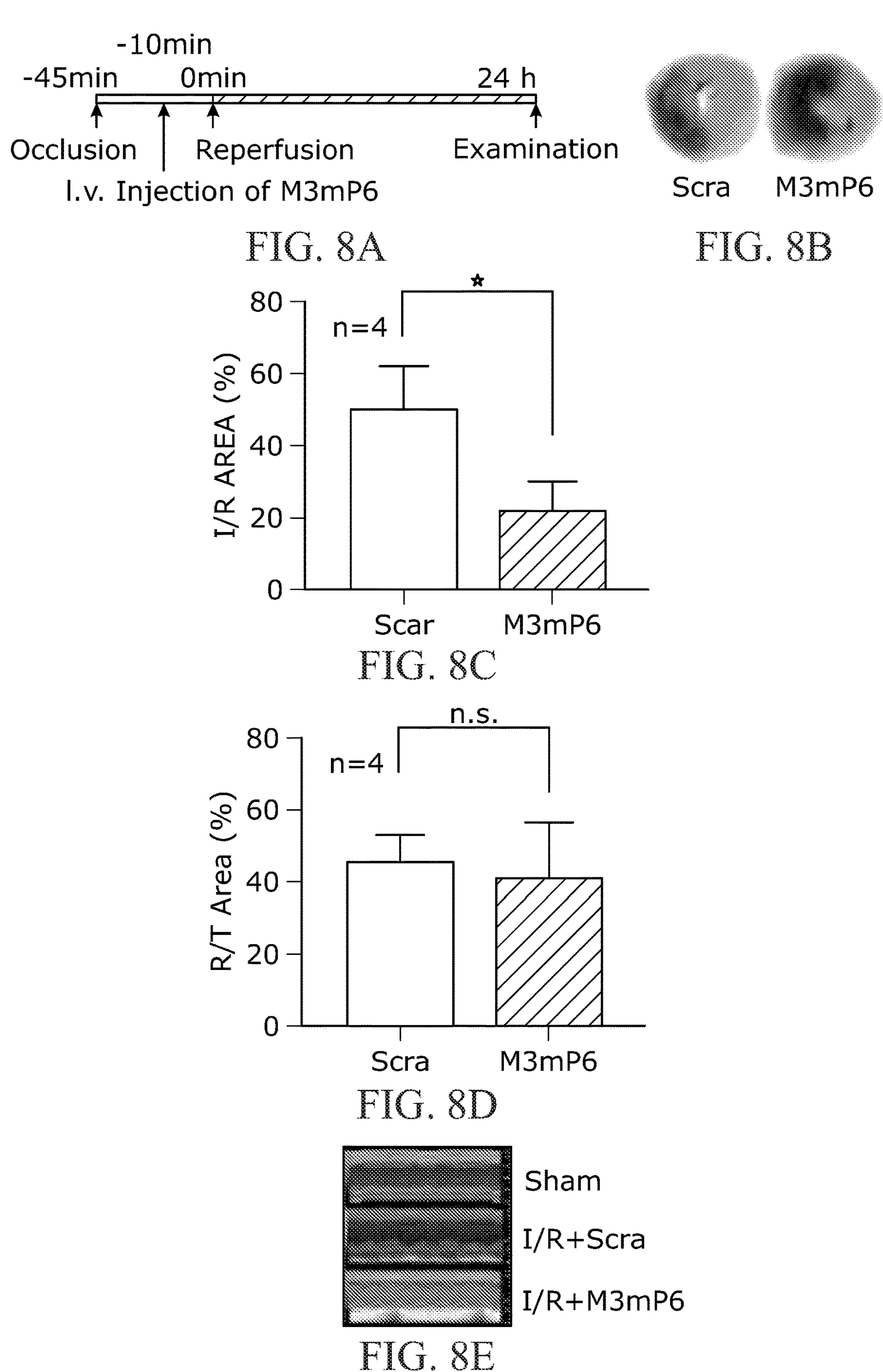
Figure 8F:
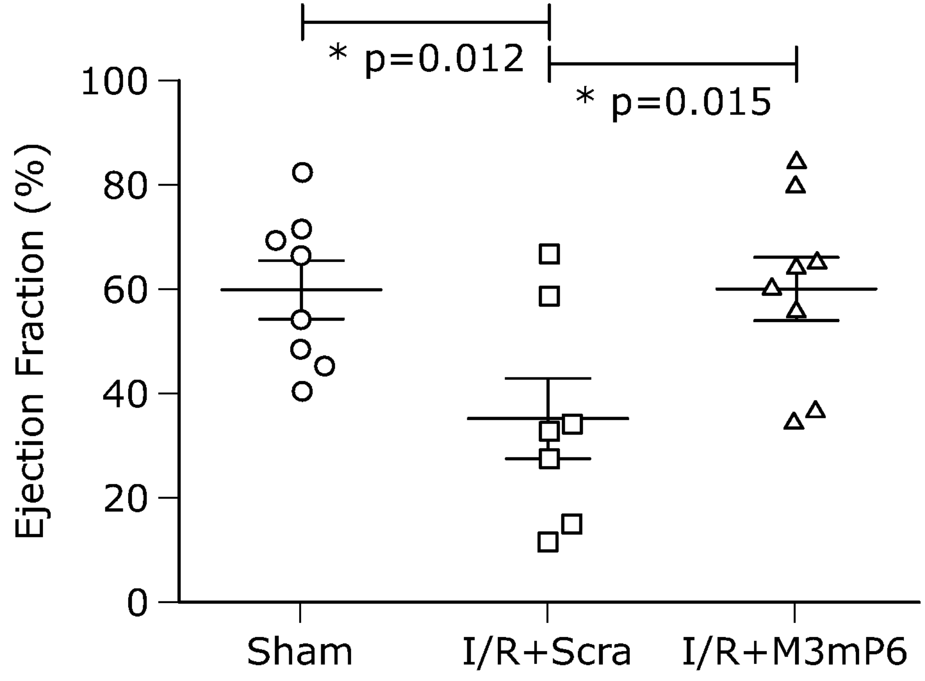
Figure 8I:
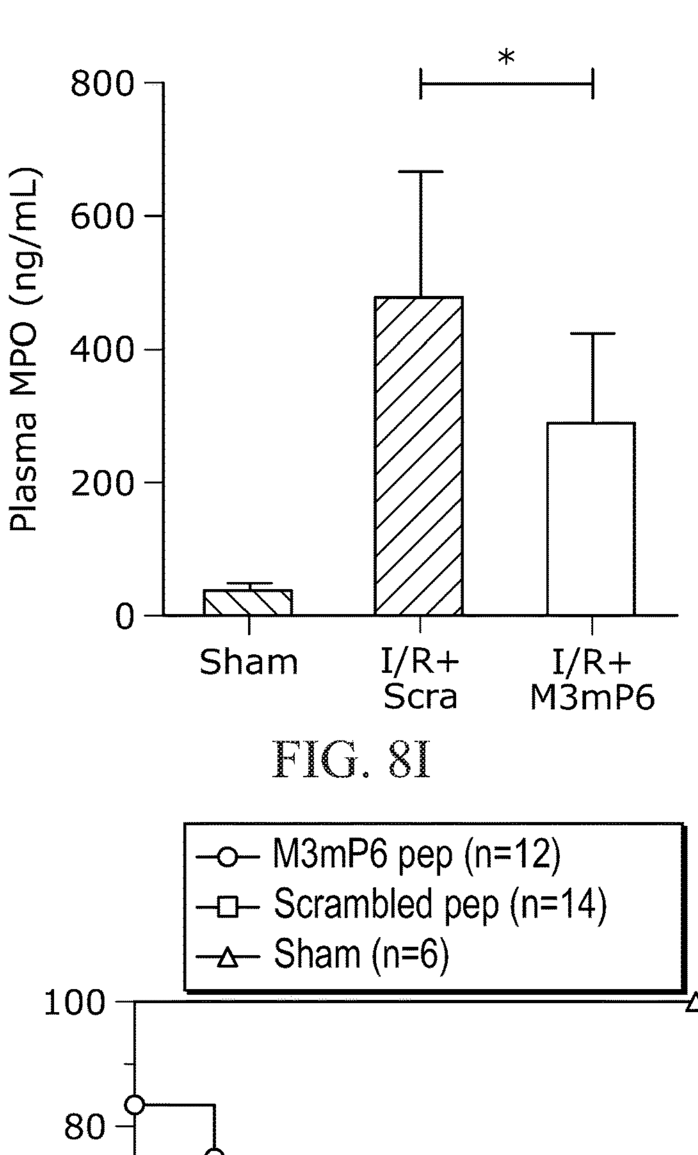
Figure 8J:
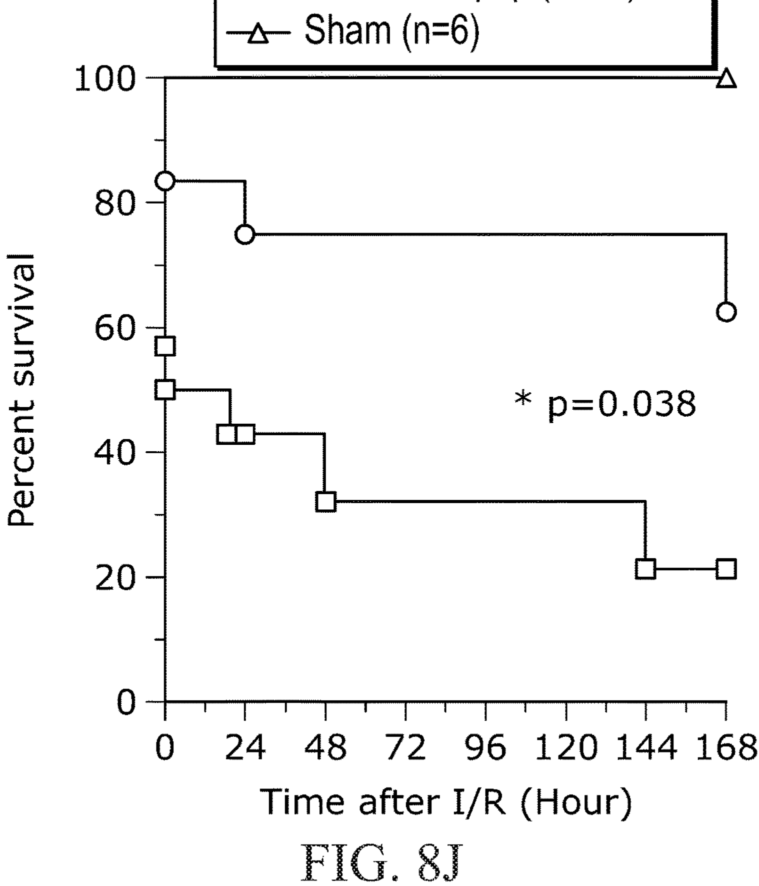
Figures 8K, 8L:
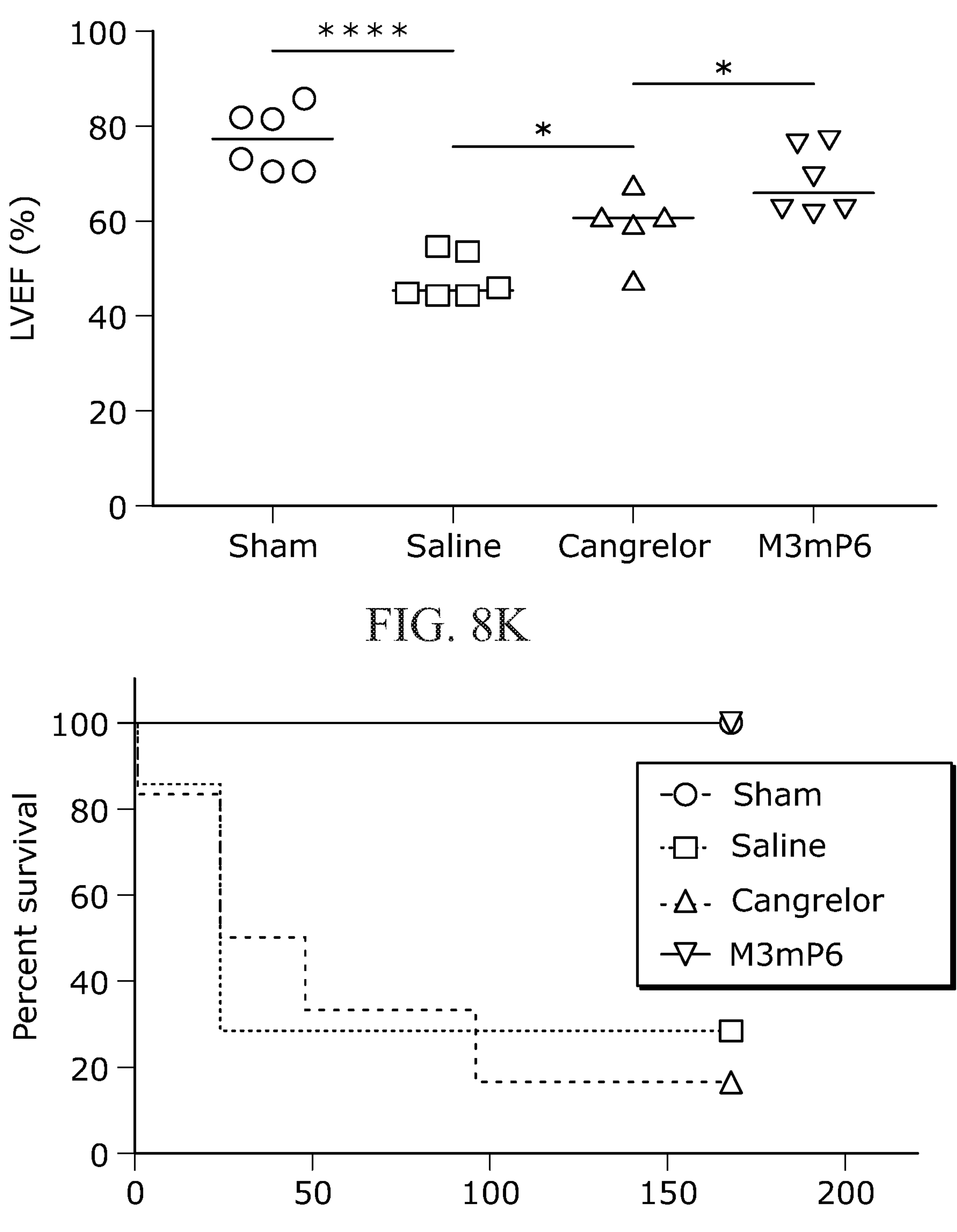

Example 10: Treatment of Myocardial Infarction-Reperfusion (MIR) Injury with M3mP6 HLPN The current prevailing treatment for myocardial infarction/ischemia (MI) is to perform surgical or percutaneous coronary interventions to physically reopen the occluded artery. Reperfusion of ischemic tissues however, may cause myocardial ischemia/reperfusion (MI/R) injury, where an acute thrombo-inflammatory reaction of the ischemically injured tissues occurs upon re-exposure to oxygenated blood, resulting in damage to cardiac function and death. To evaluate the therapeutic effect of M3mP6 HLPN in treating MI and MI/R injury under conditions mimicking the clinical process of MI, severe mouse MI was induced by ligating the left anterior descending branch (LAD) of the coronary artery for 45 minutes before reopening to allow reperfusion. To mimic clinical treatment, M3mP6 or control HLPN were post-ischemically injected 35 minutes after the induction of MI (FIG. 8A). Compared with the control group, the M3mP6 HLPN treatment group showed significantly lower infarct area/risk area ration as indicated by triphenyltetrazolium chloride (TTC)/Evans Blue staining (FIG. 8B-8D), and prevented damage of cardiac function as indicated by echo cardioagraphy performed at 24 hours after the procedure (FIG. 8E and F). Histoimmunochemistry study indicate that MI/R-induced microvascular thrombosis (FIG. 8G) and interestingly neutrophil infiltration (FIG. 8H) in the reperfused cardiac tissue was significantly reduced by M3mP6 HLPN treatment. M3mP6 also reduced plasma MPO levels (FIG. 8I), which is an indicator of neutrophil activation, in MI/R mice. Importantly, M3mP6 greatly reduced mortality rate during the 7-day post-procedure monitoring (FIG. 8J). M3mP6 was also found to improve MI/R survival rate and is significantly more effective than cangrelor in treating myocardial ischemia/reperfusion injury (FIGS. 8K-8L). These data indicate that M3mP6 is an effective treatment of MIR-induced thrombosis/inflammation and cardiac injury in the mouse model.

Figures 9A, 9B, 9C:
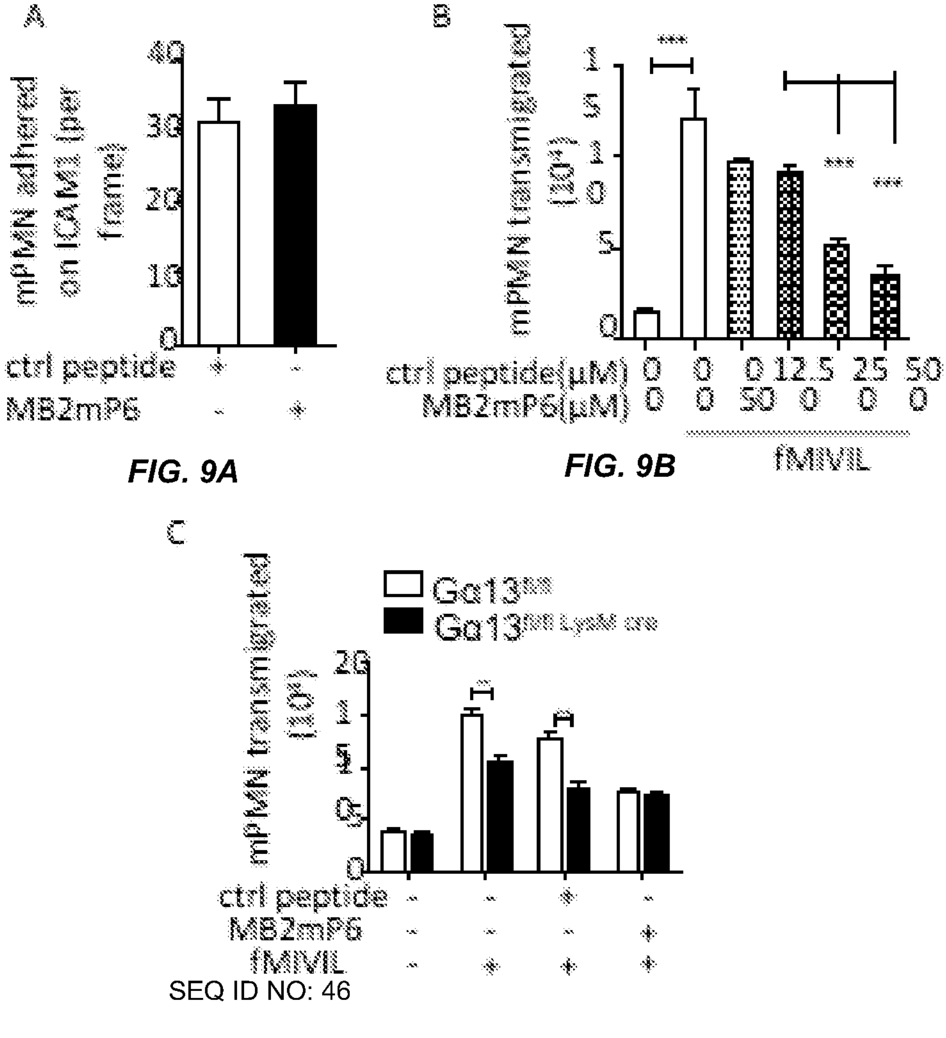
FIGS. 9A-9C shows that the EXE motif peptide MB2mP6 derived from integrin β2 cytoplasmic domain does not affect neutrphil adhesion, but inhibits neutrophil migration.
Figure 10A:
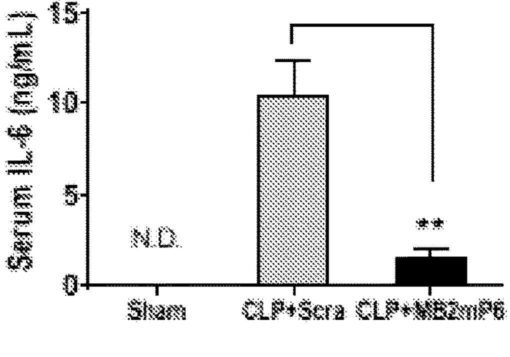
FIGS. 10A-10D shows that MB2mP6 inhibits cytokine expression in septic mice induced by CLP.
Figure 10B:
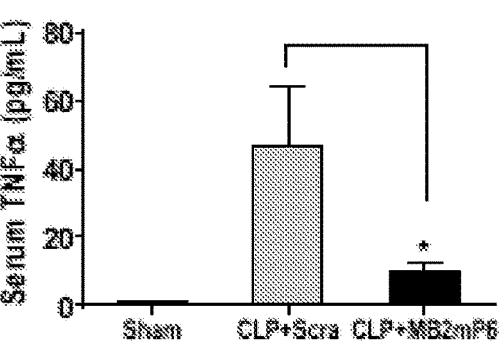
Figure 10C:
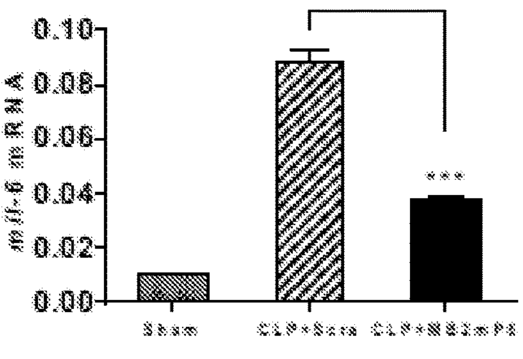
Figure 10D:
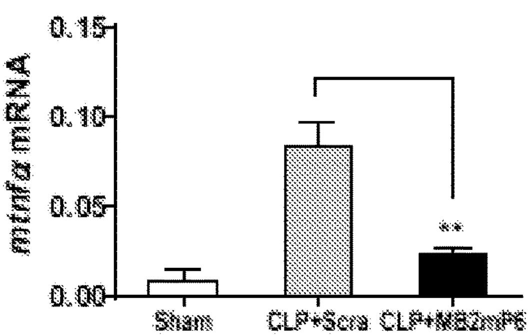
Figure 11:
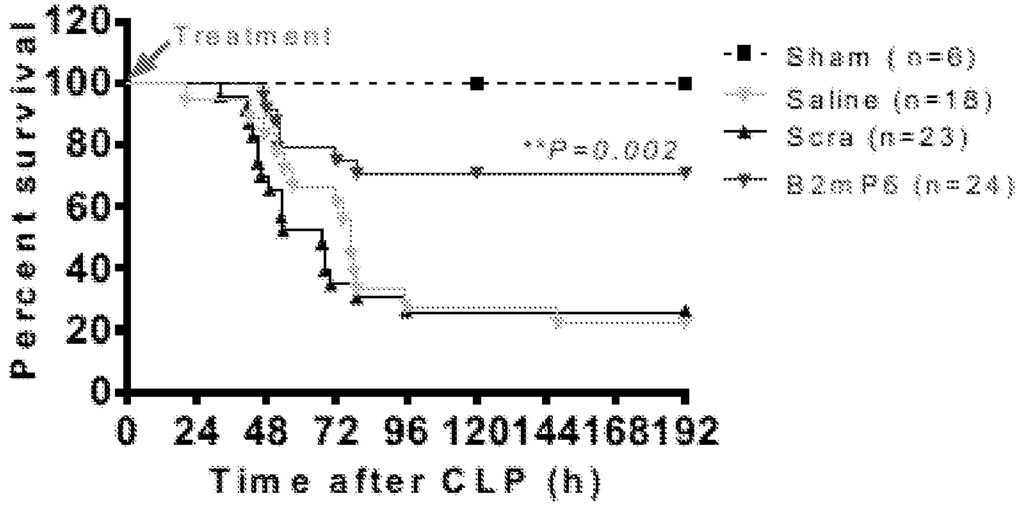
FIG. 11 shows that MB2mP6 protects mice against death in CLP sepsis model and prevents sepsis induced organ injury. a, MB2mP6 treatment immediately after CLP surgery enhanced the survive of septic C57BL/6 mice in CLP model compared to scrambled peptide or saline treatment groups. All mice in sham group survived. Significance analysis was determined by Log-rank (Mantel-Cox) test using the GraphPad Prism software. Sham, n=6; Scra, n=23; MB2mP6, n=24; Saline, n=18.

Example 11: Effects of ExE Motif Peptides on Leukocyte Function and Systemic Inflammation The Gα13 binding ExE motif is conserved in different integrin R subunits including the leukocyte specific β2 integrin subunit, with sequence variations. Thus, a myristoylated peptide derived from the Gα13 binding motif of 32 cytoplasmic domain, Myr-FEKEKL (SEQ ID NO: 27) (MB2mP6), and the lipid-stabilized high MB2mP6 loading nanoparticles was made in order to investigate the effect of MB2mP6 on leukocyte function and inflammation. Preincubation of MB2mP6 nanoparticles significantly attenuated transendothelial migration of peripheral blood neutrophil induced by bacterial chemotractent peptide (fMIVIL (SEQ ID NO: 46)) (FIGS. 9A-9C), indicating that the MB2mP6 indeed inhibited leukocyte function. To determine the effect of MB2mP6 on systemic inflammation, sepsis was induced in mice using the standard cecal ligation puncture (CLP) model, and compared the the control group with the MB2mP6-treated group in mortality induced by sepsis. MB2mP6 significantly reduced inflammation induced by CLP as indicated by proinflammatory cytokine levels (FIGS. 10A-10D) and reduced mortality induced by sepsis (FIG. 11). Consistent with this observation, it also observed that M3mP6 inhibited neutrophil infiltration into reperfused cardiac tissue following myocardial ischemia (FIG. 8H). These data provide evidence that the ExE peptides as described in this patent are effective anti-inflammation drugs, which is not previously known.

Figures 12A, 12B, 12C, 12D, 12E:
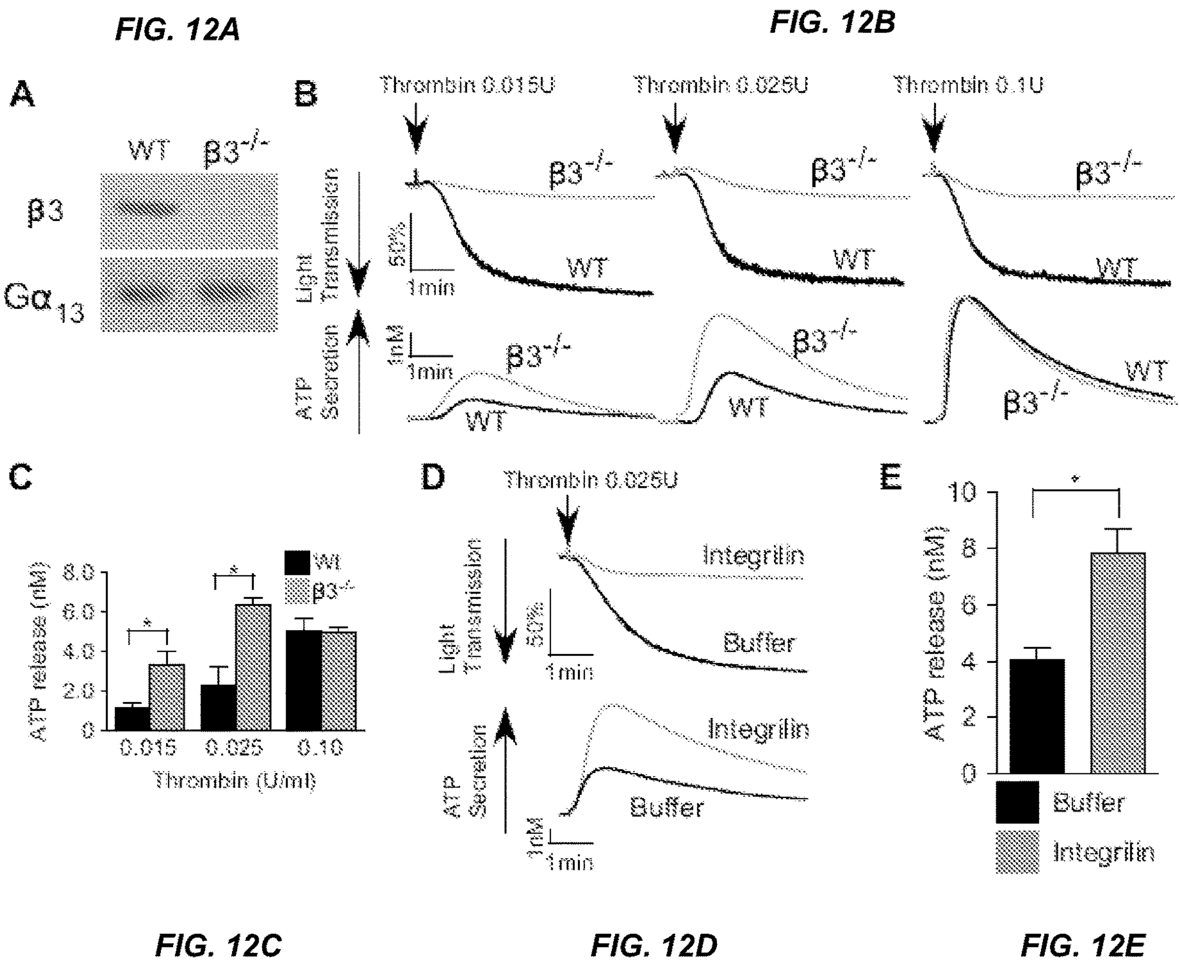
FIGS. 12A-12E show that platelet secretion induced by thrombin is enhanced in integrin β3−/− platelets and by integrin antagonist Integrilin.

Example 12: Defective Ligand Binding Function of Integrin αIIbβ3 Enhances Thrombin-Induced Platelet Granule Secretion To study the mechanisms of integrin αIIbβ3 outside-in signaling in regulating platelet granule secretion, granule secretion of wild type and β3−/− platelets were compared (FIG. 1A). β3−/− platelets stimulated by low concentrations of thrombin showed an enhanced ATP secretion response despite of a defective aggregation (FIGS. 12B and 12C). At higher thrombin concentrations, however, no difference in ATP release was observed between wile-type and β3−/− platelets (FIGS. 12B and 12C). To determine whether the effect of β3 deficiency on platelet secretion was caused by defects in platelet development or defective ligand binding to integrins, wild type mouse or human platelets were treated with the integrin antagonist, Integrilin, and then stimulated with low dose thrombin. Integrilin enhanced platelet granule secretion in a manner similar to β3 deficiency (FIGS. 12D and 12E). Thus, ligand binding to integrin αIIbβ3 appears to negatively regulate granule secretion, which apparently contradicts the knowledge that ligand binding to integrin αIIbβ3 promotes platelet granule secretion.

Figure 13A:
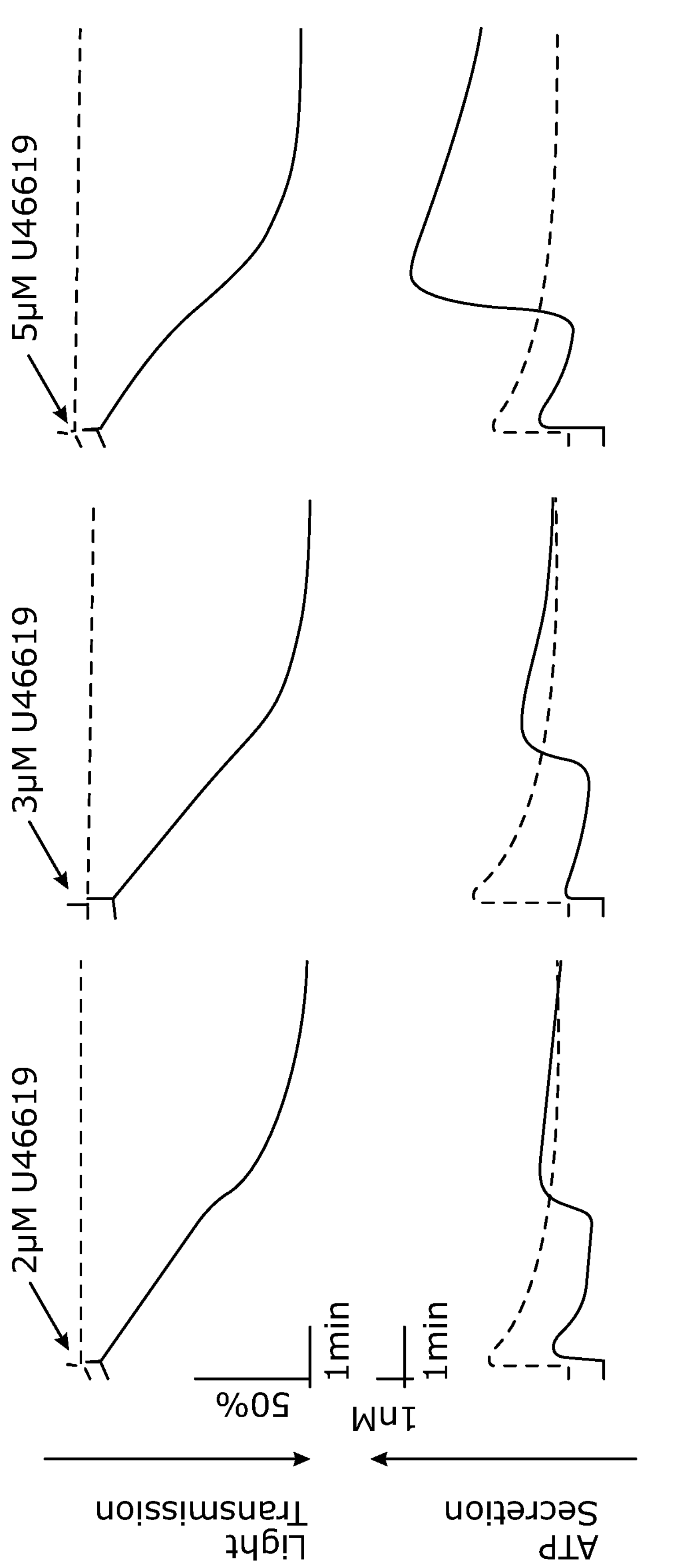
FIGS. 13A-13E show the dual roles of integrin αIIbβ3 in regulating platelet granule secretion.
Figures 13B, 13C:
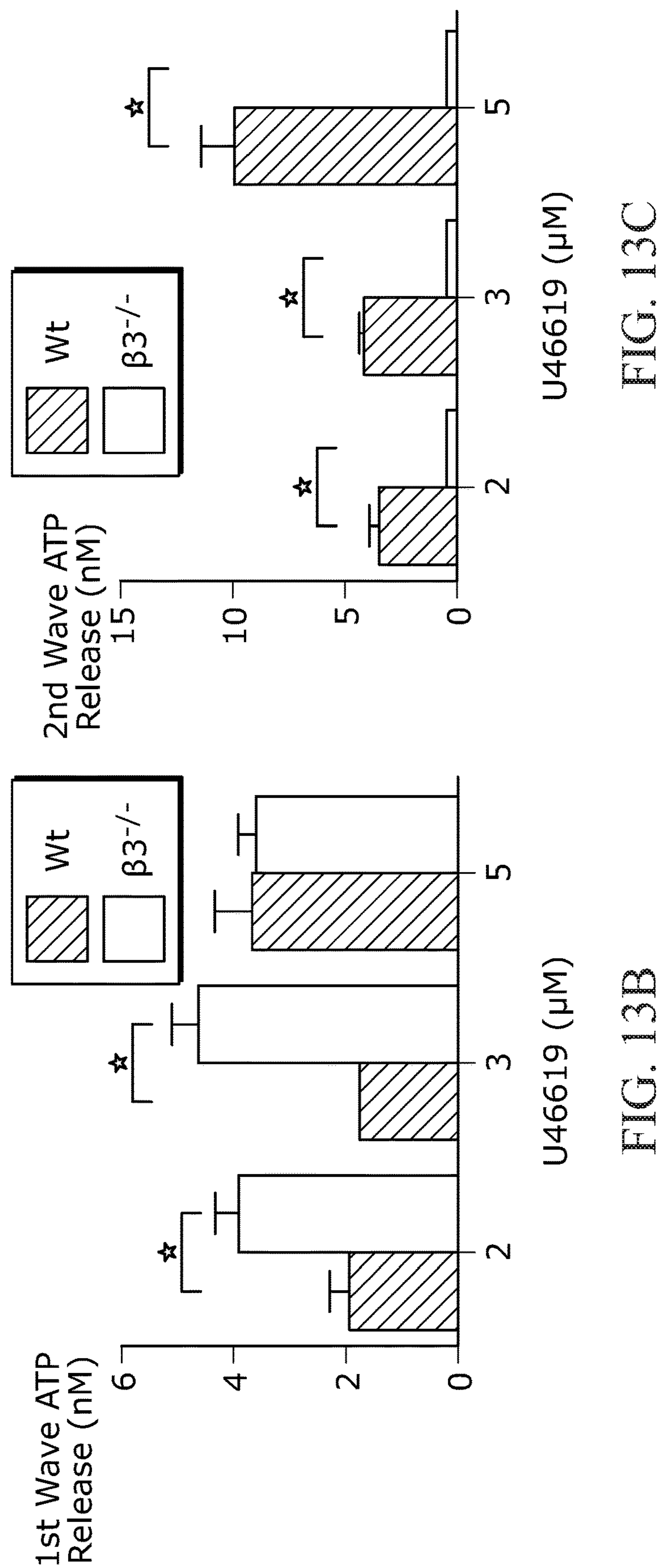
Figures 13D, 13E:
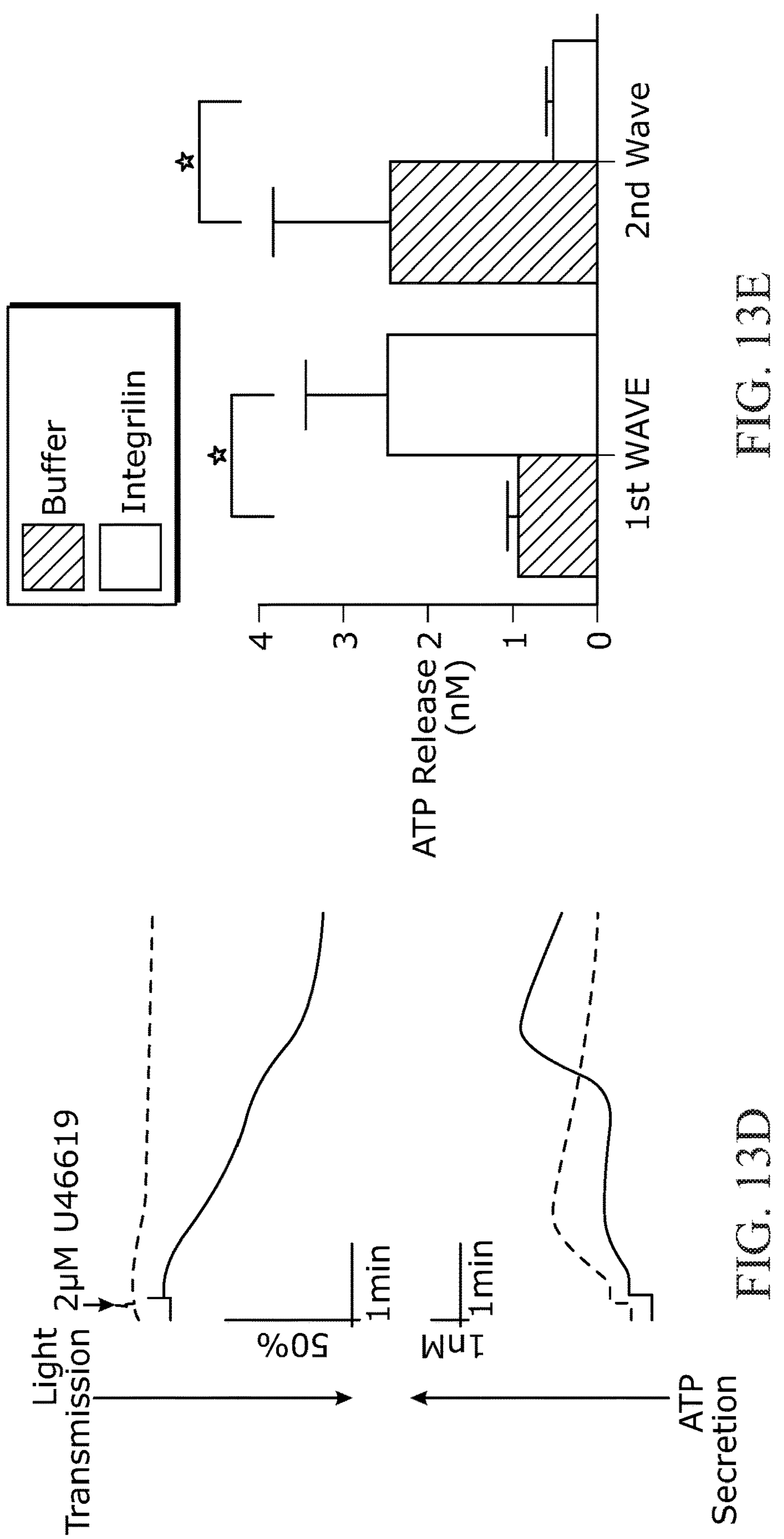

Example 13: Dual Roles of Integrin αIIbβ3 in Regulating Platelet Granule Secretion It is known that platelet granule secretion can be mediated by two distinct pathways: integrin-dependent granule secretion induced by agonist receptor signaling and integrin-independent granule secretion consequent to outside-in signaling. When platelets are stimulated with thrombin, secretions induced by these two pathways normally do not separate. However, platelet granule secretion induced by a stable thromboxane A2 analogue, U46619, shows distinct separation of integrin-independent and integrin-dependent waves. Thus, U46619 was used to stimulate platelets and examine the effect of αIIbβ3 deficiency on integrin-independent first wave and integrin-dependent second wave granule secretion. The first wave of granule secretion was significantly enhanced in both β3−/− mouse platelets (FIGS. 13A and 13B) and Integrilin-treated mouse and human platelets (FIGS. 13D and 13E). In contrast, the integrin-dependent second wave of secretion was diminished in β3−/− (FIGS. 13A and 13C) and Integrilin-treated platelets (FIGS. 13D and 13E). These data suggest that ligand binding to integrin αIIbβ3 negatively regulates integrin-independent first wave of granule secretion induced by GPCR signaling but stimulates integrin-dependent granule secretion.

Figures 14A, 14B, 14C, 14D, 14E:
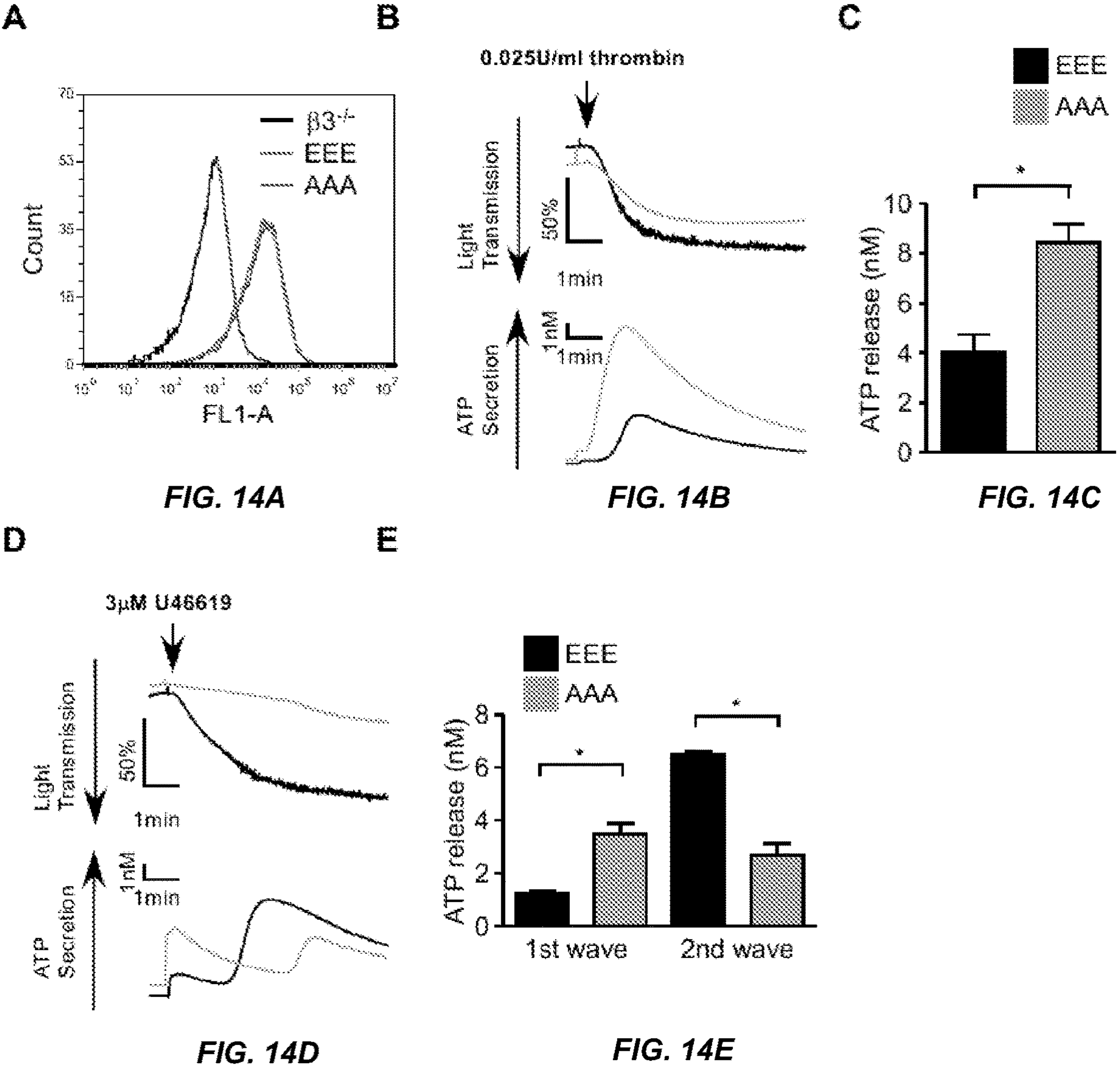
FIGS. 14A-14E show the dual roles of Gα13-β3 interaction in platelet granule secretion.
Figures 15A, 15B, 15C, 15D, 15E:
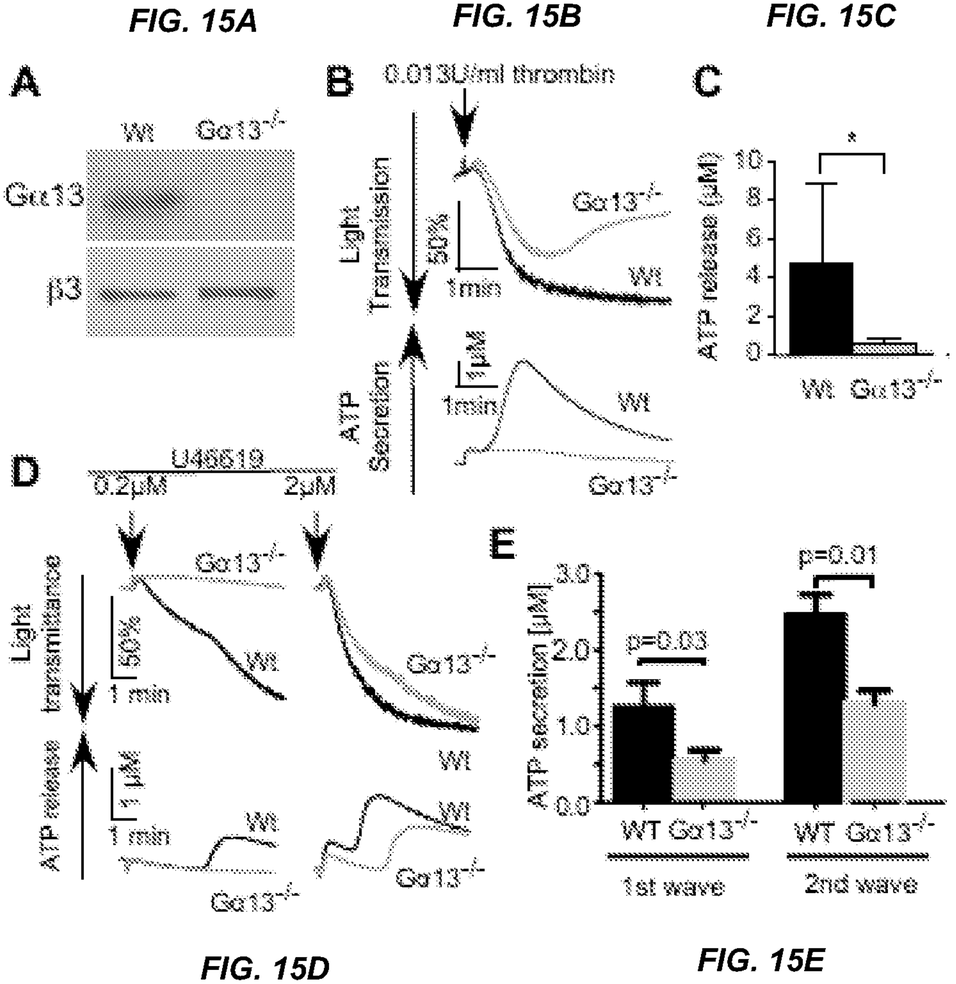
FIGS. 15A-15E show the role of Gα13 in integrin-independent and integrin-dependent platelet granule secretion.

Example 14: The Binding of Gα13 to Integrin β3 Cytoplasmic Domain Mediates the Dual Role of Integrins in Platelet Granule Secretion Integrin-dependent platelet granule secretion requires outside-in signaling. It has been previously shown that early phase of integrin outside-in signaling is mediated by the direct binding of Gα13 to the cytoplasmic domain of integrin β3 subunit. It has also been shown that Gα13 interacts with an EEE motif in the cytoplasmic domain of β3, and mutating these glutamic acid residues to alanine (AAA mutation) abolished Gα13-β3 interaction and selectively abolished integrin outside-in signaling without affecting inside-out signaling and ligand binding to integrins. To investigate whether Gα13-integrin interaction is important for regulating platelet granule secretion, β3−/−mice were lethally irradiated and transplanted with bone marrow stem cells expressing wild type or AAA mutant β3, respectively. Flow cytometry data indicate that wild type and AAA mutant platelets expressed similar levels of integrin β3 (FIG. 14A). As expected, platelets expressing this outside-in signaling-deficient β3 mutant (AAA) showed reduced aggregation compared to wild type platelets (FIG. 14B) when stimulated with low dose thrombin. However, ATP secretion was enhanced in AAA platelets rather than diminished (FIGS. 14B and 14C), which was similar to β3−/− mouse platelets and Integrilin-treated human platelets. Furthermore, in U46619-stimulated platelets, the integrin-dependent second wave of granule secretion was selectively abolished in AAA mutant platelets (FIGS. 14D and 14E). In contrast, the integrin-independent first wave of platelet granule secretion was enhanced in AAA mutant platelets in comparison with wild type β3 expressing platelets (FIGS. 14D and 14E), suggesting that Gα13-integrin interaction selectively inhibited integrin-independent platelet granule secretion, but stimulated integrin-dependent granule secretion.

Figure 17:
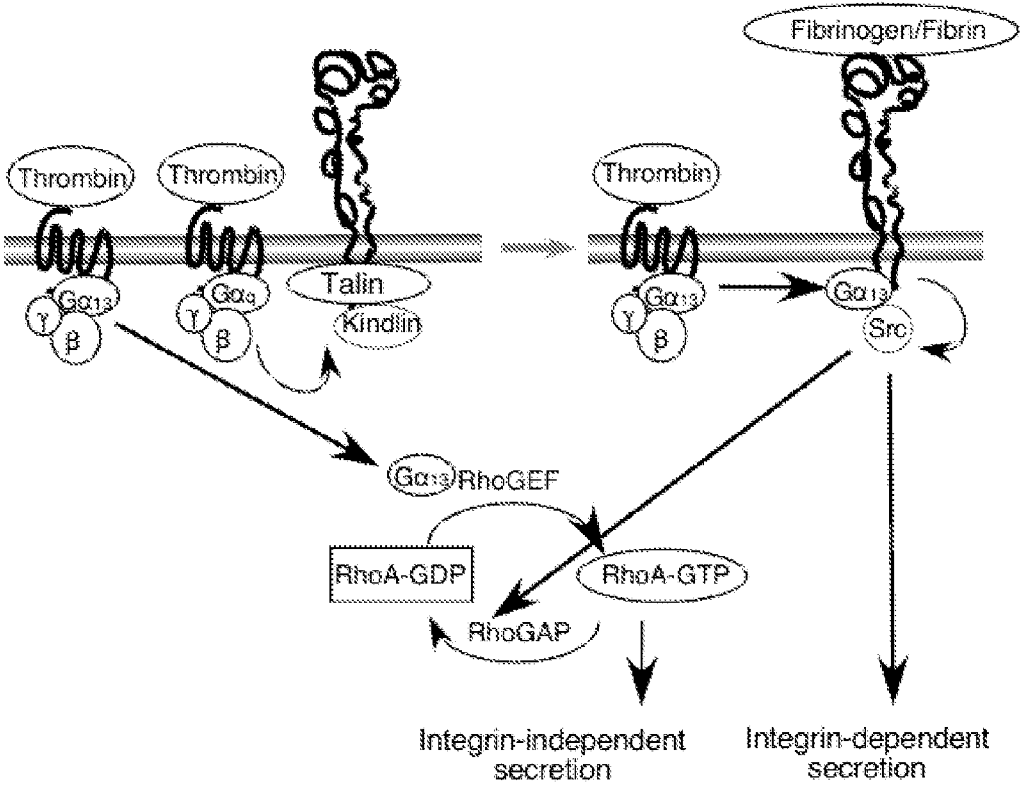
FIG. 17 is a schematic of integrin- and Gα13-dependent dual regulation of platelet granule secretion.
Figure 18A:
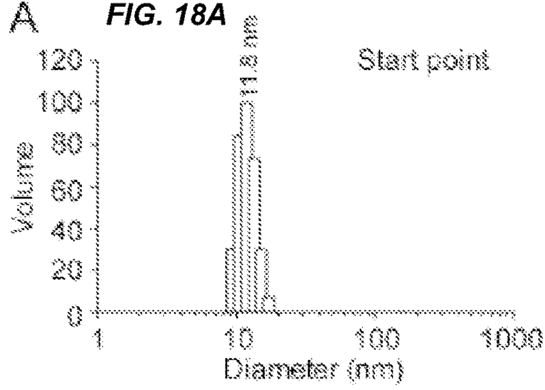
FIGS. 18A-18F show the stability of M3mP6 HLPN during storage.
Figure 18B:
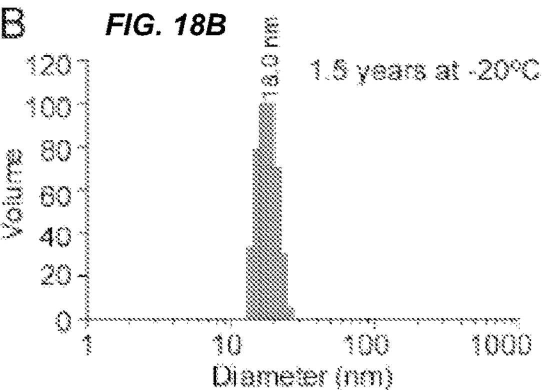
Figure 18C:
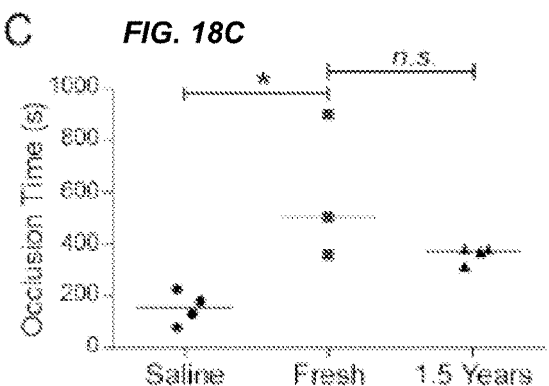
Figure 18D:
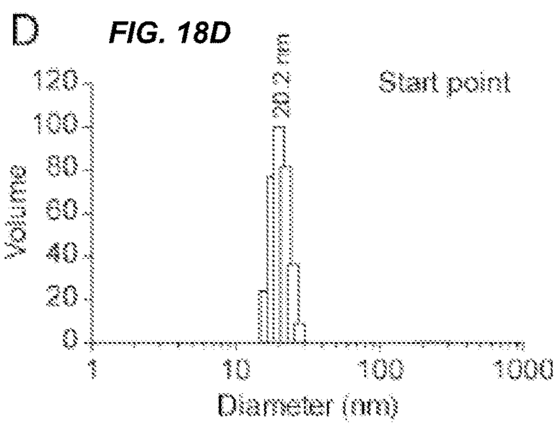
Figure 18E:
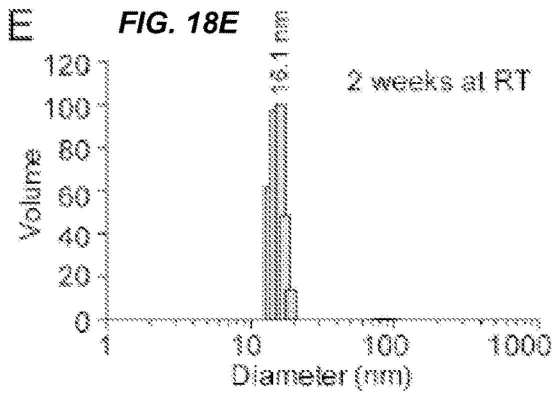
Figure 18F:
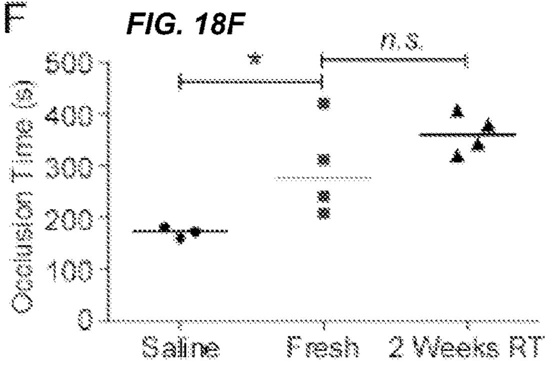

Example 15: The Effects of Gα13 Inhibiting Peptide, mP6 and mP5, on Platelet Granule Secretion Gα13 plays important roles in both integrin-independent and dependent granule secretion (FIGS. 15A-15E). In these studies on Gα13-integrin interaction, 2 integrin-based peptide inhibitors, mP5 (myr-EEERA (SEQ ID NO: 22)) and mP6 (myr-FEEERA (SEQ ID NO: 23)) were made, which inhibit Gα13-integrin interaction and outside-in signaling without affecting the talin-integrin interaction and ligand binding to integrins. Thus, the effects of these two inhibitors on platelet granule secretion were evaluated. Pretreatment of washed platelets with mP5 partially inhibited platelet aggregation induced by thrombin as expected, but enhanced platelet ATP secretion (FIGS. 16A-16E). Consistent with the results obtained with platelet expressing AAA mutant of 03, mP5 significantly enhanced first wave of ATP secretion induced by U46619 but reduced integrin-dependent second wave of ATP secretion (FIGS. 16A and 16B). These results, together with the data obtained using Gα13−/− platelets, suggest that myr-EEERA (SEQ ID NO: 22) selectively inhibited integrin-Gα13 interaction without abolishing the overall function of Gα13. These data also support the conclusion that Gα13-integrin interaction negatively regulates integrin-independent granules secretion but stimulates integrin-dependent granule secretion in mouse and also in human platelets (FIG. 17).

In contrast to mP5, pretreatment of platelets with mP6 potently inhibited thrombin-induced platelet aggregation and also significantly inhibited ATP secretion induced by thrombin (FIGS. 5A and 5B), suggesting that both integrin-dependent and independent components of platelet granule secretion was inhibited. Indeed, the U46619-induced integrin-independent first wave of granule secretion and the integrin-dependent second wave secretion were both diminished in mP6-treated platelets (FIGS. 5A-5D), which is in contrast to the mP5-treated platelets. These results demonstrate that mP6 inhibits the function of Gα13 to stimulate integrin-independent and dependent granule secretion.

The data provided herein demonstrates that exemplary M3mP6 HLPN is not only itself a potent anti-thrombotic but also exerts a significant synergistic effect when used in combination with the current standard of care, P2Y12 inhibitors with or without aspirin. This synergistic effect occurred with clopidogrel and with the more potent new direct P2Y12 inhibitors ticagrelor and cangrelor, even at the highest clinical doses. These synergistic effects suggest that the integrin-dependent secondary amplification of thrombus formation requires release of known agonists such as ADP and thromboxane A2 (TXA2) and also activation of additional signaling pathways that are not inhibited by ADP receptor antagonists or inhibitors of the TXA2 synthesis pathway. Because M3mP6 HLPN did not increase the bleeding risks of aspirin and P2Y12 inhibitors, this synergistic effect also suggests that combination use of M3mP6 HLPN with a P2Y12 inhibitor has the potential to increase anti-thrombotic efficacy to an extent that is not currently possible with anti-platelet therapy without devastating bleeding risk. Consistent with this notion, it was demonstrated that combination use of M3mP6 with low-dose cangrelor not only enhanced anti-thrombotic efficacy more potently than the highest clinical dose of cangrelor but also significantly reduced bleeding associated with high-dose cangrelor. Thus, combination use of M3mP6 HLPN with lower doses of a P2Y12 inhibitor represents a novel anti-thrombotic strategy that has significant implications for clinical outcomes, because it enhances anti-thrombotic efficacy and mitigates the life-threatening bleeding risk caused by the anti-platelet drugs currently in clinical use. These data further suggest that this fast-acting new drug can be used as an effective post-ischemic treatment for acute myocardial ischemia/reperfusion (I/R) injury. Post-ischemia injection of M3mP6 HLPN inhibited both microvascular thrombosis and inflammation in reperfused cadiac tissue, and improved cardiac function and survival rate in a mouse model of myocardial ischemia/reperfusion.

Figures 25A, 25C, 25D:
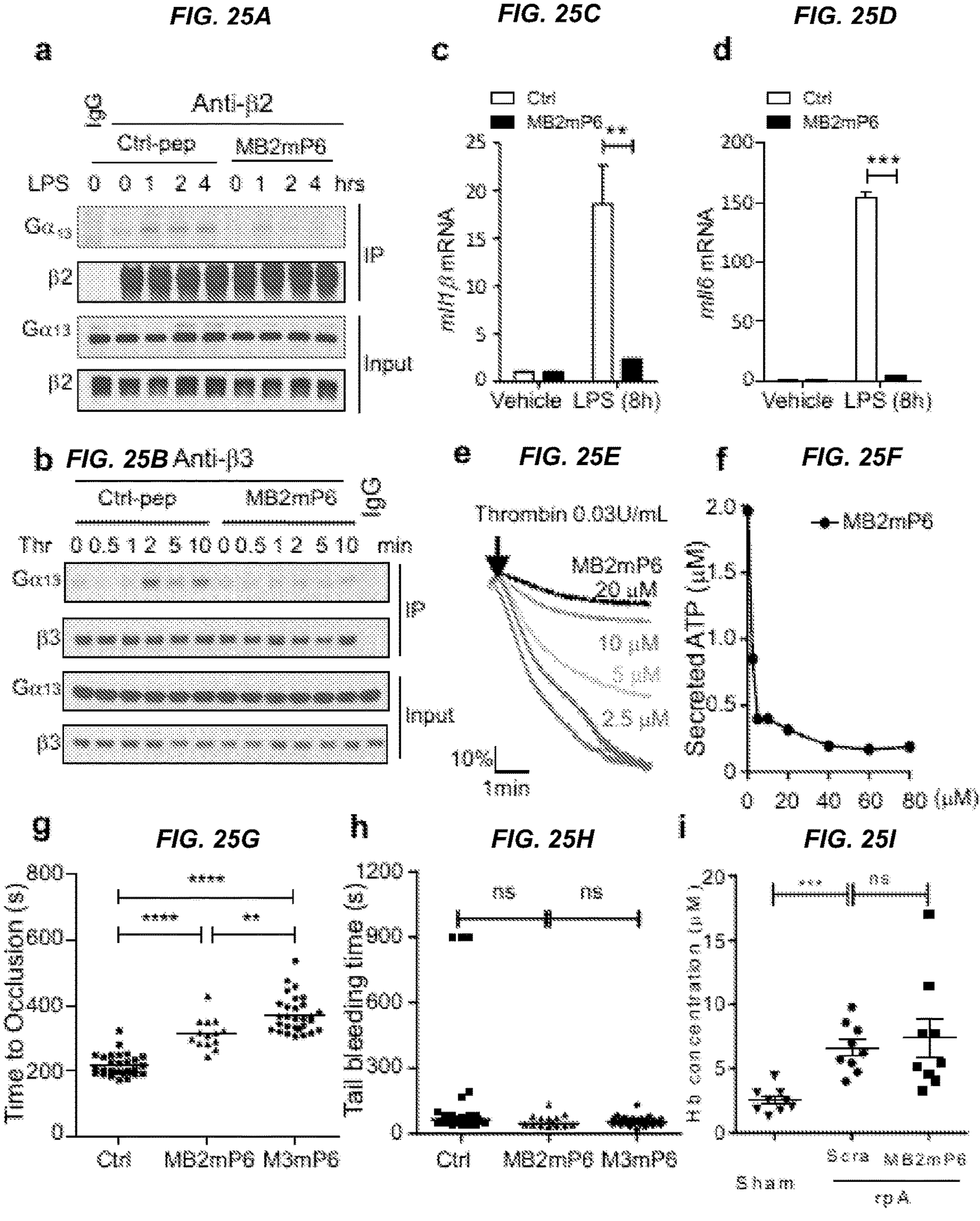

Example 16: MB2mP6 Blocks Gα13 Interactions with β2 and β3 Integrins and Inhibits Macrophage and Platelet Function without Causing Bleeding Integrins play critical roles in platelet and leukocyte functions. Current anti-platelet drugs either inhibit "inside-out" signaling blocking integrin activation or block ligand binding to integrins. Because integrin αIIbβ3-mediated primary platelet adhesion/aggregation is important in hemostasis, these drugs exacerbate hemorrhage. Ligand binding to integrins stimulates "outside-in signaling", important for platelet-mediated thrombus expansion, leukocyte trafficking and inflammation. Ligand binding to integrin αIIbβ3 induces binding of a G-protein subunit, Gα13, to 03, transmitting outside-in signaling (14,15). Because outside-in signaling is a post-adhesion amplification mechanism, inhibiting this process minimally affects primary integrin-mediated platelet aggregation and hemostasis (16). Gα13 binds to a cytoplasmic ExE motif which is homologous among β2 and β3 integrins (16). Thus, an inhibitory peptide, MB2mP6 (Myr-FEKEKL (SEQ ID NO: 27)) was designed, based on the ExE sequence of integrin β2. MB2mP6 potently inhibited Gα13 co-immunoprecipitation with β2 integrins in LPS-stimulated macrophages differentiated from the human monocytic leukemia cell line (THP-1) (17) (FIG. 25A), and also cross-inhibited the co-immunoprecipitation of Gα13 with β3 in thrombin-stimulated human platelets (FIG. 25B). MB2mP6 potently inhibited LPS-induced expression of proinflammatory cytokines IL-10 and IL-6 in mouse bone marrow derived macrophages (BMDM; FIGS. 25C and 25D), suggesting that Gα13-integrin interaction is important in macrophage proinflammatory function. Furthermore, MB2mP6 inhibited human platelet aggregation and secretion in vitro (FIGS. 25E and 25F), and $FeCl_3$-induced mouse carotid artery thrombosis in vivo, although the anti-thrombotic effect appeared less potent than the 03-derived M3mP6 peptide (FIG. 25G). Importantly, MB2mP6 neither affected injury-induced tail-bleeding time (FIG. 25H), nor inflammation-induced hemorrhage in the reverse passive Arthus (rpA) reaction in mice (FIG. 25I). These data demonstrate that MB2mP6 is anti-inflammatory and anti-thrombotic but does not exacerbate hemorrhage.

Figure 26A:
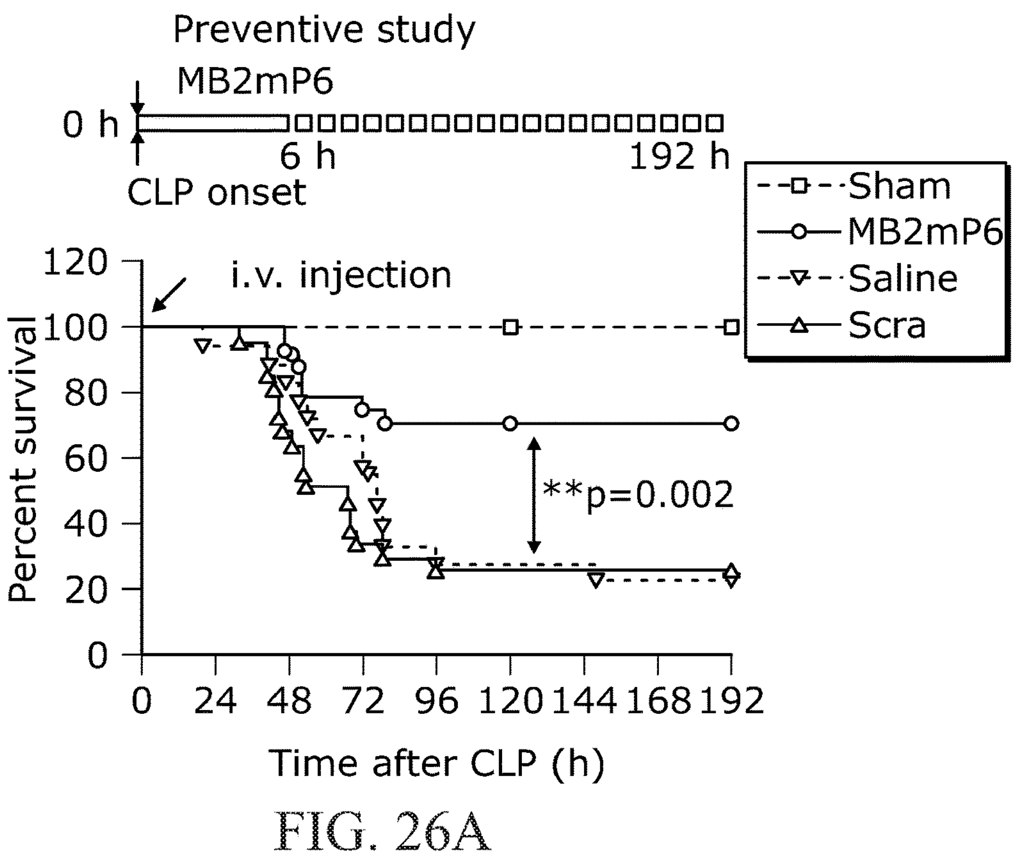
FIGS. 26A-26F show that MB2mP6 enhances survival in a CLP sepsis model and prevents sepsis-induced organ injury.
Figure 26B:
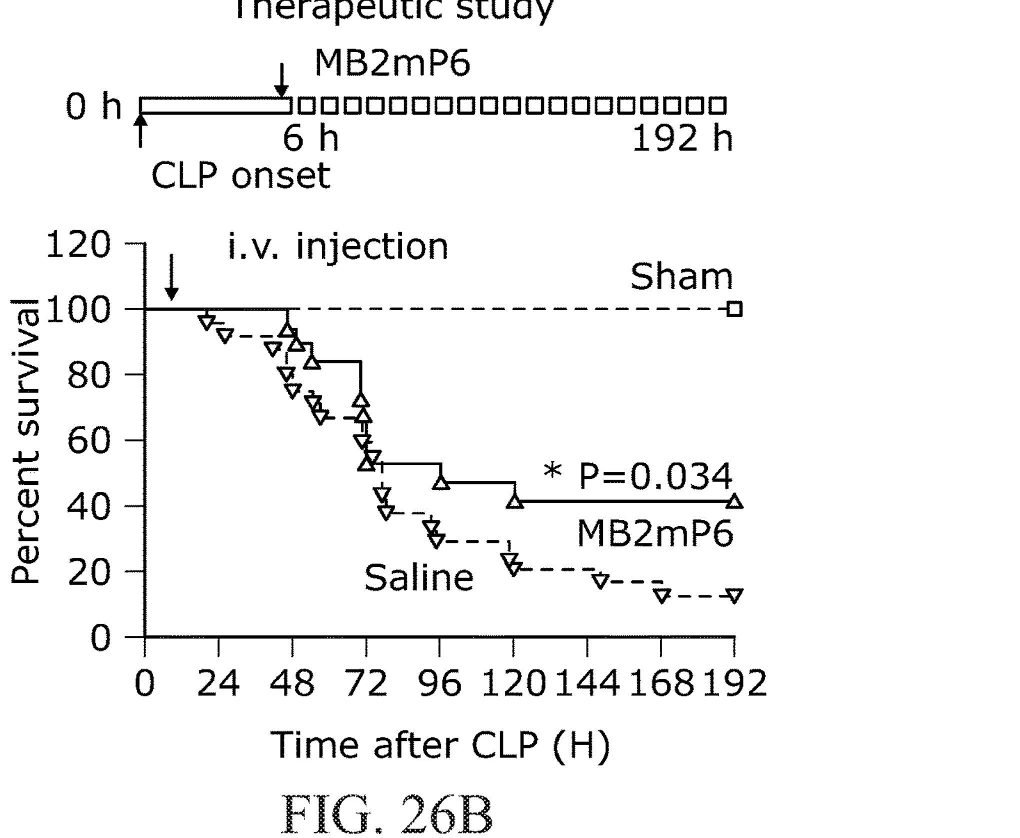
Figure 26C:
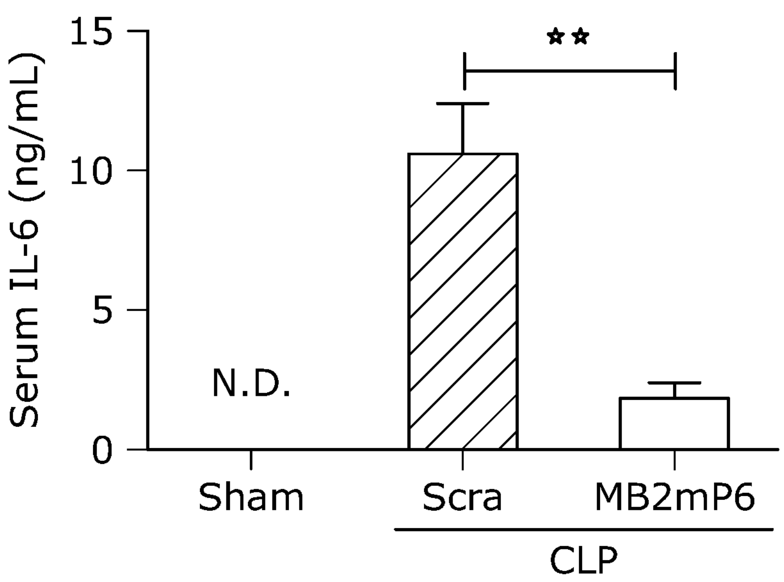
Figure 26D:
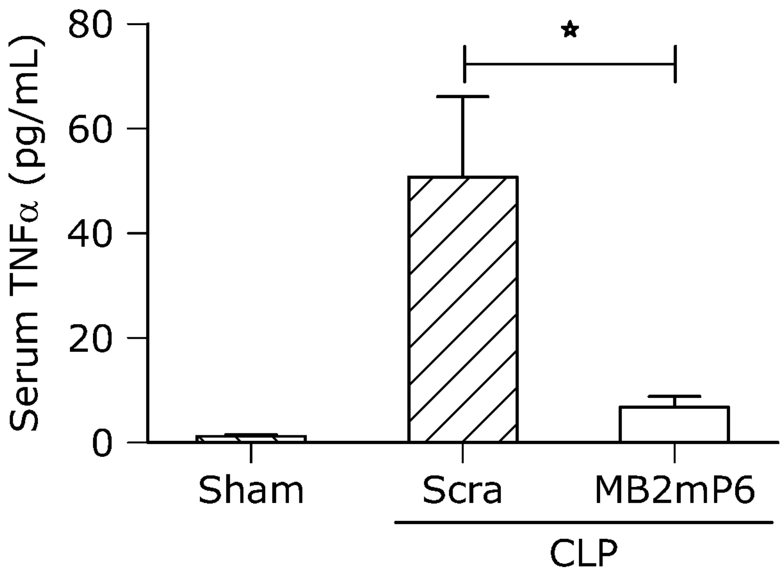
Figure 26E:
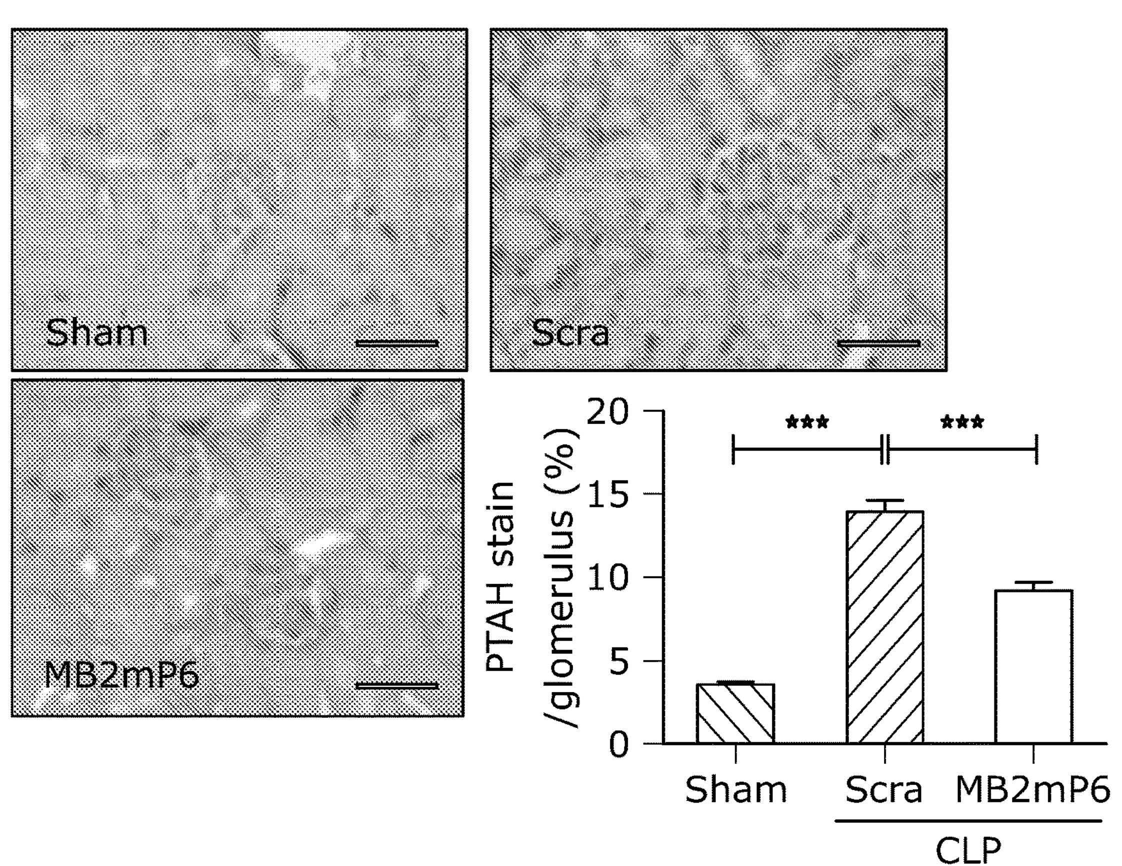
Figure 26F:
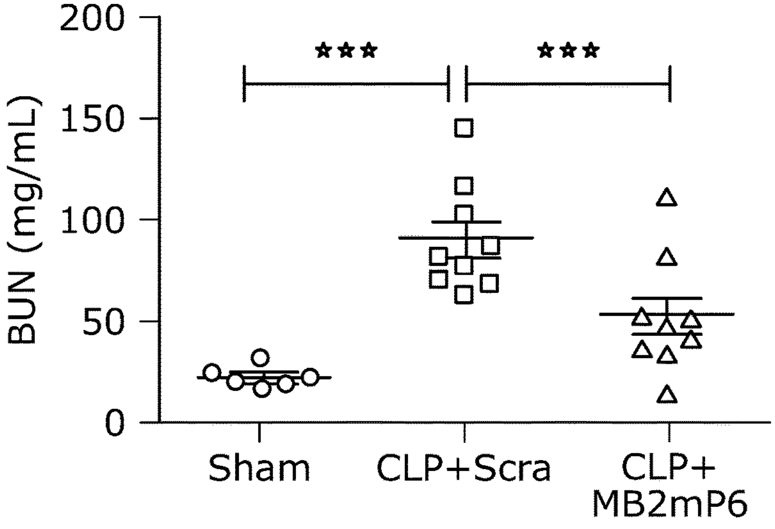

Example 17: MB2mP Enhances Survival in a CLP Sepsis Model and Prevents Sepsis-Induced Organ Injury A mouse cecal ligation and puncture (CLP) model of severe polymicrobial sepsis was used to test the possible therapeutic effects of MB2mP6 on systemic inflammation. MB2mP6 or a scrambled control peptide in a micellar nanoparticle formulation were infused i.v. immediately after CLP at a rate of 1.25 μmol/kg/hour through a pre-placed jugular vein cannula. The MB2mP6 group showed a significant improvement in survival probability (survival rate 71% in the MB2mP6 group vs 26% in the control peptide group at 192 h (8 days); p=0.002 (FIG. 26A). The control peptide group was similar to the saline treatment group (FIG. 26A). To more closely mimic the clinical conditions in sepsis treatment, MB2mP6 infusion was started 6 hours after CLP onset. Under this condition, MB2mP6 still significantly improved the 8-day survival probability (survival rate 42% in the MB2mP6 group vs 12.5% in the control group, p=0.034, FIG. 26B). Thus MB2mP6 effectively improves the survival probability of septic mice even when injected after a 6 hour delay. To assess the effect of MB2mP6 on inflammation during sepsis in vivo, pro-inflammatory cytokine levels were tested in mouse serum collected 24 hours after CLP. Control mice showed significantly increased secretion of IL-6 and TNFα, which were significantly reduced by MB2mP6 treatment (FIGS. 26C and 26D). Similarly, expression of IL-6 and TNFα transcripts in septic mouse lung were also induced by CLP and significantly suppressed by MB2mP6 infusion. These data demonstrate that MB2mP6 has potent anti-inflammatory effects in vivo during severe sepsis.

Figures 29A, 29B, 29C, 29D:
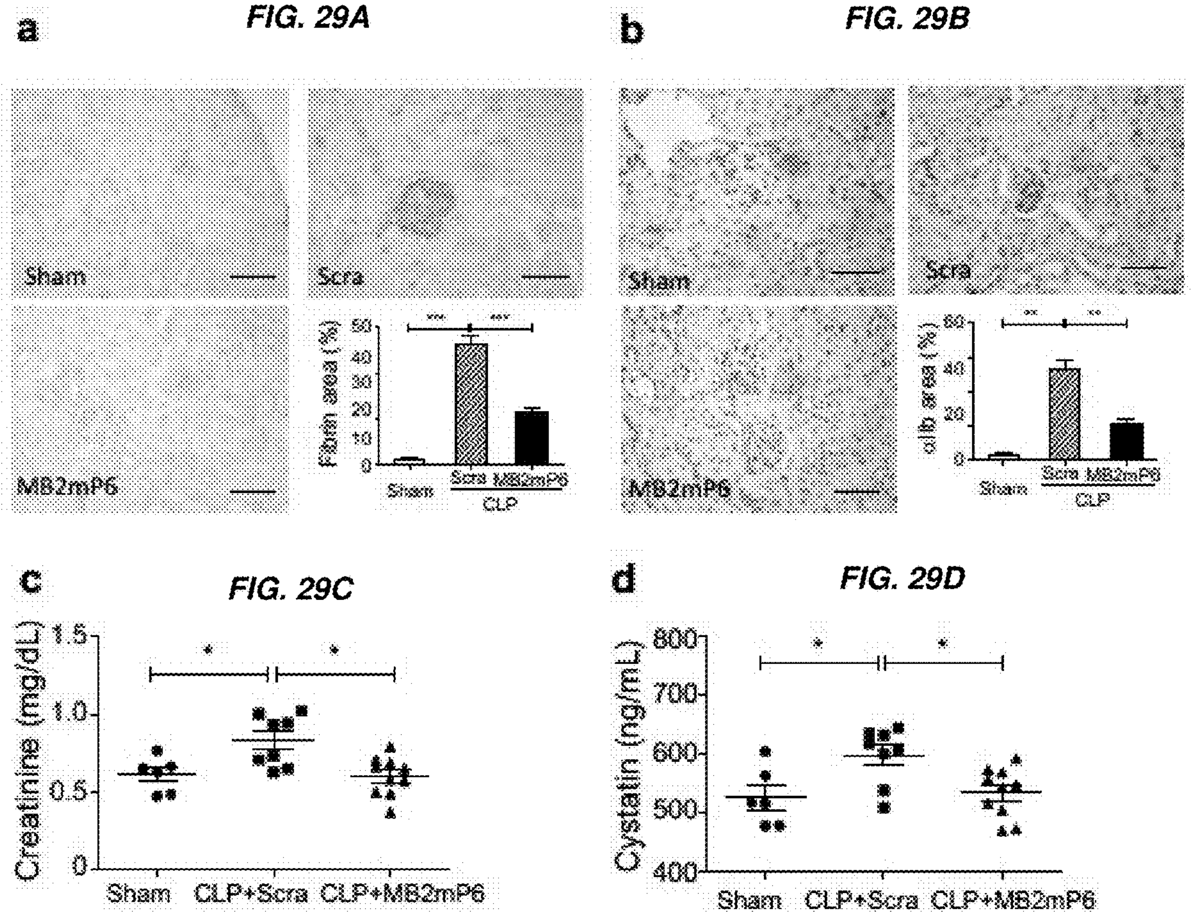
FIGS. 29A-29D show that MB2mP6 inhibits mouse kidney glomerulus microvascular thrombosis and kidney function impairment in CLP septic mice.

Severe sepsis causes microvascular thrombosis in kidney glomeruli, damaging kidney function (18,19). Indeed, in CLP septic mice, microvascular thrombosis was observed in kidney glomeruli, as indicated by Mallory's phosphotungstic acid hematoxylin (PTAH) (FIG. 26E), anti-fibrin staining of fibrin deposition and anti-αIIb staining of platelets (FIGS. 29A and 29B). CLP sepsis also impaired renal function as indicated by elevation of BUN, creatinine and cystatin C (FIG. 26F and FIGS. 29C and 29D) in the control group 24 hours after CLP. MB2mP6 treatment significantly inhibited glomerular thrombosis and reduced BUN, creatinine and cystatin C (FIGS. 26E-26F and FIGS. 29A-29D). Thus, MB2mP6 inhibits both inflammation and renal thrombosis and improves survival probability in septic mice.

Figure 27D:
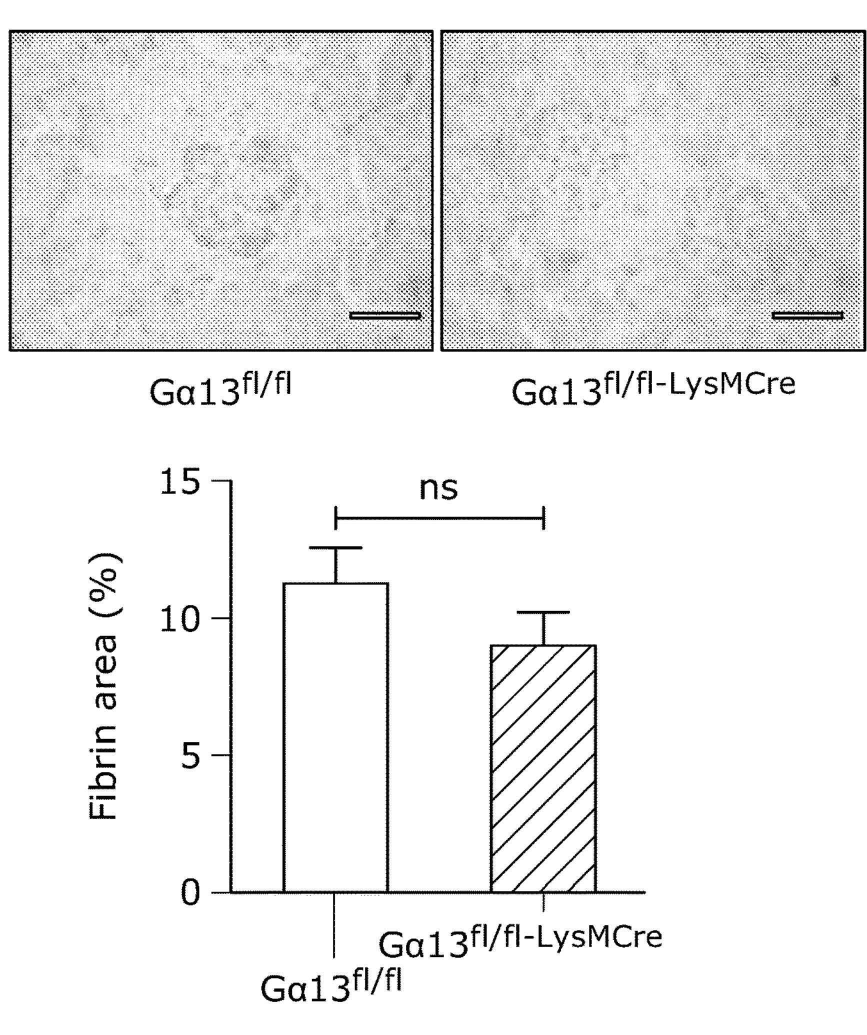
Figure 27E:
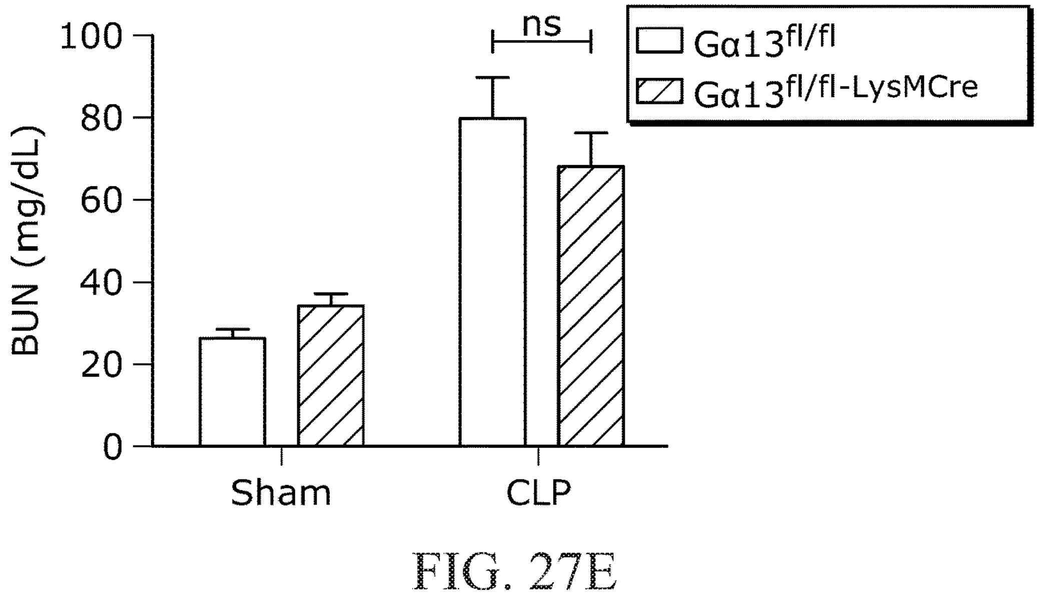

Example 18: Leukocyte- or Platelet-Specific Gα13 Knockout Reduces Mortality in CLP-Induced Septic Mice To determine the role of leukocyte Gα13 in systemic inflammation and to assess the contribution of leukocyte Gα13 in the therapeutic effect of MB2mP6, leukocyte-specific Gα13 knockout mice were generated by mating Gα$13^{fl/fl}$ mice as described in *Nat Med* 9, 1418-1422 (2003) (20), with LysM-Cre mice. Western blotting analysis confirmed the absence of Gα13 protein in both macrophages and neutrophils but not platelets of Gα$13^{fl/fl\text{-}LysMCre}$ mice (FIGS. 30A and 30B). Leukoctye-specific Gα13 knockout (Gα$13^{fl/fl\text{-}LysMCre}$) mice had a moderately but significantly improved 8-day survival rate in CLP-induced sepsis as compared with control groups (44% in MB2mP6 group vs 19% in the control group, p=0.0475) (FIG. 27A). However, the survival rate in leukocyte-specific Gα13-knockout mice was significantly lower than that in the MB2mP6-treated mice (FIG. 26A vs FIG. 27A). Importantly, the elevation of serum cytokines IL-6 and TNFα levels 24 hours after CLP were significantly inhibited in Gα$13^{fl/fl\text{-}LysMCre}$ mice (FIGS. 27B and 27C), suggesting that leukocyte Gα13 plays an major role in the inflammatory state induced by sepsis. In contrast, glomerular microvascular thrombosis as indicated by fibrin deposition was slightly but not significantly decreased in Gα$13^{fl/fl\text{-}LysMCre}$ mice compared with control Gα13$^{fl/fl}$ mice (FIG. 27D) and the elevation of the kidney damage marker BUN was also not reduced in the blood of Gα13$^{fl/fl\text{-}LysM\text{-}Cre}$ septic mice (FIG. 27E). These data suggest that leukocyte Gα13 is not a critical factor in kidney microvascular thrombosis and damage and that the protective effect of leukocyte-specific Gα13 knockout on septic systemic inflammation was mainly due to inhibition of leukocyte-mediated cytokine secretion and inflammation.

Figure 27F:
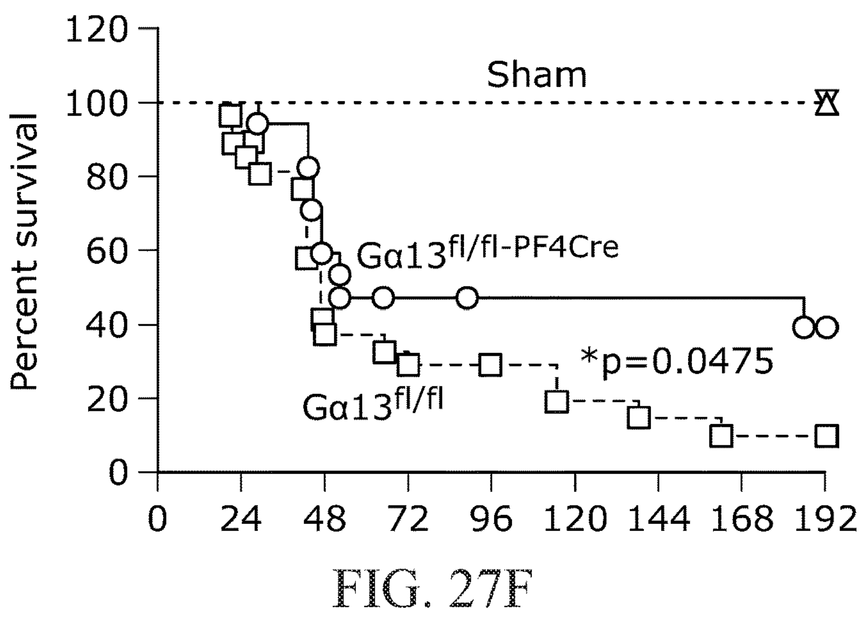
Figure 27G:
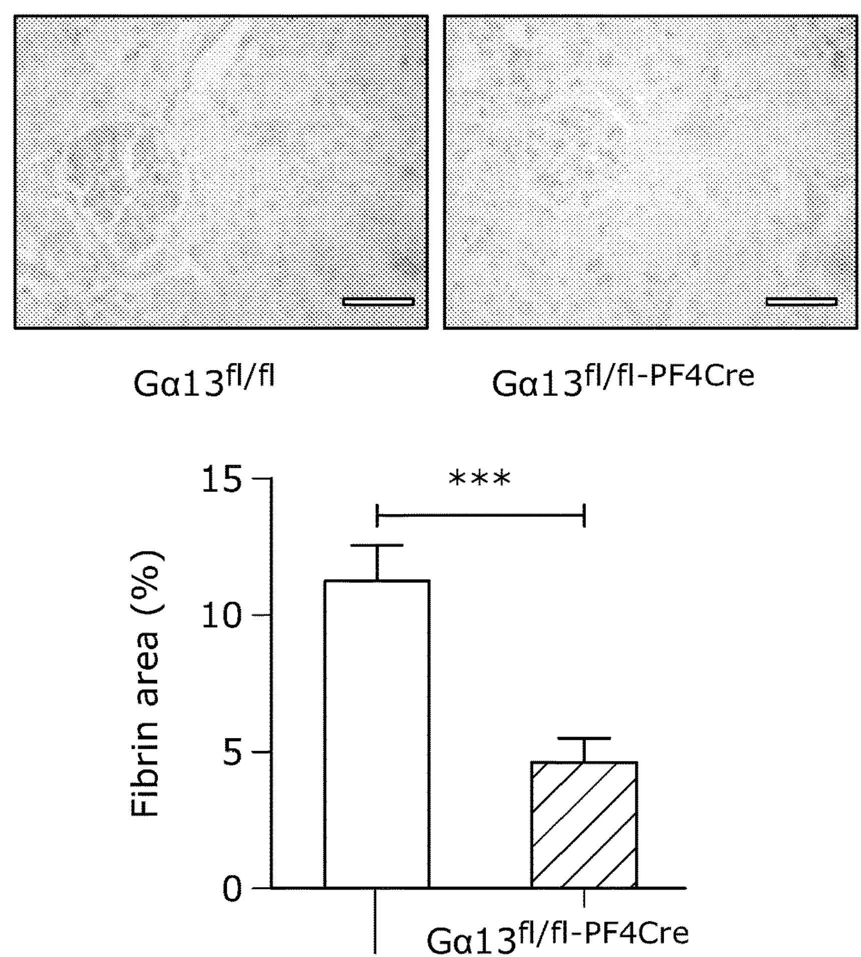
Figures 27H, 27I, 27J:
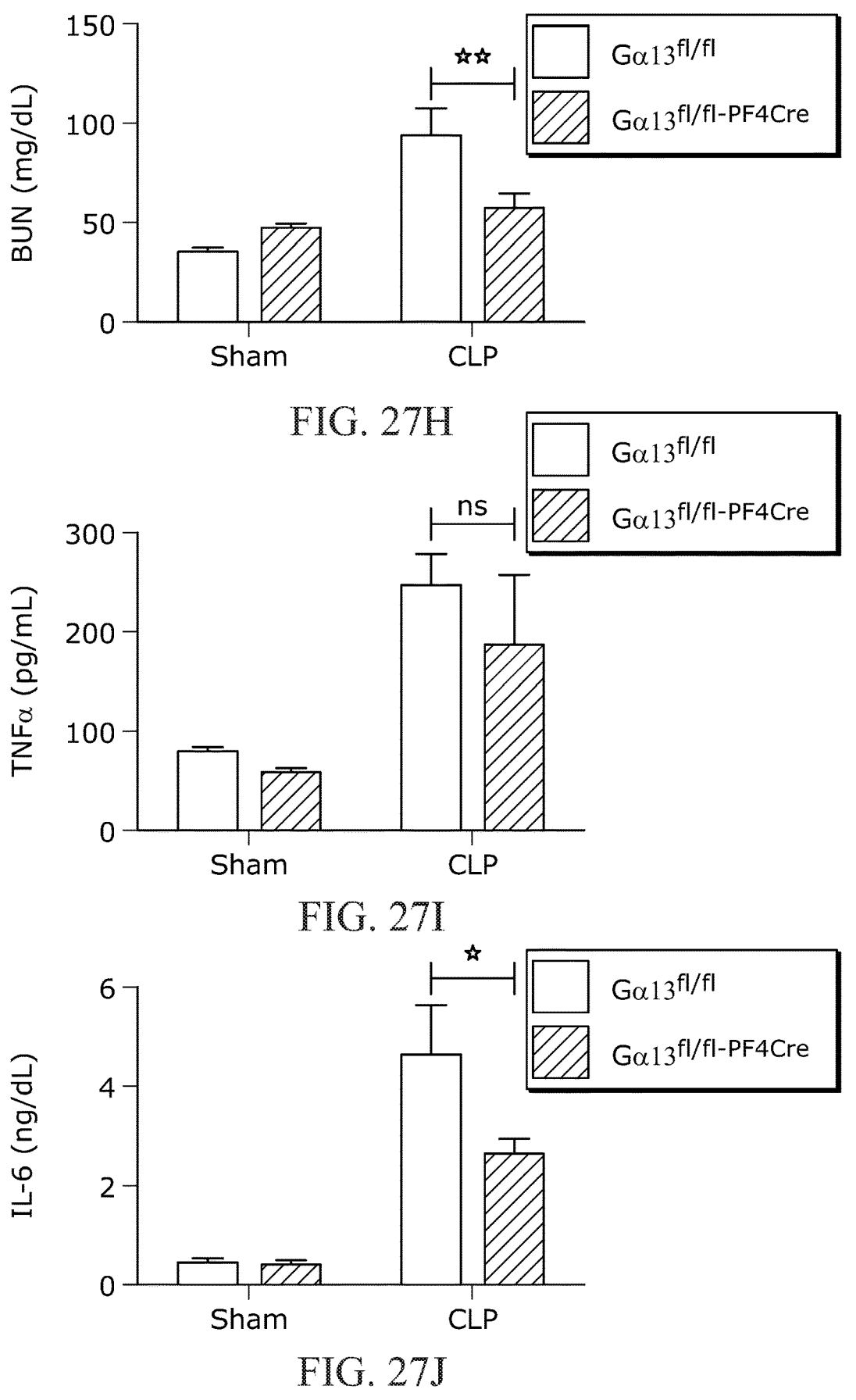

To assess the contribution of platelet Gα13 to the therapeutic effect of MB2mP6, and its role in systemic inflammation, platelet-specific knockout mice were generated by mating Gα13flox/flox mice with PF4-Cre mice (FIGS. 30A and 30B). The 8-day (192 h) survival rate in the platelet-specific Gα13 knockout (Gα13$^{fl/fl\text{-}PF4Cre}$) mice after CLP sepsis was moderately but significantly improved compared with control Gα13$^{fl/fl}$ mice (39.2% vs 9.6% in the control group; p=0.0475) (FIG. 27F), but significantly lower than MB2mP6-treated mice (FIG. 26A vs FIG. 27F). In contrast to leukocyte Gα13 knockout, the CLP-induced glomerular microvascular thrombosis and kidney function impairment (indicated by blood BUN levels 24 hours after CLP) were both markedly reduced in Gα13$^{fl/fl\text{-}PF4Cre}$ mice compared with Gα13$^{fl/fl}$ mice (FIGS. 27G and 27H). Thus platelet Gα13 plays an important role in glomerular microvascular thrombosis and kidney injury during sepsis, and is likely responsible for the therapeutic effect of MB2mP6 on glomerular thrombosis and kidney injury. However, the serum level of the inflammatory cytokine TNFα was not significantly reduced in Gα13$^{fl/fl\text{-}PF4Cre}$ mice (FIG. 27I), although cytokine IL-6, levels in mouse serum were partially (and significantly) reduced (FIG. 27J), Thus, it appears that platelet specific Gα13 knockout moderately protected mice septic death mainly by inhibiting microvascular thrombosis, although platelet Gα13 may also contribute to the exacerbation of the inflammatory state.

Figure 28A:
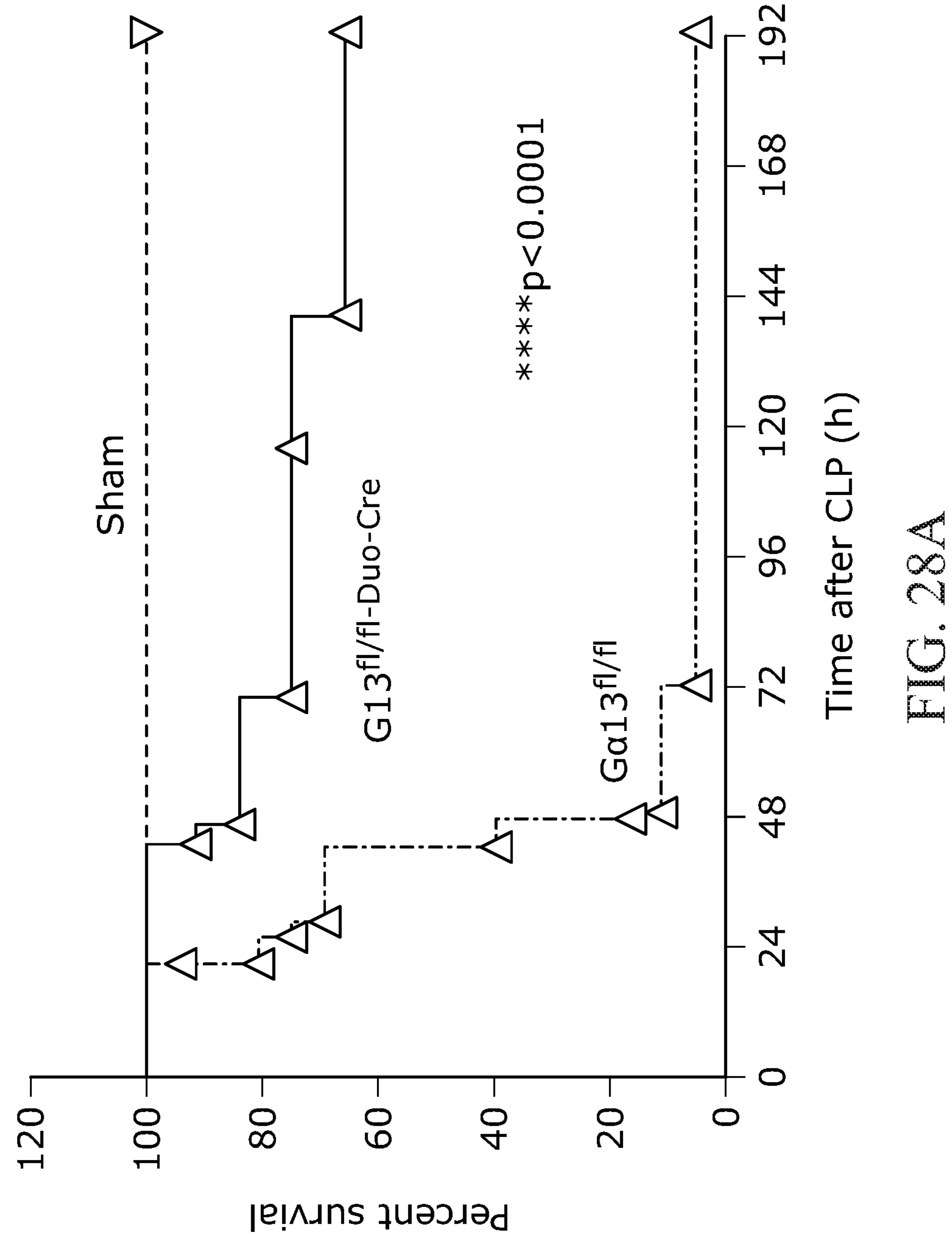

Example 19: Platelet and Leukocyte Duo-Specific Gα13 Knockout Protects Mice from Deathin CLP Sepsis Model To further determine whether Gα13 in platelets and in leukocytes has independent roles in sepsis-induced mortality and organ damage, platelet/leukocyte dual Gα13 knockout mice were generated (Gα13$^{fl/fl\text{-}LysM}$/PF4 double Cre mice, FIGS. 30A and 30B). The 8-day survival rate after CLP in the dual Gα13 knockout mice was 66% (FIG. 28A), similar to that of septic wild type mice treated with MB2mP6 (71%; FIG. 28A), and significantly higher than not only the control mice but also platelet-specific Gα13 knockout (39%) (FIG. 27F vs. FIG. 28A) and leukocyte-specific Gα13 knockout mice (44%) (FIG. 27A vs. FIG. 28A). Consistent with these results, the elevation of kidney injury marker BUN (FIG. 26F) and cytokines IL-6 (FIG. 26C) or TNFα (FIG. 26D) in the blood of control mice 24 hours after CLP were markedly inhibited in the dual Gα13 knockout mice (FIGS. 28B, 28C and 28D). The CLP-induced glomerular microvascular thrombosis was also significantly reduced in the dual Gα13 knockout mice as indicated by greatly reduced fibrin deposition (FIG. 28E). These data not only further support the distinct roles of Gα13 in platelets and leukocytes in septic systemic inflammation, but also demonstrate that their roles in sepsis are additive. Furthermore, these data demonstrate that the effectiveness of MB2mP6 in treating septic systemic inflammation in the CLP model is likely due to its ability to inhibit Gα13-integrin interaction in both platelets and leukocytes.

Taken together, these experimental results unambiguously demonstrate that thrombosis and inflammation play additive roles in exacerbating systemic inflammation, which provides an explanation for past failures of purely anti-inflammatory drugs in treating sepsis, and importantly provides strong support for a new approach to the treatment of systemic inflammation including sepsis with simultaneous anti-thrombotic and anti-inflammatory therapy. However, all current anti-thrombotic approaches carry significant risks of excessive hemorrhage, which have already been shown to outweigh beneficial effect of Xigris (3,6). In contrast, it is demonstrated that MB2mP6 targeting the outside-in signaling of integrins both in leukocytes and platelets, does not exacerbate hemorrhage. Importantly, it is demonstrated that MB2mP6 is effective in treating septic systemic inflammation in the CLP mouse model, reducing both inflammation an thrombosis to enhance survival. It is important to note that MB2mP6's effectiveness is not limited to preventing the onset of CLP sepsis, but also had significant therapeutic effects when administered 6 hours after CLP in mice. In mice, sepsis-induced increases in most cytokines as well as lung neutrophil recruitment, alveolar leak, endothelial damage, liver neutrophil and platelet recruitment with impaired sinusoidal perfusion, and acute kidney injury are all well established by 4-6 h post-CLP (21-25). Thus, MB2mP6 is not purely preventative, but rather disrupts the natural progression of systemic inflammation. If the patients/experimental animals have succumbed to the consequences of inflammation and thrombosis (e.g., multiple organ dysfunction), they are unlikely to be revived with these (or likely any other) drugs. Indeed, infusion of MB2mP6 immediately after sepsis onset resulted in better survival compared to infusion 6 hours after CLP. Thus, use of this type of drug early is likely to be effective in disrupting the progression of systemic inflammation into the irreversible phase. Overall, this data reveals the independent and interdependent roles of inflammation, hemorrhage and thrombosis in systemic inflammation and provides a new concept and new drug for simultaneous anti-inflammatory and anti-thrombotic therapy without causing vascular leakage and hemorrhage. This new therapeutic concept should help our defense against systemic inflammation, which is increasingly a challenge to human health such as in the recent SARS-coronavirus-2 infection.

Example 20: The Importance of Gα13 in the Transendothelial Migration of Neutrophils A myeloid lineage-selective knockout mouse model was to study the importance of $G\alpha_{13}$ in neutrophil migration (Moers et al., *Nat Med* 9, 1418-1422 (2003)). We crossed C57BL/6 mice expressing Cre under control of the murine lysozyme 2 promoter (LysM cre) and homozygous mice with a loxP flanked Gα13 allele ($G\alpha_{13}{}^{fl/fl}$) to generate myeloid lineage-specific conditional $G\alpha_{13}$ knockout mice ($G\alpha_{13}{}^{fl/fl\text{-}LysMcre}$). In these mice, $G\alpha_{13}$ expression was defective in neutrophils but is normally expressed in platelets (FIG. 31A). The number of neutrophils in both peripheral blood and bone marrow were similar in both $G\alpha_{13}{}^{fl/fl\text{-}LysMcre}$ and $G\alpha_{13}{}^{fl/fl}$ mice (FIGS. 31B-31C). Transwell chambers (Corning, Lowell, MA) with endothelial monolayers grown on top of the gelatin-coated filter membrane were used to analyze neutrophil transendothelial migration. The endothelial cells were treated with 10 ng/mL of both TNF-α and INF-γ to induce expression of $\beta_2$ integrin ligand intercellular adhesion molecule 1 (ICAM1), which is important for neutrophil transmigration. Neutrophils from control $G\alpha_{13}{}^{fl/fl}$ ($G\alpha_{13}^{+/+}$) or $G\alpha_{13}^{fl/fl\text{-}LysMcre}$ ($G\alpha_{13}^{-/-}$) mice were loaded into the upper chambers and various concentrations of a chemoattractant (a formyl peptide derived from *L. monocytogenes*, fMIVIL(SEQ ID NO: 46) (N-formyl-Met-Ile-Val-Ile-Leu)(Southgate et al., 2008) were added to the lower chamber to induce neutrophil migration across the endothelial monolayer. A small number of control $G\alpha_{13}^{+/+}$ neutrophils migrated across the endothelial monolayer without fMIVIL (SEQ ID NO: 46) stimulation, but the number of migrated $G\alpha_{13}^{-/-}$ neutrophils was even less (FIG. 31D). The number of migrated control $G\alpha_{13}^{+/+}$ neutrophils markedly increased with increasing fMIVIL (SEQ ID NO: 46) concentrations, peaking at 10 nM fMIVIL (SEQ ID NO: 46) (FIG. 31D), and then decreasing at higher fMIVIL (SEQ ID NO: 46) concentrations (FIG. 31D), a typical chemotactic response. However, the number of $G\alpha_{13}$-deficient neutrophils migrating into the lower chamber with 10 nM fMIVIL (SEQ ID NO: 46) was significantly lower compared to control $G\alpha_{13}^{+/+}$ neutrophils and the peak response wasn't achieved until a much higher fMIVIL (SEQ ID NO: 46) concentration (100 nM), and was still significantly reduced compared with the peak achieved by control neutrophils at 10 nM fMIVIL (SEQ ID NO: 46) (FIG. 31D). Thus, $G\alpha_{13}$ is important in neutrophil transendothelial migration.

Figure 32A:
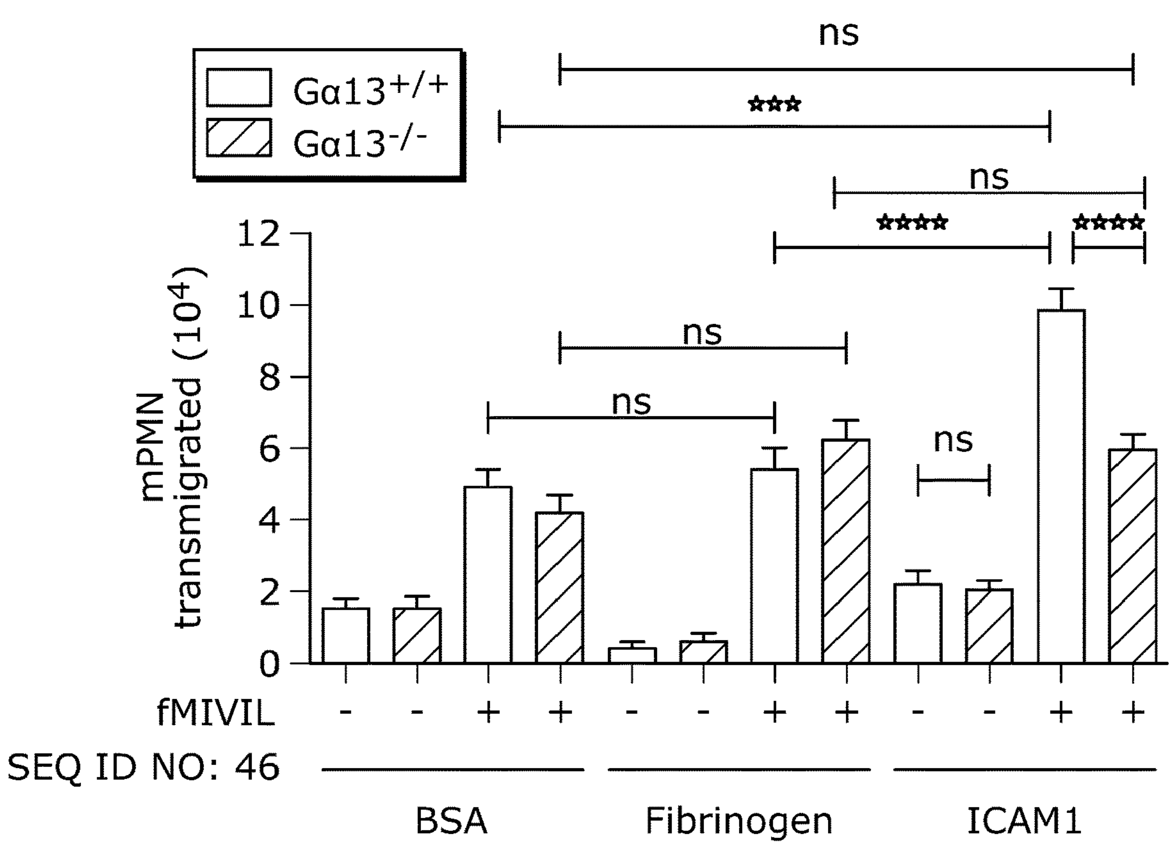
FIGS. 32A-32B: The importance of ICAM1 and β2 integrins in Gα13-dependent transendothelial migration.
Figure 32B:
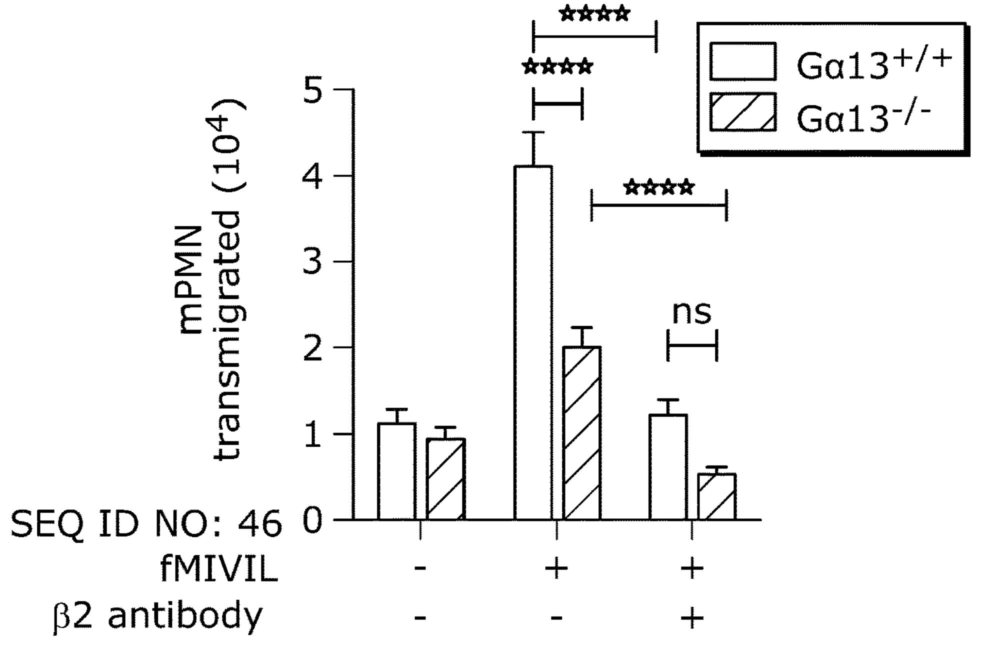

Example 21: The Importance of ICAM1 and $\beta_2$ Integrins in $G\alpha_{13}$-Dependent Transendothelial Migration To determine if the $G\alpha_{13}$-dependent neutrophil transendothelial migration is mediated through $\beta_2$ integrin interaction with integrin ligand ICAM1 on the endothelial cell surface, transmigration of neutrophils across the transwell filters coated with purified ICAM1, were tested. There were very low numbers of neutrophils migrated across the ICAM1-coated filter without chemoattractant fMIVIL (SEQ ID NO: 46) as compared with BSA-coated filters, which were similar between control or $G\alpha_{13}$-deficient mice. Transwell migration of control neutrophils through ICAM1-coated filters, however, was significantly increased when stimulated with fMIVIL (SEQ ID NO: 46) (FIG. 32A) as compared with BSA or fibrinogen-coated surfaces, even though migration through BSA- and fibrinogen-coated wells was also increased in the presence of fMIVIL (SEQ ID NO: 46). In contrast, the migration of $G\alpha_{13}$-deficient neutrophils through the ICAM1-coated filter in the presence of 10 nM fMIVIL (SEQ ID NO: 46) was significantly lower than that of control $G\alpha_{13}^{+/+}$ neutrophils (FIG. 32A), and was similar or perhaps slightly increased when compared with fMIVIL (SEQ ID NO: 46)-stimulated neutrophil migration through the control BSA-coated surfaces. $\beta_2$ integrin also binds fibrinogen and this binding has been shown to be important in bacterial clearance (Flick et al., 2004). Whether $G\alpha_{13}$ is also important in leukocyte migration on fibrinogen was also investigated. Interestingly, fMIVIL (SEQ ID NO: 46)-induced migration of control neutrophils through fibrinogen-coated filters was similar to fMIVIL (SEQ ID NO: 46)-induced cell migration on BSA surfaces, and the response did not differ between control and $G\alpha_{13}$ knockout neutrophils, suggesting that leukocyte migration on fibrinogen via a mechanism distinct from the ICAM1 and does not require the $G\alpha_{13}$-dependent outside-in signaling. Together, these data indicate the selective importance of $G\alpha_{13}$ in ICAM1-dependent transendothelial migration of neutrophils but not in neutrophil migration on another β2 integrin ligand fibrinogen or on control BSA. To further verify the dependence of transendothelial migration of neutrophils on β2 integrins, transendothelial migration assays were performed in the presence of a functional blocking anti-β2 monoclonal antibody compared with IgG control. Gα13-dependent neutrophil transendothelial migration was inhibited by the anti-β2 antibody (FIG. 32B). These data are consistent with the previously established findings that transendothelial migration of leukocytes requires $\beta_2$ integrins (Ding et al., 1999), and further indicating that the $G\alpha_{13}$ is important in $\beta_2$ integrin-dependent neutrophil transendothelial migration.

Example 22: The Role of Gα13 in Neutrophil Migration Speed and Directionality on ICAM1

Figures 33A, 33B, 33C, 33D, 33E:
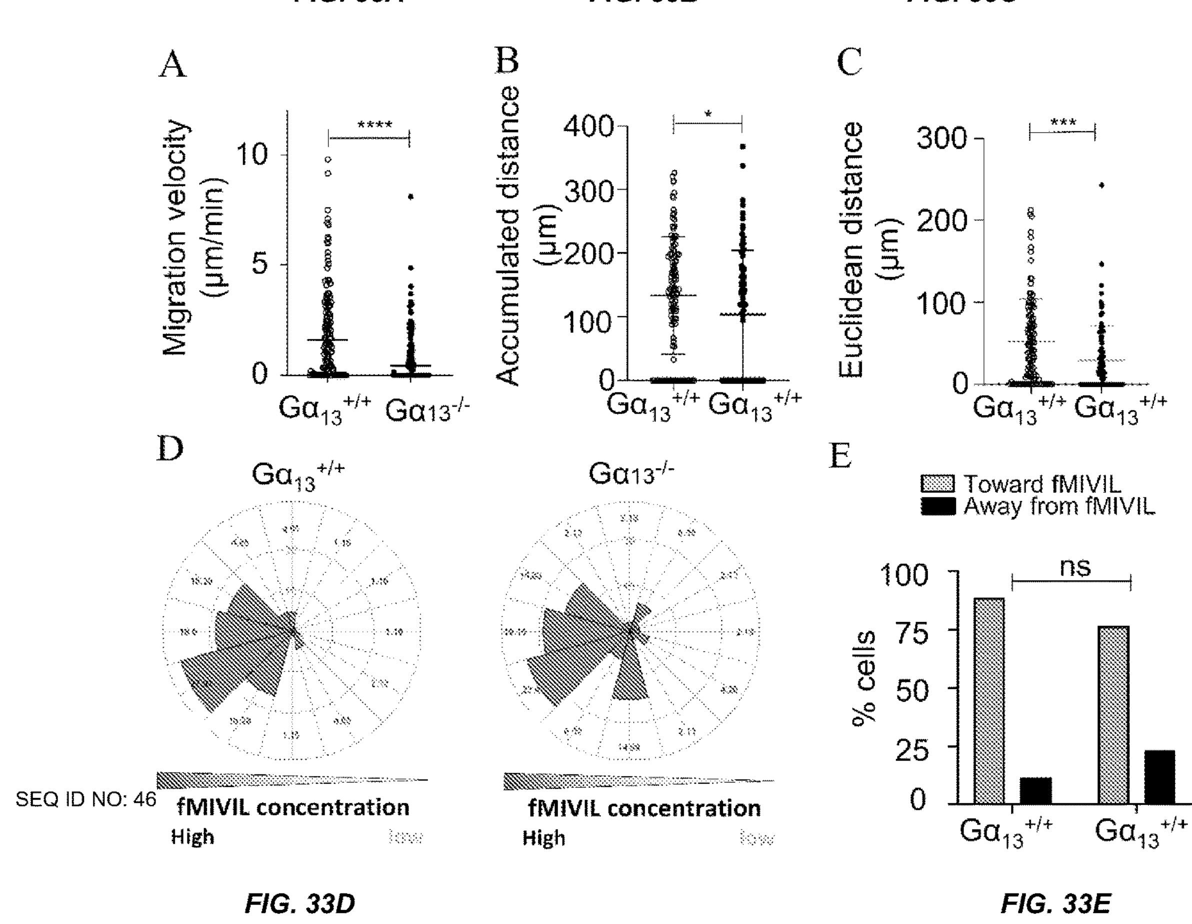
FIGS. 33A-33E: The role of $G\alpha_{13}$ in neutrophil migration on the surface of ICAM1.

Cell migration towards a chemoattractant involves both sensing of chemoattractant signals for direction, which is often GPCR-dependent, and the coordination of migration machinery driving cell movement, in which integrins play an important role. To determine whether Gα13 is important in directional sensing, and/or in driving cell movement, a microfluidic chamber was used to measure the speed and directionality of neutrophil migration in the chemoattractant gradient. As compared with control neutrophils, Gα13-knockout neutrophils exhibited significantly reduced velocity in migrating toward chemoattractant fMIVIL (SEQ ID NO: 46) (FIG. 33A). Also, the total travel distance and Euclidean distance (distance between initial and final point) were significantly reduced in Gα13-deficient neutrophils (FIGS. 33B-33C). However, the percentage of neutrophils that migrated toward the chemoattractant were not significantly different in control and knockout neutrophils (FIGS. 33D, 33E). These data indicate that Gα13 knockout is mainly associated with a defect in chemoattractant-stimulated, integrin-dependent neutrophil motility but not directionality.

Figures 34A, 34B:
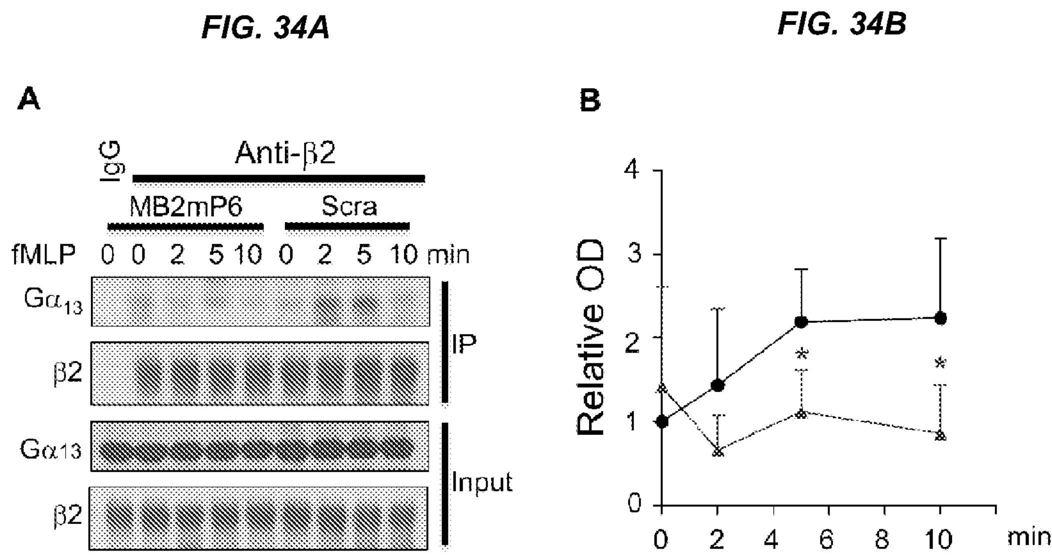
FIGS. 34A-34B: MB2mP6 blocks $G\alpha_{13}$ interactions with $\beta_2$ integrin in human neutrophils.

Example 23: An Inhibitor Peptide Derived from the $G\alpha_{13}$-Binding ExE Motif of Integrin $\beta_2$ Subunit Inhibits $G\alpha_{13}$- and Integrin-Dependent Interaction and Neutrophil Transendothelial Migration It was previously demonstrated that Gα13 directly interacts with R subunits via an ExE motif found in several integrin β subunits.(Haixia Gong, Bo Shen, Panagiotis Flevaris, Christina Chow, Stephen C.-T. Lam, Tatyana A. Voyno-Yasenetskaya, Tohru Kozasa, 2010; Shen et al., 2015, 2013). To further explore the role of $G\alpha_{13}$-$\beta_2$ interaction in transendothelial migration of neutrophils, the effect of a synthetic peptide derived from the $\beta_2$ ExE motif, myr-FEKEKL (SEQ ID NO: 27) (MB2mP6), or control peptide (myr-FKKEKL (SEQ ID NO: 47)) on neutrophil migration, was studied. MB2mP6 inhibited Gα13 interaction with $\beta_2$ integrin in formal peptide-stimulated human neutrophils as compared with a control peptide (FIGS. 34A-34B).

However, MB2mP6 (50 μM) had no significant effect on neutrophil adhesion to ICAM1 compared to control peptide (FIG. 35A), indicating that $G\alpha_{13}$-integrin interaction was neither important in inside-out signaling nor in ligand binding function of $\beta_2$ integrins. In contrast, neutrophil transendothelial migration was dose-dependently inhibited by MB2mP6 (FIG. 35B). To determine whether the effect of the peptide is $G\alpha_{13}$-dependent, the effect of MB2mP6 on transendothelial migration of $G\alpha_{13}^{-/-}$ neutrophils was also tested. As before, $G\alpha_{13}^{-/-}$ neutrophils showed significantly reduced transwell migration compared to control $G\alpha_{13}^{+/+}$ neutrophils, but MB2mP6 treatment did not further inhibit the transendothelial migration of $G\alpha_{13}^{-/-}$ neutrophils (FIG. 35C), suggesting that the inhibitory effect on control neutrophils is likely $G\alpha_{13}$-dependent. Furthermore, MB2mP6 inhibited wild type neutrophil transmigration on either endothelial cells or ICAM1 coated transwell filters, but neutrophil migration on fibrinogen-coated transwells was not affected by MB2mP6 (FIG. 35D), a result consistent with that of $G\alpha_{13}^{-/-}$ neutrophils (FIG. 32A-32B). These data support the notion that $G\alpha_{13}$-β2 interaction selectively mediates integrin/ICAM1-dependent migration of neutrophils.

Example 24: Gα13 Deficiency Did not Affect Neutrophil Adhesion to ICAM1, but Inhibited the Spreading of Adherent Neutrophils The above data have showed that knockout of $G\alpha_{13}$ inhibited integrin-dependent neutrophil transendothelial migration. To further distinguish whether this effect was due to the importance of $G\alpha_{13}$ (1) in regulating integrin-dependent cell adhesion or (2) in mediating ICAM1-induced integrin outside-in signaling, the adhesion of both Gα13+/+ and $G\alpha_{13}^{-/-}$ neutrophils to ICAM1 coated surfaces were tested and found there was no significant difference between $G\alpha_{13}^{+/+}$ and $G\alpha_{13}^{-/-}$ neutrophils in adhesion to ICAM1 (FIG. 36A). Thus, $G\alpha_{13}$ is not required for the ICAM1-binding function of $\beta_2$ integrins. To assess whether $G\alpha_{13}$ is important in integrin outside-in signaling, it was investigated whether $G\alpha_{13}$ knockout affected neutrophil spreading on ICAM1-coated surfaces. It is established that cell spreading (lamellipodia formation) in the leading edge of a cell is a cell response to integrin outside-in signaling and important in the process of integrin-dependent cell migration. $G\alpha_{13}$ has been shown to mediate outside-in signaling leading to cell spreading in platelets (Shen et al., 2015, 2013). The data revealed that the size of the $G\alpha_{13}$ deficient neutrophils were similar to control neutrophils prior to cell adhesion to ICAM1. However, whereas control neutrophils rather quickly spread on ICAM1-coated surfaces, the spreading of $G\alpha_{13}$-knockout neutrophils was reduced (FIGS. 36B, 36C). Consequently, control neutrophils adherent to ICAM1 were significantly larger as compared with $G\alpha_{13}$ knockout neutrophils or control neutrophils treated with MB2mP6 (FIGS. 36B-36F). These data are consistent with knowledge that neutrophil migration is associated with coordinated spreading and retraction, and that $G\alpha_{13}$ plays an important role in outside-in signaling leading to integrin-dependent cell spreading. These data further support the idea that $G\alpha_{13}$ plays an important role in integrin-dependent cell migration by mediating integrin outside-in signaling.

Example 25: The Role of Gα13 in Neutrophil Migration In Vivo

Figures 37A, 37B:
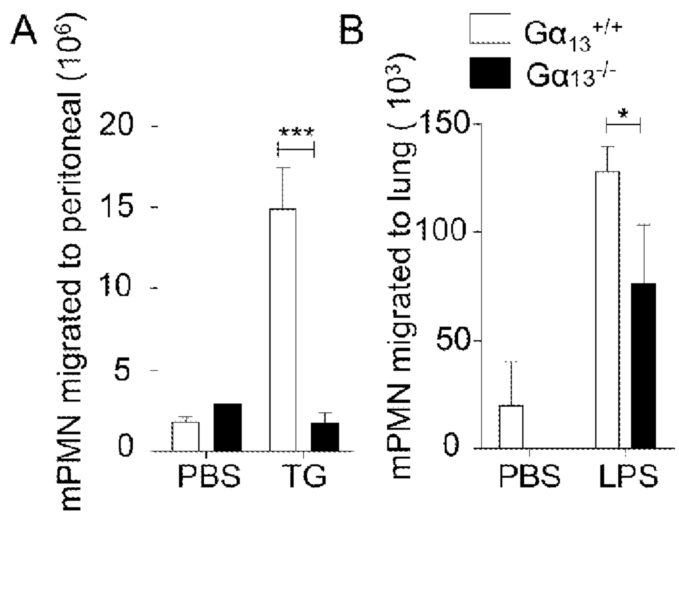
FIGS. 37A-37B: The role of Gα13 in neutrophil migration in vivo.

To determine the in vivo importance of the Gα13-dependent transendothelial migration, the role of Gα13 in neutrophil migration to the site of inflammation outside of blood vessels in vivo were further investigated using two mouse models. In the thioglycollate-induced peritonitis model, neutrophil migration into the peritoneal cavity was significantly reduced in the Gα13−/− mice compared to control $G\alpha13^{+/+}$ mice (FIG. 37A). In the LPS-induced lung inflammation model, neutrophil infiltration into the lungs 6 h after intratracheal LPS instillation was significantly reduced in $G\alpha13^{-/-}$ mice compared to the $G\alpha13^{+/+}$ mice (FIG. 37B). These data suggest that Gα13 plays an important role in neutrophil migration to the sites of inflammation outside of blood vessels in vivo.

Example 26: MB2mP6 Inhibits CLP-Induced Microvascular Thrombosis and Vascular Leakage in Septic Mouse Lungs Acute respiratory distress syndrome (ARDS) can be caused by severe viral infections, COVID-19 infection and bacterial infection such as in sepsis.

The effect of ExE motif peptides in high-loading peptide nanoparticle (HLPN) formulation on vascular leakage in the lung and thrombosis were evaluated in a mouse model of systemic inflammation (sepsis).

Figure 38A:
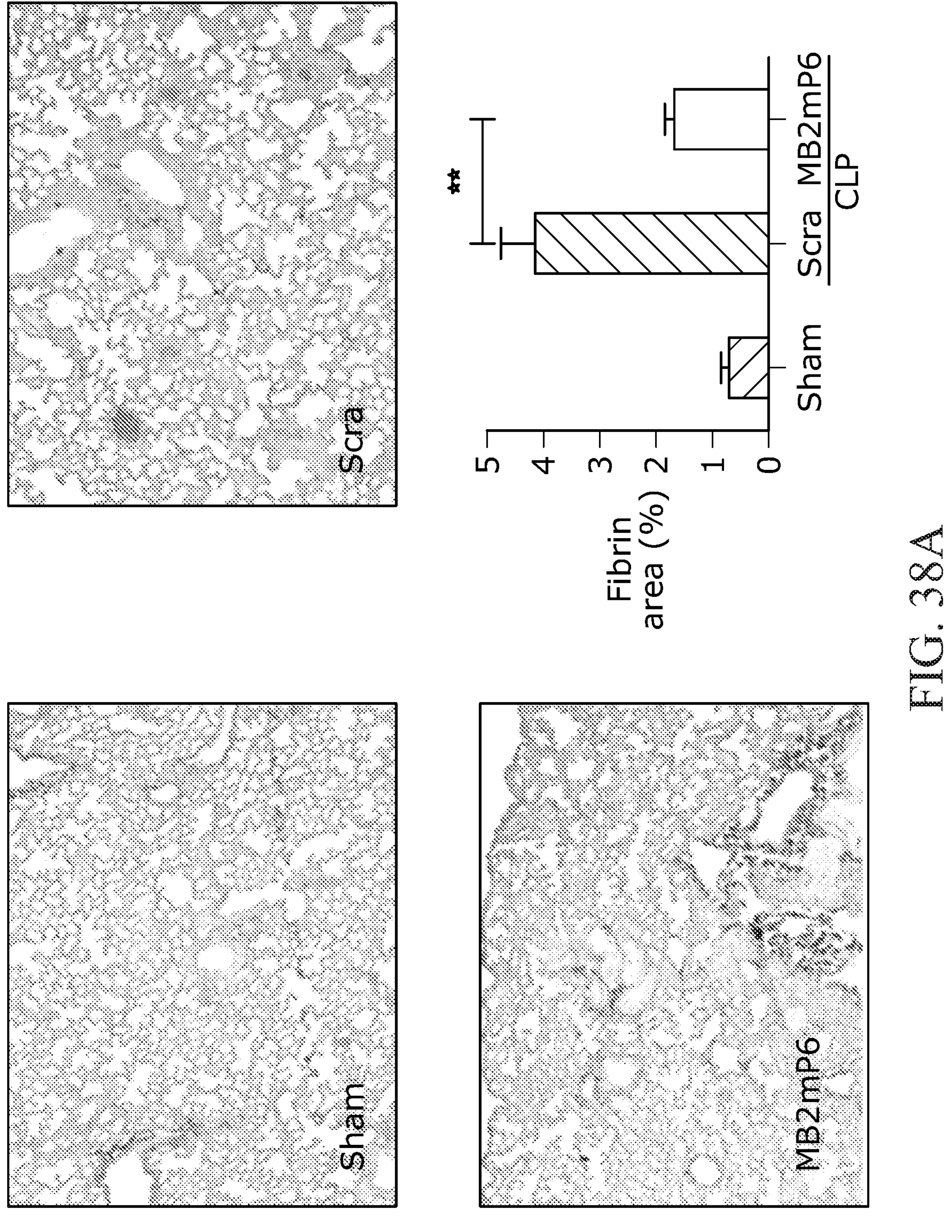

Briefly, C57BL mice were infused with MB2mP6 or scrambled peptides immediately after CLP onset. After 24 h, lungs were removed and sections cut and stained with phosphotungstic acid hematoxylin (PTAH) for fibrin (blue stain) (FIG. 38A). C57BL mice were infused with MB2mP6 or saline immediately after (FIG. 38B) or 6 h after CLP (FIG. 38C). After 23 h, mice were i.v. injected with Evans blue albumin (EBA; 1%, 25 mg/kg body weight). After 1 h, mouse lungs were harvested and Evans blue was extracted with formamide at 60° C. for 18 h and quantitated by absorbance at 620 nm.

As shown in FIGS. 38A-38C, ExE motif peptides in high-loading peptide nanoparticle (HLPN) formulation significantly reduced the vascular leakage in the lung and thrombosis in addition to its anti-inflammatory effect in a mouse model of sepsis. The ExE peptides are effective drugs for treating ARDS.

This disclosure provides examples of the role for $G\alpha_{13}$ in integrin $\beta_2$-mediated transendothelial neutrophil migration, and that this role is selectively important in neutrophil migration on ICAM1, an endothelial $\beta_2$ ligand, but not on fibrinogen, another β2 integrin ligand. These data further demonstrate that the primary role of $G\alpha_{13}$ is to enhance integrin-dependent neutrophil motility without affecting the directionality of neutrophil migration, which is known to be mediated via GPCR and integrin inside-out signaling. Furthermore, this effect of $G\alpha_{13}$ is inhibited by a peptide derived from the $\beta_2$ integrin $G\alpha_{13}$-binding sequence that blocks $G\alpha_{13}$-integrin interaction, suggesting it is likely to be mediated via $G\alpha_{13}$ interaction with $\beta_2$ integrins. Importantly, the role of $G\alpha_{13}$ in neutrophil migration was also observed in vivo using two different in vivo models. Together with previous studies, these data suggest that while integrin inside-out signaling and consequent cell adhesion induced by GPCR is important for directionality of neutrophil migration and for inducing outside-in signaling, $G\alpha_{13}$-dependent outside-in signaling is selectively important for cell motility, which is also required for neutrophil migration on β2 integrin ligand. Thus, targeting $G\alpha_{13}$ is a new approach for anti-inflammation therapy that does not affect adhesion function of $\beta_2$ integrins.

Integrin $\beta_2$ as well as $G\alpha_{13}$ were independently reported to play a role in cell migration (Kolaczkowska and Kubes, 2013; Kourtzelis et al., 2017; Nourshargh and Alon, 2014; Radhika et al., 2004; Shan et al., 2006; Tan et al., 2006). However, the possible connection between $\beta_2$ and $G\alpha_{13}$ in leukocyte migration has not been studied. Currently, the importance of $G\alpha_{13}$ in leukocyte function has been attributed to its role in transmitting canonical GPCR signaling, which is important in cytokine-mediated leukocyte activation and chemotaxis (Chen et al., 2012; Dorward et al., 2015; Francis et al., 2006; Goulimari et al., 2005; Surve et al., 2016). However, the data herein demonstrate that $G\alpha_{13}$ knockout in neutrophils does not affect the directionality of neutrophil migration nor cell adhesion, but selectively inhibits integrin-dependent cell motility and cell spreading. Thus the studies described herein show that $G\alpha_{13}$ plays an important role in neutrophil transendothelial migration via the integrin outside-in signaling pathway.

Neutrophils migrate via two different mechanisms: slow integrin-dependent migration and fast ameboid movement which is independent of integrins. (Lammermann and Sixt, 2009; Shen et al., 2013) The transendothelial migration of circulating blood neutrophils out of the vasculature requires a tightly regulated $\beta_2$ integrin-dependent process (Huttenlocher and Horwitz, 2011). The data show that $G\alpha_{13}$ is important in neutrophil migration on $\beta_2$ integrin ligand ICAM1 and in transendothelial migration which is ICAM1-dependent. Transendothelial migration of neutrophils was blocked by a specific monoclonal anti-$\beta_2$ antibody, further supporting the notion that the $G\alpha_{13}$-dependent neutrophil migration is also $\beta_2$-dependent migration. The data demonstrate that $G\alpha_{13}$ is not important for neutrophil migration on surfaces coated with BSA, which is not an integrin ligand, and interestingly, it was also found that $G\alpha_{13}$ is not involved in neutrophil migration on fibrinogen, which is a $\beta_2$ ligand in plasma and at the sites of vascular wound. This finding is intriguing, suggesting that not only is the role of $G\alpha_{13}$ selectively important in integrin-dependent cell migration, but is also selective for certain ligands of $\beta_2$, and this selective role appears to be important, as neutrophils migrate faster on ICAM1 than on fibrinogen-coated surfaces. It was reported in an early study that fibrinogen-mediated leukocyte adhesion to vascular endothelium is ICAM1-dependent (Languino et al., 1993), suggesting an important role for ICAM1 not only directly interacts with $\beta_2$ integrins to mediate $G\alpha_{13}$-dpendent leukocyte migration but is also important in fibrinogen (another $\beta_2$ ligand)-mediated leukocyte interaction with the endothelium. Thus, it is possible that fibrinogen may enhance leukocyte adhesion to the endothelium and leukocyte migration by modulating integrin-ICAM1 interaction and consequent outside-in signaling. In this respect, it was reported that conformational changes in $\alpha_L$ I domain can greatly enhances affinity between ICAM1 and I domain (McDowall et al., 1998), suggesting a potential mechanism for the modulating role of fibrinogen. Although, fibrinogen per se may also mediate slower neutrophil migration independently of $G\alpha_{13}$, in a way similar to BSA. Integrins, including $\beta_2$ integrins, transmit signals bidirectionally: Chemoattractants and cytokines induce "inside-out" signals which activate or enhance ligand binding to integrins. Ligand binding not only mediates cell adhesion, but also induces "outside-in" signals into the cell, leading to additional cellular responses, including cell spreading and cell retraction. Coordinated cell spreading (mainly in the leading edge) and retraction (mainly in the trailing edge) is thought to be responsible for driving integrin-dependent cell migration. Consistent with this notion, proteins that mediate integrin inside-out signaling, such as talin-1, kindlin-3 and RIAM were reported to play an important role in the directionality of migration of neutrophil-like cells (Lagarrigue et al., 2016b; Yamahashi et al., 2015). Thus, directionality of neutrophil migration requires GPCR-induced integrin activation and adhesion. Herein it is shown that $G\alpha_{13}$ plays an important role in enhancing the motility but not the directionality of integrin-dependent neutrophil migration, suggesting that, whereas directionality is determined by where integrin is activated and ligated, the motility is determined by integrin-mediated outside-in signaling. This is supported by the data that $G\alpha_{13}$ knockout did not affect adhesion of leukocytes to ICAM1, but significantly affected the cell spreading on ICAM1 during migration. Importantly, this data demonstrated that a peptide derived from the ExE motif of $\beta_2$ integrin subunit (the site that binds to $G\alpha_{13}$), significantly inhibited $\beta_2$ integrin-dependent neutrophil transendothelial migration, similar to the effect of $G\alpha_{13}$ knockout. As previously established, the importance of the ExE motif in $G\alpha_{13}$-integrin interaction and outside-in signaling in other cell types (Shen et al., 2015, 2013), these results suggest that $G\alpha_{13}$ plays an important role in the outside-in signaling-dependent machinery of neutrophil motility, and is thus critically important for $\beta_2$ integrin-dependent neutrophil transendothelial migration. Because neutrophil transendothelial migration plays critical roles in inflammation, targeting $G\alpha_{13}$ represents a new approach for developing novel types of anti-inflammatory drugs that do not totally abolish integrin function and leukocyte function in immunity.

In summary, disclosed herein is an engineered lipid-stabilized HLPN to efficiently deliver an inhibitor peptide of integrin outside-in signaling in vivo, which is a fast acting, reversible and potent anti-thrombotic drug without the adverse effect of bleeding. Importantly, post-ischemic injection of this new drug effectively treats MI/R injury and significantly reduces MI/R mortality. Furthermore, an anti-platelet strategy was developed in which M3mP6 HLPNs in combination with current anti-platelet drugs significantly enhances anti-thrombotic efficacy and reduces bleeding risk. The studies described herein were carried out in mouse models, in which the relevant $\beta_3$ cytoplasmic domain sequence is identical to humans.

Although preferred embodiments, uses and modifications of the disclosure have been depicted and disclosed, such description is to be considered illustrative rather than limiting, particularly since those of ordinary skill in the art would understand that various modifications and changes may be made in the disclosure without departing from the spirit and scope of the claims which follow.

REFERENCES

The following represents a listing of the references cited in the background and examples 1-15.

1. K. Fosgerau, T. Hoffmann, Peptide therapeutics: current status and future directions. *Drug Discov Today* 20, 122-128 (2015).
2. M. L. Tan, P. F. Choong, C. R. Dass, Recent developments in liposomes, microparticles and nanoparticles for protein and peptide drug delivery. *Peptides* 31, 184-193 (2010).
3. E. J. Benjamin, M. J. Blaha, S. E. Chiuve, M. Cushman, S. R. Das, R. Deo, S. D. de Ferranti, J. Floyd, M. Fornage, C. Gillespie, C. R. Isasi, M. C. Jimenez, L. C. Jordan, S. E. Judd, D. Lackland, J. H. Lichtman, L. Lisabeth, S. Liu, C. T. Longenecker, R. H. Mackey, K. Matsushita, D. Mozaffarian, M. E. Mussolino, K. Nasir, R. W. Neumar, L. Palaniappan, D. K. Pandey, R. R. Thiagarajan, M. J. Reeves, M. Ritchey, C. J. Rodriguez, G. A. Roth, W. D. Rosamond, C. Sasson, A. Towfighi, C. W. Tsao, M. B. Turner, S. S. Virani, J. H. Voeks, J. Z. Willey, J. T. Wilkins, J. H. Wu, H. M. Alger, S. S. Wong, P. Muntner, C. American Heart Association Statistics, S. Stroke Statistics, Heart Disease and Stroke Statistics-2017 Update: A Report From the American Heart Association. *Circulation* 135, e146-e603 (2017).
4. B. S. Coller, Historical perspective and future directions in platelet research. *J Thromb Haemost* 9 Suppl 1, 374-395 (2011).
5. Z. M. Ruggeri, Platelets in atherothrombosis. *Nat Med* 8, 1227-1234. (2002).

6. P. Libby, Mechanisms of acute coronary syndromes and their implications for therapy. *N Engl J Med* 368, 2004-2013 (2013).
7. K. Bledzka, S. S. Smyth, E. F. Plow, Integrin alphaIIb-beta3: from discovery to efficacious therapeutic target. *Circ Res* 112, 1189-1200 (2013).
8. S. J. Shattil, C. Kim, M. H. Ginsberg, The final steps of integrin activation: the end game. *Nat Rev Mol Cell Biol* 11, 288-300 (2010).
9. P. T. O'Gara, F. G. Kushner, D. D. Ascheim, D. E. Casey, Jr., M. K. Chung, J. A. de Lemos, S. M. Ettinger, J. C. Fang, F. M. Fesmire, B. A. Franklin, C. B. Granger, H. M. Krumholz, J. A. Linderbaum, D. A. Morrow, L. K. Newby, J. P. Ornato, N. Ou, M. J. Radford, J. E. Tamis-Holland, C. L. Tommaso, C. M. Tracy, Y. J. Woo, D. X. Zhao, J. L. Anderson, A. K. Jacobs, J. L. Halperin, N. M. Albert, R. G. Brindis, M. A. Creager, D. DeMets, R. A. Guyton, J. S. Hochman, R. J. Kovacs, E. M. Ohman, W. G. Stevenson, C. W. Yancy, 2013 ACCF/AHA guideline for the management of ST-elevation myocardial infarction: a report of the American College of Cardiology Foundation/American Heart Association Task Force on Practice Guidelines. *J Am Coll Cardiol* 61, e78-140 (2013).
10. P. Metharom, M. C. Berndt, R. I. Baker, R. K. Andrews, Current state and novel approaches of antiplatelet therapy. *Arterioscler Thromb Vasc Biol* 35, 1327-1338 (2015).
11. P. B. Berger, D. L. Bhatt, V. Fuster, P. G. Steg, K. A. Fox, M. Shao, D. M. Brennan, W. Hacke, G. Montalescot, S. R. Steinhubl, E. J. Topol, C. Investigators, Bleeding complications with dual antiplatelet therapy among patients with stable vascular disease or risk factors for vascular disease: results from the Clopidogrel for High Atherothrombotic Risk and Ischemic Stabilization, Management, and Avoidance (CHARISMA) trial. *Circulation* 121, 2575-2583 (2010).
12. B. Estevez, B. Shen, X. Du, Targeting integrin and integrin signaling in treating thrombosis. *Arterioscler Thromb Vasc Biol* 35, 24-29 (2015).
13. J. Mehilli, A. Kastrati, S. Schulz, S. Frungel, S. G. Nekolla, W. Moshage, F. Dotzer, K. Huber, J. Pache, J. Dirschinger, M. Seyfarth, S. Martinoff, M. Schwaiger, A. Schomig, I. Bavarian Reperfusion Alternatives Evaluation-3 Study, Abciximab in patients with acute ST-segment-elevation myocardial infarction undergoing primary percutaneous coronary intervention after clopidogrel loading: a randomized double-blind trial. *Circulation* 119, 1933-1940 (2009).
14. D. M. Safley, L. Venkitachalam, K. F. Kennedy, D. J. Cohen, Impact of Glycoprotein IIb/IIIa Inhibition in Contemporary Percutaneous Coronary Intervention for Acute Coronary Syndromes: Insights From the National Cardiovascular Data Registry. *JACC Cardiovasc Interv* 8, 1574-1582 (2015).
15. G. Ndrepepa, A. Kastrati, Bleeding complications in patients undergoing percutaneous coronary interventions: current status and perspective. *Coron Artery Dis* 25, 247-257 (2014).
16. R. Mehran, S. Pocock, E. Nikolsky, G. D. Dangas, T. Clayton, B. E. Claessen, A. Caixeta, F. Feit, S. V. Manoukian, H. White, M. Bertrand, E. M. Ohman, H. Parise, A. J. Lansky, A. M. Lincoff, G. W. Stone, Impact of bleeding on mortality after percutaneous coronary intervention results from a patient-level pooled analysis of the REPLACE-2 (randomized evaluation of PCI linking angiomax to reduced clinical events), ACUITY (acute catheterization and urgent intervention triage strategy), and HORIZONS-AMI (harmonizing outcomes with revascularization and stents in acute myocardial infarction) trials. *JACC Cardiovasc Interv* 4, 654-664 (2011).
17. G. Ndrepepa, E. Guerra, S. Schulz, M. Fusaro, S. Cassese, A. Kastrati, Weight of the bleeding impact on early and late mortality after percutaneous coronary intervention. *J Thromb Thrombolysis* 39, 35-42 (2015).
18. M. Moscucci, Frequency and costs of ischemic and bleeding complications after percutaneous coronary interventions: rationale for new antithrombotic agents. *J Invasive Cardiol* 14 Suppl B, 55B-64B (2002).
19. S. L. French, J. F. Arthur, H. A. Tran, J. R. Hamilton, Approval of the first protease-activated receptor antagonist: Rationale, development, significance, and considerations of a novel anti-platelet agent. *Blood Rev* 29, 179-189 (2015).
20. P. C. Wong, D. Seiffert, J. E. Bird, C. A. Watson, J. S. Bostwick, M. Giancarli, N. Allegretto, J. Hua, D. Harden, J. Guay, M. Callejo, M. M. Miller, R. M. Lawrence, J. Banville, J. Guy, B. D. Maxwell, E. S. Priestley, A. Marinier, R. R. Wexler, M. Bouvier, D. A. Gordon, W. A. Schumacher, J. Yang, Blockade of protease-activated receptor-4 (PAR4) provides robust antithrombotic activity with low bleeding. *Sci Transl Med* 9, (2017).
21. B. Shen, X. Zhao, K. A. O'Brien, A. Stojanovic-Terpo, M. K. Delaney, K. Kim, J. Cho, S. C. Lam, X. Du, A directional switch of integrin signalling and a new anti-thrombotic strategy. *Nature* 503, 131-135 (2013).
22. H. Gong, B. Shen, P. Flevaris, C. Chow, S. C. Lam, T. A. Voyno-Yasenetskaya, T. Kozasa, X. Du, G protein subunit Galpha13 binds to integrin alphaIIbbeta3 and mediates integrin "outside-in" signaling. *Science* 327, 340-343 (2010).
23. D. L. Bhatt, A. M. Lincoff, C. M. Gibson, G. W. Stone, S. McNulty, G. Montalescot, N. S. Kleiman, S. G. Goodman, H. D. White, K. W. Mahaffey, C. V. Pollack, Jr., S. V. Manoukian, P. Widimsky, D. P. Chew, F. Cura, I. Manukov, F. Tousek, M. Z. Jafar, J. Arneja, S. Skerjanec, R. A. Harrington, C. P. Investigators, Intravenous platelet blockade with cangrelor during PCI. *N Engl J Med* 361, 2330-2341 (2009).
24. D. L. Bhatt, G. W. Stone, K. W. Mahaffey, C. M. Gibson, P. G. Steg, C. W. Hamm, M. J. Price, S. Leonardi, D. Gallup, E. Bramucci, P. W. Radke, P. Widimsky, F. Tousek, J. Tauth, D. Spriggs, B. T. McLaurin, D. J. Angiolillo, P. Genereux, T. Liu, J. Prats, M. Todd, S. Skerjanec, H. D. White, R. A. Harrington, C. P. Investigators, Effect of platelet inhibition with cangrelor during PCI on ischemic events. *N Engl J Med* 368, 1303-1313 (2013).
25. A. Pang, Y. Cui, Y. Chen, N. Cheng, M. K. Delaney, M. Gu, A. Stojanovic-Terpo, C. Zhu, X. Du, Shear-induced integrin signaling in platelet phosphatidylserine exposure, microvesicle release, and coagulation. *Blood* 132, 533-543 (2018).
26. R. Jasuja, B. Furie, B. C. Furie, Endothelium-derived but not platelet-derived protein disulfide isomerase is required for thrombus formation in vivo. *Blood* 116, 4665-4674 (2010).
27. L. Ivanciu, S. Krishnaswamy, R. M. Camire, New insights into the spatiotemporal localization of prothrombinase in vivo. *Blood* 124, 1705-1714 (2014).
28. Z. Li, M. K. Delaney, K. A. O'Brien, X. Du, Signaling During Platelet Adhesion and Activation. *Arterioscler Thromb Vasc Biol* 30, 2341-2349 (2010).

29. B. Estevez, X. Du, New Concepts and Mechanisms of Platelet Activation Signaling. *Physiology* (*Bethesda*) 32, 162-177 (2017).
30. R. O. Hynes, Integrins: bidirectional, allosteric signaling machines. *Cell* 110, 673-687. (2002).
31. H. Yin, A. Stojanovic-Terpo, W. Xu, A. Corken, A. Zakharov, F. Qian, S. Pavlovic, A. Krbanjevic, A. V. Lyubimov, Z. J. Wang, J. Ware, X. Du, Role for platelet glycoprotein Ib-IX and effects of its inhibition in endotoxemia-induced thrombosis, thrombocytopenia, and mortality. *Arterioscler Thromb Vasc Biol* 33, 2529-2537 (2013).
32. A. J. Donovan, J. Kalkowski, S. A. Smith, J. H. Morrissey, Y. Liu, Size-controlled synthesis of granular polyphosphate nanoparticles at physiologic salt concentrations for blood clotting. *Biomacromolecules* 15, 3976-3984 (2014).
33. Z. Li, G. Zhang, G. C. Le Breton, X. Gao, A. B. Malik, X. Du, Two waves of platelet secretion induced by thromboxane A2 receptor and a critical role for phosphoinositide 3-kinases. *J Biol Chem* 278, 30725-30731 (2003).
34. B. Estevez, A. Stojanovic-Terpo, M. K. Delaney, K. A. O'Brien, M. C. Berndt, C. Ruan, X. Du, LIM kinase-1 selectively promotes glycoprotein Ib-IX-mediated TXA2 synthesis, platelet activation, and thrombosis. *Blood* 121, 4586-4594 (2013).
35. B. Shen, B. Estevez, Z. Xu, B. Kreutz, A. Karginov, Y. Bai, F. Qian, U. Norifumi, D. Mosher, X. Du, The interaction of Galphal3 with integrin betal mediates cell migration by dynamic regulation of RhoA. *Mol Biol Cell* 26, 3658-3670 (2015).
36. B. Estevez, K. Kim, M. K. Delaney, A. Stojanovic-Terpo, B. Shen, C. Ruan, J. Cho, Z. M. Ruggeri, X. Du, Signaling-mediated cooperativity between glycoprotein Ib-IX and protease-activated receptors in thrombin-induced platelet activation. *Blood* 127, 626-636 (2016).
37. S. M. Day, J. L. Reeve, D. D. Myers, W. P. Fay, Murine thrombosis models. *Thromb Haemost* 92, 486-494 (2004).
38. K. A. O'Brien, A. Stojanovic-Terpo, N. Hay, X. Du, An important role for Akt3 in platelet activation and thrombosis. *Blood* 118, 4215-4223 (2011).
39. J. A. Marjanovic, Z. Li, A. Stojanovic, X. Du, Stimulatory roles of nitric-oxide synthase 3 and guanylyl cyclase in platelet activation. *J Biol Chem* 280, 37430-37438 (2005).
40. M. Brooks, J. Catalfamo, Buccal mucosa bleeding time is prolonged in canine models of primary hemostatic disorders. *Thromb Haemost* 70, 777-780 (1993).
41. Z. Xu, J. Alloush, E. Beck, N. Weisleder, A murine model of myocardial ischemia-reperfusion injury through ligation of the left anterior descending artery. *J Vis Exp*, (2014).
42. L. Zhu, C. Xu, X. Huo, H. Hao, Q. Wan, H. Chen, X. Zhang, R. M. Breyer, Y. Huang, X. Cao, D. P. Liu, G. A. FitzGerald, M. Wang, The cyclooxygenase-1/mPGES-1/endothelial prostaglandin EP4 receptor pathway constrains myocardial ischemia-reperfusion injury. *Nat Commun* 10, 1888 (2019).

The following represents a listing of the references cited in examples 16-19:

1. Angus, D. C. & van der Poll, T. Severe sepsis and septic shock. *N Engl J Med* 369, 840-851 (2013).
2. Levi, M. & van der Poll, T. Inflammation and coagulation. *Crit Care Med* 38, S26-34 (2010).
3. Esmon, C. T. Crosstalk between inflammation and thrombosis. *Maturitas* 61, 122-131 (2008).
4. Davis, R. P., Miller-Dorey, S. & Jenne, C. N. Platelets and coagulation in infection. *Clin Trans Immunol* 5, e89 (2016).
5. Fink, M. P. & Warren, H. S. Strategies to improve drug development for sepsis. *Nat Rev Drug Discov* 13, 741-758 (2014).
6. Bernard, G. R., et al. Efficacy and safety of recombinant human activated protein C for severe sepsis. *N Engl J Med* 344, 699-709 (2001).
7. Winning, J., et al. Antiplatelet drugs and outcome in mixed admissions to an intensive care unit. *Crit Care Med* 38, 32-37 (2010).
8. Seidel, M., Winning, J., Claus, R. A., Bauer, M. & Losche, W. Beneficial effect of clopidogrel in a mouse model of polymicrobial sepsis. *J Thromb Haemost* 7, 1030-1032 (2009).
9. Storey, R. F., et al. Lower mortality following pulmonary adverse events and sepsis with ticagrelor compared to clopidogrel in the PLATO study. *Platelets* 25, 517-525 (2014).
10. Liverani, E., Rico, M. C., Tsygankov, A. Y., Kilpatrick, L. E. & Kunapuli, S. P. P2Y12 Receptor Modulates Sepsis-Induced Inflammation. *Arterioscler Thromb Vasc Biol* 36, 961-971 (2016).
11. Tsai, M. J., et al. Association of prior antiplatelet agents with mortality in sepsis patients: a nationwide population-based cohort study. *Intensive Care Med* 41, 806-813 (2015).
12. Tsai, M. J., Shih, C. J. & Chen, Y. T. Association of prior antiplatelet agents with mortality in sepsis patients. *Intensive Care Med* 42, 605-607 (2016).
13. Benefield, R. J., Drevets, D. A., Huycke, M. M. & Gentry, C. A. A multicenter evaluation of the safety of drotrecogin alfa (activated) in patients with baseline bleeding precautions. Curr *Drug Saf* 7, 3-7 (2012).
14. Coller, B. S. Anti-GPIIb/IIIa drugs: current strategies and future directions. *Thromb Haemost* 86, 427-443 (2001).
15. Estevez, B., Shen, B. & Du, X. Targeting integrin and integrin signaling in treating thrombosis. *Arterioscler Thromb Vasc Biol* 35, 24-29 (2015).
16. Shen, B., et al. A directional switch of integrin signalling and a new anti-thrombotic strategy. *Nature* 503, 131-135 (2013).
17. Auwerx, J. The human leukemia cell line, THP-1: a multifacetted model for the study of monocyte-macrophage differentiation. *Experientia* 47, 22-31 (1991).
18. Levi, M., Schultz, M. & van der Poll, T. Sepsis and thrombosis. *Semin Thromb Hemost* 39, 559-566 (2013).
19. Semeraro, N., Ammollo, C. T., Semeraro, F. & Colucci, M. Sepsis, thrombosis and organ dysfunction. *Thromb Res* 129, 290-295 (2012).
20. Moers, A., et al. G13 is an essential mediator of platelet activation in hemostasis and thrombosis. *Nat Med* 9, 1418-1422 (2003).
21. Seemann, S., Zohles, F. & Lupp, A. Comprehensive comparison of three different animal models for systemic inflammation. *J Biomed Sci* 24, 60 (2017).
22. Speyer, C. L., et al. Novel chemokine responsiveness and mobilization of neutrophils during sepsis. *Am J Pathol* 165, 2187-2196 (2004).
23. Bhargava, R., et al. Acute lung injury and acute kidney injury are established by four hours in experimental sepsis and are improved with pre, but not post, sepsis administration of TNF-alpha antibodies. *PLoS One* 8, e79037 (2013).

24. Gill, S. E., Taneja, R., Rohan, M., Wang, L. & Mehta, S. Pulmonary microvascular albumin leak is associated with endothelial cell death in murine sepsis-induced lung injury in vivo. *PLoS One* 9, e88501 (2014).

25. Singer, G., Urakami, H., Specian, R. D., Stokes, K. Y. & Granger, D. N. Platelet recruitment in the murine hepatic microvasculature during experimental sepsis: role of neutrophils. *Microcirculation* 13, 89-97 (2006).

26. Davis, B. K. Isolation, culture, and functional evaluation of bone marrow-derived macrophages. *Methods Mol Biol* 1031, 27-35 (2013).

27. Yin, H., et al. Role for platelet glycoprotein Ib-IX and effects of its inhibition in endotoxemia-induced thrombosis, thrombocytopenia, and mortality. *Arterioscler Thromb Vasc Biol* 33, 2529-2537 (2013).

28. Estevez, B., et al. LIM kinase-1 selectively promotes glycoprotein Ib-IX-mediated TXA2 synthesis, platelet activation, and thrombosis. *Blood* 121, 4586-4594 (2013).

29. Pang, A., et al. Shear-induced integrin signaling in platelet phosphatidylserine exposure, microvesicle release, and coagulation. *Blood* 132, 533-543 (2018).

30. Gong, H., et al. G protein subunit Galpha13 binds to integrin alphallbbeta3 and mediates integrin "outside-in" signaling. *Science* 327, 340-343 (2010).

31. Shen, B., et al. The interaction of Galpha13 with integrin betal mediates cell migration by dynamic regulation of RhoA. *Mol Biol Cell* 26, 3658-3670 (2015).

32. Cuenca, A. G., Delano, M. J., Kelly-Scumpia, K. M., Moldawer, L. L. & Efron, P. A. Cecal ligation and puncture. *Curr Protoc Immunol* Chapter 19, Unit 19 13 (2010).

33. Cheng, N., Liang, Y., Du, X. & Ye, R. D. Serum amyloid A promotes LPS clearance and suppresses LPS-induced inflammation and tissue injury. *EMBO Rep* 19(2018).

The following represents a listing of the references cited in examples 20-26:

1. Bargatze BRF, Kurk S, Butcher E C, Jutila M A. 1994. Neutrophils Roll on Adherent Neutrophils Bound to Cytokine-induced Endothelial Cells via L-Selectin on the rolling cells. J Exp Med 180:1785-1792.

2. Bian D, Mahanivong C, Yu J, Frisch S M, Pan Z K, Ye R D, Huang S. 2006. The G12/13-RhoA signaling pathway contributes to efficient lysophosphatidic acid-stimulated cell migration. Oncogene 25:2234-2244. doi:10.1038/sj.onc.1209261

3. Call D R, Nemzek J A, Ebong S J, Bolgos G L, Newcomb D E, Remick D G. 2001. Ratio of local to systemic chemokine concentrations regulates neutrophil recruitment. Am J Pathol 158:715-721. doi:10.1016/50002-9440(10)64014-X 4. Chen Z, Guo L, Hadas J, Gutowski S, Sprang S R, Sternweis P C. 2012. Activation of p115-RhoGEF requires direct association of Gα13and the Dbl homology domain. J Biol Chem 287:25490-25500. doi:10.1074/jbc.M111.333716

5. Diacovo T G, Roth S J, Buccola J M, Bainton D F, Springer T a. 1996. Neutrophil rolling, arrest, and transmigration across activated, surface-adherent platelets via sequential action of P-selectin and the beta 2-integrin CD11b/CD18. Blood 88:146-157.

6. Ding Z M, Babensee J E, Simon S I, Lu H, Perrard J L, Bullard D C, Dai X Y, Bromley S K, Dustin M L, Entman M L, Smith C W, Ballantyne C M. 1999. Relative contribution of LFA-1 and Mac-1 to neutrophil adhesion and migration. J Immunol 163:5029-38.

7. Dorward D A, Lucas C D, Chapman G B, Haslett C, Dhaliwal K, Rossi A G. 2015. The role of formylated peptides and formyl peptide receptor 1 in governing neutrophil function during acute inflammation. Am J Pathol 185:1172-1184. doi:10.1016/j.ajpath.2015.01.020

8. Flick M J, Du X L, Witte D P, Jirouskovi M, Soloviev D A, Busuttil S J, Plow E F, Degen J L. 2004. Leukocyte engagement of fibrin(ogen) via the integrin receptor aMP2/Mac-1 is critical for host inflammatory response in vivo. J Clin Invest 113:1596-1606. doi:10.1172/JCI20741

9. Francis S A, Shen X, Young J B, Kaul P, Lerner D J. 2006. Rho GEF Lsc is required for normal polarization, migration, and adhesion of formyl-peptide-stimulated neutrophils.

Blood 107:1627-1635. doi:10.1182/blood-2005-03-1164

10. Goulimari P, Kitzing™, Knieling H, Brandt D T, Offermanns S, Grosse R. 2005. Gα12/13 is essential for directed cell migration and localized rho-dial function. J Biol Chem 280:42242-42251. doi:10.1074/jbc.M508690200

11. Haixia Gong, Bo Shen, Panagiotis Flevaris, Christina Chow, Stephen C.-T. Lam, Tatyana A. Voyno-Yasenetskaya, Tohru Kozasa and X Du. 2010. G Protein Subunit Gα13 Binds to Integrin αIIbb3 and Mediates Integrin "Outside-In" Signaling. Science (80-) 327:342.

12. Haixia Gong, Bo Shen, Panagiotis Flevaris, Christina Chow S C-T L, Tatyana A. Voyno-Yasenetskaya, Tohru Kozasa X Du. 2010. G Protein Subunit Gα13 Binds to integrin alpha I I b beta III and mediates "Outside-In" Signaling. Science (80-) 327:340-343.

13. Heit B, Tavener S, Raharjo E, Kubes P. 2002. An intracellular signaling hierarchy determines direction of migration in opposing chemotactic gradients. J Cell Biol 159:91-102. doi:10.1083/jcb.200202114

14. Hind L E, Vincent WJB, Huttenlocher A. 2016. Leading from the Back: The Role of the Uropod in Neutrophil Polarization and Migration. Dev Cell 38:161-169. doi:10.1016/j.devcel.2016.06.031

15. Huttenlocher A, Horwitz A R. 2011. Integrins in cell migration. Cold Spring Harb Perspect Biol 3 V N-re:1-16. doi:10.1101/cshperspect.a005074

16. Hynes R O. 2004. The emergence of integrins: A personal and historical perspective. Matrix Biol 23:333-340. doi:10.1016/j.matbio.2004.08.001

17. Hynes R O. 2002. Integrins: Bidirectional, allosteric signaling machines. Cell 110:673-687. doi:10.1016/S0092-8674(02)00971-6

18. Hynes R O. 1987. Integrins: A family of cell surface receptors. Cell 48:549-554. doi:10.1016/0092-8674(87)90233-9

19. Kiosses W B, Shattil S J, Pampori N, Schwartz M A. 2001. Rac recruits high-affinity integrin α v R 3 to lamellipodia in endothelial cell migration. Nat cell 3(3).

20. Kolaczkowska E, Kubes P. 2013. Neutrophil recruitment and function in health and inflammation. Nat Rev Immunol 13:159-175. doi:10.1038/nri3399

21. Kourtzelis I, Mitroulis I, Renesse J Von, Hajishengallis G, Chavakis T. 2017. From leukocyte recruitment to resolution of inflammation: the cardinal role of integrins. J Leukoc Biol 102:677-683. doi:10.1189/jlb.3MR0117-024R 22. Kozasa T, Hajicek N, Chow C R, Suzuki N. 2011. Signalling mechanisms of RhoGTPase regulation by the heterotrimeric G proteins G12 and G13. J Biochem 150: 357-369. doi:10.1093/jb/mvr105

23. Kreutz B, Hajicek N, Yau D M, Nakamura S, Kozasa T. 2007. Distinct regions of Gα13 participate in its regulatory interactions with RGS homology domain-containing RhoGEFs. Cell Signal 19:1681-1689. doi:10.1016/j.cellsig.2007.03.004

24. Kroon J, Schaefer A, van Rijssel J, Hoogenboezem M, van Alphen F, Hordijk P, Stroes ESG, Stromblad S, van Rheenen J, van Buul J D. 2018. Inflammation-Sensitive Myosin-X Functionally Supports Leukocyte Extravasation by Cdc42-Mediated ICAM-1-Rich Endothelial Filopodia Formation. J Immunol ji1700702. doi:10.4049/jimmunol.1700702

25. Kumar S, Xu J, Perkins C, Guo F, Snapper S, Finkelman F D, Zheng Y, Filippi M. 2012. Cdc42 regulates neutrophil migration via crosstalk between WASp, CD11b, and microtubules. Blood 120:2-4. doi:10.1182/blood-2012-04-426981. The 26. Lagarrigue F, Kim C, Ginsberg M H. 2016a. The Rap l-RIAM-talin axis of integrin activation and blood cell function. Blood 128:479-487. doi:10.1182/blood-2015-12-638700

27. Lagarrigue F, Kim C, Ginsberg M H. 2016b. The Rap l-RIAM-talin axis of integrin activation and blood cell function. Blood 128:479-488. doi:10.1182/blood-2015-12-638700.cytoplasmic 28. Lammermann T, Bader B L, Monkley S J, Worbs T, Wedlich-Soldner R, Hirsch K, Keller M, Forster R, Critchley D R, Fassler R, Sixt M. 2008. Rapid leukocyte migration by integrin-independent flowing and squeezing. Nature 453:51-55. doi:10.1038/nature06887

29. Lammermann T, Sixt M. 2009. Mechanical modes of "amoeboid" cell migration. Cuff Opin Cell Biol. doi: 10.1016/j.ceb.2009.05.003

30. Languino L R, Plescia J, Duperray A, Brian A A, Plow E F, Geltosky J E, Altieri D C. 1993. Fibrinogen mediates leukocyte adhesion to vascular endothelium through an ICAM-1-dependent pathway. Cell 73:1423-1434. doi:10.1016/0092-8674(93)90367-Y 31. Ley K, Laudanna C, Cybulsky M I, Nourshargh S. 2007. Getting to the site of inflammation: The leukocyte adhesion cascade updated. Nat Rev Immunol 7:678-689. doi: 10.1038/nri2156

32. Li Z, Delaney M K, O'Brien K A, Du X. 2010. Signaling during platelet adhesion and activation. Arterioscler Thromb Vasc Biol 30:2341-2349. doi:10.1161/ATVBAHA.110.207522

33. Luscinskas F W. 2008. Assays of Transendothelial Migration in vitro. Methods Enzymol 6879:155-176. doi: 10.1016/S0076-6879(08)02009-0.Assays 34. Margadant C, Sonnenberg A. 2010. Integrin-TGF-beta crosstalk in fibrosis, cancer and wound healing. EMBO Rep 11:97-105. doi:10.1038/embor.2009.276

35. McDowall A, Leitinger B, Stanley P, Bates P A, Randi A M, Hogg N. 1998. The I domain of integrin leukocyte function-associated antigen-1 is involved in a conformational change leading to high affinity binding to ligand intercellular adhesion molecule 1 (ICAM-1). J Biol Chem 273:27396-27403. doi:10.1074/jbc.273.42.27396

36. Moers A, Nieswandt B, Massberg S, Wettschureck N, Gruner S, Konrad I, Schulte V, Aktas B, Gratacap M P, Simon M I, Gawaz M, Offermanns S. 2003. G13 is an essential mediator of platelet activation in hemostasis and thrombosis. Nat Med 9:1418-1422. doi:10.1038/nm943

37. Nourshargh S, Alon R. 2014. Leukocyte Migration into Inflamed Tissues. Immunity 41:694-707. doi:10.1016/j.immuni.2014.10.008

38. Nuzzi, Paul;Lokuta, Mary; Huttenlocher A. 2007. Analysis of Neutrophil Chemotaxis, second edi. ed. Totowa, N J: Humana Press Inc.

39. Radhika V, Onesime D, Ji H H, Dhanasekaran N. 2004. Gα13 stimulates cell migration through cortactin-interacting protein Hax-1. J Biol Chem 279:49406-49413. doi:10.1074/jbc.M408836200

40. Ray A, Dittel B N. 2010. Isolation of mouse peritoneal cavity cells. J Vis Exp 9-11. doi:10.3791/1488

41. Reutershan J. 2005. Sequential recruitment of neutrophils into lung and bronchoalveolar lavage fluid in LPS-induced acute lung injury. AJP Lung Cell Mol Physiol 289:L807-L815. doi:10.1152/ajplung.00477.2004

42. Rieken S, Sassmann A, Herroeder S, Wallenwein B, Moers A, Offermanns S, Wettschureck N. 2006. G 12/G 13 Family G Proteins Regulate Marginal Zone B Cell Maturation, Migration, and Polarization. J Immunol 177: 2985-2993. doi:10.4049/jimmunol.177.5.2985

43. RStudio Team. 2020. Citing RStudio—RStudio Support. RStudio Integr Dev R RStudio.

44. Seguin L, Desgrosellier J S, Weis S M, Cheresh D A. 2015. Integrins and cancer: Regulators of cancer stemness, metastasis, and drug resistance. Trends Cell Biol 25:234-240. doi:10.1016/j.tcb.2014.12.006

45. Shan D, Chen L, Wang D, Tan Y C, Gu J L, Huang X Y. 2006. The G Protein Gα13 Is Required for Growth Factor-Induced Cell Migration. Dev Cell 10:707-718. doi:10.1016/j.devcel.2006.03.014

46. Shen B, Estevez B, Xu Z, Kreutz B, Karginov A, Bai Y, Qian F, Norifumi U, Mosher D, Du X. 2015. The interaction of G 13 with integrin β1 mediates cell migration by dynamic regulation of RhoA. Mol Biol Cell 26:3658-3670. doi:10.1091/mbc.E15-05-0274

47. Shen B, Zhao X, O'Brien K A, Stojanovic-Terpo A, Delaney M K, Kim K, Cho J, Lam SCT, Du X. 2013. A directional switch of integrin signalling and a new anti-thrombotic strategy. Nature 503:131-135. doi:10.1038/naturel2613

48. Southgate E L, He R L, Gao J, Philip M, Nanamori M, Ye R D, Southgate E L, He R L, Gao J, Murphy P M, Nanamori M, Ye R D. 2008. Identification of Formyl Peptides from Listeria monocytogenes and Staphylococcus aureus as Potent Chemoattractants for Mouse Neutrophils. J Immunol 181:1429-1437. doi:10.4049/jimmunol.181.2.1429

49. Surve C R, To J Y, Malik S, Kim M, Smrcka A V. 2016. Dynamic regulation of neutrophil polarity and migration by the heterotrimeric G protein subunits G alpha i-GTP and G beta gamma. Sci Signal 9:1-10. doi:10.1126/scisignal.aad8163

50. Suzuki N, Nakamura S, Mano H, Kozasa T. 2003. Gα12 activates Rho GTPase through tyrosine-phosphorylated leukemia-associated RhoGEF. Proc Natl Acad Sci USA 100:733-738. doi:10.1073/pnas.0234057100

51. Szczur K, Zheng Y, Filippi M D. 2009. The small Rho GTPase Cdc42 regulates neutrophil polarity via CD11b integrin signaling. Blood 114:4527-4537. doi:10.1182/blood-2008-12-195164

52. Tan W, Martin D, Gutkind J S. 2006. The Gα13-Rho signaling axis is required for SDF-1-induced migration through CXCR. J Biol Chem 281:39542-39549. doi: 10.1074/jbc.M609062200

53. Thelen M, Stein J V. 2008. How chemokines invite leukocytes to dance. Nat Immunol 9:953-959. doi: 10.1038/ni.f.207

54. Vestweber D. 2015. Review: How leukocytes cross the vascular endothelium. Nat Rev Immunol 15:692-704.

55. Weckmann M, Becker T, Nissen G, Pech M, Kopp M V. 2017. SiMA: A simplified migration assay for analyzing neutrophil migration. Cytom Part A 91:675-685. doi: 10.1002/cyto.a.23114

56. Yamahashi Y, Cavnar P J, Hind L E, Berthier E, Bennin D A, Beebe D, Huttenlocher A. 2015. Integrin associated proteins differentially regulate neutrophil polarity and directed migration in 2D and 3D. Biomed Microdevices 17. doi:10.1007/s10544-015-9998-x

The invention claimed is:

1. An engineered, lipid-stabilized, high-loading peptide nanoparticle comprising a) a peptide, b) one or more lipids free of a water-soluble polymer, and c) one or more lipids covalently attached to a water-soluble polymer, wherein:

i) greater than 10 mole percent of the total nanoparticle mass is the peptide;

ii) 2 to 20 mole percent of the total nanoparticle mass is the of one or more lipids free of a water-soluble polymer; and iii) 10 to 60 mole percent of the total nanoparticle mass is the one or more lipids covalently attached to a water-soluble polymer, wherein the peptide is a lipidated peptide, amphiphilic peptide, or a peptide conjugated to a hydrophobic molecule, and wherein the peptide consists of 5 to 50 amino acid residues.

2. The engineered, lipid-stabilized, high-loading peptide nanoparticle of claim 1, wherein the peptide is a lipidated peptide which is conjugated or covalently attached to a fatty acid.

3. The engineered, lipid-stabilized, high-loading peptide nanoparticle of claim 2, wherein the lipidated peptide is myristoylated.

4. The engineered, lipid-stabilized, high-loading peptide nanoparticle of claim 1, wherein the one or more lipids free of a water-soluble polymer is phosphatidylcholine (PC), phosphatidylglycerol (PG), phosphatidyl-inositol (PI), phosphatidyl-serine (PS), phosphatidylethanolamine (PE), or mixtures thereof and the one or more lipids covalently attached to a water-soluble polymer is PEG-phosphatidylethanolamine (PEG-PE), PEG-phosphatidylcholine(PEG-PC), PEG-phosphatidylglycerol (PEG-PG), PEG-phosphatidyl-inositol (PEG-PI), PEG-phosphatidyl-serine (PEG-PS), PEG-1,2-distearoyl-sn-glycero-3-phosphoethanolamine-N-[amino(polyethyleneglycol)] (PEG-DSPE), or a mixture thereof.

5. The engineered, lipid-stabilized, high-loading peptide nanoparticle of claim 1, wherein the one or more lipids covalently attached to a water-soluble polymer is PEG-DSPE and the one or more lipids free of a water-soluble polymer is phosphatidylcholine.

6. The engineered, lipid-stabilized, high-loading peptide nanoparticle according to claim 5, wherein 2 to 10 mole percent of the total nanoparticle mass is the one or more lipids free of a water-soluble polymer.

7. The engineered, lipid-stabilized, high-loading peptide nanoparticle of claim 1, wherein the peptide comprises the amino acid sequence $FEX_1ERX_2$ (SEQ ID NO: 1) wherein $X_1$ and $X_2$ are natural or unnatural amino acids, wherein the peptide is a 6-mer, 7-mer, 8-mer or 9-mer, and wherein the peptide inhibits both the integrin-dependent and integrin-independent platelet granule secretion or wherein the peptide inhibits leukocyte integrin outside-in signaling.

8. The engineered, lipid-stabilized, high-loading peptide nanoparticle of claim 6, wherein $X_1$ is glutamic acid or lysine and/or $X_2$ is leucine, isoleucine, alanine, methionine or lysine.

9. The engineered, lipid-stabilized, high-loading peptide nanoparticle of claim 6, wherein the peptide is myristoylated.

10. The engineered, lipid-stabilized, high-loading peptide nanoparticle of claim 1, wherein the peptide comprises one of the amino acid sequences: FEEERI (SEQ ID NO: 2), FEKEKI (SEQ ID NO: 3), FEKERI (SEQ ID NO: 4), RGT, EEERA (SEQ ID NO: 5), FEEERA (SEQ ID NO: 6), FEEERM (SEQ ID NO: 7), FEEERL (SEQ ID NO: 8), FEKEKM (SEQ ID NO: 9), FEKEKL (SEQ ID NO: 10), FEKERM (SEQ ID NO: 11), FEKERL (SEQ ID NO: 12), CFEEERAC (SEQ ID NO: 13), FEEERAR (SEQ ID NO: 14), FEEERARA (SEQ ID NO: 15), SIRYSGHpSL (SEQ ID NO: 16), KFEEERARAKWDT (SEQ ID NO: 17), LLARRPTKGIHEY (SEQ ID NO: 18), myristoyl-FEEERI (SEQ ID NO: 19), myristoyl-FEKEKI (SEQ ID NO: 20), myristoyl-FEKERI (SEQ ID NO: 21), myristoyl-RGT, myristoyl-EEERA (SEQ ID NO: 22), myristoyl-FEEERA (SEQ ID NO: 23), myristoyl-FEEERM (SEQ ID NO: 24), myristoyl-FEEERL (SEQ ID NO: 25), myristoyl-FEKEKM (SEQ ID NO: 26), myristoyl-FEKEKL (SEQ ID NO: 27), myristoyl-FEKERM (SEQ ID NO: 28), myristoyl-FEKERL (SEQ ID NO: 29), myristoyl-CFEEERAC (SEQ ID NO: 30), myristoyl-FEEERAR (SEQ ID NO: 31), myristoyl-FEEERARA (SEQ ID NO: 32), myristoyl-SIRYSGHpSL (SEQ ID NO: 33), myristoyl-KFEEERARAKWDT (SEQ ID NO: 34), or myristoyl-LLARRPTKGIHEY (SEQ ID NO: 35).

11. The engineered, lipid-stabilized, high-loading peptide nanoparticle according to claim 9, wherein the peptide is myristoyl-FEEERL (SEQ ID NO: 25) or myristoyl-FEKEKL (SEQ ID NO: 27).

12. The engineered, lipid-stabilized, high-loading peptide nanoparticle according to claim 1, wherein 10 to 80 mole percent of the total nanoparticle mass is the peptide.

13. A pharmaceutical composition comprising the engineered, lipid-stabilized, high-loading nanoparticle of claim 1, and a pharmaceutically acceptable carrier, diluent, or excipient.

14. A method for preparing the engineered, lipid-stabilized, high-loading peptide nanoparticle of claim 1, wherein the method comprises contacting a) a peptide with b) one or more lipids free of a water-soluable polymer and c) one or more lipids covalently attached to a water-soluable polymer, where the peptide consists of 5 to 50 amino acid reduces wherein the peptide is a lipidated peptide, amphiphilic peptide, or a peptide conjugated to a hydrophobic molecule, and wherein i) greater than 10 mole percent of the total nanoparticle mass is the peptide;

ii) 2 to 20 mole percent of the total nanoparticle mass is the one or more lipids free of a water-soluble polymer; and iii) 10 to 60 mole percent of the total nanoparticle mass is the one or more lipids covalently attached to a water-soluble polymer.

15. A method of treating a thrombotic condition, an inflammatory condition, or a stroke or heart attack in a subject in need thereof comprising administering to the subject an effective amount of the engineered lipid-stabilized, high-loadig peptide nanoparticle of claim 1.

16. The method of claim 14, wherein the inflammatory condition is sepsis, acute respiratory distress syndrome (ARDS), autoimmune diseases, AV Fistula for hemodialysis, organ transplantation, atherosclerosis, vasculitis, deep vein thrombosis, or ischemia-reperfusion injury, and the thrombotic condition is arterial thrombosis, venous thrombosis and microvascular thrombosis, artificial valve thrombosis, AV-Fistura thrombosis, heart attack, or ischemic stroke.

* * * * *